(12) United States Patent
Allen et al.

(10) Patent No.: US 6,218,167 B1
(45) Date of Patent: Apr. 17, 2001

(54) STABLE BIOCATALYSTS FOR ESTER HYDROLYSIS

(75) Inventors: Larry Allen, Northfield; John Aikens, LaGrange Park; David DeMirjian, Chicago; Veronika Vonstein, Chicago; Michael Fonstein, Chicago; Malcolm Casadaban, Chicago, all of IL (US)

(73) Assignee: ThermoGen, Inc., Chicago, IL (US)

( * ) Notice: Subject to any disclaimer, the term of this patent is extended or adjusted under 35 U.S.C. 154(b) by 0 days.

(21) Appl. No.: 09/058,260

(22) Filed: Apr. 10, 1998

Related U.S. Application Data

(63) Continuation-in-part of application No. 08/827,810, filed on Apr. 11, 1997, now abandoned, which is a continuation-in-part of application No. 08/781,802, filed on Jan. 10, 1997, now Pat. No. 5,969,121, which is a continuation-in-part of application No. 08/694,078, filed on Aug. 8, 1996.

(60) Provisional application No. 60/019,580, filed on Jun. 12, 1996, and provisional application No. 60/009,704, filed on Jan. 11, 1996.

(51) Int. Cl.[7] .............................. C12N 1/20; C12N 9/16; C12N 15/00; C07H 21/04

(52) U.S. Cl. ................................. 435/252.3; 435/320.1; 435/252.33; 435/196; 536/23.2

(58) Field of Search ............................ 435/196, 320.1, 435/252.33, 252.3; 536/23.2

*Primary Examiner*—Rebecca E. Prouty
*Assistant Examiner*—M. Monshipouri
(74) *Attorney, Agent, or Firm*—McDonnell Boehnen Hulbert & Berghoff

(57) ABSTRACT

The instant invention encompasses isolated stable esterase enzymes characterized by the ability to remain stable at certain temperatures, substrate specificities, and activity profile; the expression vectors which can express, nucleic acids which encode for, and corresponding protein amino acid sequence of such proteins.

4 Claims, 55 Drawing Sheets

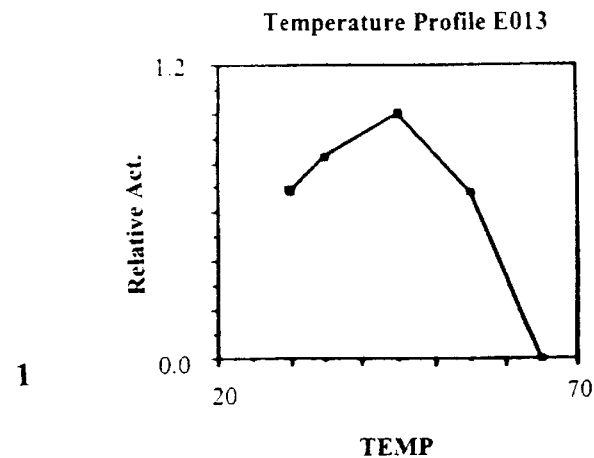
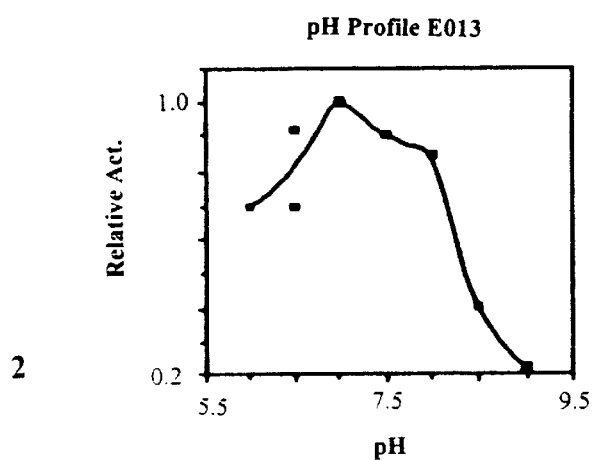
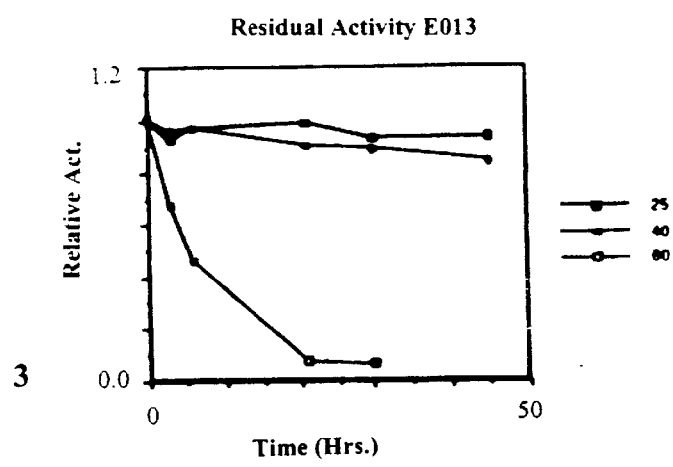
FIGURE 1A

Fig. 2A
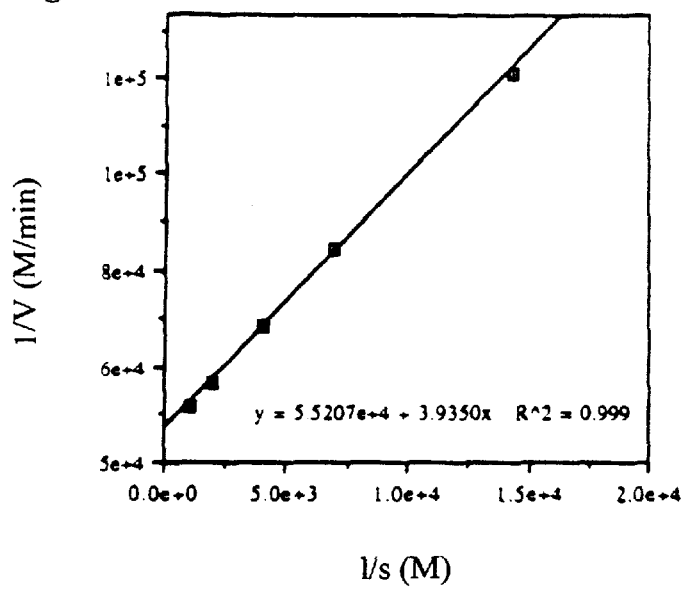
Fig. 2B
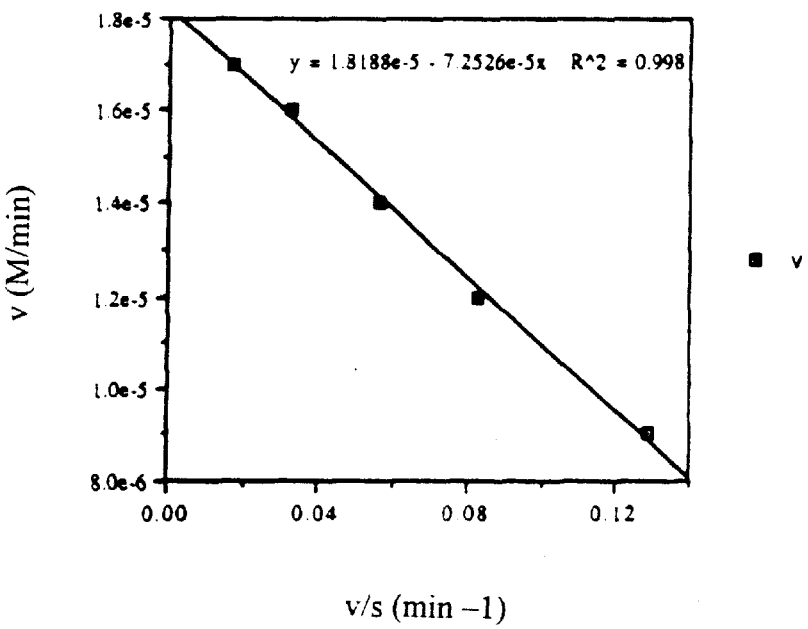
FIGURE 2

Fig. 3A
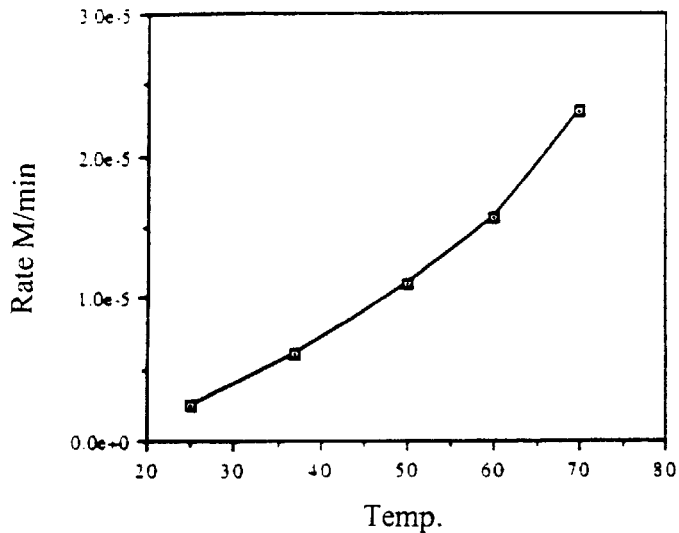
Fig. 3B
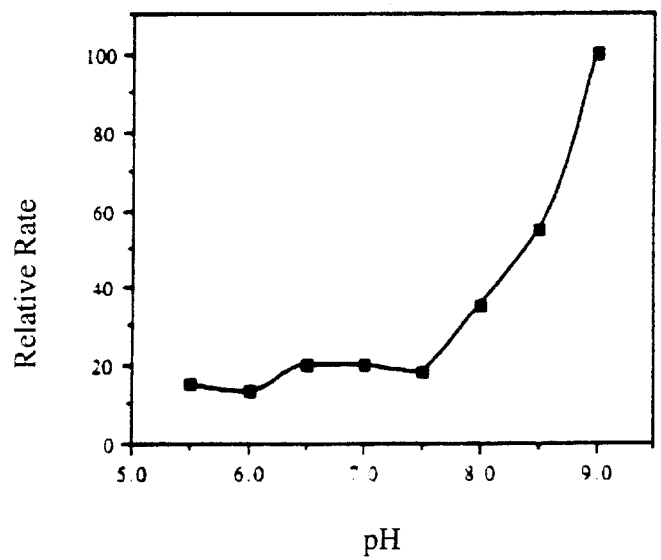
FIGURE 3

FIGURE 5A
Type I. Chirality on Carboxylate
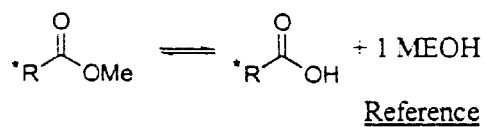 + 1 MEOH
| | Reference |
|---|---|
| 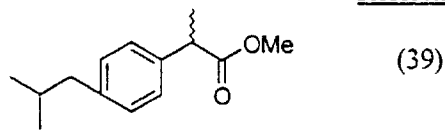 | (39) |
| 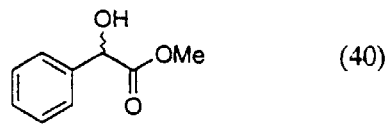 | (40) |
|  | (40) |
|  | (41) |
|  | (42) |
Type II. Chirality on Alcohol
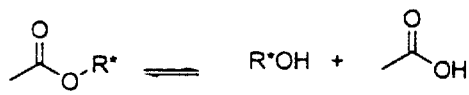
| | Reference |
|---|---|
| 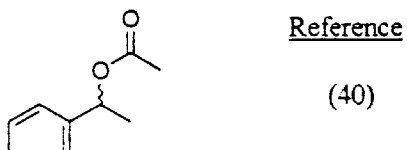 | (40) |
| 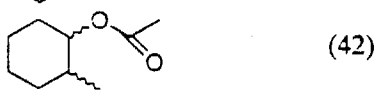 | (42) |
| 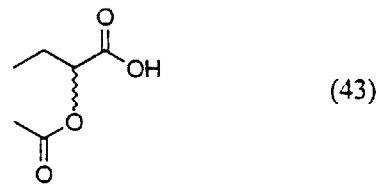 | (43) |
|  | (44) |

FIGURE 5B
TYPE III. Chiral Resolution of a Prochiral Center
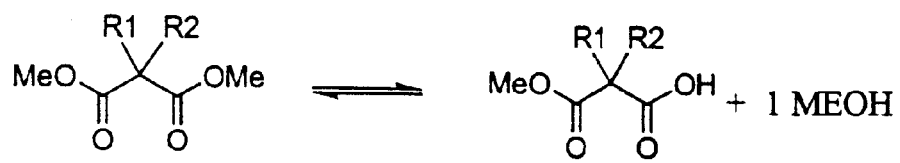
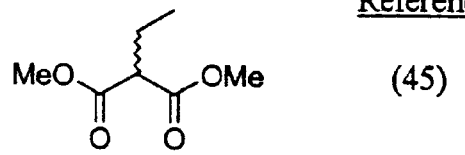
Reference
(45)
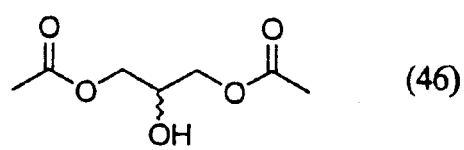
(46)
TYPE IV. Resolution of *Meso* Compounds
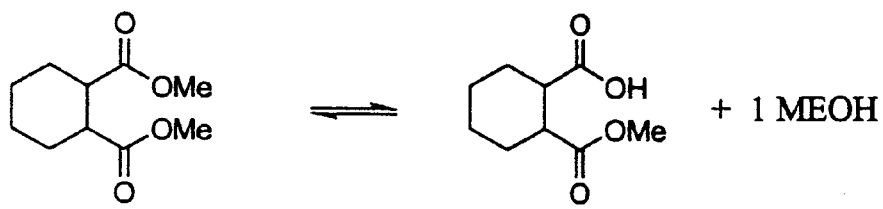
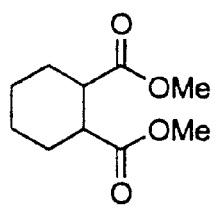
Reference
(42)
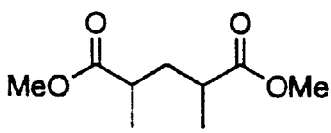
Reference
(49)
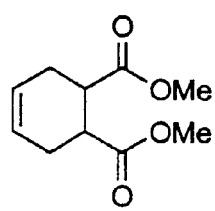
(47) (48)
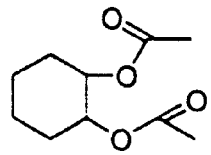
(50)
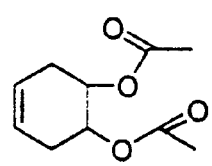
(51)

Fig. 6A-1

```
GATCAAGTGGCGATCGACCGCGCGTTGATTGAACTTGACGGCACGGAAAACAAAGGAAAGCTTGGGGC
GAATGCTATTTTAGGCGTGTCGCTCGCGGTCGCTCGCGCTGCGGCTGATGAGCTTGGCTTGCCGTTGT
ACCAATACTTGGGCGGCTTTAACGCTAAAACGCTGCCTGTACCGATGATGAACATTTTAAACGGCGGC
GCGCATGCGGACAACAACGTTGACATTCAAGAATTCATGATCATGCCGGTCGGTGCGGAAAGCTTCCG
TGAAGCGCTGCGCATGGGTGCAGAAATTTTCCATAGCTTAAAAGCTGTGTTAAAAGCGAAAGGCTACA
ACACGGCTGTCGGTGACGAAGGCGGATTTGCTCCGAACTTAAAATCGAACGAAGAAGCGCTGCAAACG
ATCATTGAAGCGATCGAAAAAGCCGGCTACAAACCAGGCGAACAAGTGATGCTCGCTATGGACGTTGC
TTCGTCGGAGCTGTACAACAAAGAAGATGGCAAATATCATTTGGAAGGCGAAGGCGTCGTCAAAACAT
CAGAAGAAATGGTTGCTTGGTATGAAGAGCTTGTGTCGAAATATCCGATCATCTCGATCGAAGACGGA
CTTGACGAAAATGACTGGGAAGGCCATAAACTGCTTACTGAGCGCCTTGGCCACAAAGTGCAGCTCGT
CGGTGACGACTTGTTTGTAACGAACACGAAAAAACTGGCCGAAGGCATTGAAAAAGGCGTCGGCAACT
CGATTTTAATTAAAGTGAACCAAATCGGTACACTGACGGAAACGTTCGATGCCATTGAGATGGCCAAA
                                                                1► GlnT
CGCGCCGGCTACACGGCGGTTGTGTCGCACCGTTCCGGTGAAACGGAAGACAGCACGATTGCCGATAT
hrArgArgLeuHisGlyGlyCysValAlaProPheArg•••AsnGlyArgGlnHisAspCysArgTyr
CGCTGTCGCAACAAACGCTGGCCAAATCAAAACGGGAGCACCGTCGCGTACGGACCGCGTCGCAAAAT
ArgCysArgAsnLysArgTrpProAsnGlnAsnGlySerThrValAlaTyrGlyProArgArgLysIl
ACAACCAGCTGCTCCGCATTGAAGACGAACTTGGCCACACGGCTATTTACCAAGGCATTCGTTCGTTT
eGlnProAlaAlaProHis•••ArgArgThrTrpProHisGlyTyrLeuProArgHisSerPheValL
TACAATTTGAAAAAATAACGGGAATCAACAACAAAGGGTGTCTCCAACGTTGCCGAGACACCCTCTTTA
euGlnPheGluLysIleThrGlyIleAsnAsnLysGlyCysLeuGlnArgCysGluThrProSerLeu
ATTACGGGAAACAGAAATGATTTCCTATCGATAGCAAAAAATGGACGTGGGTAAACCATTCGTTTATA
IleThrGlyAsnArgAsnAspPheLeuSerIleAlaLysAsnGlyArgGly•••ThrIleArgLeu••
ATATCTTTTTGTAATCGTTAGAATA TTG AAA AAG GGG ATG GGA ACC GTG ATC
•TyrLeuPheValIleValArgIle► Leu Lys Lys Gly Met Gly Thr Val  Ile
GTG GAA ACA AAG TAC GGT CGG TTG CGC GGG GGA ACA AAT GAA
Val Glu Thr Lys Tyr Gly Arg Leu Arg Gly Gly Thr Asn Glu
GGG GTT TTC TAT TGG AAA GGG ATT CCG TAC GCG AAA GCG CCG
Gly Val Phe Tyr Trp Lys Gly Ile Pro Tyr Ala Lys Ala Pro
GTC GGT GAA CGC CGT TTT TTG CCG CCG GAA CCG CCC GAT GCA
Val Gly Glu Arg Arg Phe Leu Pro Pro Glu Pro Pro Asp Ala
TGG GAC GGA GTG CGT GAG GCG ACA TCG TTT GGA CCG GTC GTC
Trp Asp Gly Val Arg Glu Ala Thr Ser Phe Gly Pro Val Val
ATG CAG CCG TCC GAT TCG ATG TTC AGC CAG CTG CTC GGA CGG
Met Gln Pro Ser Asp Ser Met Phe Ser Gln Leu Leu Gly Arg
ATG AAT GAA CCA ATG AGC GAG GAT GGG TTG TAT CTG AAC ATT
Met Asn Glu Pro Met Ser Glu Asp Gly Leu Tyr Leu Asn Ile
TGG TCA CCG GCG GCG GAT GGG AAG AAG CGC CCG GTA TTG TTT
Trp Ser Pro Ala Ala Asp Gly Lys Lys Arg Pro Val Leu Phe
TGG ATT CAT GGC GGC GCT TTT TTA TTC GGC TCC GGT TCA TTT
Trp Ile His Gly Gly Ala Phe Leu Phe Gly Ser Gly Ser Phe
CCA TGG TAT GAT GGA ACG GCG TTT GCC AAA CAC GGC GAT GTC
Pro Trp Tyr Asp Gly Thr Ala Phe Ala Lys His Gly Asp Val
GTT GTC GTG ACG ATC AAC TAC CGG ATG AGC GTG TTT GGC TTT
Val Val Val Thr Ile Asn Tyr Arg Met Ser Val Phe Gly Phe
TTG TAT TTG GGA GAT GCG TTT GGC GAA ACG TAT GCC CAG GCG
Leu Tyr Leu Gly Asp Ala Phe Gly Glu Thr Tyr Ala Gln Ala
GGA AAT CTT GGC ATA TTG GAT CAA GTG GCG GCG CTG CGC TGG
Gly Asn Leu Gly Ile Leu Asp Gln Val Ala Ala Leu Arg Trp
GTG AAA GAG AAC ATT GAG GCG TTC GGC GGT GAT CCG GAC AAC
Val Lys Glu Asn Ile Glu Ala Phe Gly Gly Asp Pro Asp Asn
```

Fig. 6A-2

```
ATT ACG ATT TTT GGC GAA TCA GCC GGA GCG GCA AGC GTT GGC
Ile Thr Ile Phe Gly Glu Ser Ala Gly Ala Ala Ser Val Gly
GTG CTG TTG TCG CTT CCG GAA GCA AGC GGG CTG TTT CGA CGC
Val Leu Leu Ser Leu Pro Glu Ala Ser Gly Leu Phe Arg Arg
GCT ATA TTG CAA AGC GGA TCG GGT TCG CTT CTT CTT CGT TCT
Ala Ile Leu Gln Ser Gly Ser Gly Ser Leu Leu Leu Arg Ser
CCG GAG ACG GCG ATG GCT CTG ACT GAA CGC ATT TTA GAA CGT
Pro Glu Thr Ala Met Ala Leu Thr Glu Arg Ile Leu Glu Arg
GCC GGC ATC CGT CCG GGT GAC CGC GAT CGG CTG CTG TCG ATT
Ala Gly Ile Arg Pro Gly Asp Arg Asp Arg Leu Leu Ser Ile
CCA GCA GCA GAG CTA TTG CAG GCG GCG ATG TCG CTC GGC CCA
Pro Ala Ala Glu Leu Leu Gln Ala Ala Met Ser Leu Gly Pro
GGA ATC ACG TAC GGT CCG GTG GTT GAC GGA CAT GTG TTG CGA
Gly Ile Thr Tyr Gly Pro Val Val Asp Gly His Val Leu Arg
CGC CAT CCG ATC GAA GCG CTC CAC GAC GGG GCA GCA AGT GAT
Arg His Pro Ile Glu Ala Leu His Asp Gly Ala Ala Ser Asp
ATT CCA ATC CTA ATT GGC GTG ACG AAA GAC GAA TAC AAT TTG
Ile Pro Ile Leu Ile Gly Val Thr Lys Asp Glu Tyr Asn Leu
TTT TCA TTG ACT GAT CCG TCA TTG ACA AGA CTC GAA GAA AAA
Phe Ser Leu Thr Asp Pro Ser Leu Thr Arg Leu Glu Glu Lys
GAA CTG CTT GAC CGG ATG AAC CGT GAG GTC GGG CCT ATT CCG
Glu Leu Leu Asp Arg Met Asn Arg Glu Val Gly Pro Ile Pro
GAG GAG GCG GTA CGC TAT TAC GCG GAA ACA GCG GAT CGG TCG
Glu Glu Ala Val Arg Tyr Tyr Ala Glu Thr Ala Asp Arg Ser
GCA CCC GCG TGG CAA ACA TGG CTG CGC ATC ATG ACG TAC CTT
Ala Pro Ala Trp Gln Thr Trp Leu Arg Ile Met Thr Tyr Leu
GTT TTT GTC GAC GGA ATG TTG CGA ACG GCG GAT GCC CAA GCA
Val Phe Val Asp Gly Met Leu Arg Thr Ala Asp Ala Gln Ala
GCG CAA GGG GCG AAT GTG TAC ATG TAT CGG TTT GAT TAT GAA
Ala Gln Gly Ala Asn Val Tyr Met Tyr Arg Phe Asp Tyr Glu
ACG CCG GCG TTC GGT GGA CAA CTG AAA GCG TGC CAT ACG CTC
Thr Pro Ala Phe Gly Gly Gln Leu Lys Ala Cys His Thr Leu
GAG TTG CCG TTT GTG TTT CAT AAC CTC CAT CAG CCT GGT GTC
Glu Leu Pro Phe Val Phe His Asn Leu His Gln Pro Gly Val
GAG AAT TTC GTC GGC AAC CGA CCA GAG CGT GAG GCG ATT GCC
Glu Asn Phe Val Gly Asn Arg Pro Glu Arg Glu Ala Ile Ala
AGC GAA ATG CAT GGT GCC TGG CTT TCG TTC GCC CGC ACC GGC
Ser Glu Met His Gly Ala Trp Leu Ser Phe Ala Arg Thr Gly
AAC CCG AAC GGC GCT CAT TTA CCA GAG AAG TGG CCC GTA TAC
Asn Pro Asn Gly Ala His Leu Pro Glu Lys Trp Pro Val Tyr
ACA AAA GAG CAC AAA CCG GTG TTT GTC TTT TCG GCT GCG AGC
Thr Lys Glu His Lys Pro Val Phe Val Phe Ser Ala Ala Ser
CAT GTG GAA GAC GAT CCG TTC GGT CGC GAG CGG GAA GCG TGG
His Val Glu Asp Asp Pro Phe Gly Arg Glu Arg Glu Ala Trp
CAA GGA CGC CTT TGA CGAAAAATCCATAAGCAACATGTGTTCTTTGTCTGAACACGAT
Gln Gly Arg Leu ***
CAAGGTACGCGCATTTTCGCGGAAAAAGACCGTGGGCAAACGTTCGCCTTTACCTCTAAAAGGAATGA
CGCAACATGTCTGCACTTCACAGGAAAGAGGACGAAACGGTTGGTTTTCAGAATAGGAAAAGGTGTCC
```

Fig. 6A-3

```
CGTTTTTTGGGACACCTTCTTCTATGTATCGCTCAATCATTTGCTTCTGTGGCAGGAAGCCCGAATCG
CTCGGCGAGTGCCGGATCACGATCGATCGCCTCAATCAGTTTCCGCATGACGTTCACATCAAACGTAA
AATTCGAACCGATTGGCGAGGTGACGAAAATTTTCCCTTCTTTCGCCTCGCGTGCTCGTTTAAATTGA
TAGCCGTCAATCGCAATGACGACTCGTTCGTCTGGCCTTGCCATTAGGAATCCCTCCATCGCTGTTTT
TTCTTTCATTGTACTTGATTTTGAGGATGAACACCAACGTTCATGACACGCTCTTAAGGATAACGGAT
GGGAGAGCGTTAGAGGGCGGTGAATTTCATCAAGAACGTAGCACAAAACGACATTTTTTTCATTATAGA
CGTCTTGATGTTTGGAATGATCGGAAAAGGCGATTGTTAGGCGGGGATCATGATCCACTAGCGGATGA
AAGTGAAGAGCAACGAAATAGTCTCTTTTGTTTCACAACAAATGAATTGGTGCCATTCAGGGCGGAGAC
AGGTGAGACAGTTGCTGCAAACGATAATGTATGGTATAGTAAAAATATTGCAACGTAGGTCGTTGGAG
GTGTCAGGCATGCATGCCTTGCTTGTGA
```

Fig. 6B-1

```
TCTAATTCACGCTGGATCTTTCCTTTGTGTTTTAAAACTTAAAGCACCGGATTGCCGGCTGTATGGTCCGG
 Ser Asn Ser Arg Trp Ile Phe Pro Leu Cys Phe Lys Thr ••• Ser Thr Gly Leu Pro Ala Val Trp Ser Gl
TTGGATATTGTCATCACATCGTGGATATCAGTGGATCCGGTGCGATGGATTGCTTCAGGGGAACTTTTAAA
y Trp Ile Leu Ser Ser His Ser Arg Gly Tyr Gln Trp Ile Arg Cys Asp Gly Leu Leu Gln Gly Asn Phe ••• T
CACTTGAGTTTGACAACCACTCCTTAATCATTTAAGATTTAAATGAAAATTAAAATAAATCAAAAAGA
hr Leu Glu Phe Asp Asn His Ser Leu Ile Ile ••• Asp Leu Asn Glu Asn ••• Asn Lys Ser Lys Arg
```

<u>TTG</u> ATT CAA <u>ATG</u> AAT ACG <u>TTG</u> GTG GAA ACC CGT TTT GGG AAA GTG
Leu Ile Gln Met Asn Thr Leu Val Glu Thr Arg Phe Gly Lys Val
CAA GGC GGT ACA GAC GGA GAG GTT TGT TTT TGG AAA GGG ATT CCT
Gln Gly Gly Thr Asp Gly Glu Val Cys Phe Trp Lys Gly Ile Pro
TAT GCG AAA CCT CCG GTG GGA AAA CGC CGC TTT CAA AAA CCG GAA
Tyr Ala Lys Pro Pro Val Gly Lys Arg Arg Phe Gln Lys Pro Glu
CCG CCG GAG AAA TGG GAT GGC GTT TGG GAG GCC ACC CGG TTC CGG
Pro Pro Glu Lys Trp Asp Gly Val Trp Glu Ala Thr Arg Phe Arg
TCC ATG GTG ATG CAG CCG TCC GGC ACC ACC TTC AGC ACC GTG CTC
Ser Met Val Met Gln Pro Ser Gly Thr Thr Phe Ser Thr Val Leu
GGG GAA GCG GAT CTT CCT GTG AGC GAA GAC GGT CTT TAT CTG AAT
Gly Glu Ala Asp Leu Pro Val Ser Glu Asp Gly Leu Tyr Leu Asn
ATC TGG TCG CCG GCA GCC GAC GGA AAA AAG CGG CCG GTG CTC TTC
Ile Trp Ser Pro Ala Ala Asp Gly Lys Lys Arg Pro Val Leu Phe
TGG ATC CAT GGC GGC GCC TAC CAG TTT GGG TCC GGC GCT TCC CCC
Trp Ile His Gly Gly Ala Tyr Gln Phe Gly Ser Gly Ala Ser Pro
TGG TAT GAC GGG ACG GAG TTT GCC AAA AAC GGA GAT GTG GTG GTT
Trp Tyr Asp Gly Thr Glu Phe Ala Lys Asn Gly Asp Val Val Val
GTC ACG ATC AAC TAC CGG TTG AAC GCG TTT GGA TTT TTG TAC TTG
Val Thr Ile Asn Tyr Arg Leu Asn Ala Phe Gly Phe Leu Tyr Leu
GCA GAT TGG TTC GGC GAC GAA TTT TCA GCG TCG GGC AAC CTG GGA
Ala Asp Trp Phe Gly Asp Glu Phe Ser Ala Ser Gly Asn Leu Gly
ATT TTG GAC CAA GTC GCT GCA CTG CGC TGG GTG AAA GAA AAC ATT
Ile Leu Asp Gln Val Ala Ala Leu Arg Trp Val Lys Glu Asn Ile
TCG GCA TTC GGC GGC GAC CCG GAG CAA ATC ACC ATC TTC GGG GAG
Ser Ala Phe Gly Gly Asp Pro Glu Gln Ile Thr Ile Phe Gly Glu
TCG GCC GGA GCC GGA AGC GTC GGG GTT CTG CTT TCC CTC CCG GAA
Ser Ala Gly Ala Gly Ser Val Gly Val Leu Leu Ser Leu Pro Glu
ACC AAA GGG CTG TTT CAA CGG GCG ATC TTG CAA AGC GGA TCG GGT
Thr Lys Gly Leu Phe Gln Arg Ala Ile Leu Gln Ser Gly Ser Gly
GCC ATT TTG CTC CGT TCC TCT CAG ACA GCC TCG GGC ATC GCG GAA
Ala Ile Leu Leu Arg Ser Ser Gln Thr Ala Ser Gly Ile Ala Glu
CAA ATT CTT ACG AAA GCC GGC ATT CGA AAA GGA GAC CGC GAC CGG
Gln Ile Leu Thr Lys Ala Gly Ile Arg Lys Gly Asp Arg Asp Arg
TTG TTA TCC ATC CCG GCC GGT GAA CTC CTT GAA GCC GCA CAA TCC
Leu Leu Ser Ile Pro Ala Gly Glu Leu Leu Glu Ala Ala Gln Ser
GTG AAT CCG GGA ATG GTT TTT GGT CCC GTT GTG GAC GGC ACC GTA
Val Asn Pro Gly Met Val Phe Gly Pro Val Val Asp Gly Thr Val
TTG AAA ACC CAT CCG ATT GAA GCG TTG GAA ACC GGA GCC GCC GGC
Leu Lys Thr His Pro Ile Glu Ala Leu Glu Thr Gly Ala Ala Gly
GAT ATC CCG ATC ATC ATC GGG GTG ACA AAG GAT GAG TAC AAT TTA
Asp Ile Pro Ile Ile Ile Gly Val Thr Lys Asp Glu Tyr Asn Leu

Fig. 6B-2

```
TTT ACA CTG ACT GAC CCT TCC TGG ACG ACA GCG GGA AAA GAA GAA
Phe Thr Leu Thr Asp Pro Ser Trp Thr Thr Ala Gly Lys Glu Glu
CTG ATG GAC CGG ATC GAA CAG GAA ATC GGG CCG GTT CCG GAA AAA
Leu Met Asp Arg Ile Glu Gln Glu Ile Gly Pro Val Pro Glu Lys
GTT TTT CCA TAT TAC TTA TCT TTT GGG GAT CCA TCG CAA CCG GTA
Val Phe Pro Tyr Tyr Leu Ser Phe Gly Asp Pro Ser Gln Pro Val
TGG CAA AAG CTG TTG CGC GCC ATG ACC TAC CAC ATC TTT ACC CGG
Trp Gln Lys Leu Leu Arg Ala Met Thr Tyr His Ile Phe Thr Arg
GGC ATG TTA AAA ACG GCT GAC GCC CAA ATC AAG CAA GGC GGG AAG
Gly Met Leu Lys Thr Ala Asp Ala Gln Ile Lys Gln Gly Gly Lys
GTT TGG GTT TAC CGG TTT GAT TAC GAA ACC CCG CTC TTT GAC GGT
Val Trp Val Tyr Arg Phe Asp Tyr Glu Thr Pro Leu Phe Asp Gly
CGG TTG AAA GCA TGT CAC GCA CTG GAA ATC CCC TTT GTC TTT CAC
Arg Leu Lys Ala Cys His Ala Leu Glu Ile Pro Phe Val Phe His
AAC CTG CAT CAA CCG GGG GTC GAT GTG TTC ACC GGC ACA CAT CCG
Asn Leu His Gln Pro Gly Val Asp Val Phe Thr Gly Thr His Pro
AAG CGG GAG CTA ATT TCC CGG CAA ATG CAT GAA GCA TGG ATT GCC
Lys Arg Glu Leu Ile Ser Arg Gln Met His Glu Ala Trp Ile Ala
TTT GCC CGG ACA GGG GAT CCG AAC GGC GAC CAT CTC CCC GAT GCG
Phe Ala Arg Thr Gly Asp Pro Asn Gly Asp His Leu Pro Asp Ala
TGG TTG CCC TTT GCA CAA AAA GAC CGG CCG GCC ATG GTC TTT GAC
Trp Leu Pro Phe Ala Gln Lys Asp Arg Pro Ala Met Val Phe Asp
ACC GAA ACC AGA GCG GAA AAG CAT CTG TTT GAC CGC GAG CAG GAA
Thr Glu Thr Arg Ala Glu Lys His Leu Phe Asp Arg Glu Gln Glu
CTG TGG GAA TCA AAG GCT TGA GTGATTTGCTCAAGCCTTTTTTGCATTTCACGTATGTA
Leu Trp Glu Ser Lys Ala ***
TTCGGATTTGGAATTAAACAATGGTGCTTTTATCGAAATGGGGAGTGTTTGCTTATAATGAACGGGTTTAC
AAAGCTTGTTTTGGTACCGGATTACTGAAATGATCCGTGTTTATCATTTGGATGCTTTCTATTGGAAACCG
```

Fig. 6C-1

```
GATCTTTCCTTTGTGTTTTAAAACTTAAAGCACCGGATTGCCGGCTGTATGGTCCGGTTGGATATTGT
 IlePheProLeuCysPheLysThr***SerThrGlyLeuProAlaValTrpSerGlyTrpIleLeuS
CATCACATCGTGGATATCAGTGGATCCGGTGCGATGGATTGCTTCAGGGGAACTTTTAAACACTTGAG
erSerHisArgGlyTyrGlnTrpIleArgCysAspGlyLeuLeuGlnGlyAsnPhe***ThrLeuGlu
TTTGACAACCACTCCTTAATCATTTAAGATTTAAATGAAAATTAAAATAAATCAAAAAGA GTG
PheAspAsnHisSerLeuIleIle***AspLeuAsnGluAsn***AsnLysSerLysArg Val
```

| ATT | CAA | ATG | AAT | ACG | TTG | GTG | GAA | ACC | CGT | TTT | GGG | AAA | GTG |
|---|---|---|---|---|---|---|---|---|---|---|---|---|---|
| Ile | Gln | Met | Asn | Thr | Leu | Val | Glu | Thr | Arg | Phe | Gly | Lys | Val |
| CAA | GGC | GGT | ACA | GAC | GGA | GAG | GTT | TGT | TTT | TGG | AAA | GGG | ATT |
| Gln | Gly | Gly | Thr | Asp | Gly | Glu | Val | Cys | Phe | Trp | Lys | Gly | Ile |
| CCT | TAT | GCG | AAA | CCT | CCG | GTG | GGA | AAA | CGC | CGC | TTT | CAA | AAA |
| Pro | Tyr | Ala | Lys | Pro | Pro | Val | Gly | Lys | Arg | Arg | Phe | Gln | Lys |
| CCG | GAA | CCG | CCG | GAG | AAA | TGG | GAT | GGC | GTT | TGG | GAG | GCC | ACC |
| Pro | Glu | Pro | Pro | Glu | Lys | Trp | Asp | Gly | Val | Trp | Glu | Ala | Thr |
| CGG | TTC | CGG | TCC | ATG | GTG | ATG | CAG | CCG | TCC | GGC | ACC | ACC | TTC |
| Arg | Phe | Arg | Ser | Met | Val | Met | Gln | Pro | Ser | Gly | Thr | Thr | Phe |
| AGC | ACC | GTG | CTC | GGG | GAA | GCG | GAT | CTT | CCT | GTG | AGC | GAA | GAC |
| Ser | Thr | Val | Leu | Gly | Glu | Ala | Asp | Leu | Pro | Val | Ser | Glu | Asp |
| GGT | CTT | TAT | CTG | AAT | ATC | TGG | TCG | CCG | GCA | GCC | GAC | GGA | AAA |
| Gly | Leu | Tyr | Leu | Asn | Ile | Trp | Ser | Pro | Ala | Ala | Asp | Gly | Lys |
| AAG | CGG | CCG | GTG | CTC | TTC | TGG | ATC | CAT | GGC | GGC | GCC | TAC | CAG |
| Lys | Arg | Pro | Val | Leu | Phe | Trp | Ile | His | Gly | Gly | Ala | Tyr | Gln |
| TTT | GGG | TCC | GGC | GCT | TCC | CCC | TGG | TAT | GAC | GGG | ACG | GAG | TTT |
| Phe | Gly | Ser | Gly | Ala | Ser | Pro | Trp | Tyr | Asp | Gly | Thr | Glu | Phe |
| GCC | AAA | AAC | GGA | GAT | GTG | GTG | GTT | GTC | ACG | ATC | AAC | TAC | CGG |
| Ala | Lys | Asn | Gly | Asp | Val | Val | Val | Val | Thr | Ile | Asn | Tyr | Arg |
| TTG | AAC | GCG | TTT | GGA | TTT | TTG | TAC | TTG | GCA | GAT | TGG | TTC | GGC |
| Leu | Asn | Ala | Phe | Gly | Phe | Leu | Tyr | Leu | Ala | Asp | Trp | Phe | Gly |
| GAC | GAA | TTT | TCA | GCG | TCG | GGC | AAC | CTG | GGA | ATT | TTG | GAC | CAA |
| Asp | Glu | Phe | Ser | Ala | Ser | Gly | Asn | Leu | Gly | Ile | Leu | Asp | Gln |
| GTC | GCT | GCA | CTG | CGC | TGG | GTG | AAA | GAA | AAC | ATT | TCG | GCA | TTC |
| Val | Ala | Ala | Leu | Arg | Trp | Val | Lys | Glu | Asn | Ile | Ser | Ala | Phe |
| GGC | GGC | GAC | CCG | GAG | CAA | ATC | ACC | ATC | TTC | GGG | GAG | TCG | GCC |
| Gly | Gly | Asp | Pro | Glu | Gln | Ile | Thr | Ile | Phe | Gly | Glu | Ser | Ala |
| GGA | GCC | GGA | AGC | GTC | GGG | GTT | CTG | CTT | TCC | CTC | CCG | GAA | ACC |
| Gly | Ala | Gly | Ser | Val | Gly | Val | Leu | Leu | Ser | Leu | Pro | Glu | Thr |
| AAA | GGG | CTG | TTT | CAA | CGG | GCG | ATC | TTG | CAA | AGC | GGA | TCG | GGT |
| Lys | Gly | Leu | Phe | Gln | Arg | Ala | Ile | Leu | Gln | Ser | Gly | Ser | Gly |
| GCC | ATT | TTG | CTC | CGT | TCC | TCT | CAG | ACA | GCC | TCG | GGC | ATC | GCG |
| Ala | Ile | Leu | Leu | Arg | Ser | Ser | Gln | Thr | Ala | Ser | Gly | Ile | Ala |
| GAA | CAA | ATT | CTT | ACG | AAA | GCC | GGC | ATT | CGA | AAA | GGA | GAC | CGC |
| Glu | Gln | Ile | Leu | Thr | Lys | Ala | Gly | Ile | Arg | Lys | Gly | Asp | Arg |
| GAC | CGG | TTG | TTA | TCC | ATC | CCG | GCC | GGT | GAA | CTC | CTT | GAA | GCC |
| Asp | Arg | Leu | Leu | Ser | Ile | Pro | Ala | Gly | Glu | Leu | Leu | Glu | Ala |
| GCA | CAA | TCC | GTG | AAT | CCG | GGA | ATG | GTT | TTT | GGT | CCC | GTT | GTG |
| Ala | Gln | Ser | Val | Asn | Pro | Gly | Met | Val | Phe | Gly | Pro | Val | Val |

Fig. 6C-2

```
GAC GGC ACC GTA TTG AAA ACC CAT CCG ATT GAA GCG TTG GAA
Asp Gly Thr Val Leu Lys Thr His Pro Ile Glu Ala Leu Glu
ACC GGA GCC GCC GGC GAT ATC CCG ATC ATC ATC GGG GTG ACA
Thr Gly Ala Ala Gly Asp Ile Pro Ile Ile Ile Gly Val Thr
AAG GAT GAG TAC AAT TTA TTT ACA CTG ACT GAC CCT TCC TGG
Lys Asp Glu Tyr Asn Leu Phe Thr Leu Thr Asp Pro Ser Trp
ACG ACA GCG GGA AAA GAA GAA CTG ATG GAC CGG ATC GAA CAG
Thr Thr Ala Gly Lys Glu Glu Leu Met Asp Arg Ile Glu Gln
GAA ATC GGG CCG GTT CCG GAA AAA GTT TTT CCA TAT TAC TTA
Glu Ile Gly Pro Val Pro Glu Lys Val Phe Pro Tyr Tyr Leu
TCT TTT GGG GAT CCA TCG CAA CCG GTA TGG CAA AAG CTG TTG
Ser Phe Gly Asp Pro Ser Gln Pro Val Trp Gln Lys Leu Leu
CGC GCC ATG ACC TAC CAC ATC TTT ACC CGG GGC ATG TTA AAA
Arg Ala Met Thr Tyr His Ile Phe Thr Arg Gly Met Leu Lys
ACG GCT GAC GCC CAA ATC AAG CAA GGC GGG AAG GTT TGG GTT
Thr Ala Asp Ala Gln Ile Lys Gln Gly Gly Lys Val Trp Val
TAC CGG TTT GAT TAC GAA ACC CCG CTC TTT GAC GGT CGG TTG
Tyr Arg Phe Asp Tyr Glu Thr Pro Leu Phe Asp Gly Arg Leu
AAA GCA TGT CAC GCA CTG GAA ATC CCC TTT GTC TTT CAC AAC
Lys Ala Cys His Ala Leu Glu Ile Pro Phe Val Phe His Asn
CTG CAT CAA CCG GGG GTC GAT GTG TTC ACC GGC ACA CAT CCG
Leu His Gln Pro Gly Val Asp Val Phe Thr Gly Thr His Pro
AAG CGG GAG CTA ATT TCC CGG CAA ATG CAT GAA GCA TGG ATT
Lys Arg Glu Leu Ile Ser Arg Gln Met His Glu Ala Trp Ile
GCC TTT GCC CGG ACA GGG GAT CCG AAC GGC GAC CAT CTC CCC
Ala Phe Ala Arg Thr Gly Asp Pro Asn Gly Asp His Leu Pro
GAT GCG TGG TTG CCC TTT GCA CAA AAA GAC CGG CCG GCC ATG
Asp Ala Trp Leu Pro Phe Ala Gln Lys Asp Arg Pro Ala Met
GTC TTT GAC ACC GAA ACC AGA GCG GAA AAG CAT CTG TTT GAC
Val Phe Asp Thr Glu Thr Arg Ala Glu Lys His Leu Phe Asp
CGC GAG CAG GAA CTG TGG GAA TCA AAG GCT TGA GTGATTTGCT
Arg Glu Gln Glu Leu Trp Glu Ser Lys Ala ***
CAAGCCTTTT TTGCATTTCA CGTATGTATT CGGATTTGGA ATTAAACAAT GGTGCTTTTA
TCGAAATGGG GAGTGTTTGC TTATAATGAA CGGGTTTACA AAGCTTGTTT TGGTACCGGA
TTACTGAAAT GATCAGAAGG AAATATCATG ACGTAATAAT CAGGGGATCT TGAGAAAGAA
ATACATGGAG TGTTATGTCC CTTGAAAAAC AGAGACGCCG GTGGCATCAC CATCACAGGG
```

Fig. 6D-1

```
GATCCGCTTC ATCCAGCAGG TCCTGGAGCA GCGGGAGCGG GAGGACACCT TCCGCCTCAA
GCGCATCAAG GGCAAGATCG AGGCCCGGGA AGCGGAGGAG GGGGGGCGGC CCAACCCCCA
CCTGGAGATC GGAGCGGGCC TCTAAGGCCG CCCCAGCTTG AGCCACCCCC CAGGCTTCCC
CTGGGGGGTT TACCCTTGAC CCGGTCAAG GTTTTCGGGT AGGCTCCTCC TCGGAGGGAA
AACC ATG AGG CGG CTT TTG GGG CTC CTT TTG TTC CTG GCC TTG GCC TTG
     Met Arg Arg Leu Leu Gly Leu Leu Leu Phe Leu Ala Leu Ala Leu
      1               5                  10                  15

GCG CAA GGC CTT GGC CCT TAC TGG CAG GAG GTT CAG GCC CAG GGT ACG
Ala Gln Gly Leu Gly Pro Tyr Trp Gln Glu Val Gln Ala Gln Gly Thr
                 20                  25                  30

GTC TGC TCG GAC GGC TCC CCC TGG CGG TTC TAC GTG AGC CCG GGG GAC
Val Cys Ser Asp Gly Ser Pro Trp Arg Phe Tyr Val Ser Pro Gly Asp
             35                  40                  45

CCC AAG AAG GTC CTT CTG GAC TTC CAG GGG GGC GGG GCC TGC TGG GAC
Pro Lys Lys Val Leu Leu Asp Phe Gln Gly Gly Gly Ala Cys Trp Asp
         50                  55                  60

GCC CAG ACC TGC GGT CCC CAG AGC CAG ACC TAC CGG AAG CGG GTG GAC
Ala Gln Thr Cys Gly Pro Gln Ser Gln Thr Tyr Arg Lys Arg Val Asp
     65                  70                  75

GTG CAG GAA CTC CTC CTG GCC CAG GGG ATC TAC AAC CGG GCG AGC ATC
Val Gln Glu Leu Leu Leu Ala Gln Gly Ile Tyr Asn Arg Ala Ser Ile
 80                  85                  90                  95

GCC AAC CCC TTC TTC GGC TGG ACC CAC GTC TTC ATC CCC TAC TGC ACG
Ala Asn Pro Phe Phe Gly Trp Thr His Val Phe Ile Pro Tyr Cys Thr
                100                 105                 110

GGG GAC CTG CAC GTG GGC CGG GCC ACG GTG GAC TAC GGC GGC TTT AAG
Gly Asp Leu His Val Gly Arg Ala Thr Val Asp Tyr Gly Gly Phe Lys
             115                 120                 125

GTC CAC CAC CAG GGG GCG CGA AAC GCC CTG GCC GCC TTG GAG TAC GTC
Val His His Gln Gly Ala Arg Asn Ala Leu Ala Ala Leu Glu Tyr Val
         130                 135                 140

TTC AAG AAC TAC CCC AAG GCA GAG CGG GTC TTC GTC ACC GGG TGC AGC
Phe Lys Asn Tyr Pro Lys Ala Glu Arg Val Phe Val Thr Gly Cys Ser
     145                 150                 155

GCC GGG GGG TAC GGG GCG GTC TTC TGG GCG GAC AAG GTC CTT GCC ACC
Ala Gly Gly Tyr Gly Ala Val Phe Trp Ala Asp Lys Val Leu Ala Thr
160                 165                 170                 175

TAC AAA AGC GCC CAG ATC GCC GTT TGC GGG GAC GCC GCC TTG GGC GTG
Tyr Lys Ser Ala Gln Ile Ala Val Cys Gly Asp Ala Ala Leu Gly Val
                180                 185                 190

AGC ACA TCG GAC TTC CCC GGG AGC CGG GTT TGG AAC GCC CGC CTG CCC
Ser Thr Ser Asp Phe Pro Gly Ser Arg Val Trp Asn Ala Arg Leu Pro
             195                 200                 205
```

Fig. 6D-2

```
GAG CTT CCC GGC CTG GGC CCG AAC CCC AGC GTG GAG GAG ATC TAC CGG
Glu Leu Pro Gly Leu Gly Pro Asn Pro Ser Val Glu Glu Ile Tyr Arg
        210                 215                 220

GCC CTG GCC CGG GCC TAC CCC GGC GCG GCC TTC GCC CAG TAC ACC ACC
Ala Leu Ala Arg Ala Tyr Pro Gly Ala Ala Phe Ala Gln Tyr Thr Thr
        225                 230                 235

CAG CTG GAC GGG ACC CAG ATC TAC TTC TAC GCC CTC ATG AAG AAG GAG
Gln Leu Asp Gly Thr Gln Ile Tyr Phe Tyr Ala Leu Met Lys Lys Glu
240                 245                 250                 255

GTA CCC CCC TCC GAG GCC ACC GCC CGG GAG TGG GCC GTC CGG GCC CAG
Val Pro Pro Ser Glu Ala Thr Ala Arg Glu Trp Ala Val Arg Ala Gln
                260                 265                 270

ACC AGC CTC CAG AGC CTG GCC CAG GAG TCC AAC TTC ACC TAC TAC CTG
Thr Ser Leu Gln Ser Leu Ala Gln Glu Ser Asn Phe Thr Tyr Tyr Leu
        275                 280                 285

GCC CCG GGG AGC CAA CAC TGC ATC CTG CCC CGG CCC GAG CTC TAC ACC
Ala Pro Gly Ser Gln His Cys Ile Leu Pro Arg Pro Glu Leu Tyr Thr
        290                 295                 300

CTG AAG GTG GGG GAG GTG AGC GTT CTG GAC TGG CTC AGG AGC CTG GCG
Leu Lys Val Gly Glu Val Ser Val Leu Asp Trp Leu Arg Ser Leu Ala
        305                 310                 315

GAG AAG GGG CAG GCC CCC CGC GTA GGT CCG TGAGGTCGGG GAGGGCCTCG
Glu Lys Gly Gln Ala Pro Arg Val Gly Pro
320                 325
```

```
AGGAGGACCC GGTACGCCTC CTTGGGGGAG GGGGCCTGGA GGAGGGCCCG GAGGACCCCC
TCCCCTTTCG CCACCAGGAC GTCCGCCTTC AGGGCGAAGA CCCCTTGGAA GTAGAGGGCG
TCCGCCAGGC TGGTGCGGAG CCGGTCATAG GCGCTGAGGC GGGGGTTGGG GGGTCTTAGC
CGGGCGAGGA GGCGCGCCCA GGCCAGGTAA AGGGGGTACC GCTCAGGGTA GGCCCCCTTC
AGGGCGAAGA GGAAGAGGTA GTTGGCCAGG AACTCGTCCA GCCAGCGGCG GCCGGTCCTG
AGCCGCCAGG CCACCTGGAC CGCGTGGGCG TGCTCGTGCC CCAGGGTGAG GTCCAAGAAC
TCCTCCAGCG CCCCGGGGAG ACCCTCCTCC GCCACAGGCA GGAGGACCTG GCGCAGGCGG
TGGAGGAGGC GCTCGGGGTA GACCAGAGGG ACGAAGAGGT AAAGCCGGGT CCGGCTCGTC
CTCTGGAAGG GGAGGCCGTA GGGCACCCGG TCCTCTCCC GCCAGTCCCT CTCCGAGAGG
ACGAAGAGGG TCACGGGGGG AAGGGGGCGG TAGCGGGCCA GGAGGCGGTG GAGCCCCTCC
```

Fig. 6E-1

```
ACGATTGCCGATATCGCTGTCGCAACAAACGCTGGCCAAATCAAAACGGGAGCACCGTCGCGTACGGA
Thr IleAlaAspIleAlaValAlaThrAsnAlaGlyGlnIleLysThrGlyAlaProSerArgThrAs
CCGCGTCGCAAAATACAACCAGTTGCTCCGCATTGAAGACGAACTTGGCCACACGGCTATTTACCAAG
pArgValAlaLysTyrAsnGlnLeuLeuArgIleGluAspGluLeuGlyHisThrAlaIleTyrGlnG
GCATTCGTTCGTTTTACAATTTGAAAAAATAACGGGAATCAACAACAAAGGGTGTCTCCAACGTTGCG
lyIleArgSerPheTyrAsnLeuLysLys***◁IGlyIleAsnAsnLysGlyCysLeuGlnArgCysG
AGACACCCTCTTTAATTACGGGAAACAGAAATGATTTCCTATCGATAGCAAAAAATGGACGTGGGTAA
luThrProSerLeuIleThrGlyAsnArgAsnAspPheLeuSerIleAlaLysAsnGlyArgGly***
ACCATTCGTTTATAATATCTTTTTTGTAATCGTTAGAATA TTG AAA AAG GGG ATG GGA
ThrIleArgLeu***TyrLeuPheValIleValArgIle▷ Leu Lys Lys Gly Met Gly
ACC GTG ATC GTG GAA ACA AAG TAC GGT CGG TTG CGC GGG GGA
Thr Val Ile Val Glu Thr Lys Tyr Gly Arg Leu Arg Gly Gly
ACA AAT GAA GGG GTT TTC TAT TGG AAA GGG ATT CCG TAC GCG
Thr Asn Glu Gly Val Phe Tyr Trp Lys Gly Ile Pro Tyr Ala
AAA GCG CCG GTC GGT GAA CGC CGT TTT TTG CCG CCG GAA CCG
Lys Ala Pro Val Gly Glu Arg Arg Phe Leu Pro Pro Glu Pro
CCC GAT GCA TGG GAC GGA GTG CGT GAG GCG ACA TCG TTT GGA
Pro Asp Ala Trp Asp Gly Val Arg Glu Ala Thr Ser Phe Gly
CCG GTC GTC ATG CAG CCG TCC GAT TCG ATG TTC AGC CAG CTG
Pro Val Val Met Gln Pro Ser Asp Ser Met Phe Ser Gln Leu
CTC GGA CGG ATG AAT GAA CCA ATG AGC GAG GAT GGG TTG TAT
Leu Gly Arg Met Asn Glu Pro Met Ser Glu Asp Gly Leu Tyr
CTG AAC ATT TGG TCA CCG GCG GCG GAT GGG AAG AAG CGC CCG
Leu Asn Ile Trp Ser Pro Ala Ala Asp Gly Lys Lys Arg Pro
GTA TTG TTT TGG ATT CAT GGC GGC GCT TTT TTA TTC GGC TCC
Val Leu Phe Trp Ile His Gly Gly Ala Phe Leu Phe Gly Ser
GGT TCA TTT CCA TGG TAT GAT GGA ACG GCG TTT GCC AAA CAC
Gly Ser Phe Pro Trp Tyr Asp Gly Thr Ala Phe Ala Lys His
GGC GAT GTC GTT GTC GTG ACG ATC AAC TAC CGG ATG AGC GTG
Gly Asp Val Val Val Val Thr Ile Asn Tyr Arg Met Ser Val
TTT GGC TTT TTG TAT TTG GGA GAT GCG TTT GGC GAA ACG TAT
Phe Gly Phe Leu Tyr Leu Gly Asp Ala Phe Gly Glu Thr Tyr
GCC CAG GCG GGA AAT CTT GGC ATA TTG GAT CAA GTG GCG GCG
Ala Gln Ala Gly Asn Leu Gly Ile Leu Asp Gln Val Ala Ala
CTG CGC TGG GTG AAA GAG AAC ATT GAG GCG TTC GGC GGT GAT
Leu Arg Trp Val Lys Glu Asn Ile Glu Ala Phe Gly Gly Asp
CCG GAC AAC ATT ACG ATT TTT GGC GAA TCA GCC GGA GCG GCA
Pro Asp Asn Ile Thr Ile Phe Gly Glu Ser Ala Gly Ala Ala
AGC GTT GGC GTG CTG TTG TCG CTT CCG GAA GCA AGC GGG CTG
Ser Val Gly Val Leu Leu Ser Leu Pro Glu Ala Ser Gly Leu
TTT CGA CGC GCT ATA TTG CAA AGC GGA TCG GGT TCG CTT CTT
Phe Arg Arg Ala Ile Leu Gln Ser Gly Ser Gly Ser Leu Leu
CTT CGT TCT CCG GAG ACG GCG ATG GCT CTG ACT GAA CGC ATT
Leu Arg Ser Pro Glu Thr Ala Met Ala Leu Thr Glu Arg Ile
TTA GAA CGT GCC GGC ATC CGT CCG GGT GAC CGC GAT CGG CTG
Leu Glu Arg Ala Gly Ile Arg Pro Gly Asp Arg Asp Arg Leu
CTG TCG ATT CCA GCA GCA GAG CTA TTG CAG GCG GCG ATG TCG
Leu Ser Ile Pro Ala Ala Glu Leu Leu Gln Ala Ala Met Ser
```

Fig. 6E-2

```
CTC GGC CCA GGA ATC ACG TAC GGT CCG GTG GTT GAC GGA CAT
Leu Gly Pro Gly Ile Thr Tyr Gly Pro Val Val Asp Gly His
GTG TTG CGA CGC CAT CCG ATC GAA GCG CTC CAC GAC GGG GCA
Val Leu Arg Arg His Pro Ile Glu Ala Leu His Asp Gly Ala
GCA AGT GAT ATT CCA ATC CTA ATT GGC GTG ACG AAA GAC GAA
Ala Ser Asp Ile Pro Ile Leu Ile Gly Val Thr Lys Asp Glu
TAC AAT TTG TTT TCA TTG ACT GAT CCG TCA TTG ACA AGA CTC
Tyr Asn Leu Phe Ser Leu Thr Asp Pro Ser Leu Thr Arg Leu
GAA GAA AAA GAA CTG CTT GAC CGG ATG AAC CGT GAG GTC GGG
Glu Glu Lys Glu Leu Leu Asp Arg Met Asn Arg Glu Val Gly
CCT ATT CCG GAG GAG GCG GTA CGC TAT TAC GCG GAA ACA GCG
Pro Ile Pro Glu Glu Ala Val Arg Tyr Tyr Ala Glu Thr Ala
GAT CGG TCG GCA CCC GCG TGG CAA ACA TGG CTG CGC ATC ATG
Asp Arg Ser Ala Pro Ala Trp Gln Thr Trp Leu Arg Ile Met
ACG TAC CTT GTT TTT GTC GAC GGA ATG TTG CGA ACG GCG GAT
Thr Tyr Leu Val Phe Val Asp Gly Met Leu Arg Thr Ala Asp
GCC CAA GCA GCG CAA GGG GCG AAT GTG TAC ATG TAT CGG TTT
Ala Gln Ala Ala Gln Gly Ala Asn Val Tyr Met Tyr Arg Phe
GAT TAT GAA ACG CCG GCG TTT GGT GGA CAA CTG AAA GCG TGC
Asp Tyr Glu Thr Pro Ala Phe Gly Gly Gln Leu Lys Ala Cys
CAT ACG CTC GAG TTG CCG TTT GTG TTT CAT AAC CTC CAT CAG
His Thr Leu Glu Leu Pro Phe Val Phe His Asn Leu His Gln
CCT GGT GTC GAG AAT TTC GTC GGC AAC CGA CCA GAG CGT GAG
Pro Gly Val Glu Asn Phe Val Gly Asn Arg Pro Glu Arg Glu
GCG ATT GCC AGC GAA ATG CAT GGT GCC TGG CTT TCG TTC GCC
Ala Ile Ala Ser Glu Met His Gly Ala Trp Leu Ser Phe Ala
CAC ACC GGC AAC CCG AAC GGC GCT CAT TTA CCA GAG AAG TGG
His Thr Gly Asn Pro Asn Gly Ala His Leu Pro Glu Lys Trp
CCC GTA TAC ACA AAA GAG CAC AAA CCG GTG TTT GTC TTT TCG
Pro Val Tyr Thr Lys Glu His Lys Pro Val Phe Val Phe Ser
GCT GCG AGC CAT GTG GAA GAC GAT CCG TTC GGT CGC GAG CGG
Ala Ala Ser His Val Glu Asp Asp Pro Phe Gly Arg Glu Arg
GAA GCG TGG CAA GGA CGC CTT TGA CGAAAAAATCCATAAGCAACATGTGTTCTTT
Glu Ala Trp Gln Gly Arg Leu ***
GTCTGAACACGATCAAGGTACGCGCATTTTTCGCGGAAAAAGACCGTGGGCAAACGTTCGCCTTTACCT
CTAAAAGGAATGACGCAACATGTCTGCACTTCACAGGAAAGAGGACGAAACGGTTGGTTTTCAGAATA
GGAAAAGGTGTCCCGTTTTTTTGGGACACCTTCTTCTATGTATCGCTCAATCATTTGCTTCTGTGGCAG
GAAGCCCGAATCGCTCGGCGAGTGCCGGATCGGTTGAAAAAAGTGATGGATGAGATTCGCCAAGCAGG
CAACATCATTTTTGTTCATCGATGAGCTCCATACGCTAATCGGCGCTGGCGGAGCCGAAGGAGCGATCC
AAAGAATTCAAAAAGCTTCTCGAGAGTACTTCTAGAGCGGCCGCGGGCCCATCGATTTTCCACCCGGG
TGGGGTACCAGGTAAGTGTACCCAATTCGCCCTATAGTGAGTCGTATTACAAT
```

Fig. 6F-1

```
TTGAYRCCAAGCTCGAAATTAACCCTCACTAAAGGGAACAAAAGCTGGAGCTCGCGCGCCTGCA
►•••???GlnAlaArgAsn•••ProSerLeuLysGlyThrLysAlaGlyAlaArgAlaProAla
GGTCGACACTAGTGGATCCCCTTTCATTTATGATTTTGCAGCGGTCGAGCTGCTTTTATGTTGT
GlyArgHis•••TrpIleProPheHisLeu•••PheCysSerGlyArgAlaAlaPheMetLeuL
TGAATGAACTGTTCAATTTGATCATGCCGGTCGGTGCGGAAAGCTTCCGTGAAGCGCTGCGCAT
euAsnGluLeuPheAsnLeuIleMetProValGlyAlaGluSerPheArgGlyAlaLeuArgMe
GGGTGCAGAAATTTTCCATAGCTTAAAAGCTGTGTTAAAAGCGAAAGGCTACAACACGGCTGTC
tGlyAlaGluIlePheHisSerLeuLysAlaValLeuLysAlaLysGlyTyrAsnThrAlaVal
GGTGACGAAGGCGGATTTGCTCCGAACTTAAAATCGAACGAAGAAGCGCTGCAAACGATCATTG
GlyAspGluGlyGlyPheAlaProAsnLeuLysSerAsnGluGluAlaLeuGlnThrIleIleG
AAGCGATCGAAAAAGCCGGCTACAAACCAGGCGAACAAGTGATGCTCGCTATGGACGTTGCTTC
luAlaIleGluLysAlaGlyTyrLysProGlyGluGlnValMetLeuAlaMetAspValAlaSe
GTCGGAGCTGTACAACAAAGAAGATGGCAAATATCATTTGGAAGGCGAAGGCGTCGTCAAAACA
rSerGluLeuTyrAsnLysGluAspGlyLysTyrHisLeuGluGlyGluGlyValValLysThr
TCAGAAGAAATGGTTGCTTGGTATGAAGAGCTTGTGTCGAAATATCCGATCATCTCGATCGAAG
SerGluGluMetValAlaTrpTyrGluGluLeuValSerLysTyrProIleIleSerIleGluA
ACGGACTTGACGAAAATGACTGGGAAGGCCATAAACTGCTTACTGAGCGCCTTGGCCACAAAGT
spGlyLeuAspGluAsnAspTrpGluGlyHisLysLeuLeuThrGluArgLeuGlyHisLysVa
GCAGCTCGTCGGTGACGACTTGTTTGTAACGAACACGAAAAAACTGGCCGAAGGCATTGAAAAA
lGlnLeuValGlyAspAspLeuPheValThrAsnThrLysLysLeuAlaGluGlyIleGluLys
GGCGTCGGCAACTCGATTTTAATTAAAGTGAACCAAATCGGTACACTGACGGAAACGTTCGATG
GlyValGlyAsnSerIleLeuIleLysValAsnGlnIleGlyThrLeuThrGluThrPheAspA
CCATTGAGATGGCCAAACGCGCCGGCTACACGGCGGTTGTGTCGCACCGTTCCGGTGAAACGGA
laIleGluMetAlaLysArgAlaGlyTyrThrAlaValValSerHisArgSerGlyGluThrGl
AGACAGCACGATTGCCGATATCGCTGTCGCAACAAACGCTGGCCAAATCAAAACGGGAGCACCG
uAspSerThrIleAlaAspIleAlaValAlaThrAsnAlaGlyGlnIleLysThrGlyAlaPro
TCGCGTACGGACCGCGTCGCAAAATACAACCAGCTGCTCCGCATTGAAGACGAACTTGGCCACA
SerArgThrAspArgValAlaLysTyrAsnGlnLeuLeuArgIleGluAspGluLeuGlyHisT
CGGCTATTTACCAAGGCATTCGTTCGTTTTACAATTTGAAAAAATAACGGGAATCAACAACAAA
hrAlaIleTyrGlnGlyIleArgSerPheTyrAsnLeuLysLys•••◄►GlyIleAsnAsnLys
GGGTGTCTCCAACGTTGCGAGACACCCTCTTTAATTACGGGAAACAGAAATGATTTCCTATCGA
GlyCysLeuAsnArgCysGluThrProSerLeuIleThrGlyAsnArgAsnAspPheLeuSerI
TAGCAAAAAATGGACGTGGGTAAACCATTCGTTTATAATATCTTTTTTGTAATCGTTAGAATA
leAlaLysAsnGlyArgGly•••ThrIleArgLeu•••TyrLeuPheValIleValArgIle
```

| TTG | AAA | AAG | GGG | ATG | GGA | ACC | GTG | ATC | GTG | GAA | ACA | AAG |
|-----|-----|-----|-----|-----|-----|-----|-----|-----|-----|-----|-----|-----|
| Leu | Lys | Lys | Gly | Met | Gly | Thr | Val | Ile | Val | Glu | Thr | Lys |
| TAC | GGT | CGG | TTG | CGC | GGG | GGA | ACA | AAT | GAA | GGG | GTT | TTC |
| Tyr | Gly | Arg | Leu | Arg | Gly | Gly | Thr | Asn | Glu | Gly | Val | Phe |
| TAT | TGG | AAA | GGG | ATT | CCG | TAC | GCG | AAA | GCG | CCG | GTC | GGT | GAA |
| Tyr | Trp | Lys | Gly | Ile | Pro | Tyr | Ala | Lys | Ala | Pro | Val | Gly | Glu |
| CGC | CGT | TTT | TTG | CCG | CCG | GAA | CCG | CCC | GAT | GCA | TGG | GAC |
| Arg | Arg | Phe | Leu | Pro | Pro | Glu | Pro | Pro | Asp | Ala | Trp | Asp |
| GGA | GTG | CGT | GAG | GCG | ACA | TCG | TTT | GGA | CCG | GTC | GTC | ATG | CAG |
| Gly | Val | Arg | Glu | Ala | Thr | Ser | Phe | Gly | Pro | Val | Val | Met | Gln |
| CCG | TCC | GAT | TCG | ATG | TTC | AGC | CAG | CTG | CTC | GGA | CGG | ATG | AAT |
| Pro | Ser | Asp | Ser | Met | Phe | Ser | Gln | Leu | Leu | Gly | Arg | Met | Asn |
| GAA | CCA | ATG | AGC | GAG | GAT | GGG | TTG | TAT | CTG | AAC | ATT | TGG | TCA |
| Glu | Pro | Met | Ser | Glu | Asp | Gly | Leu | Tyr | Leu | Asn | Ile | Trp | Ser |
| CCG | GCG | GCG | GAT | GGG | AAG | AAG | CGC | CCG | GTA | TTG | TTT | TGG | ATT |
| Pro | Ala | Ala | Asp | Gly | Lys | Lys | Arg | Pro | Val | Leu | Phe | Trp | Ile |
| CAT | GGC | GGC | GCT | TTT | TTA | TTC | GGC | TCC | GGT | TCA | TTT | CCA | TGG |
| His | Gly | Gly | Ala | Phe | Leu | Phe | Gly | Ser | Gly | Ser | Phe | Pro | Trp |

Fig. 6F-2

```
TAT GAT GGA ACG GCG TTT GCC AAA CAC GGC GAT GTC GTT GTC
Tyr Asp Gly Thr Ala Phe Ala Lys His Gly Asp Val Val Val
GTG ACG ATC AAC TAC CGG ATG AGC GTG TTT GGC TTT TTG TAT
Val Thr Ile Asn Tyr Arg Met Ser Val Phe Gly Phe Leu Tyr
TTG GGA GAT GCG TTT GGC GAA ACG TAT GCC CAG GCG GGA AAT
Leu Gly Asp Ala Phe Gly Glu Thr Tyr Ala Gln Ala Gly Asn
CTT GGC ATA TTG GAT CAA GTG GCG GCG CTG CGC TGG GTG AAA
Leu Gly Ile Leu Asp Gln Val Ala Ala Leu Arg Trp Val Lys
GAG AAC ATT GAG GCG TTC GGC GGT GAT CCG GAC AAC ATT ACG
Glu Asn Ile Glu Ala Phe Gly Gly Asp Pro Asp Asn Ile Thr
ATT TTT GGC GAA TCA GCC GGA GCG GCA AGC GTT GGC GTG CTG
Ile Phe Gly Glu Ser Ala Gly Ala Ala Ser Val Gly Val Leu
TTG TCG CTT CCG GAA GCA AGC GGG CTG TTT CGA CGC GCT ATA
Leu Ser Leu Pro Glu Ala Ser Gly Leu Phe Arg Arg Ala Ile
TTG CAA AGC GGA TCG GGT TCG CTT CTT CTT CGT TCT CCG GAG
Leu Gln Ser Gly Ser Gly Ser Leu Leu Leu Arg Ser Pro Glu
ACG GCG ATG GCT CTG ACT GAA CGC ATT TTA GAA CGT GCC GGC
Thr Ala Met Ala Leu Thr Glu Arg Ile Leu Glu Arg Ala Gly
ATC CGT CCG GGT GAC CGC GAT CGG CTG CTG TCG ATT CCA GCA
Ile Arg Pro Gly Asp Arg Asp Arg Leu Leu Ser Ile Pro Ala
GCA GAG CTA TTG CAG GCG GCG ATG TCG CTC GGC CCA GGA ATC
Ala Glu Leu Leu Gln Ala Ala Met Ser Leu Gly Pro Gly Ile
ACG TAC GGT CCG GTG GTT GAC GGA CAT GTG TTG CGA CGC CAT
Thr Tyr Gly Pro Val Val Asp Gly His Val Leu Arg Arg His
CCG ATC GAA GCG CTC CAC GAC GGG GCA GCA AGT GAT ATT CCA
Pro Ile Glu Ala Leu His Asp Gly Ala Ala Ser Asp Ile Pro
ATC CTA ATT GGC GTG ACG AAA GAC GAA TAC AAT TTG TTT TCA
Ile Leu Ile Gly Val Thr Lys Asp Glu Tyr Asn Leu Phe Ser
TTG ACT GAT CCG TCA TTG ACA AGA CTC GAA GAA AAA GAA CTG
Leu Thr Asp Pro Ser Leu Thr Arg Leu Glu Glu Lys Glu Leu
CTT GAC CGG ATG AAC CGT GAG GTC GGG CCT ATT CCG GAG GAG
Leu Asp Arg Met Asn Arg Glu Val Gly Pro Ile Pro Glu Glu
GCG GTA CGC TAT TAC GCG GAA ACA GCG GAT CGG TCG GCA CCC
Ala Val Arg Tyr Tyr Ala Glu Thr Ala Asp Arg Ser Ala Pro
GCG TGG CAA ACA TGG CTG CGC ATC ATG ACG TAC CTT GTT TTT
Ala Trp Gln Thr Trp Leu Arg Ile Met Thr Tyr Leu Val Phe
GTC GAC GGA ATG TTG CGA ACG GCG GAT GCC CAA GCA GCG CAA
Val Asp Gly Met Leu Arg Thr Ala Asp Ala Gln Ala Ala Gln
GGG GCG AAT GTG TAC ATG TAT CGG TTT GAT TAT GAA ACG CCG
Gly Ala Asn Val Tyr Met Tyr Arg Phe Asp Tyr Glu Thr Pro
GCG TTC GGT GGA CAA CTG AAA GCG TGC CAT ACG CTC GAG TTG
Ala Phe Gly Gly Gln Leu Lys Ala Cys His Thr Leu Glu Leu
CCG TTT GTG TTT CAT AAC CTC CAT CAG CCT GGT GTC GAG AAT
Pro Phe Val Phe His Asn Leu His Gln Pro Gly Val Glu Asn
TTC GTC GGC AAC CGA CCA GAG CGT GAG GCG ATT GCC AGC GAA
Phe Val Gly Asn Arg Pro Glu Arg Glu Ala Ile Ala Ser Glu
ATG CAT GGT GCC TGG CTT TCG TTC GCC CAC ACC GGC AAC CCG
Met His Gly Ala Trp Leu Ser Phe Ala His Thr Gly Asn Pro
```

FIGURE 6F-3

```
AAC GGC GCT CAT TTA CCA GAG AAG TGG CCC GTA TAC ACA AAA
Asn Gly Ala His Leu Pro Glu Lys Trp Pro Val Tyr Thr Lys
GAG CAC AAA CCG GTG TTT GTC TTT TCG GCT GCG AGC CAT GTG
Glu His Lys Pro Val Phe Val Phe Ser Ala Ala Ser His Val
GAA GAC GAT CCG TTC GGT CGC GAG CGG GAA GCG TGG CAA GGA
Glu Asp Asp Pro Phe Gly Arg Glu Arg Glu Ala Trp Gln Gly
CGC CTT TGA CGAAAAAATCCATAAGCAACATGTGTTCTTTGTCTGAACACGATC
Arg Leu ***
```

Fig. 6G-1

```
ATTGCTTCAGGGGAACTTTTAAACACTTGAGTTTGACAACCACTCCTTAATCATTTAAGATTTAAATGAAAA
 Leu Leu Gln Gly Asn Phe *** Thr Leu Glu Phe Asp Asn His Ser Leu Ile Ile *** Asp Leu Asn Glu As
TTAAAATAAATCAAAAAGA GTG ATT CAA ATG AAT ACG TTG GTG GAA ACC CGT
n *** Asn Lys Ser Lys Arg> Val Ile Gln Met Asn Thr Leu Val Glu Thr Arg
TTT GGG AAA GTA CAA GGC GGT ACA GAC GGA GAG GTT TGT TTT TGG
Phe Gly Lys Val Gln Gly Gly Thr Asp Gly Glu Val Cys Phe Trp
AAA GGG ATT CCT TAT GCG AAA CCT CCG GTG GGA AAA CGC CGC TTT
Lys Gly Ile Pro Tyr Ala Lys Pro Pro Val Gly Lys Arg Arg Phe
CAA AAA CCG GAA CCG CCG GAG AAA TGG GAT GGC GTT TGG GAG GCC
Gln Lys Pro Glu Pro Pro Glu Lys Trp Asp Gly Val Trp Glu Ala
ACC CGG TTC CGG TCC ATG GTG ATG CAG CCG TCC GGC ACC ACC TTC
Thr Arg Phe Arg Ser Met Val Met Gln Pro Ser Gly Thr Thr Phe
AGC ACC GTG CTC GGG GAA GCG GAT CTT CCT GTG AGC GAA GAC GGT
Ser Thr Val Leu Gly Glu Ala Asp Leu Pro Val Ser Glu Asp Gly
CTT TAT CTG AAT ATC TGG TCG CCG GCA GCC GAC GGA AAA AAG CGG
Leu Tyr Leu Asn Ile Trp Ser Pro Ala Ala Asp Gly Lys Lys Arg
CCG GTG CTC TTC TGG ATC CAT GGC GGC GCC TAC CAG TTT GGA TCC
Pro Val Leu Phe Trp Ile His Gly Gly Ala Tyr Gln Phe Gly Ser
GGC GCT TCC CCC TGG TAT GAC GGG ACG GAG TTT GCC AAA AAC GGA
Gly Ala Ser Pro Trp Tyr Asp Gly Thr Glu Phe Ala Lys Asn Gly
GAT GTG GTG GTT GTC ACG ATC AAC TAC CGG TTG AAC GCG TTT GGA
Asp Val Val Val Val Thr Ile Asn Tyr Arg Leu Asn Ala Phe Gly
TTT TTG TAC TTG GCA GAT TGG TTC GGC GAC GAA TTT TCA GCG TCG
Phe Leu Tyr Leu Ala Asp Trp Phe Gly Asp Glu Phe Ser Ala Ser
GGC AAC CTG GGA ATA TTG GAC CAA GTC GCT GCA CTG CGC TGG GTG
Gly Asn Leu Gly Ile Leu Asp Gln Val Ala Ala Leu Arg Trp Val
AAA GAA AAC ATT TCC GCA TTC GGC GGC GAC CCG GAG CAA ATC ACC
Lys Glu Asn Ile Ser Ala Phe Gly Gly Asp Pro Glu Gln Ile Thr
ATC TTC GGG GAG TCG GCC GGA GCC GGA AGC GTC GGG GTT CTG CTT
Ile Phe Gly Glu Ser Ala Gly Ala Gly Ser Val Gly Val Leu Leu
TCC CTC CCG GAA ACC AAA GGG CTG TTT CAA CGG GCG ATC TTG CAA
Ser Leu Pro Glu Thr Lys Gly Leu Phe Gln Arg Ala Ile Leu Gln
AGC GGA TCG GGT GCC ATT TTG CTC CGT TCC TCT CAG ACA GCC TCG
Ser Gly Ser Gly Ala Ile Leu Leu Arg Ser Ser Gln Thr Ala Ser
GGC ATC GCG GAA CAA ATT CTT ACG AAA GCC GGC ATT CGA AAA GGA
Gly Ile Ala Glu Gln Ile Leu Thr Lys Ala Gly Ile Arg Lys Gly
GAC CGC GAC CGG TTG TTA TCC ATC CCG GCC GGT GAA CTC CTT GAA
Asp Arg Asp Arg Leu Leu Ser Ile Pro Ala Gly Glu Leu Leu Glu
GCC GCA CAA TCC GTG AAT CCG GGA ATG GTT TTT GGT CCC GTT GTG
Ala Ala Gln Ser Val Asn Pro Gly Met Val Phe Gly Pro Val Val
GAC GGC ACC GTA TTG AAA ACC CAT CCG ATT GAA GCG TTG GAA AAC
Asp Gly Thr Val Leu Lys Thr His Pro Ile Glu Ala Leu Glu Asn
GGA GCC GCC GGC GAT ATC CCG ATC ATC ATC GGG GTG ACA AAG GAT
Gly Ala Ala Gly Asp Ile Pro Ile Ile Ile Gly Val Thr Lys Asp
GAG TAC AAT TTA TTT ACA CTG ACT GAC CCT TCC TGG ACG ACA GCG
Glu Tyr Asn Leu Phe Thr Leu Thr Asp Pro Ser Trp Thr Thr Ala
```

Fig. 6G-2

```
GGA AAA GAA GAA CTG ATG GAC CGG ATC GAA CAG GAA ATC GGG TCG
Gly Lys Glu Glu Leu Met Asp Arg Ile Glu Gln Glu Ile Gly Ser
GTT CCG GAA AAA GTT TTT CCA TAT TAC TTA TCT TCC GGG GAT CCA
Val Pro Glu Lys Val Phe Pro Tyr Tyr Leu Ser Ser Gly Asp Pro
TCG CAA CCG GTA TGG CAA AAG CTG TTG CGC GCC ATG ACC TAC CAC
Ser Gln Pro Val Trp Gln Lys Leu Leu Arg Ala Met Thr Tyr His
ATC TTT ACC CGG GGC ATG TTA AAA ACG GCT GAC GCC CAA ATC AAG
Ile Phe Thr Arg Gly Met Leu Lys Thr Ala Asp Ala Gln Ile Lys
CAA GGC GGG AAG GTT TGG GTT TAC CGG TTT GAT TAC GAA ACC CCG
Gln Gly Gly Lys Val Trp Val Tyr Arg Phe Asp Tyr Glu Thr Pro
CTC TTT GAC GGT CGG TTG AAA GCA TGT CAC GCA CTG GAA ATC CCC
Leu Phe Asp Gly Arg Leu Lys Ala Cys His Ala Leu Glu Ile Pro
TTT GTC TTT CAC AAC CTG CAT CAA CCG GGG GTC GAT GTG TTC ACC
Phe Val Phe His Asn Leu His Gln Pro Gly Val Asp Val Phe Thr
GGC ACA CAT CCG AAG CGG GAG CTA ATT TCC CGG CAA ATG CAT GAA
Gly Thr His Pro Lys Arg Glu Leu Ile Ser Arg Gln Met His Glu
GCA TGG ATT GCC TTT GCC CGG ACA GGG GAT CCG AAC GGC GAC CAT
Ala Trp Ile Ala Phe Ala Arg Thr Gly Asp Pro Asn Gly Asp His
CTC CCC GAT GCG TGG TTG CCC TTT GCA CAA AAA GAC CGG CCG GCC
Leu Pro Asp Ala Trp Leu Pro Phe Ala Gln Lys Asp Arg Pro Ala
ATG GTC TTT GAC ACC GAA ACC AGA GCG GAA AAG CAT CTG TTT GAC
Met Val Phe Asp Thr Glu Thr Arg Ala Glu Lys His Leu Phe Asp
CGC GAG CAG GAA CTG TGG GAA TCA AAG GCT TGA GTGATTTGCTCAAGCCTTTTT
Arg Glu Gln Glu Leu Trp Glu Ser Lys Ala ***
TGCATTAACGTATGTATTCGGATTTGGAATTAAACAATGGNGCTTTTATCGNAATGGGGAGTGTTNGCTTAT
AATGAACGGGTT
```

Fig. 6H-1

```
CTTCAACTAACATGTTGGCTTGCGGGCGTTCATGCTCAGAAACAAGGTTGGGACAAGCACTTCCAGGCTA
LeuGlnLeuThrCysTrpLeuAlaGlyValHisAlaGlnLysGlnGlyTrpAspLysHisPheGlnAlaA
ACACAGTCAGAAATCGAAACGTACTCTCAACAGTTCGCTTAGGCATGGAAGTTTTGCGGCATTCTGGCTA
snThrValArgAsnArgAsnValLeuSerThrValArgLeuGlyMetGluValLeuArgHisSerGlyTy
CACAATAACAAGGGAAGACTTACTCGTGGCTGCAACCCTACTAGCTCAAAATTTA ATG AGG GGA
rThrIleThrArgGluAspLeuLeuValAlaAlaThrLeuLeuAlaGlnAsnLeu  Met Arg Gly
TCT CTC AGA ACA AAG TAC GGT CGG TTG CGC GGG GGA ACA AAT GAA
Ser Leu Arg Thr Lys Tyr Gly Arg Leu Arg Gly Gly Thr Asn Glu
GGG GTT TTC TAT TGG AAA GGG ATT CCG TAC GCG AAA GCG CCG GTC
Gly Val Phe Tyr Trp Lys Gly Ile Pro Tyr Ala Lys Ala Pro Val
GGT GAA CGC CGT TTT TTG CCG CCG GAA CCG CCC GAT GCA TGG GAC
Gly Glu Arg Arg Phe Leu Pro Pro Glu Pro Pro Asp Ala Trp Asp
GGA GTG CGT GAG GCG ACA TCG TTT GGA CCG GTC GTC ATG CAG CCG
Gly Val Arg Glu Ala Thr Ser Phe Gly Pro Val Val Met Gln Pro
TCC GAT TCG ATG TTC AGC CAG CTG CTC GGA CGG ATG AAT GAA CCA
Ser Asp Ser Met Phe Ser Gln Leu Leu Gly Arg Met Asn Glu Pro
ATG AGC GAG GAT GGG TTG TAT CTG AAC ATT TGG TCA CCG GCG GCG
Met Ser Glu Asp Gly Leu Tyr Leu Asn Ile Trp Ser Pro Ala Ala
GAT GGG AAG AAG CGC CCG GTA TTG TTT TGG ATT CAT GGC GGC GCT
Asp Gly Lys Lys Arg Pro Val Leu Phe Trp Ile His Gly Gly Ala
TTT TTA TTC GGC TCC GGT TCA TTT CCA TGG TAT GAT GGA ACG GCG
Phe Leu Phe Gly Ser Gly Ser Phe Pro Trp Tyr Asp Gly Thr Ala
TTT GCC AAA CAC GGC GAT GTC GTT GTC GTG ACG ATC AAC TAC CGG
Phe Ala Lys His Gly Asp Val Val Val Val Thr Ile Asn Tyr Arg
ATG AGC GTG TTT GGC TTT TTG TAT TTG GGA GAT GCG TTT GGC GAA
Met Ser Val Phe Gly Phe Leu Tyr Leu Gly Asp Ala Phe Gly Glu
ACG TAT GCC CAG GCG GGA AAT CTT GGC ATA TTG GAT CAA GTG GCG
Thr Tyr Ala Gln Ala Gly Asn Leu Gly Ile Leu Asp Gln Val Ala
GCG CTG CGC TGG GTG AAA GAG AAC ATT GAG GCG TTC GGC GGT GAT
Ala Leu Arg Trp Val Lys Glu Asn Ile Glu Ala Phe Gly Gly Asp
CCG GAC AAC ATT ACG ATT TTT GGC GAA TCA GCC GGA GCG GCA AGC
Pro Asp Asn Ile Thr Ile Phe Gly Glu Ser Ala Gly Ala Ala Ser
GTT GGC GTG CTG TTG TCG CTT CCG GAA GCA AGC GGG CTG TTT CGA
Val Gly Val Leu Leu Ser Leu Pro Glu Ala Ser Gly Leu Phe Arg
```

Fig. 6H-2

```
CGC GCT ATA TTG CAA AGC GGA TCG GGT TCG CTT CTT CTT CGT TCT
Arg Ala Ile Leu Gln Ser Gly Ser Gly Ser Leu Leu Leu Arg Ser
CCG GAG ACG GCG ATG GCT CTG ACT GAA CGC ATT TTA GAA CGT GCC
Pro Glu Thr Ala Met Ala Leu Thr Glu Arg Ile Leu Glu Arg Ala
GGC ATC CGT CCG GGT GAC CGC GAT CGG CTG CTG TCG ATT CCA GCA
Gly Ile Arg Pro Gly Asp Arg Asp Arg Leu Leu Ser Ile Pro Ala
GCA GAG CTA TTG CAG GCG GCG ATG TCG CTC GGC CCA GGA ATC ACG
Ala Glu Leu Leu Gln Ala Ala Met Ser Leu Gly Pro Gly Ile Thr
TAC GGT CCG GTG GTT GAC GGA CAT GTG TTG CGA CGC CAT CCG ATC
Tyr Gly Pro Val Val Asp Gly His Val Leu Arg Arg His Pro Ile
GAA GCG CTC CAC GAC GGG GCA GCA AGT GAT ATT CCA ATC CTA ATT
Glu Ala Leu His Asp Gly Ala Ala Ser Asp Ile Pro Ile Leu Ile
GGC GTG ACG AAA GAC GAA TAC AAT TTG TTT TCA TTG ACT GAT CCG
Gly Val Thr Lys Asp Glu Tyr Asn Leu Phe Ser Leu Thr Asp Pro
TCA TTG ACA AGA CTC GAA GAA AAA GAA CTG CTT GAC CGG ATG AAC
Ser Leu Thr Arg Leu Glu Glu Lys Glu Leu Leu Asp Arg Met Asn
CGT GAG GTC GGG CCT ATT CCG GAG GAG GCG GTA CGC TAT TAC GCG
Arg Glu Val Gly Pro Ile Pro Glu Glu Ala Val Arg Tyr Tyr Ala
GAA ACA GCG GAT CGG TCG GCA CCC GCG TGG CAA ACA TGG CTG CGC
Glu Thr Ala Asp Arg Ser Ala Pro Ala Trp Gln Thr Trp Leu Arg
ATC ATG ACG TAC CTT GTT TTT GTC GAC GGA ATG TTG CGA ACG GCG
Ile Met Thr Tyr Leu Val Phe Val Asp Gly Met Leu Arg Thr Ala
GAT GCC CAA GCA GCG CAA GGG GCG AAT GTG TAC ATG TAT CGG TTT
Asp Ala Gln Ala Ala Gln Gly Ala Asn Val Tyr Met Tyr Arg Phe
GAT TAT GAA ACG CCG GCG TTT GGT GGA CAA CTG AAA GCG TGC CAT
Asp Tyr Glu Thr Pro Ala Phe Gly Gly Gln Leu Lys Ala Cys His
ACG CTC GAG TTG CCG TTT GTG TTT CAT AAC CTC CAT CAG CCT GGT
Thr Leu Glu Leu Pro Phe Val Phe His Asn Leu His Gln Pro Gly
GTC GAG AAT TTC GTC GGC AAC CGA CCA GAG CGT GAG GCG ATT GCC
Val Glu Asn Phe Val Gly Asn Arg Pro Glu Arg Glu Ala Ile Ala
AGC GAA ATG CAT GGT GCC TGG CTT TCG TTC GCC CAC ACC GGC AAC
Ser Glu Met His Gly Ala Trp Leu Ser Phe Ala His Thr Gly Asn
CCG AAC GGC GCT CAT TTA CCA GAG AAG TGG CCC GTA TAC ACA AAA
Pro Asn Gly Ala His Leu Pro Glu Lys Trp Pro Val Tyr Thr Lys
GAG CAC AAA CCG GTG TTT GTC TTT TCG GCT GCG AGC CAT GTG GAA
Glu His Lys Pro Val Phe Val Phe Ser Ala Ala Ser His Val Glu
GAC GAT CCG TTC GGT CGC GAG CGG GAA GCG TGG CAA GGA CGC CTT
Asp Asp Pro Phe Gly Arg Glu Arg Glu Ala Trp Gln Gly Arg Leu
TGA CGAAAAAATCCATAAGCAACATGTGTTCTTTGTCTGAACACGATCAAGGTACGCGCATTTTCGCG
***
GAAAAAGACCGTGGGCAAACGTTCGCCTTTTACCTCTAAAAGGAATGACGCAACATGTCTGCACTTCACAG
GAAAGAGGACGAAACGGTTGGTTTTCAGAATAGGAAAAGGTGTCCCGTTTTTTGGGACACCTTCTTCTAT
GTATCGCTCAATCATTTGCTTCTGTGGCAGGAAGCCCGAATCGCTCGGCGAGTGCCGGATCACGATCGAT
CGCCTCAATCAGTTTCCGCATGACGTTCACATCAAACGTAAAATTCGAACCGATTGGCGAGGTGACGAAA
ATTTTTCCCTTCTTTCGCCTCGCGTGCTCGTTTAAATTGATAGCCGTCAATCGCAATGACGACTCGTTCGT
CTGGCCTTGCCATTAGGAATCCCTCCATCGCTGTTTTTTTCTTTCATTGTACTTGATTTTGAGGATGAACA
CCAACGTTCATGACACGCTCTTAAGGATAACGGATGGGAGAGCGTTAGAGGGCGGTGAATTTCATCAAGA
ACGTGGCACAAAACGACATTTTTTTTCATTATAGACGTCTTGATGTTTGGAATGATCGGAAAAGGCGATTGT
TAGGCGGGGATCATGATCCACTAGCGGA
```

Fig. 6I-1

```
CCCAACGACCCCCGCCCATTGACGTCAATAATGACGTATGTTCCCATAGTAACGCCAATAGGGACTTTCCAT
ProAsnAspProArgProLeuThrSerIleMetThrTyrValProIleValThrProIleGlyThrPheHis
TGACGTCAATGGGTGGAGTATTTACGGTAAACTGCCCACTTGGCAGTACATCAA GTG TAT CAT
*ArgGlnTrpValGluTyrLeuArg*ThrAlaHisLeuAlaValHisGln> Val Tyr His
```

| ATG | CCA | AGT | ACG | CCC | CCT | ATT | GAC | GTC | AAT | GAC | GGT | AAA | TGG | CCC |
|---|---|---|---|---|---|---|---|---|---|---|---|---|---|---|
| Met | Pro | Ser | Thr | Pro | Pro | Ile | Asp | Val | Asn | Asp | Gly | Lys | Trp | Pro |
| GCC | TGG | CAT | TAT | GCC | CAG | TAC | ATG | ACC | TTA | TGG | GAC | TTT | CCT | ACT |
| Ala | Trp | His | Tyr | Ala | Gln | Tyr | Met | Thr | Leu | Trp | Asp | Phe | Pro | Thr |
| TGG | CAG | TAC | ATC | TAC | GTA | TTA | GTC | ATC | GCT | ATT | ACC | ATG | GTG | AAG |
| Trp | Gln | Tyr | Ile | Tyr | Val | Leu | Val | Ile | Ala | Ile | Thr | Met | Val | Lys |
| CAG | CCG | TCC | GGC | ACC | ACC | TTC | AGC | ACC | GTG | CTC | GGG | GAA | GCG | GAT |
| Gln | Pro | Ser | Gly | Thr | Thr | Phe | Ser | Thr | Val | Leu | Gly | Glu | Ala | Asp |
| CTT | CCT | GTG | AGC | GAA | GAC | GGT | CTT | TAT | CTG | AAT | ATC | TGG | TCG | CCG |
| Leu | Pro | Val | Ser | Glu | Asp | Gly | Leu | Tyr | Leu | Asn | Ile | Trp | Ser | Pro |
| GCA | GCC | GAC | GGA | AAA | AAG | CGG | CCG | GTG | CTC | TTC | TGG | ATC | CAT | GGC |
| Ala | Ala | Asp | Gly | Lys | Lys | Arg | Pro | Val | Leu | Phe | Trp | Ile | His | Gly |
| GGC | GCC | TAC | CAG | TTT | GGG | TCC | GGC | GCT | TCC | CCC | TGG | TAT | GAC | GGG |
| Gly | Ala | Tyr | Gln | Phe | Gly | Ser | Gly | Ala | Ser | Pro | Trp | Tyr | Asp | Gly |
| ACG | GAG | TTT | GCC | AAA | AAC | GGA | GAT | GTG | GTG | GTT | GTC | ACG | ATC | AAC |
| Thr | Glu | Phe | Ala | Lys | Asn | Gly | Asp | Val | Val | Val | Val | Thr | Ile | Asn |
| TAC | CGG | TTG | AAC | GCG | TTT | GGA | TTT | TTG | TAC | TTG | GCA | GAT | TGG | TTC |
| Tyr | Arg | Leu | Asn | Ala | Phe | Gly | Phe | Leu | Tyr | Leu | Ala | Asp | Trp | Phe |
| GGC | GAC | GAA | TTT | TCA | GCG | TCG | GGC | AAC | CTG | GGA | ATT | TTG | GAC | CAA |
| Gly | Asp | Glu | Phe | Ser | Ala | Ser | Gly | Asn | Leu | Gly | Ile | Leu | Asp | Gln |
| GTC | GCT | GCA | CTG | CGC | TGG | GTG | AAA | GAA | AAC | ATT | TCG | GCA | TTC | GGC |
| Val | Ala | Ala | Leu | Arg | Trp | Val | Lys | Glu | Asn | Ile | Ser | Ala | Phe | Gly |
| GGC | GAC | CCG | GAG | CAA | ATC | ACC | ATC | TTC | GGG | GAG | TCG | GCC | GGA | GCC |
| Gly | Asp | Pro | Glu | Gln | Ile | Thr | Ile | Phe | Gly | Glu | Ser | Ala | Gly | Ala |
| GGA | AGC | GTC | GGG | GTT | CTG | CTT | TCC | CTC | CCG | GAA | ACC | AAA | GGG | CTG |
| Gly | Ser | Val | Gly | Val | Leu | Leu | Ser | Leu | Pro | Glu | Thr | Lys | Gly | Leu |
| TTT | CAA | CGG | GCG | ATC | TTG | CAA | AGC | GGA | TCG | GGT | GCC | ATT | TTG | CTC |
| Phe | Gln | Arg | Ala | Ile | Leu | Gln | Ser | Gly | Ser | Gly | Ala | Ile | Leu | Leu |
| CGT | TCC | TCT | CAG | ACA | GCC | TCG | GGC | ATC | GCG | GAA | CAA | ATT | CTT | ACG |
| Arg | Ser | Ser | Gln | Thr | Ala | Ser | Gly | Ile | Ala | Glu | Gln | Ile | Leu | Thr |
| AAA | GCC | GGC | ATT | CGA | AAA | GGA | GAC | CGC | GAC | CGG | TTG | TTA | TCC | ATC |
| Lys | Ala | Gly | Ile | Arg | Lys | Gly | Asp | Arg | Asp | Arg | Leu | Leu | Ser | Ile |
| CCG | GCC | GGT | GAA | CTC | CTT | GAA | GCC | GCA | CAA | TCC | GTG | AAT | CCG | GGA |
| Pro | Ala | Gly | Glu | Leu | Leu | Glu | Ala | Ala | Gln | Ser | Val | Asn | Pro | Gly |
| ATG | GTT | TTT | GGT | CCC | GTT | GTG | GAC | GGC | ACC | GTA | TTG | AAA | ACC | CAT |
| Met | Val | Phe | Gly | Pro | Val | Val | Asp | Gly | Thr | Val | Leu | Lys | Thr | His |

Fig. 6I-2

```
CCG ATT GAA GCG TTG GAA ACC GGA GCC GCC GGC GAT ATC CCG ATC
Pro Ile Glu Ala Leu Glu Thr Gly Ala Ala Gly Asp Ile Pro Ile
ATC ATC GGG GTG ACA AAG GAT GAG TAC AAT TTA TTT ACA CTG ACT
Ile Ile Gly Val Thr Lys Asp Glu Tyr Asn Leu Phe Thr Leu Thr
GAC CCT TCC TGG ACG ACA GCG GGA AAA GAA GAA CTG ATG GAC CGG
Asp Pro Ser Trp Thr Thr Ala Gly Lys Glu Glu Leu Met Asp Arg
ATC GAA CAG GAA ATC GGG CCG GTT CCG GAA AAA GTT TTT CCA TAT
Ile Glu Gln Glu Ile Gly Pro Val Pro Glu Lys Val Phe Pro Tyr
TAC TTA TCT TTT GGG GAT CCA TCG CAA CCG GTA TGG CAA AAG CTG
Tyr Leu Ser Phe Gly Asp Pro Ser Gln Pro Val Trp Gln Lys Leu
TTG CGC GCC ATG ACC TAC CAC ATC TTT ACC CGG GGC ATG TTA AAA
Leu Arg Ala Met Thr Tyr His Ile Phe Thr Arg Gly Met Leu Lys
ACG GCT GAC GCC CAA ATC AAG CAA GGC GGG AAG GTT TGG GTT TAC
Thr Ala Asp Ala Gln Ile Lys Gln Gly Gly Lys Val Trp Val Tyr
CGG TTT GAT TAC GAA ACC CCG CTC TTT GAC GGT CGG TTG AAA GCA
Arg Phe Asp Tyr Glu Thr Pro Leu Phe Asp Gly Arg Leu Lys Ala
TGT CAC GCA CTG GAA ATC CCC TTT GTC TTT CAC AAC CTG CAT CAA
Cys His Ala Leu Glu Ile Pro Phe Val Phe His Asn Leu His Gln
CCG GGG GTC GAT GTG TTC ACC GGC ACA CAT CCG AAG CGG GAG CTA
Pro Gly Val Asp Val Phe Thr Gly Thr His Pro Lys Arg Glu Leu
ATT TCC CGG CAA ATG CAT GAA GCA TGG ATT GCC TTT GCC CGG ACA
Ile Ser Arg Gln Met His Glu Ala Trp Ile Ala Phe Ala Arg Thr
GGG GAT CCG AAC GGC GAC CAT CTC CCC GAT GCG TGG TTG CCC TTT
Gly Asp Pro Asn Gly Asp His Leu Pro Asp Ala Trp Leu Pro Phe
GCA CAA AAA GAC CGG CCG GCC ATG GTC TTT GAC ACC GAA ACC AGA
Ala Gln Lys Asp Arg Pro Ala Met Val Phe Asp Thr Glu Thr Arg
GCG GAA AAG CAT CTG TTT GAC CGC GAG CAG GAA CTG TGG GAA TCA
Ala Glu Lys His Leu Phe Asp Arg Glu Gln Glu Leu Trp Glu Ser
AAG GCT TGA GTGATTTGCTCAAGCCTTTTTTTGCATTTCACGTATGTATTCGGATTTGGAATTAAACA
Lys Ala ***   ValIleCysSerSerLeuPheCysIleSerArgMetTyrSerAspLeuGluLeuAsnA
ATGGTGCTTTTATCGAAATGGGGAGTGTTTGCTTATAATGAACGGGTTTACAAAGCTTGTTTTGGTACCGGA
snGlyAlaPheIleGluMet
TTACTGAAATGATCAGAAGGAAATATCATGACGTAATAATCAGGGGATCTTGAGAAAGAAATACATGGAGTG
TTATGTCCCTTGAAAAACAGAGACGCCGGTGGCATCACCATCACAGGGTCTTTCTTTTCAAATCATGGTTTG
TAGTTTTATAATGCAAACTAATTAATCATACATATGGAGTGTGGGTTCCATTGATGCCCCTTTAAGG
```

Fig. 6J-1

```
CTTCAGGGGAACTTTTAAACACTTGAGTTTGACAACCACTCCTTAATCATTTAAGATTTAAATGAAAAT
LeuGlnGlyAsnPhe***ThrLeuGluPheAspAsnHisSerLeuIleIle***AspLeuAsnGluAsn
TAAAATAAATCAAAAAGA GTG ATT CAA ATG AAT ACG TTG GTG GAA ACC
***AsnLysSerLysArg  Val Ile Gln Met Asn Thr Leu Val Glu Thr
CGT TTT GGG AAA GTG CAA GGC GGT ACA GAC GGA GAG GTT TGT TTT
Arg Phe Gly Lys Val Gln Gly Gly Thr Asp Gly Glu Val Cys Phe
TGG AAA GGG ATT CCT TAT GCG AAA CCT CCG GTG GGA AAA CGC CGC
Trp Lys Gly Ile Pro Tyr Ala Lys Pro Pro Val Gly Lys Arg Arg
TTT CAA AAA CCG GAA CCG CCG GAG AAA TGG GAT GGC GTT TGG GAG
Phe Gln Lys Pro Glu Pro Pro Glu Lys Trp Asp Gly Val Trp Glu
GCC ACC CGG TTC CGG TCC ATG GTG ATG CAG CCG TCC GGC ACC ACC
Ala Thr Arg Phe Arg Ser Met Val Met Gln Pro Ser Gly Thr Thr
TTC AGC ACC GTG CTC GGG GAA GCG GAT CTT CCT GTG AGC GAA GAC
Phe Ser Thr Val Leu Gly Glu Ala Asp Leu Pro Val Ser Glu Asp
GGT CTT TAT CTG AAT ATC TGG TCG CCG GCA GCC GAC GGA AAA AAG
Gly Leu Tyr Leu Asn Ile Trp Ser Pro Ala Ala Asp Gly Lys Lys
CGG CCG GTG CTC TTC TGG ATC CAT GGC GGC GCC TAC CAG TTT GGG
Arg Pro Val Leu Phe Trp Ile His Gly Gly Ala Tyr Gln Phe Gly
TCC GGC GCT TCC CCC TGG TAT GAC GGG ACG GAG TTT GCC AAA AAC
Ser Gly Ala Ser Pro Trp Tyr Asp Gly Thr Glu Phe Ala Lys Asn
GGA GAT GTG GTG GTT GTC ACG ATC AAC TAC CGG TTG AAC GCG TTT
Gly Asp Val Val Val Val Thr Ile Asn Tyr Arg Leu Asn Ala Phe
GGA TTT TTG TAC TTG GCA GAT TGG TTC GGC GAC GAA TTT TCA GCG
Gly Phe Leu Tyr Leu Ala Asp Trp Phe Gly Asp Glu Phe Ser Ala
TCG GGC AAC CTG GGA ATT TTG GAC CAA GTC GCT GCA CTG CGC TGG
Ser Gly Asn Leu Gly Ile Leu Asp Gln Val Ala Ala Leu Arg Trp
GTG AAA GAA AAC ATT TCG GCA TTC GGC GGC GAC CCG GAG CAA ATC
Val Lys Glu Asn Ile Ser Ala Phe Gly Gly Asp Pro Glu Gln Ile
ACC ATC TTC GGG GAG TCG GCC GGA GCC GGA AGC GTC GGG GTT CTG
Thr Ile Phe Gly Glu Ser Ala Gly Ala Gly Ser Val Gly Val Leu
CTT TCC CTC CCG GAA ACC AAA GGG CTG TTT CAA CGG GCG ATC TTG
Leu Ser Leu Pro Glu Thr Lys Gly Leu Phe Gln Arg Ala Ile Leu
CAA AGC GGA TCG GGT GCC ATT TTG CTC CGT TCC TCT CAG ACA GCC
Gln Ser Gly Ser Gly Ala Ile Leu Leu Arg Ser Ser Gln Thr Ala
TCG GGC ATC GCG GAA CAA ATT CTT ACG AAA GCC GGC ATT CGA AAA
Ser Gly Ile Ala Glu Gln Ile Leu Thr Lys Ala Gly Ile Arg Lys
GGA GAC CGC GAC CGG TTG TTA TCC ATC CCG GCC GGT GAA CTC CTT
Gly Asp Arg Asp Arg Leu Leu Ser Ile Pro Ala Gly Glu Leu Leu
GAA GCC GCA CAA TCC GTG AAT CCG GGA ATG GTT TTT GGT CCC GTT
Glu Ala Ala Gln Ser Val Asn Pro Gly Met Val Phe Gly Pro Val
```

Fig. 6J-2

```
GTG GAC GGC ACC GTA TTG AAA ACC CAT CCG ATT GAA GCG TTG GAA
Val Asp Gly Thr Val Leu Lys Thr His Pro Ile Glu Ala Leu Glu
ACC GGA GCC GCC GGC GAT ATC CCG ATC ATC ATC GGG GTG ACA AAG
Thr Gly Ala Ala Gly Asp Ile Pro Ile Ile Ile Gly Val Thr Lys
GAT GAG TAC AAT TTA TTT ACA CTG ACT GAC CCT TCC TGG ACG ACA
Asp Glu Tyr Asn Leu Phe Thr Leu Thr Asp Pro Ser Trp Thr Thr
GCG GGA AAA GAA GAA CTG ATG GAC CGG ATC GAA CAG GAA ATC GGG
Ala Gly Lys Glu Glu Leu Met Asp Arg Ile Glu Gln Glu Ile Gly
CCG GTT CCG GAA AAA GTT TTT CCA TAT TAC TTA TCT TTT GGG GAT
Pro Val Pro Glu Lys Val Phe Pro Tyr Tyr Leu Ser Phe Gly Asp
CCA TCG CAA CCG GTA TGG CAA AAG CTG TTG CGC GCC ATG ACC TAC
Pro Ser Gln Pro Val Trp Gln Lys Leu Leu Arg Ala Met Thr Tyr
CAC ATC TTT ACC CGG GGC ATG TTA AAA ACG GCT GAC GCC CAA ATC
His Ile Phe Thr Arg Gly Met Leu Lys Thr Ala Asp Ala Gln Ile
AAG CAA GGC GGG AAG GTT TGG GTT TAC CGG TTT GAT TAC GAA ACC
Lys Gln Gly Gly Lys Val Trp Val Tyr Arg Phe Asp Tyr Glu Thr
CCG CTC TTT GAC GGT CGG TTG AAA GCA TGT CAC GCA CTG GAA ATC
Pro Leu Phe Asp Gly Arg Leu Lys Ala Cys His Ala Leu Glu Ile
CCC TTT GTC TTT CAC AAC CTG CAT CAA CCG GGG GTC GAT GTG TTC
Pro Phe Val Phe His Asn Leu His Gln Pro Gly Val Asp Val Phe
ACC GGC ACA CAT TCG AAG CGG GAG CTA ATT TCC CGG CAA ATG CAT
Thr Gly Thr His Ser Lys Arg Glu Leu Ile Ser Arg Gln Met His
GAA GCA TGG ATT GCC TTT GCC CGG ACA GGG GAT CCG AAC GGC GAC
Glu Ala Trp Ile Ala Phe Ala Arg Thr Gly Asp Pro Asn Gly Asp
CAT CTC CCC GAT GCG TGG TTG CCC TTT GCA CAA AAA GAC CGG CCG
His Leu Pro Asp Ala Trp Leu Pro Phe Ala Gln Lys Asp Arg Pro
GCC ATG GTC TTT GAC ACC GAA ACC AGA GCG GAA AAG CAT CTG TTT
Ala Met Val Phe Asp Thr Glu Thr Arg Ala Glu Lys His Leu Phe
GAC CGC GAG CAG GAA CTG TGG GAA TCA AAG GCT TGA GTGATTTGCTCAA
Asp Arg Glu Gln Glu Leu Trp Glu Ser Lys Ala ***
GCCTTTTTTTGCATTTCACGTATGTATTCGGATTTGGAATTAAACAATGGTGCTTTTATCGAAATGGGGA
GTGTTTGCTTATAATGAACGGGTTTACAAAGCTTGTTTTGGTACCGGATTACTGAAATGATCAGAAGGA
AATATCATGACGTAATAATCAGGGGATCTTGAGAAAGAAATACATGGAGTGTTATGTCCCTTGAAAAAC
AGAGACGCCGGTGGCATCACCATCACAGGGTCTTTCTTTTCAAATCATGGTTTGTAGTTTATAATGCAA
ACTAGTTTAATCATACATATTGGAAGTGTGGTTCCATTTGATGCCCTTTTAAGGAAATGGCAAAAACTT
GAATTA
```

Fig. 6K-1

```
ATCACATCGTGGATATCAGTGGATCCGGTGCGATGGATTGCTTCAGGGGAACTTTTAAACACTTGAGTTT
▶ SerHisArgGlyTyrGlnTrpIleArgCysAspGlyLeuLeuGlnGlyAsnPhe***ThrLeuGluPhe
GACAACCACTCCTTAATCATTTAAGATTTAAATGAAAATTAAAAATAAATCAAAAAGA GTG ATT
AspAsnHisSerLeuIleIle***AspLeuAsnGluAsn***AsnLysSerLysArg↓ Val  Ile
```

| CAA | ATG | AAT | ACG | TTG | GTG | GAA | ACC | CGT | TTT | GGG | AAA | GTG | CAA |
|---|---|---|---|---|---|---|---|---|---|---|---|---|---|
| Gln | Met | Asn | Thr | Leu | Val | Glu | Thr | Arg | Phe | Gly | Lys | Val | Gln |
| GGC | GGT | ACA | GAC | GGA | GAG | GTT | TGT | TTT | TGG | AAA | GGG | ATT | CCT | TAT |
| Gly | Gly | Thr | Asp | Gly | Glu | Val | Cys | Phe | Trp | Lys | Gly | Ile | Pro | Tyr |
| GCG | AAA | CCT | CCG | GTG | GGA | AAA | CGC | CGC | TTT | CAA | AAA | CCG | GAA | CCG |
| Ala | Lys | Pro | Pro | Val | Gly | Lys | Arg | Arg | Phe | Gln | Lys | Pro | Glu | Pro |
| CCG | GAG | AAA | TGG | GAT | GGC | GTT | TGG | GAG | GCC | ACC | CGG | TTC | CGG | TCC |
| Pro | Glu | Lys | Trp | Asp | Gly | Val | Trp | Glu | Ala | Thr | Arg | Phe | Arg | Ser |
| ATG | GTG | ATG | CAG | CCG | TCC | GGC | ACC | ACC | TTC | AGC | ACC | GTG | CTC | GGG |
| Met | Val | Met | Gln | Pro | Ser | Gly | Thr | Thr | Phe | Ser | Thr | Val | Leu | Gly |
| GAA | GCG | GAT | CTT | CCT | GTG | AGC | GAA | GAC | GGT | CTT | TAT | CTG | AAT | ATC |
| Glu | Ala | Asp | Leu | Pro | Val | Ser | Glu | Asp | Gly | Leu | Tyr | Leu | Asn | Ile |
| TGG | TCG | CCG | GCA | GCC | GAC | GGA | AAA | AAG | CGG | CCG | GTG | CTC | TTC | TGG |
| Trp | Ser | Pro | Ala | Ala | Asp | Gly | Lys | Lys | Arg | Pro | Val | Leu | Phe | Trp |
| ATC | CAT | GGC | GGC | GCC | TAC | CAG | TTT | GGG | TCC | GGC | GCT | TCC | CCC | TGG |
| Ile | His | Gly | Gly | Ala | Tyr | Gln | Phe | Gly | Ser | Gly | Ala | Ser | Pro | Trp |
| TAT | GAC | GGG | ACG | GAG | TTT | GCC | AAA | AAC | GGA | GAT | GTG | GTG | GTT | GTC |
| Tyr | Asp | Gly | Thr | Glu | Phe | Ala | Lys | Asn | Gly | Asp | Val | Val | Val | Val |
| ACG | ATC | AAC | TAC | CGG | TTG | AAC | GCG | TTT | GGA | TTT | TTG | TAC | TTG | GCA |
| Thr | Ile | Asn | Tyr | Arg | Leu | Asn | Ala | Phe | Gly | Phe | Leu | Tyr | Leu | Ala |
| GAT | TGG | TTC | GGC | GAC | GAA | TTT | TCA | GCG | TCG | GGC | AAC | CTG | GGA | ATT |
| Asp | Trp | Phe | Gly | Asp | Glu | Phe | Ser | Ala | Ser | Gly | Asn | Leu | Gly | Ile |
| TTG | GAC | CAA | GTC | GCT | GCA | CTG | CGC | TGG | GTG | AAA | GAA | AAC | ATT | TCG |
| Leu | Asp | Gln | Val | Ala | Ala | Leu | Arg | Trp | Val | Lys | Glu | Asn | Ile | Ser |
| GCA | TTC | GGC | GGC | GAC | CCG | GAG | CAA | ATC | ACC | ATC | TTC | GGG | GAG | TCG |
| Ala | Phe | Gly | Gly | Asp | Pro | Glu | Gln | Ile | Thr | Ile | Phe | Gly | Glu | Ser |
| GCC | GGA | GCC | GGA | AGC | GTC | GGG | GTT | CTG | CTT | TCC | CTC | CCG | GAA | ACC |
| Ala | Gly | Ala | Gly | Ser | Val | Gly | Val | Leu | Leu | Ser | Leu | Pro | Glu | Thr |
| AAA | GGG | CTG | TTT | CAA | CGG | GCG | ATC | TTG | CAA | AGC | GGA | TCG | GGT | GCC |
| Lys | Gly | Leu | Phe | Gln | Arg | Ala | Ile | Leu | Gln | Ser | Gly | Ser | Gly | Ala |
| ATT | TTG | CTC | CGT | TCC | TCT | CAG | ACA | GCC | TCG | GGC | ATC | GCG | GAA | CAA |
| Ile | Leu | Leu | Arg | Ser | Ser | Gln | Thr | Ala | Ser | Gly | Ile | Ala | Glu | Gln |
| ATT | CTT | ACG | AAA | GCC | GGC | ATT | CGA | AAA | GGA | GAC | CGC | GAC | CGG | TTG |
| Ile | Leu | Thr | Lys | Ala | Gly | Ile | Arg | Lys | Gly | Asp | Arg | Asp | Arg | Leu |
| TTA | TCC | ATC | CCG | GCC | GGT | GAA | CTC | CTT | GAA | GCC | GCA | CAA | TCC | GTG |
| Leu | Ser | Ile | Pro | Ala | Gly | Glu | Leu | Leu | Glu | Ala | Ala | Gln | Ser | Val |
| AAT | CCG | GGA | ATG | GTT | TTT | GGT | CCC | GTT | GTG | GAC | GGC | ACC | GTA | TTG |
| Asn | Pro | Gly | Met | Val | Phe | Gly | Pro | Val | Val | Asp | Gly | Thr | Val | Leu |
| AAA | ACC | CAT | CCG | ATT | GAA | GCG | TTG | GAA | ACC | GGA | GCC | GCC | GGC | GAT |
| Lys | Thr | His | Pro | Ile | Glu | Ala | Leu | Glu | Thr | Gly | Ala | Ala | Gly | Asp |
| ATC | CCG | ATC | ATC | ATC | GGG | GTG | ACA | AAG | GAT | GAG | TAC | AAT | TTA | TTT |
| Ile | Pro | Ile | Ile | Ile | Gly | Val | Thr | Lys | Asp | Glu | Tyr | Asn | Leu | Phe |

Fig. 6K-2

```
ACA CTG ACT GAC CCT TCC TGG ACG ACA GCG GGA AAA GAA GAA CTG
Thr Leu Thr Asp Pro Ser Trp Thr Thr Ala Gly Lys Glu Glu Leu
ATG GAC CGG ATC GAA CAG GAA ATC GGG CCG GTT CCG GAA AAA GTT
Met Asp Arg Ile Glu Gln Glu Ile Gly Pro Val Pro Glu Lys Val
TTT CCA TAT TAC TTA TCT TTT GGG GAT CCA TCG CAA CCG GTA TGG
Phe Pro Tyr Tyr Leu Ser Phe Gly Asp Pro Ser Gln Pro Val Trp
CAA AAG CTG TTG CGC GCC ATG ACC TAC CAC ATC TTT ACC CGG GGC
Gln Lys Leu Leu Arg Ala Met Thr Tyr His Ile Phe Thr Arg Gly
ATG TTA AAA ACG GCT GAC GCC CAA ATC AAG CAA GGC GGG AAG GTT
Met Leu Lys Thr Ala Asp Ala Gln Ile Lys Gln Gly Gly Lys Val
TGG GTT TAC CGG TTT GAT TAC GAA ACC CCG CTC TTT GAC GGT CGG
Trp Val Tyr Arg Phe Asp Tyr Glu Thr Pro Leu Phe Asp Gly Arg
TTG AAA GCA TGT CAC GCA CTG GAA ATC CCC TTT GTC TTT CAC AAC
Leu Lys Ala Cys His Ala Leu Glu Ile Pro Phe Val Phe His Asn
CTG CAT CAA CCG GGG GTC GAT GTG TTC ACC GGC ACA CAT CCG AAG
Leu His Gln Pro Gly Val Asp Val Phe Thr Gly Thr His Pro Lys
CGG GAG CTA ATT TCC CGG CAA ATG CAT GAA GCA TGG ATT GCC TTT
Arg Glu Leu Ile Ser Arg Gln Met His Glu Ala Trp Ile Ala Phe
GCC CGG ACA GGG GAT CCG AAC GGC GAC CAT CTC CCC GAT GCG TGG
Ala Arg Thr Gly Asp Pro Asn Gly Asp His Leu Pro Asp Ala Trp
TTG CCC TTT GCA CAA AAA GAC CGG CCG GCC ATG GTC TTT GAC ACC
Leu Pro Phe Ala Gln Lys Asp Arg Pro Ala Met Val Phe Asp Thr
GAA ACC AGA GCG GAA AAG CAT CTG TTT GAC CGC GAG CAG GAA CTG
Glu Thr Arg Ala Glu Lys His Leu Phe Asp Arg Glu Gln Glu Leu
TGG GAA TCA AAG GCT TGA GTGATTTGCTCAAGCCTTTTTTGCATTTCACGTATGTATTCG
Trp Glu Ser Lys Ala ***
GATTTGGAATTAAACAATGGTGCTTTTATCGAAATGGGGAGTGTTTGCTTATAATGAACGGGTTTACAAA
GCTTGTTT
```

Fig. 6L-1

```
ATCACATCGTGGATATCAGTGGATCCGGTGCGATGGATTGCTTCAGGGGAACTTTTAAACACTTGAGTTTG
▶ Ser HisArgGlyTyrGlnTrpIleArgCysAspGlyLeuLeuGlnGlyAsnPhe***ThrLeuGluPheA
ACAACCACTCCTTAATCATTTAAGATTTAAATGAAAATTAAAATAAATCAAAAAGA GTG ATT CAA
spAsnHisSerLeuIleIle***AspLeuAsnGluAsn***AsnLysSerLysArg  Val  Ile Gln
ATG AAT ACG TTG GTG GAA ACC CGT TTT GGG AAA GTG CAA GGC
Met Asn Thr Leu Val Glu Thr Arg Phe Gly Lys Val Gln Gly
GGT ACA GAC GGA GAG GTT TGT TTT TGG AAA GGG ATT CCT TAT GCG
Gly Thr Asp Gly Glu Val Cys Phe Trp Lys Gly Ile Pro Tyr Ala
AAA CCT CCG GTG GGA AAA CGC CGC TTT CAA AAA CCG GAA CCG CCG
Lys Pro Pro Val Gly Lys Arg Arg Phe Gln Lys Pro Glu Pro Pro
GAG AAA TGG GAT GGC GTT TGG GAG GCC ACC CGG TTC CGG TCC ATG
Glu Lys Trp Asp Gly Val Trp Glu Ala Thr Arg Phe Arg Ser Met
GTG ATG CAG CCG TCC GGC ACC ACC TTC AGC ACC GTG CTC GGG GAA
Val Met Gln Pro Ser Gly Thr Thr Phe Ser Thr Val Leu Gly Glu
GCG GAT CTT CCT GTG AGC GAA GAC GGT CTT TAT CTG AAT ATC TGG
Ala Asp Leu Pro Val Ser Glu Asp Gly Leu Tyr Leu Asn Ile Trp
TCG CCG GCA GCC GAC GGA AAA AAG CGG CCG GTG CTC TTC TGG ATC
Ser Pro Ala Ala Asp Gly Lys Lys Arg Pro Val Leu Phe Trp Ile
CAT GGC GGC GCC TAC CAG TTT GGG TCC GGC GCT TCC CCC TGG TAT
His Gly Gly Ala Tyr Gln Phe Gly Ser Gly Ala Ser Pro Trp Tyr
GAC GGG ACG GAG TTT GCC AAA AAC GGA GAT GTG GTG GTT GTC ACG
Asp Gly Thr Glu Phe Ala Lys Asn Gly Asp Val Val Val Val Thr
ATC AAC TAC CGG TTG AAC GCG TTT GGA TTT TTG TAC TTG GCA GAT
Ile Asn Tyr Arg Leu Asn Ala Phe Gly Phe Leu Tyr Leu Ala Asp
TGG TTC GGC GAC GAA TTT TCA GCG TCG GGC AAC CTG GGA ATT TTG
Trp Phe Gly Asp Glu Phe Ser Ala Ser Gly Asn Leu Gly Ile Leu
GAC CAA GTC GCT GCA CTG CGC TGG GTG AAA GAA AAC ATT TCG GCA
Asp Gln Val Ala Ala Leu Arg Trp Val Lys Glu Asn Ile Ser Ala
TTC GGC GGC GAC CCG GAG CAA ATC ACC ATC TTC GGG GAG TCG GCC
Phe Gly Gly Asp Pro Glu Gln Ile Thr Ile Phe Gly Glu Ser Ala
GGA GCC GGA AGC GTC GGG GTT CTG CTT TCC CTC CCG GAA ACC AAA
Gly Ala Gly Ser Val Gly Val Leu Leu Ser Leu Pro Glu Thr Lys
GGG CTG TTT CAA CGG GCG ATC TTG CAA AGC GGA TCG GGT GCC ATT
Gly Leu Phe Gln Arg Ala Ile Leu Gln Ser Gly Ser Gly Ala Ile
TTG CTC CGT TCC TCT CAG ACA GCC TCG GGC ATC GCG GAA CAA ATT
Leu Leu Arg Ser Ser Gln Thr Ala Ser Gly Ile Ala Glu Gln Ile
CTT ACG AAA GCC GGC ATT CGA AAA GGA GAC CGC GAC CGG TTG TTA
Leu Thr Lys Ala Gly Ile Arg Lys Gly Asp Arg Asp Arg Leu Leu
TCC ATC CCG GCC GGT GAA CTC CTT GAA GCC GCA CAA TCC GTG AAT
Ser Ile Pro Ala Gly Glu Leu Leu Glu Ala Ala Gln Ser Val Asn
CCG GGA ATG GTT TTT GGT CCC GTT GTG GAC GGC ACC GTA TTG AAA
Pro Gly Met Val Phe Gly Pro Val Val Asp Gly Thr Val Leu Lys
ACC CAT CCG ATT GAA GCG TTG GAA ACC GGA GCC GCC GGC GAT ATC
Thr His Pro Ile Glu Ala Leu Glu Thr Gly Ala Ala Gly Asp Ile
CCG ATC ATC ATC GGG GTG ACA AAG GAT GAG TAC AAT TTA TTT ACA
Pro Ile Ile Ile Gly Val Thr Lys Asp Glu Tyr Asn Leu Phe Thr
```

Fig. 6L-2

```
CTG ACT GAC CCT TCC TGG ACG ACA GCG GGA AAA GAA GAA CTG ATG
Leu Thr Asp Pro Ser Trp Thr Thr Ala Gly Lys Glu Glu Leu Met
GAC CGG ATC GAA CAG GAA ATC GGG CCG GTT CCG GAA AAA GTT TTT
Asp Arg Ile Glu Gln Glu Ile Gly Pro Val Pro Glu Lys Val Phe
CCA TAT TAC TTA TCT TTT GGG GAT CCA TCG CAA CCG GTA TGG CAA
Pro Tyr Tyr Leu Ser Phe Gly Asp Pro Ser Gln Pro Val Trp Gln
AAG CTG TTG CGC GCC ATG ACC TAC CAC ATC TTT ACC CGG GGC ATG
Lys Leu Leu Arg Ala Met Thr Tyr His Ile Phe Thr Arg Gly Met
TTA AAA ACG GCT GAC GCC CAA ATC AAG CAA GGC GGG AAG GTT TGG
Leu Lys Thr Ala Asp Ala Gln Ile Lys Gln Gly Gly Lys Val Trp
GTT TAC CGG TTT GAT TAC GAA ACC CCG CTC TTT GAC GGT CGG TTG
Val Tyr Arg Phe Asp Tyr Glu Thr Pro Leu Phe Asp Gly Arg Leu
AAA GCA TGT CAC GCA CTG GAA ATC CCC TTT GTC TTT CAC AAC CTG
Lys Ala Cys His Ala Leu Glu Ile Pro Phe Val Phe His Asn Leu
CAT CAA CCG GGG GTC GAT GTG TTC ACC GGC ACA CAT CCG AAG CGG
His Gln Pro Gly Val Asp Val Phe Thr Gly Thr His Pro Lys Arg
GAG CTA ATT TCC CGG CAA ATG CAT GAA GCA TGG ATT GCC TTT GCC
Glu Leu Ile Ser Arg Gln Met His Glu Ala Trp Ile Ala Phe Ala
CGG ACA GGG GAT CCG AAC GGC GAC CAT CTC CCC GAT GCG TGG TTG
Arg Thr Gly Asp Pro Asn Gly Asp His Leu Pro Asp Ala Trp Leu
CCC TTT GCA CAA AAA GAC CGG CCG GCC ATG GTC TTT GAC ACC GAA
Pro Phe Ala Gln Lys Asp Arg Pro Ala Met Val Phe Asp Thr Glu
ACC AGA GCG GAA AAG CAT CTG TTT GAC CGC GAG CAG GAA CTG TGG
Thr Arg Ala Glu Lys His Leu Phe Asp Arg Glu Gln Glu Leu Trp
GAA TCA AAG GCT TGA GTGATTTGCTCAAGCCTTTTTTGCATTTCACGTATGTATTCGGATTT
Glu Ser Lys Ala ***
GGAATTAAACAATGGTGCTTTTTATCGAAATGGGGAGTGTTTGCTTATAATGAACGGGTTTACAAAGCTTGT
TTTGGTACCGGATTACTGAAAATGA
```

Fig. 6.M-1

```
GTCTCCAACGTTGCGAGACACCCCTCTTTAATTACGGGAACCAGAAATGATTTCCTATCGATAGCAAAAA
 ysLeuGlnArgCysGluThr ProLeuPheAsnTyr GlyAsnGlnLys***PheProIleAspSerLysLy
ATGGACGTGGGTAAACCATTCGTTAATAATATCTTTTGTAATCGTTAGAATA TTG AAA AAG
sTrpThr TrpValAsnHisSerLeuIleIleSer PheValIleValArgIle Leu Lys Lys
GGG ATG GGA CCC GTG ATC GTG GAA ACA AAG TAC GGT CGG TTG
Gly Met Gly Pro Val Ile Val Glu Thr Lys Tyr Gly Arg Leu
CGC GGG GGA ACA AAT GAA GGG GTT TTC TAT TGG AAA GGG ATT CCG
Arg Gly Gly Thr Asn Glu Gly Val Phe Tyr Trp Lys Gly Ile Pro
TAC GCG AAA GCG CCG GTC GGT GAA CGC CGT TTT TTG CCG CCG GAA
Tyr Ala Lys Ala Pro Val Gly Glu Arg Arg Phe Leu Pro Pro Glu
CCG CCC GAT GCA TGG GAC GGA GTG CGT GAG GCG ACA TCG TTT GGA
Pro Pro Asp Ala Trp Asp Gly Val Arg Glu Ala Thr Ser Phe Gly
CCG GTC GTC ATG CAG CCG TCC GAT TCG ATG TTC AGC CAG CTG CTC
Pro Val Val Met Gln Pro Ser Asp Ser Met Phe Ser Gln Leu Leu
GGA CGG ATG AAT GAA CCA ATG AGC GAG GAT GGG TTG TAT CTG AAC
Gly Arg Met Asn Glu Pro Met Ser Glu Asp Gly Leu Tyr Leu Asn
ATT TGG TCA CCG GCG GCG GAT GGG AAG AAG CGC CCG GTA TTG TTT
Ile Trp Ser Pro Ala Ala Asp Gly Lys Lys Arg Pro Val Leu Phe
TGG ATT CAT GGC GGC GCT TTT TTA TTC GGC TCC GGT TCA TTT CCA
Trp Ile His Gly Gly Ala Phe Leu Phe Gly Ser Gly Ser Phe Pro
TGG TAT GAT GGA ACG GCG TTT GCC AAA CAC GGC GAT GTC GTT GTC
Trp Tyr Asp Gly Thr Ala Phe Ala Lys His Gly Asp Val Val Val
GTG ACG ATC AAC TAC CGG ATG AGC GTG TTT GGC TTT TTG TAT TTG
Val Thr Ile Asn Tyr Arg Met Ser Val Phe Gly Phe Leu Tyr Leu
GGA GAT GCG TTT GGC GAA ACG TAT GCC CAG GCG GGA AAT CTT GGC
Gly Asp Ala Phe Gly Glu Thr Tyr Ala Gln Ala Gly Asn Leu Gly
ATA TTG GAT CAA GTG GCG GCG CTG CGC TGG GTG AAA GAG AAC ATT
Ile Leu Asp Gln Val Ala Ala Leu Arg Trp Val Lys Glu Asn Ile
GAG GCG TTC GGC GGT GAT CCG GAC AAC ATT ACG ATT TTT GGC GAA
Glu Ala Phe Gly Gly Asp Pro Asp Asn Ile Thr Ile Phe Gly Glu
TCA GCC GGA GCG GCA AGC GTT GGC GTG CTG TTG TCG CTT CCG GAA
Ser Ala Gly Ala Ala Ser Val Gly Val Leu Leu Ser Leu Pro Glu
GCA AGC GGG CTG TTT CGA CGC GCT ATA TTG CAA AGC GGA GCG GGT
Ala Ser Gly Leu Phe Arg Arg Ala Ile Leu Gln Ser Gly Ala Gly
TCG CTT CTT CTT CGT TCT CCG GAG ACG GCG ATG GCT CTG ACT GAA
Ser Leu Leu Leu Arg Ser Pro Glu Thr Ala Met Ala Leu Thr Glu
CGC ATT TTA GAA CGT GCC GGC ATC CGT CCG GGT GAC CGC GAT CGG
Arg Ile Leu Glu Arg Ala Gly Ile Arg Pro Gly Asp Arg Asp Arg
CTG CTG TCG ATT CCA GCA GCA GAG CTA TTG CAG GCG GCG ATG TCG
Leu Leu Ser Ile Pro Ala Ala Glu Leu Leu Gln Ala Ala Met Ser
CTC GGC CCA GGA ATC ACG TAC GGT CCG GTG GTT GAC GGA CAT GTG
Leu Gly Pro Gly Ile Thr Tyr Gly Pro Val Val Asp Gly His Val
TTG CGA CGC CAT CCG ATC GAA GCG CTC CAC GAC GGG GCA GCA AGT
Leu Arg Arg His Pro Ile Glu Ala Leu His Asp Gly Ala Ala Ser
```

Fig. 6M-2

```
GAT ATT CCA ATC CTA ATT GGC GTG ACG AAA GAC GAA TAC AAT TTG
Asp Ile Pro Ile Leu Ile Gly Val Thr Lys Asp Glu Tyr Asn Leu
TTT TCA TTG ACT GAT CCG TCA TTG ACA AGA CTC GAA GAA AAA GAA
Phe Ser Leu Thr Asp Pro Ser Leu Thr Arg Leu Glu Glu Lys Glu
CTG CTT GAC CGG ATG AAC CGT GAG GTC GGG CCT ATT CCG GAG AAG
Leu Leu Asp Arg Met Asn Arg Glu Val Gly Pro Ile Pro Glu Lys
CCG GTA CGC TAT TAC GCG GAA ACA GCG GAT CGG TCG GCA CCC GCG
Pro Val Arg Tyr Tyr Ala Glu Thr Ala Asp Arg Ser Ala Pro Ala
TGG CAA ACA TGG CTG CGC ATC ATG ACG TAC CTT GTT TTT GTC GAC
Trp Gln Thr Trp Leu Arg Ile Met Thr Tyr Leu Val Phe Val Asp
GGA ATG TTG CGA ACG GCG GAT GCC CAA GCA GCG CAA GGG GCG AAT
Gly Met Leu Arg Thr Ala Asp Ala Gln Ala Ala Gln Gly Ala Asn
GTG TAC ATG TAT CGG TTT GAT TAT GAA ACG CCG GCG TTC GGT GGA
Val Tyr Met Tyr Arg Phe Asp Tyr Glu Thr Pro Ala Phe Gly Gly
CAA CTG AAA GCG TGC CAT ACG CTC GAG TTG CCG TTT GTG TTT CAT
Gln Leu Lys Ala Cys His Thr Leu Glu Leu Pro Phe Val Phe His
AAC CTC CAT CAG CCT GGT GTC GAG AAT TTC GTC GGC AAC CGA CCA
Asn Leu His Gln Pro Gly Val Glu Asn Phe Val Gly Asn Arg Pro
GAG CGT GAG GCG ATT GCC AGC GAA ATG CAT GGT GCC TGG CTT TCG
Glu Arg Glu Ala Ile Ala Ser Glu Met His Gly Ala Trp Leu Ser
TTC GCC CAC ACC GGC AAC CCG AAC GGC GCT CAT TTA CCA GAG AAG
Phe Ala His Thr Gly Asn Pro Asn Gly Ala His Leu Pro Glu Lys
TGG CCC GTA TAC ACA AAA GAG CAC AAA CCG GTG TTT GTC TTT TCG
Trp Pro Val Tyr Thr Lys Glu His Lys Pro Val Phe Val Phe Ser
GCT GCG AGC CAT GTG GAA GAC GAT CCG TTC GGT CGC GAG CGG GAA
Ala Ala Ser His Val Glu Asp Asp Pro Phe Gly Arg Glu Arg Glu
GCG TGG CAA GGA CGC CTT TGA CGAAAAAATCCATAAGCAACATGTGTTCTTTGTCTGAA
Ala Trp Gln Gly Arg Leu ***
CACGATCCAAAGAATTCAAAAAGCTTCTCGAGAGTACTTCTAGAGCGGCCGCGGGCCCATCGATTTTCCA
CCCGGGTGGGGTACCAGGTAAGTGTACCCAATTCG
```

Fig. 6N-1

```
CCGTCGCGTACGGACCGCGTCGCAAAATACAACCAGTTGCTCCGCATTGAAGACGAACTTGGCCACA
 ProSerArgThrAspArgValAlaLysTyrAsnGlnLeuLeuArgIleGluAspGluLeuGlyHisT
CGGCTATTTACCAAGGCATTCGTTCGTTTTACAATTTGAAAAAATAACGGGAATCAACAACAAAGGG
 hrAlaIleTyrGlnGlyIleArgSerPheTyrAsnLeuLysLys***
TGTCTCCAACGTTGCGAGACACCCTCTTTAATTACGGGAAACAGAAATGATTTCCTATCGATAGCAA
                       1▶ThrGlyAsnArgAsnAspPheLeuSerIleAlaL
AAAATGGACGTGGGTAAACCATTCGTTTATAATATCTTTTTGTAATCGTTAGAATA TTG AAA
 ysAsnGlyArgGly***ThrIleArgLeu***TyrLeuPheValIleValArgIl▶ Leu Lys
```

| AAG | GGG | ATG | GGA | ACC | GTG | ATC | GTG | GAA | ACA | AAG | TAC | GGT | CGG |
|-----|-----|-----|-----|-----|-----|-----|-----|-----|-----|-----|-----|-----|-----|
| Lys | Gly | Met | Gly | Thr | Val | Ile | Val | Glu | Thr | Lys | Tyr | Gly | Arg |

| TTG | CGC | GGG | GGA | ACA | AAT | GAA | GGG | GTT | TTC | TAT | TGG | AAA | GGG |
| Leu | Arg | Gly | Gly | Thr | Asn | Glu | Gly | Val | Phe | Tyr | Trp | Lys | Gly |

| ATT | CCG | TAC | GCG | AAA | GCG | CCG | GTC | GGT | GAA | CGC | CGT | TTT | TTG |
| Ile | Pro | Tyr | Ala | Lys | Ala | Pro | Val | Gly | Glu | Arg | Arg | Phe | Leu |

| CCG | CCG | GAA | CCG | CCC | GAT | GCA | TGG | GAC | GGA | GTG | CGT | GAG | GCG |
| Pro | Pro | Glu | Pro | Pro | Asp | Ala | Trp | Asp | Gly | Val | Arg | Glu | Ala |

| ACA | TCG | TTT | GGA | CCG | GTC | GTC | ATG | CAG | CCG | TCC | GAT | TCG | ATG |
| Thr | Ser | Phe | Gly | Pro | Val | Val | Met | Gln | Pro | Ser | Asp | Ser | Met |

| TTC | AGC | CAG | CTG | CTC | GGA | CGG | ATG | AAT | GAA | CCA | ATG | AGC | GAG |
| Phe | Ser | Gln | Leu | Leu | Gly | Arg | Met | Asn | Glu | Pro | Met | Ser | Glu |

| GAT | GGG | TTG | TAT | CTG | AAC | ATT | TGG | TCA | CCG | GCG | GCG | GAT | GGG |
| Asp | Gly | Leu | Tyr | Leu | Asn | Ile | Trp | Ser | Pro | Ala | Ala | Asp | Gly |

| AAG | AAG | CGC | CCG | GTA | TTG | TTT | TGG | ATT | CAT | GGC | GGC | GCT | TTT |
| Lys | Lys | Arg | Pro | Val | Leu | Phe | Trp | Ile | His | Gly | Gly | Ala | Phe |

| TTA | TTC | GGC | TCC | GGT | TCA | TTT | CCA | TGG | TAT | GAT | GGA | ACG | GCG |
| Leu | Phe | Gly | Ser | Gly | Ser | Phe | Pro | Trp | Tyr | Asp | Gly | Thr | Ala |

| TTT | GCC | AAA | CAC | GGC | GAT | GTC | GTT | GTC | GTG | ACG | ATC | AAC | TAC |
| Phe | Ala | Lys | His | Gly | Asp | Val | Val | Val | Val | Thr | Ile | Asn | Tyr |

| CGG | ATG | AGC | GTG | TTT | GGC | TTT | TTG | TAT | TTG | GGA | GAT | GCG | TTT |
| Arg | Met | Ser | Val | Phe | Gly | Phe | Leu | Tyr | Leu | Gly | Asp | Ala | Phe |

| GGC | GAA | ACG | TAT | GCC | CAG | GCG | GGA | AAT | CTT | GGC | ATA | TTG | GAT |
| Gly | Glu | Thr | Tyr | Ala | Gln | Ala | Gly | Asn | Leu | Gly | Ile | Leu | Asp |

| CAA | GTG | GCG | GCG | CTG | CGC | TGG | GTG | AAA | GAG | AAC | ATT | GAG | GCG |
| Gln | Val | Ala | Ala | Leu | Arg | Trp | Val | Lys | Glu | Asn | Ile | Glu | Ala |

| TTC | GGC | GGT | GAT | CCG | GAC | AAC | ATT | ACG | ATT | TTT | GGC | GAA | TCA |
| Phe | Gly | Gly | Asp | Pro | Asp | Asn | Ile | Thr | Ile | Phe | Gly | Glu | Ser |

| GCC | GGA | GCG | GCA | AGC | GTT | GGC | GTG | CTG | TTG | TCG | CTT | CCG | GAA |
| Ala | Gly | Ala | Ala | Ser | Val | Gly | Val | Leu | Leu | Ser | Leu | Pro | Glu |

| GCA | AGC | GGG | CTG | TTT | CGA | CGC | GCT | ATA | TTG | CAA | AGC | GGA | TCG |
| Ala | Ser | Gly | Leu | Phe | Arg | Arg | Ala | Ile | Leu | Gln | Ser | Gly | Ser |

| GGT | TCG | CTT | CTT | CTT | CGT | TCT | CCG | GAG | ACG | GCG | ATG | GCT | CTG |
| Gly | Ser | Leu | Leu | Leu | Arg | Ser | Pro | Glu | Thr | Ala | Met | Ala | Leu |

| ACT | GAA | CGC | ATT | TTA | GAA | CGT | GCC | GGC | ATC | CGT | CCG | GGT | GAC |
| Thr | Glu | Arg | Ile | Leu | Glu | Arg | Ala | Gly | Ile | Arg | Pro | Gly | Asp |

Fig. 6N-2

```
CGC GAT CGG CTG CTG TCG ATT CCA GCA GCA GAG CTA TTG CAG
Arg Asp Arg Leu Leu Ser Ile Pro Ala Ala Glu Leu Leu Gln
GCG GCG ATG TCG CTC GGC CCA GGA ATC ACG TAC GGT CCG GTG
Ala Ala Met Ser Leu Gly Pro Gly Ile Thr Tyr Gly Pro Val
GTT GAC GGA CAT GTG TTG CGA CGC CAT CCG ATC GAA GCG CTC
Val Asp Gly His Val Leu Arg Arg His Pro Ile Glu Ala Leu
CAC GAC GGG GCA GCA AGT GAT ATT CCA ATC CTA ATT GGC GTG
His Asp Gly Ala Ala Ser Asp Ile Pro Ile Leu Ile Gly Val
ACG AAA GAC GAA TAC AAT TTG TTT TCA TTG ACT GAT CCG TCA
Thr Lys Asp Glu Tyr Asn Leu Phe Ser Leu Thr Asp Pro Ser
TTG ACA AGA CTC GAA GAA AAA GAA CTG CTT GAC CGG ATG AAC
Leu Thr Arg Leu Glu Glu Lys Glu Leu Leu Asp Arg Met Asn
CGT GAG GTC GGG CCT ATT CCG GAG GAG GCG GTA CGC TAT TAC
Arg Glu Val Gly Pro Ile Pro Glu Glu Ala Val Arg Tyr Tyr
GCG GAA ACA GCG GAT CGG TCG GCA CCC GCG TGG CAA ACA TGG
Ala Glu Thr Ala Asp Arg Ser Ala Pro Ala Trp Gln Thr Trp
CTG CGC ATC ATG ACG TAC CTT GTT TTT GTC GAC GGA ATG TTG
Leu Arg Ile Met Thr Tyr Leu Val Phe Val Asp Gly Met Leu
CGA ACG GCG GAT GCC CAA GCA GCG CAA GGG GCG AAT GTG TAC
Arg Thr Ala Asp Ala Gln Ala Ala Gln Gly Ala Asn Val Tyr
ATG TAT CGG TTT GAT TAT GAA ACG CCG GCG TTT GGT GGA CAA
Met Tyr Arg Phe Asp Tyr Glu Thr Pro Ala Phe Gly Gly Gln
CTG AAA GCG TGC CAT ACG CTC GAG TTG CCG TTT GTG TTT CAT
Leu Lys Ala Cys His Thr Leu Glu Leu Pro Phe Val Phe His
AAC CTC CAT CAG CCT GGT GTC GAG AAT TTC GTC GGC AAC CGA
Asn Leu His Gln Pro Gly Val Glu Asn Phe Val Gly Asn Arg
CCA GAG CGT GAG GCG ATT GCC AGC GAA ATG CAT GGT GCC TGG
Pro Glu Arg Glu Ala Ile Ala Ser Glu Met His Gly Ala Trp
CTT TCG TTC GCC CAC ACC GGC AAC CCG AAC GGC GCT CAT TTA
Leu Ser Phe Ala His Thr Gly Asn Pro Asn Gly Ala His Leu
CCA GAG AAG TGG CCC GTA TAC ACA AAA GAG CAC AAA CCG GTG
Pro Glu Lys Trp Pro Val Tyr Thr Lys Glu His Lys Pro Val
TTT GTC TTT TCG GCT GCG AGC CAT GTG GAA GAC GAT CCG TTC
Phe Val Phe Ser Ala Ala Ser His Val Glu Asp Asp Pro Phe
GGT CGC GAG CGG GAA GCG TGG CAA GGA CGC CTT TGACGAAAAAATCCAT
Gly Arg Glu Arg Glu Ala Trp Gln Gly Arg Leu
AAGCAACATGTGTTCTTTGTCTGAACACGATCAAGGTACGCGCATTTTCGCGGAAAAAGACCGTGGG
CAAACGTTCGCCTTTACCTCTAAAAGGAATGACGCAACATGTCTGCACTTCACAGGAAAGAGGACGA
AACGGTTGGTTTTCAGAATAGGAAAAGGTGTCCCGTTTTTTGGGACACCTTCTTCTATGTATCGCTC
AATCATTTGCTTCTGTGGCAGGAAGCCCGAATCGCTCGGCGAGTGCCGGATCACGATCGATCGCCTC
AATCAGTTTCCGCATGACGTTCACATCAAACGTAAAATTCGAACCGATTGGCGAGGTGACGAAAATT
TTCCCTTCTTTCGCCTCGCGTGCTCGTTTAAATTGATAGCCGTCAATCGCAATGACGACTCGTTCGT
CTGGCCTTGCCATTAGGAATCCCTCCATCGCTGTTTTTTCTTTCATTGTACTTGATTTTGAGGATGA
ACACCAACGTTCATGACACGCTCTTAAGGATAACGGATGGGACAGCGTTAGAGGGCGGTGAATTTCA
TCAAGAACGTGGCACAAAACGACATTTTTTTCATTATAGACGTCTTGATGTTTGGAATGATCGGAAAA
GGCGATTGTTAGGCGGGGATC
```

Fig. 6O-1

```
AAAAACGGGAGCACCGTCGCGTACGGACCGCGTCGCAAAATACAACCAGCTGCTCCGCATTGAAGACGAACT
LysAsnGlySerThrValAlaTyrGlyProArgArgLysIleGlnProAlaAlaProHis***ArgArgThr
TGGCCACACGGCTATTTACCAAGGCATTCGTTCGTTTTACAATTTGAAAAAATAACGGGAATCAACAACAAA
TrpProHisGlyTyrLeuProArgHisSerPheValLeuGlnPheGluLysIleThrGlyIleAsnAsnLys
GGGTGTCTCCAACGTTGCGAGACACCCTCTTTAATTACGGGAAACAGAAATGATTTCCTATCGATAGCAAAA
GlyCysLeuGlnArgCysGluThrProSerLeuIleThrGlyAsnArgAsnAspPheLeuSerIleAlaLys
AATGGACGTGGGTAAACCATTCGTTTATAATATCTTTTTGTAATCGTTAGAATA TTG AAA AAG
AsnGlyArgGly***ThrIleArgLeu***TyrLeuPheValIleValArgIle  Leu Lys Lys
```

| GGG | ATG | GGA | ACC | GTG | ATC | GTG | GAA | ACA | AAG | TAC | GGT | CGG | TTG | CGC |
|---|---|---|---|---|---|---|---|---|---|---|---|---|---|---|
| Gly | Met | Gly | Thr | Val | Ile | Val | Glu | Thr | Lys | Tyr | Gly | Arg | Leu | Arg |
| GGG | GGA | ACA | AAT | GAA | GGG | GTT | TTC | TAT | TGG | AAA | GGG | ATT | CCG | TAC |
| Gly | Gly | Thr | Asn | Glu | Gly | Val | Phe | Tyr | Trp | Lys | Gly | Ile | Pro | Tyr |
| GCG | AAA | GCG | CCG | GTC | GGT | GAA | CGC | CGT | TTT | TTG | CCG | CCG | GAA | CCG |
| Ala | Lys | Ala | Pro | Val | Gly | Glu | Arg | Arg | Phe | Leu | Pro | Pro | Glu | Pro |
| CCC | GAT | GCA | TGG | GAC | GGA | GTG | CGT | GAG | GCG | ACA | TCG | TTT | GGA | CCG |
| Pro | Asp | Ala | Trp | Asp | Gly | Val | Arg | Glu | Ala | Thr | Ser | Phe | Gly | Pro |
| GTC | GTC | ATG | CAG | CCG | TCC | GAT | TCG | ATG | TTC | AGC | CAG | CTG | CTC | GGA |
| Val | Val | Met | Gln | Pro | Ser | Asp | Ser | Met | Phe | Ser | Gln | Leu | Leu | Gly |
| CGG | ATG | AAT | GAA | CCA | ATG | AGC | GAG | GAT | GGG | TTG | TAT | CTG | AAC | ATT |
| Arg | Met | Asn | Glu | Pro | Met | Ser | Glu | Asp | Gly | Leu | Tyr | Leu | Asn | Ile |
| TGG | TCA | CCG | GCG | GCG | GAT | GGG | AAG | AAG | CGC | CCG | GTA | TTG | TTT | TGG |
| Trp | Ser | Pro | Ala | Ala | Asp | Gly | Lys | Lys | Arg | Pro | Val | Leu | Phe | Trp |
| ATT | CAT | GGC | GGC | GCT | TTT | TTA | TTC | GGC | TCC | GGT | TCA | TTT | CCA | TGG |
| Ile | His | Gly | Gly | Ala | Phe | Leu | Phe | Gly | Ser | Gly | Ser | Phe | Pro | Trp |
| TAT | GAT | GGA | ACG | GCG | TTT | GCC | AAA | CAC | GGC | GAT | GTC | GTT | GTC | GTG |
| Tyr | Asp | Gly | Thr | Ala | Phe | Ala | Lys | His | Gly | Asp | Val | Val | Val | Val |
| ACG | ATC | AAC | TAC | CGG | ATG | AGC | GTG | TTT | GGC | TTT | TTG | TAT | TTG | GGA |
| Thr | Ile | Asn | Tyr | Arg | Met | Ser | Val | Phe | Gly | Phe | Leu | Tyr | Leu | Gly |
| GAT | GCG | TTT | GGC | GAA | ACG | TAT | GCC | CAG | GCG | GGA | AAT | CTT | GGC | ATA |
| Asp | Ala | Phe | Gly | Glu | Thr | Tyr | Ala | Gln | Ala | Gly | Asn | Leu | Gly | Ile |
| TTG | GAT | CAA | GTG | GCG | GCG | CTG | CGC | TGG | GTG | AAA | GAG | AAC | ATT | GAG |
| Leu | Asp | Gln | Val | Ala | Ala | Leu | Arg | Trp | Val | Lys | Glu | Asn | Ile | Glu |
| GCG | TTC | GGC | GGT | GAT | CCG | GAC | AAC | ATT | ACG | ATT | TTT | GGC | GAA | TCA |
| Ala | Phe | Gly | Gly | Asp | Pro | Asp | Asn | Ile | Thr | Ile | Phe | Gly | Glu | Ser |
| GCC | GGA | GCG | GCA | AGC | GTT | GGC | GTG | CTG | TTG | TCG | CTT | CCG | GAA | GCA |
| Ala | Gly | Ala | Ala | Ser | Val | Gly | Val | Leu | Leu | Ser | Leu | Pro | Glu | Ala |
| AGC | GGG | CTG | TTT | CGA | CGC | GCT | ATA | TTG | CAA | AGC | GGA | TCG | GGT | TCG |
| Ser | Gly | Leu | Phe | Arg | Arg | Ala | Ile | Leu | Gln | Ser | Gly | Ser | Gly | Ser |
| CTT | CTT | CTT | CGT | TCT | CCG | GAG | ACG | GCG | ATG | GCT | CTG | ACT | GAA | CGC |
| Leu | Leu | Leu | Arg | Ser | Pro | Glu | Thr | Ala | Met | Ala | Leu | Thr | Glu | Arg |
| ATT | TTA | GAA | CGT | GCC | GGC | ATC | CGT | CCG | GGT | GAC | CGC | GAT | CGG | CTG |
| Ile | Leu | Glu | Arg | Ala | Gly | Ile | Arg | Pro | Gly | Asp | Arg | Asp | Arg | Leu |
| CTG | TCG | ATT | CCA | GCA | CCA | GAG | CTA | TTG | CAG | GCG | GCG | ATG | TCG | CTC |
| Leu | Ser | Ile | Pro | Ala | Pro | Glu | Leu | Leu | Gln | Ala | Ala | Met | Ser | Leu |
| GGC | CCA | GGA | ATC | ACG | TAC | GGT | CCG | GTG | GTT | GAC | GGA | CAT | GTG | TTG |
| Gly | Pro | Gly | Ile | Thr | Tyr | Gly | Pro | Val | Val | Asp | Gly | His | Val | Leu |
| CGA | CGC | CAT | CCG | ATC | GAA | GCG | CTC | CAC | GAC | GGG | GCA | GCA | AGT | GAT |
| Arg | Arg | His | Pro | Ile | Glu | Ala | Leu | His | Asp | Gly | Ala | Ala | Ser | Asp |

Fig. 60-2

```
ATT CCA ATC CTA ATT GGC GTG ACG AAA GAC GAA TAC AAT TTG TTT
Ile Pro Ile Leu Ile Gly Val Thr Lys Asp Glu Tyr Asn Leu Phe
TCA TTG ACT GAT CCG TCA TTG ACA AGA CTC GAA GAA AAA GAA CTG
Ser Leu Thr Asp Pro Ser Leu Thr Arg Leu Glu Glu Lys Glu Leu
CTT GAC CGG ATG AAC CGT GAG GTC GGG CCT ATT CCG GAG GAG GCG
Leu Asp Arg Met Asn Arg Glu Val Gly Pro Ile Pro Glu Glu Ala
GTA CGC TAT TAC GCG GAA ACA GCG GAT CGG TCG GCA CCC GCG TGG
Val Arg Tyr Tyr Ala Glu Thr Ala Asp Arg Ser Ala Pro Ala Trp
CAA ACA TGG CTG CGC ATC ATG ACG TAC CTT GTT TTT GTC GAC GGA
Gln Thr Trp Leu Arg Ile Met Thr Tyr Leu Val Phe Val Asp Gly
ATG TTG CGA ACG GCG GAT GCC CAA GCA GCG CAA GGG GCG AAT GTG
Met Leu Arg Thr Ala Asp Ala Gln Ala Ala Gln Gly Ala Asn Val
TAC ATG TAT CGG TTT GAT TAT GAA ACG CCG GCG TTC GGT GGA CAA
Tyr Met Tyr Arg Phe Asp Tyr Glu Thr Pro Ala Phe Gly Gly Gln
CTG AAA GCG TGC CAT ACG CTC GAG TTG CCG TTT GTG TTT CAT AAC
Leu Lys Ala Cys His Thr Leu Glu Leu Pro Phe Val Phe His Asn
CTC CAT CAG CCT GGT GTC GAG AAT TTC GTC GGC AAC CGA CCA GAG
Leu His Gln Pro Gly Val Glu Asn Phe Val Gly Asn Arg Pro Glu
CGT GAG GCG ATT GCC AGC GAA ATG CAT GGT GCC TGG CTT TCG TTC
Arg Glu Ala Ile Ala Ser Glu Met His Gly Ala Trp Leu Ser Phe
GCC CAC ACC GGC AAC CCG AAC GGC GCT CAT TTA CCA GAG AAG TGG
Ala His Thr Gly Asn Pro Asn Gly Ala His Leu Pro Glu Lys Trp
CCC GTA TAC ACA AAA GAG CAC AAA CCG GTG TTT GTC TTT TCG GCT
Pro Val Tyr Thr Lys Glu His Lys Pro Val Phe Val Phe Ser Ala
GCG AGC CAT GTG GAA GAC GAT CCG TTC GGT CGC GAG CGG GAA GCG
Ala Ser His Val Glu Asp Asp Pro Phe Gly Arg Glu Arg Glu Ala
TGG CAA GGA CGC CTT TGA CGAAAAAATCCATAAGCAACATGTGTTCTTTGTCTGAACACGAT
Trp Gln Gly Arg Leu ***
CCAAAGAATTCAAAAAGCTTCTCGAGAGTACTTCTAGAGCGGCCGCGGGCCCATCGATTTTCCACCCGGGTG
GGGTACCAGGTAAGTGTACCCAATTC
```

Fig. 6P-1

```
ACATCACATCGTGGATATCAGTGGATCCGGTGCGATGGATTGCTTCAGGGGAACTTTTAAACACTTG
Thr Ser His Arg Gly Tyr Gln Trp Ile Arg Cys Asp Gly Leu Leu Gln Gly Asn Phe *** Thr Leu G
AGTTTGACAACCACTCCTTAATCATTTAAGATTTAAATGAAAATTAAAATAAATCAAAAAGA GTG
l uPheAspAsnHisSerLeuIle Ile***AspLeuAsnGluAsn***AsnLysSerLysArg Val
```

| ATT | CAA | ATG | AAT | ACG | TTG | GTG | GAA | ACC | CGT | TTT | GGG | AAA | GTG |
|---|---|---|---|---|---|---|---|---|---|---|---|---|---|
| Ile | Gln | Met | Asn | Thr | Leu | Val | Glu | Thr | Arg | Phe | Gly | Lys | Val |
| CAA | GGC | GGT | ACA | GAC | GGA | GAG | GTT | TGT | TTT | TGG | AAA | GGG | ATT |
| Gln | Gly | Gly | Thr | Asp | Gly | Glu | Val | Cys | Phe | Trp | Lys | Gly | Ile |
| CCT | TAT | GCG | AAA | CCT | CCG | GTG | GGA | AAA | CGC | CGC | TTT | CAA | AAA |
| Pro | Tyr | Ala | Lys | Pro | Pro | Val | Gly | Lys | Arg | Arg | Phe | Gln | Lys |
| CCG | GAA | CCG | CCG | GAG | AAA | TGG | GAT | GGC | GTT | TGG | GAG | GCC | ACC |
| Pro | Glu | Pro | Pro | Glu | Lys | Trp | Asp | Gly | Val | Trp | Glu | Ala | Thr |
| CGG | TTC | CGG | TCC | ATG | GTG | ATG | CAG | CCG | TCC | GGC | ACC | ACC | TTC |
| Arg | Phe | Arg | Ser | Met | Val | Met | Gln | Pro | Ser | Gly | Thr | Thr | Phe |
| AGC | ACC | GTG | CTC | GGG | GAA | GCG | GAT | CTT | CCT | GTG | AGC | GAA | GAC |
| Ser | Thr | Val | Leu | Gly | Glu | Ala | Asp | Leu | Pro | Val | Ser | Glu | Asp |
| GGT | CTT | TAT | CTG | AAT | ATC | TGG | TCG | CCG | GCA | GCC | GAC | GGA | AAA |
| Gly | Leu | Tyr | Leu | Asn | Ile | Trp | Ser | Pro | Ala | Ala | Asp | Gly | Lys |
| AAG | CGG | CCG | GTG | CTC | TTC | TGG | ATC | CAT | GGC | GGC | GCC | TAC | CAG |
| Lys | Arg | Pro | Val | Leu | Phe | Trp | Ile | His | Gly | Gly | Ala | Tyr | Gln |
| TTT | GGG | TCC | GGC | GCT | TCC | CCC | TGG | TAT | GAC | GGG | ACG | GAG | TTT |
| Phe | Gly | Ser | Gly | Ala | Ser | Pro | Trp | Tyr | Asp | Gly | Thr | Glu | Phe |
| GCC | AAA | AAC | GGA | GAT | GTG | GTG | GTT | GTC | ACG | ATC | AAC | TAC | CGG |
| Ala | Lys | Asn | Gly | Asp | Val | Val | Val | Val | Thr | Ile | Asn | Tyr | Arg |
| TTG | AAC | GCG | TTT | GGA | TTT | TTG | TAC | TTG | GCA | GAT | TGG | TTC | GGC |
| Leu | Asn | Ala | Phe | Gly | Phe | Leu | Tyr | Leu | Ala | Asp | Trp | Phe | Gly |
| GAC | GAA | TTT | TCA | GCG | TCG | GGC | AAC | CTG | GGA | ATT | TTG | GAC | CAA |
| Asp | Glu | Phe | Ser | Ala | Ser | Gly | Asn | Leu | Gly | Ile | Leu | Asp | Gln |
| GTC | GCT | GCA | CTG | CGC | TGG | GTG | AAA | GAA | AAC | ATT | TCG | GCA | TTC |
| Val | Ala | Ala | Leu | Arg | Trp | Val | Lys | Glu | Asn | Ile | Ser | Ala | Phe |
| GGC | GGC | GAC | CCG | GAG | CAA | ATC | ACC | ATC | TTC | GGG | GAG | TCG | GCC |
| Gly | Gly | Asp | Pro | Glu | Gln | Ile | Thr | Ile | Phe | Gly | Glu | Ser | Ala |
| GGA | GCC | GGA | AGC | GTC | GGG | GTT | CTG | CTT | TCC | CTC | CCG | GAA | ACC |
| Gly | Ala | Gly | Ser | Val | Gly | Val | Leu | Leu | Ser | Leu | Pro | Glu | Thr |
| AAA | GGG | CTG | TTT | CAA | CGG | GCG | ATC | TTG | CAA | AGC | GGA | TCG | GGT |
| Lys | Gly | Leu | Phe | Gln | Arg | Ala | Ile | Leu | Gln | Ser | Gly | Ser | Gly |
| GCC | ATT | TTG | CTC | CGT | TCC | TCT | CAG | ACA | GCC | TCG | GGC | ATC | GCG |
| Ala | Ile | Leu | Leu | Arg | Ser | Ser | Gln | Thr | Ala | Ser | Gly | Ile | Ala |
| GAA | CAA | ATT | CTT | ACG | AAA | GCC | GGC | ATT | CGA | AAA | GGA | GAC | CGC |
| Glu | Gln | Ile | Leu | Thr | Lys | Ala | Gly | Ile | Arg | Lys | Gly | Asp | Arg |
| GAC | CGG | TTG | TTA | TCC | ATC | CCG | GCC | GGT | GAA | CTC | CTT | GAA | GCC |
| Asp | Arg | Leu | Leu | Ser | Ile | Pro | Ala | Gly | Glu | Leu | Leu | Glu | Ala |
| GCA | CAA | TCC | GTG | AAT | CCG | GGA | ATG | GTT | TTT | GGT | CCC | GTT | GTG |
| Ala | Gln | Ser | Val | Asn | Pro | Gly | Met | Val | Phe | Gly | Pro | Val | Val |
| GAC | GGC | ACC | GTA | TTG | AAA | ACC | CAT | CCG | ATT | GAA | GCG | TTG | GAA |
| Asp | Gly | Thr | Val | Leu | Lys | Thr | His | Pro | Ile | Glu | Ala | Leu | Glu |

Fig. 6P-2

```
ACC GGA GCC GCC GGC GAT ATC CCG ATC ATC ATC GGG GTG ACA
Thr Gly Ala Ala Gly Asp Ile Pro Ile Ile Ile Gly Val Thr
AAG GAT GAG TAC AAT TTA TTT ACA CTG ACT GAC CCT TCC TGG
Lys Asp Glu Tyr Asn Leu Phe Thr Leu Thr Asp Pro Ser Trp
ACG ACA GCG GGA AAA GAA GAA CTG ATG GAC CGG ATC GAA CAG
Thr Thr Ala Gly Lys Glu Glu Leu Met Asp Arg Ile Glu Gln
GAA ATC GGG CCG GTT CCG GAA AAA GTT TTT CCA TAT TAC TTA
Glu Ile Gly Pro Val Pro Glu Lys Val Phe Pro Tyr Tyr Leu
TCT TTT GGG GAT CCA TCG CAA CCG GTA TGG CAA AAG CTG TTG
Ser Phe Gly Asp Pro Ser Gln Pro Val Trp Gln Lys Leu Leu
CGC GCC ATG ACC TAC CAC ATC TTT ACC CGG GGC ATG TTA AAA
Arg Ala Met Thr Tyr His Ile Phe Thr Arg Gly Met Leu Lys
ACG GCT GAC GCC CAA ATC AAG CAA GGC GGG AAG GTT TGG GTT
Thr Ala Asp Ala Gln Ile Lys Gln Gly Gly Lys Val Trp Val
TAC CGG TTT GAT TAC GAA ACC CCG CTC TTT GAC GGT CGG TTG
Tyr Arg Phe Asp Tyr Glu Thr Pro Leu Phe Asp Gly Arg Leu
AAA GCA TGT CAC GCA CTG GAA ATC CCC TTT GTC TTT CAC AAC
Lys Ala Cys His Ala Leu Glu Ile Pro Phe Val Phe His Asn
CTG CAT CAA CCG GGG GTC GAT GTG TTC ACC GGC ACA CAT CCG
Leu His Gln Pro Gly Val Asp Val Phe Thr Gly Thr His Pro
AAG CGG GAG CTA ATT TCC CGG CAA ATG CAT GAA GCA TGG ATT
Lys Arg Glu Leu Ile Ser Arg Gln Met His Glu Ala Trp Ile
GCC TTT GCC CGG ACA GGG GAT CCG AAC GGC GAC CAT CTC CCC
Ala Phe Ala Arg Thr Gly Asp Pro Asn Gly Asp His Leu Pro
GAT GCG TGG TTG CCC TTT GCA CAA AAA GAC CGG CCG GCC ATG
Asp Ala Trp Leu Pro Phe Ala Gln Lys Asp Arg Pro Ala Met
GTC TTT GAC ACC GAA ACC AGA GCG GAA AAG CAT CTG TTT GAC
Val Phe Asp Thr Glu Thr Arg Ala Glu Lys His Leu Phe Asp
CGC GAG CAG GAA CTG TGG GAA TCA AAG GCT TGA GTGATTTGCTCAAGC
Arg Glu Gln Glu Leu Trp Glu Ser Lys Ala ***
CTTTTTTTGCATTTCACGTATGTATTCGGATTTGGAATTAAACAATGGTGCTTTTATCGAAATGGGGA
GTGTTTGCTTATAATGAACGGGTTTACAAAGCTTGTTTT
```

E007
5'> CTAGTGATT CCCTCCTT--TCGTG CCCATTA-GTACTTT CGGTTGCGGGTG-A
ACAAATGAAGGGGTT TTCTATTGGAAAAGGGATTCCGTACGCGAAA GCTCCGGTCGGTGAA
CGCCGATTTTTGCCG CCGGAACCGCCCGAT GCATGGGACG--ATG CGTGAGGCCGACATC
gggCAAGCTTCTACA TGCATCGCCCCgAGC ATGaaacGTCGGcgT CCGGTGGAAAActgA
ACGGGTgccaTACAC GAGGGTTTCTCGTTTCGGATTCataaCCTT AATGAACCCCTTgtc
gAgaaTTTCCGCGTA AACTG <3'

>E002
5'> AAATTTTAAA CCGAAGCCACCGCAA AGCCAAAGAAGAAAGGGG
AAAAAATTTTCAAGGTCAACCTTTAGCCA AATCGGCCGGTTCCAA AACGCCGTTTTTTAC
GGTTTTAATGTGAAA CGTCAATCGGAAAGA CTGAATTAAGGCGATCCGAATCGGTGGATAA
CGGGCGTCACTTAGC CCGACGATTACGGGG CTTTCCCTGCCACAG AAGCAAATGATTTGA
GCGAATACATAGAAG

Fig. 6S

```
GAACGGGCGTTTGCCA AACACGGGCGATGTCG TTGTCGTGACGATCA ACTACCGGATGAGCG
TGTTTGGCTTTTTGT ATTTGGGAGATGCGTGCGGTGATCCGGACA ACATTACGATTTTTG
GCGAATCAAGCCGGA GCGGCAAGCGTTGGC GTGCTGTTGTCGCTT TCGGAGCGGTGATCCGGACA
ACATTACGATTTTTG GCGAATCAAGCCGGA GCGGCAAGCGTTGGC GTGCTGTTGTCGCTT
TCGGAGCGGTGATCCGGACA ACATTACGATTTTTG GCGAATCAAGCCGGA GCGGCAAGCGTTGGC
GTGCTGTTGTCGCTT TCGGAgAACGCATTTTATA AACCGTGCCCGGTAA TTTCGTTCCGGTTGG
ACCCGCAATCCGGCT GCTTGTTCTTTCCAA GCAACTAAGCGCATTTTATA AACCGTGCCCGGTAA
TTTCGTTCCGGTTGG ACCCGCAATCCGGCT GCTTGTTCTTTCCAA GCAACTAAGCGCATTTTATA
AACCGTGCCCGGTAA TTTCGTTCCGGTTGG ACCCGCAATCCGGCT GCTTGTTCTTTCCAA
GCAACTCAATCCGGCT GCTTGTTCTTCCAA GCAACTgACCTTTTGCAAGCGGCTAATGTT
CCTCTCGGGCCCCAG GAAATCACGgtaCGTT CCCGtgGTC <3'
```

Fig. 6T

```
>E014, 3' END
CCTGCACAAAT CCGATGTGAAATGTT TTGGGATATTCGGC TTGCCTTCCTTTCA TTAAAGCCA
GTAACATCCCTTGAT T TAACAGAGTAAACGA GTCGCCGCGGGTAGT CACG-GTTTTCAGAT
CGAAATATTTCTTCA ACAGCGAATCGCTCTTCAGTGGCTTGAACGTC AGTA—ACCGTCAG
ATTCAGATGG TTGAGATTCATCATCGAA TCTCCTCTCATGATTTTTTGTAAA AATG-ATCGCTGTTT
TAGTGATCCTTAACG ATGGCTTTCATGTA CAAATTTACAATCGCTTCAAGGTCTTTTGGGTATCA
GGTTGTTGGGGTGGA CGGTGTCGACAAAT GAGTCCGGCAAGCAG
GATATAAAGTAAGCCGAATGGGGTCCGACAA <3'
```

Fig. 6U

RAW DATA

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.354 | 0.202 | 0.358 | 0.236 | 0.322 | 0.09 | 0.223 | 0.042 | 0.107 | 0.252 | 0.039 | 0.084 | 0.051 | 0.051 | 0.043 | 0.45 | 0.039 | 0 | 0.134 | 0.344 |
| 40 | 0.457 | 0.235 | 0.456 | 0.312 | 0.488 | 0.165 | 0.33 | 0.099 | 0.189 | 0.39 | 0.054 | 0.143 | 0.079 | 0.079 | 0.052 | 0.729 | 0.067 | 0 | 0.22 | 0.638 |
| 80 | 0.612 | 0.318 | 0.556 | 0.452 | 0.599 | 0.236 | 0.441 | 0.155 | 0.273 | 0.528 | 0.074 | 0.2 | 0.108 | 0.108 | 0.062 | 0.97 | 0.097 | 0 | 0.308 | 0.929 |
| 120 | 0.797 | 0.411 | 0.651 | 0.585 | 0.768 | 0.309 | 0.555 | 0.215 | 0.36 | 0.666 | 0.096 | 0.266 | 0.147 | 0.147 | 0.072 | 1.206 | 0.134 | 0 | 0.399 | 1.216 |
| 160 | 0.976 | 0.501 | 0.741 | 0.73 | 0.938 | 0.393 | 0.668 | 0.275 | 0.445 | 0.801 | 0.118 | 0.327 | 0.19 | 0.19 | 0.083 | 1.407 | 0.175 | 0 | 0.492 | 1.495 |
| 200 | 1.148 | 0.594 | 0.825 | 0.874 | 1.105 | 0.46 | 0.781 | 0.334 | 0.533 | 0.931 | 0.142 | 0.391 | 0.236 | 0.236 | 0.095 | 1.599 | 0.221 | 0 | 0.583 | 1.772 |
| 240 | 1.321 | 0.687 | 0.902 | 1.016 | 1.27 | 0.547 | 0.893 | 0.395 | 0.619 | 1.059 | 0.167 | 0.454 | 0.289 | 0.289 | 0.108 | 1.781 | 0.271 | 0 | 0.674 | 2.042 |
| 280 | 1.477 | 0.776 | 0.974 | 1.155 | 1.432 | 0.623 | 1.004 | 0.457 | 0.705 | 1.184 | 0.193 | 0.517 | 0.346 | 0.346 | 0.121 | 1.954 | 0.323 | 0 | 0.763 | 2.319 |
| 320 | 1.637 | 0.865 | 1.043 | 1.283 | 1.592 | 0.69 | 1.114 | 0.52 | 0.792 | 1.303 | 0.22 | 0.58 | 0.407 | 0.407 | 0.134 | 2.125 | 0.381 | 0 | 0.854 | 2.613 |
| 360 | 1.791 | 0.956 | 1.108 | 1.414 | 1.75 | 0.769 | 1.222 | 0.583 | 0.877 | 1.42 | 0.248 | 0.641 | 0.474 | 0.474 | 0.149 | 2.299 | 0.442 | 0 | 0.943 | 2.963 |
| 400 | 1.937 | 1.044 | 1.169 | 1.542 | 1.908 | 0.848 | 1.328 | 0.65 | 0.96 | 1.534 | 0.278 | 0.701 | 0.544 | 0.544 | 0.164 | 2.442 | 0.506 | 0 | 1.033 | 3.571 |
| 440 | 2.101 | 1.132 | 1.226 | 1.664 | 2.057 | 0.919 | 1.434 | 0.72 | 1.045 | 1.645 | 0.308 | 0.762 | 0.617 | 0.617 | 0.18 | 2.594 | 0.573 | 0 | 1.123 | 3.673 |
| 480 | | | 1.278 | | | 0.99 | 1.542 | 0.789 | 1.129 | 1.756 | 0.34 | 0.822 | 0.695 | 0.695 | 0.195 | 2.761 | 0.642 | 0 | 1.213 | 3.672 |
| 520 | | | 1.325 | | | 1.066 | 1.646 | 0.857 | 1.212 | 1.865 | 0.371 | 0.882 | 0.776 | 0.776 | 0.212 | 2.943 | 0.714 | 0 | 1.304 | 3.672 |
| 560 | | | 1.366 | | | 1.143 | 1.752 | 0.926 | 1.297 | 1.978 | 0.404 | 0.941 | 0.86 | 0.86 | 0.229 | 3.19 | 0.788 | 0 | 1.395 | 3.672 |
| 600 | | | 1.403 | | | 1.218 | 1.858 | 0.996 | 1.381 | 2.089 | 0.438 | 1 | 0.947 | 0.947 | 0.247 | 3.46 | 0.864 | 0 | 1.485 | 3.673 |
| rate/min | 0.242 | 0.121 | 0.136 | 0.195 | 0.237 | 0.114 | 0.168 | 0.088 | 0.128 | 0.202 | 0.032 | 0.093 | 0.060 | 0.060 | 0.016 | 0.333 | 0.058 | 0.000 | 0.135 | 0.425 |

Average of the first four minutes note: enzyme E009 is an 80X dilution compared to the other enzymes
reaction conditions: estimated 0.1 u/1 ml reaction, 500 µg/ml substrate

FIGURE 7B

RAW DATA

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.27 | 0.18 | 0.36 | 0.24 | 0.18 | 0.13 | 0.15 | 0.07 | 0.12 | 0.12 | 0.06 | 0.09 | 0.05 | 0.02 | 0.1 | 0.22 | 0.12 | 0.08 | 0.1 | 0.17 |
| 40 | 0.29 | 0.22 | 0.46 | 0.32 | 0.25 | 0.17 | 0.23 | 0.11 | 0.23 | 0.24 | 0.08 | 0.12 | 0.07 | 0.03 | 0.07 | 0.23 | 0.1 | 0.05 | 0.14 | 0.24 |
| 80 | 0.38 | 0.26 | 0.56 | 0.4 | 0.32 | 0.21 | 0.31 | 0.14 | 0.34 | 0.35 | 0.09 | 0.15 | 0.09 | 0.04 | 0.08 | 0.28 | 0.12 | 0.05 | 0.18 | 0.32 |
| 120 | 0.46 | 0.3 | 0.65 | 0.48 | 0.38 | 0.25 | 0.39 | 0.18 | 0.44 | 0.46 | 0.11 | 0.18 | 0.1 | 0.05 | 0.09 | 0.32 | 0.13 | 0.05 | 0.22 | 0.4 |
| 160 | 0.54 | 0.34 | 0.74 | 0.55 | 0.45 | 0.29 | 0.46 | 0.21 | 0.55 | 0.56 | 0.13 | 0.21 | 0.12 | 0.06 | 0.11 | 0.37 | 0.15 | 0.05 | 0.26 | 0.47 |
| 200 | 0.62 | 0.38 | 0.83 | 0.62 | 0.52 | 0.33 | 0.54 | 0.25 | 0.65 | 0.65 | 0.14 | 0.23 | 0.13 | 0.08 | 0.12 | 0.42 | 0.17 | 0.05 | 0.3 | 0.55 |
| 240 | 0.7 | 0.42 | 0.9 | 0.68 | 0.58 | 0.37 | 0.61 | 0.28 | 0.75 | 0.74 | 0.16 | 0.26 | 0.15 | 0.09 | 0.13 | 0.46 | 0.19 | 0.05 | 0.34 | 0.62 |
| 280 | 0.77 | 0.46 | 0.97 | 0.74 | 0.64 | 0.41 | 0.68 | 0.32 | 0.85 | 0.82 | 0.17 | 0.29 | 0.16 | 0.11 | 0.14 | 0.51 | 0.21 | 0.05 | 0.38 | 0.69 |
| 320 | 0.84 | 0.5 | 1.04 | 0.8 | 0.7 | 0.45 | 0.75 | 0.35 | 0.94 | 0.89 | 0.19 | 0.31 | 0.18 | 0.13 | 0.15 | 0.55 | 0.24 | 0.05 | 0.41 | 0.76 |
| 360 | 0.9 | 0.53 | 1.11 | 0.85 | 0.76 | 0.49 | 0.81 | 0.39 | 1.02 | 0.96 | 0.2 | 0.34 | 0.19 | 0.15 | 0.16 | 0.58 | 0.26 | 0.05 | 0.45 | 0.82 |
| 400 |  | 0.57 | 1.17 | 0.9 | 0.82 | 0.53 | 0.87 | 0.42 | 1.1 | 1.03 | 0.22 | 0.36 | 0.21 | 0.17 | 0.17 | 0.62 | 0.28 | 0.05 | 0.49 | 0.89 |
| 440 |  | 0.6 | 1.23 | 0.95 | 0.87 | 0.56 | 0.93 | 0.46 | 1.17 | 1.08 | 0.23 | 0.39 | 0.22 | 0.19 | 0.18 | 0.65 | 0.3 | 0.05 | 0.53 | 0.95 |
| 480 |  | 0.64 | 1.28 | 0.99 | 0.92 | 0.6 | 0.99 | 0.49 | 1.23 | 1.14 | 0.25 | 0.41 | 0.24 | 0.21 | 0.19 | 0.68 | 0.33 | 0.06 | 0.56 | 1 |
| 520 |  | 0.67 | 1.33 | 1.03 | 0.97 | 0.64 | 1.05 | 0.53 | 1.29 | 1.19 | 0.26 | 0.43 | 0.25 | 0.23 | 0.2 | 0.71 | 0.35 | 0.06 | 0.6 | 1.06 |
| 560 |  | 0.7 | 1.37 | 1.08 | 1.02 | 0.67 | 1.1 | 0.56 | 1.35 | 1.24 | 0.28 | 0.45 | 0.26 | 0.25 | 0.22 | 0.74 | 0.38 | 0.06 | 0.64 | 1.11 |
| 600 |  |  | 1.4 | 1.11 | 1.07 | 0.7 | 1.16 | 0.6 | 1.39 | 1.28 | 0.29 | 0.48 | 0.28 | 0.27 | 0.23 | 0.77 | 0.4 | 0.06 | 0.67 | 1.16 |
| rate/min | 0.108 | 0.060 | 0.136 | 0.111 | 0.101 | 0.061 | 0.114 | 0.052 | 0.157 | 0.153 | 0.024 | 0.042 | 0.024 | 0.018 | 0.007 | 0.061 | 0.018 | -0.009 | 0.058 | 0.112 |

Average of the first four minutes note: enzyme E009 is an 80X dilution compared to the other enzymes
reaction conditions: estimated 0.1 u/1 ml reaction, 500 µg/ml substrate

FIGURE 7C

RAW DATA

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.28 | 0.15 | 0.36 | 0.13 | 0.13 | 0.14 | 0.14 | 0.07 | 0.1 | 0.11 | 0.04 | 0.13 | 0.04 | 0.04 | 0.06 | 0.17 | 0.09 | 0.02 | 0.24 | 0.28 |
| 40 | 0.39 | 0.23 | 0.47 | 0.19 | 0.21 | 0.21 | 0.22 | 0.09 | 0.16 | 0.17 | 0.05 | 0.18 | 0.05 | 0.06 | 0.07 | 0.22 | 0.11 | 0.02 | 0.34 | 0.57 |
| 80 | 0.48 | 0.28 | 0.51 | 0.23 | 0.26 | 0.27 | 0.3 | 0.11 | 0.22 | 0.22 | 0.06 | 0.24 | 0.07 | 0.08 | 0.07 | 0.26 | 0.14 | 0.02 | 0.43 | 0.84 |
| 120 | 0.56 | 0.32 | 0.53 | 0.26 | 0.32 | 0.33 | 0.39 | 0.13 | 0.28 | 0.27 | 0.07 | 0.3 | 0.08 | 0.1 | 0.08 | 0.31 | 0.17 | 0.02 | 0.52 | 1.07 |
| 160 | 0.63 | 0.37 | 0.54 | 0.29 | 0.37 | 0.4 | 0.47 | 0.15 | 0.35 | 0.31 | 0.08 | 0.35 | 0.1 | 0.13 | 0.09 | 0.35 | 0.21 | 0.02 | 0.6 | 1.19 |
| 200 | 0.69 | 0.41 | 0.54 | 0.32 | 0.42 | 0.46 | 0.55 | 0.17 | 0.41 | 0.35 | 0.09 | 0.4 | 0.11 | 0.15 | 0.09 | 0.39 | 0.24 | 0.02 | 0.69 | 1.22 |
| 240 | 0.74 | 0.45 | 0.55 | 0.34 | 0.47 | 0.52 | 0.62 | 0.19 | 0.47 | 0.38 | 0.1 | 0.46 | 0.12 | 0.18 | 0.1 | 0.43 | 0.27 | 0.02 | 0.79 | 1.25 |
| 280 | 0.77 | 0.48 | 0.55 | 0.36 | 0.51 | 0.58 | 0.69 | 0.21 | 0.53 | 0.41 | 0.11 | 0.5 | 0.13 | 0.21 | 0.1 | 0.47 | 0.31 | 0.02 | 0.85 | 1.27 |
| 320 | 0.79 | 0.51 | 0.56 | 0.37 | 0.54 | 0.63 | 0.75 | 0.22 | 0.58 | 0.43 | 0.12 | 0.55 | 0.14 | 0.25 | 0.11 | 0.5 | 0.35 | 0.02 | 0.92 | 1.29 |
| 360 | 0.81 | 0.53 | 0.56 | 0.38 | 0.57 | 0.68 | 0.8 | 0.24 | 0.64 | 0.45 | 0.13 | 0.59 | 0.15 | 0.28 | 0.11 | 0.53 | 0.38 | 0.02 | 0.98 | 1.31 |
| 400 | 0.82 | 0.55 | 0.56 | 0.39 | 0.58 | 0.73 | 0.84 | 0.26 | 0.68 | 0.47 | 0.14 | 0.63 | 0.16 | 0.32 | 0.12 | 0.56 | 0.42 | 0.02 | 1.04 | 1.32 |
| 440 | 0.83 | 0.56 | 0.57 | 0.4 | 0.59 | 0.77 | 0.88 | 0.27 | 0.73 | 0.49 | 0.15 | 0.67 | 0.17 | 0.35 | 0.13 | 0.59 | 0.46 | 0.02 | 1.09 | 1.34 |
| 480 | 0.84 | 0.57 | 0.57 | 0.41 | 0.59 | 0.81 | 0.9 | 0.29 | 0.77 | 0.51 | 0.16 | 0.7 | 0.17 | 0.39 | 0.13 | 0.61 | 0.5 | 0.02 | 1.14 | 1.35 |
| 520 | 0.85 | 0.57 | 0.57 | 0.42 | 0.6 | 0.84 | 0.92 | 0.31 | 0.81 | 0.52 | 0.17 | 0.73 | 0.18 | 0.42 | 0.14 | 0.64 | 0.54 | 0.02 | 1.18 | 1.36 |
| 560 | 0.85 | 0.58 | 0.57 | 0.43 | 0.6 | 0.87 | 0.93 | 0.32 | 0.84 | 0.53 | 0.19 | 0.75 | 0.19 | 0.45 | 0.14 | 0.66 | 0.58 | 0.02 | 1.21 | 1.37 |
| 600 | 0.86 | | 0.57 | 0.43 | 0.6 | 0.89 | 0.94 | 0.34 | 0.87 | 0.54 | 0.2 | 0.77 | 0.19 | 0.49 | 0.15 | 0.68 | 0.61 | 0.02 | 1.24 | 1.39 |
| rate/m | 0.114 | 0.073 | 0.046 | 0.053 | 0.084 | 0.029 | 0.120 | 0.030 | 0.093 | 0.068 | 0.014 | 0.082 | 0.020 | 0.035 | 0.009 | 0.065 | 0.047 | 0.000 | 0.137 | 0.242 |

Average of the first four minutes note: enzyme E009 is an 80X dilution compared to the other enzymes
reaction conditions: estimated 0.1 u/1 ml reaction, 500 µg/ml substrate

FIGURE 7D

RAW DATA

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.08 | 0.06 | 0.06 | 0.07 | 0.06 | 0.09 | 0.09 | 0.08 | 0.19 | 0.09 | 0.06 | 0.09 | 0.05 | 0.08 | 0.02 | 0.02 | 0.1 | 0 | 0.09 | 0.09 |
| 40 | 0.07 | 0.05 | 0.06 | 0.06 | 0.06 | 0.09 | 0.1 | 0.09 | 0.2 | 0.09 | 0.08 | 0.09 | 0.07 | 0.08 | 0.03 | 0.03 | 0.1 | 0 | 0.09 | 0.1 |
| 80 | 0.07 | 0.05 | 0.06 | 0.06 | 0.06 | 0.09 | 0.1 | 0.09 | 0.21 | 0.1 | 0.08 | 0.09 | 0.08 | 0.08 | 0.05 | 0.04 | 0.11 | 0 | 0.1 | 0.1 |
| 120 | 0.08 | 0.06 | 0.06 | 0.07 | 0.06 | 0.09 | 0.1 | 0.09 | 0.22 | 0.1 | 0.09 | 0.09 | 0.08 | 0.09 | 0.06 | 0.05 | 0.11 | 0 | 0.1 | 0.11 |
| 160 | 0.08 | 0.06 | 0.06 | 0.07 | 0.06 | 0.09 | 0.1 | 0.09 | 0.23 | 0.11 | 0.09 | 0.09 | 0.09 | 0.09 | 0.07 | 0.05 | 0.11 | 0 | 0.11 | 0.11 |
| 200 | 0.08 | 0.06 | 0.06 | 0.07 | 0.06 | 0.09 | 0.1 | 0.09 | 0.24 | 0.11 | 0.09 | 0.1 | 0.09 | 0.09 | 0.08 | 0.06 | 0.11 | 0 | 0.11 | 0.12 |
| 240 | 0.09 | 0.06 | 0.07 | 0.07 | 0.07 | 0.09 | 0.1 | 0.09 | 0.26 | 0.12 | 0.1 | 0.1 | 0.09 | 0.09 | 0.09 | 0.06 | 0.11 | 0 | 0.11 | 0.12 |
| 280 | 0.09 | 0.06 | 0.07 | 0.07 | 0.07 | 0.09 | 0.1 | 0.1 | 0.27 | 0.12 | 0.1 | 0.1 | 0.09 | 0.09 | 0.09 | 0.07 | 0.12 | 0 | 0.12 | 0.13 |
| 320 | 0.1 | 0.07 | 0.07 | 0.08 | 0.07 | 0.09 | 0.1 | 0.1 | 0.28 | 0.13 | 0.1 | 0.1 | 0.09 | 0.1 | 0.09 | 0.07 | 0.12 | 0 | 0.12 | 0.14 |
| 360 | 0.1 | 0.07 | 0.07 | 0.08 | 0.07 | 0.1 | 0.1 | 0.1 | 0.3 | 0.13 | 0.1 | 0.11 | 0.09 | 0.1 | 0.09 | 0.08 | 0.12 | 0 | 0.12 | 0.15 |
| 400 | 0.11 | 0.07 | 0.08 | 0.08 | 0.08 | 0.1 | 0.1 | 0.1 | 0.31 | 0.13 | 0.11 | 0.11 | 0.1 | 0.1 | 0.09 | 0.08 | 0.12 | 0 | 0.12 | 0.16 |
| 440 | 0.11 | 0.07 | 0.08 | 0.08 | 0.08 | 0.1 | 0.1 | 0.1 | 0.33 | 0.14 | 0.11 | 0.11 | 0.1 | 0.11 | 0.1 | 0.08 | 0.12 | 0 | 0.13 | 0.17 |
| 480 | 0.11 | 0.07 | 0.08 | 0.08 | 0.08 | 0.1 | 0.11 | 0.1 | 0.34 | 0.14 | 0.11 | 0.12 | 0.1 | 0.11 | 0.1 | 0.09 | 0.12 | 0 | 0.13 | 0.18 |
| 520 | 0.11 | 0.07 | 0.08 | 0.08 | 0.08 | 0.1 | 0.11 | 0.11 | 0.36 | 0.15 | 0.12 | 0.12 | 0.1 | 0.11 | 0.1 | 0.09 | 0.13 | 0 | 0.13 | 0.18 |
| 560 | 0.12 | 0.07 | 0.09 | 0.08 | 0.08 | 0.1 | 0.11 | 0.11 | 0.37 | 0.15 | 0.12 | 0.12 | 0.11 | 0.11 | 0.1 | 0.09 | 0.13 | 0 | 0.14 | 0.19 |
| 600 | 0.12 |  | 0.09 | 0.08 | 0.09 | 0.1 | 0.11 | 0.11 | 0.37 | 0.15 | 0.12 | 0.12 | 0.11 | 0.11 | 0.1 | 0.1 | 0.13 | 0 | 0.14 | 0.2 |
| rate/min | 0.003 | 0.001 | 0.001 | 0.001 | 0.001 | 0.003 | 0.002 | 0.003 | 0.017 | 0.007 | 0.009 | 0.004 | 0.010 | 0.004 | 0.017 | 0.010 | 0.004 | 0.000 | 0.006 | 0.011 |

Average of the first four minut reaction conditions: estimated 0.1 u/1 ml reaction, 500 μg/ml substrate

FIGURE 7E

RAW DATA

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.01 | 0 | 0.05 | 0.01 | 0.01 | 0 | 0 | 0 | 0.03 | 0 | 0.03 | 0.02 | 0.02 | 0.03 | 0.03 | 0.03 | 0.02 | 0 | 0.02 | 0.02 |
| 40 | 0.01 | 0 | 0.05 | 0.02 | 0.01 | 0 | 0 | 0 | 0.03 | 0 | 0.01 | 0.01 | 0 | 0.02 | 0.01 | 0.03 | 0.02 | 0 | 0.02 | 0.02 |
| 80 | 0.01 | 0 | 0.05 | 0.02 | 0.01 | 0 | 0 | 0 | 0.03 | 0 | 0.02 | 0.01 | 0 | 0.01 | 0.01 | 0.03 | 0.02 | 0 | 0.02 | 0.02 |
| 120 | 0.01 | 0 | 0.06 | 0.02 | 0.01 | 0 | 0 | 0 | 0.03 | 0 | 0.02 | 0.01 | 0 | 0.02 | 0.01 | 0.03 | 0.02 | 0 | 0.02 | 0.02 |
| 160 | 0.01 | 0.01 | 0.06 | 0.02 | 0.01 | 0 | 0 | 0 | 0.03 | 0 | 0.02 | 0.01 | 0 | 0.01 | 0.01 | 0.03 | 0.02 | 0 | 0.02 | 0.02 |
| 200 | 0.02 | 0.01 | 0.06 | 0.02 | 0.01 | 0 | 0 | 0 | 0.03 | 0 | 0.02 | 0.01 | 0 | 0.02 | 0.01 | 0.03 | 0.02 | 0 | 0.02 | 0.02 |
| 240 | 0.02 | 0.01 | 0.06 | 0.02 | 0.01 | 0 | 0 | 0 | 0.03 | 0 | 0.02 | 0.01 | 0 | 0.02 | 0.01 | 0.03 | 0.02 | 0 | 0.02 | 0.02 |
| 280 | 0.02 | 0.01 | 0.06 | 0.02 | 0.01 | 0 | 0 | 0 | 0.04 | 0 | 0.02 | 0.01 | 0 | 0.01 | 0.01 | 0.03 | 0.02 | 0 | 0.02 | 0.02 |
| 320 | 0.02 | 0.01 | 0.06 | 0.02 | 0.01 | 0 | 0 | 0 | 0.04 | 0 | 0.02 | 0.01 | 0 | 0.02 | 0.01 | 0.03 | 0.02 | 0 | 0.02 | 0.03 |
| 360 | 0.02 | 0.01 | 0.07 | 0.02 | 0.01 | 0 | 0 | 0 | 0.04 | 0 | 0.02 | 0.01 | 0 | 0.02 | 0.02 | 0.03 | 0.02 | 0 | 0.02 | 0.03 |
| 400 | 0.02 | 0.01 | 0.07 | 0.02 | 0.01 | 0 | 0 | 0 | 0.04 | 0 | 0.02 | 0.01 | 0 | 0.02 | 0.02 | 0.03 | 0.02 | 0 | 0.03 | 0.03 |
| 440 | 0.03 | 0.01 | 0.07 | 0.02 | 0.01 | 0 | 0 | 0 | 0.04 | 0 | 0.02 | 0.01 | 0 | 0.01 | 0.01 | 0.03 | 0.02 | 0 | 0.03 | 0.03 |
| 480 | 0.03 | 0.01 | 0.07 | 0.02 | 0.01 | 0 | 0 | 0 | 0.04 | 0 | 0.02 | 0.01 | 0 | 0.02 | 0.02 | 0.03 | 0.02 | 0 | 0.03 | 0.03 |
| 520 | 0.03 | 0.01 | 0.07 | 0.02 | 0.01 | 0 | 0 | 0 | 0.04 | 0 | 0.02 | 0.01 | 0 | 0.02 | 0.02 | 0.03 | 0.02 | 0 | 0.03 | 0.03 |
| 560 | 0.03 | | 0.07 | 0.02 | 0.01 | 0 | 0 | 0 | 0.04 | 0.01 | 0.02 | 0.01 | 0 | 0.02 | 0.02 | 0.03 | 0.03 | 0 | 0.03 | 0.03 |
| 600 | 0.03 | | 0.07 | 0.02 | 0.01 | 0 | 0 | 0 | 0.04 | 0.01 | 0.02 | 0.01 | 0 | 0.02 | 0.02 | 0.03 | 0.03 | 0 | 0.03 | 0.03 |
| rate/min | 0.003 | 0.002 | 0.003 | 0.001 | 0.000 | 0.000 | 0.000 | 0.000 | 0.001 | 0.000 | -0.004 | -0.004 | -0.004 | -0.004 | -0.004 | 0.000 | 0.001 | 0.000 | 0.001 | 0.002 |

Average of the first four minutes note: enzyme E009 is an 80X dilution compared to the other enzymes
reaction conditions: estimated 0.1 u/1 ml reaction, 500 µg/ml substrate

FIGURE 7F

| Time | E001 | E002 | E003 | E004 | E005 | E006 | E007 | E008 | E009 | E010 | E011 | E012 | E013 | E014 | E015 | E016 | E017 | E018 | E019 | E020 |
|---|---|---|---|---|---|---|---|---|---|---|---|---|---|---|---|---|---|---|---|---|
| 0 | 0.03 | 0 | 0 | 0 | 0.03 | 0 | 0.02 | 0 | 0.03 | 0.01 | 0 | 0 | 0.01 | 0.03 | 0 | 0 | 0.05 | 0.04 | 0.03 | 0.04 |
| 40 | 0.03 | 0 | 0 | 0 | 0.03 | 0 | 0.01 | 0 | 0.03 | 0.01 | 0 | 0 | 0.01 | 0.03 | 0 | 0.02 | 0.05 | 0.05 | 0.03 | 0.04 |
| 80 | 0.03 | 0 | 0 | 0 | 0.03 | 0 | 0.02 | 0 | 0.03 | 0.01 | 0 | 0 | 0 | 0.03 | 0 | 0.03 | 0.05 | 0.05 | 0.03 | 0.04 |
| 120 | 0.03 | 0 | 0 | 0 | 0.03 | 0 | 0.01 | 0 | 0.03 | 0 | 0 | 0 | 0 | 0.03 | 0 | 0.04 | 0.05 | 0.05 | 0.03 | 0.03 |
| 160 | 0.03 | 0 | 0 | 0 | 0.03 | 0 | 0.01 | 0 | 0.03 | 0 | 0 | 0 | 0 | 0.03 | 0 | 0.05 | 0.05 | 0.05 | 0.03 | 0.03 |
| 200 | 0.02 | 0 | 0 | 0 | 0.03 | 0 | 0.01 | 0 | 0.03 | 0 | 0 | 0 | 0 | 0.03 | 0 | 0.07 | 0.05 | 0.05 | 0.03 | 0.03 |
| 240 | 0.03 | 0 | 0 | 0 | 0.04 | 0 | 0.01 | 0 | 0.04 | 0 | 0 | 0 | 0 | 0.03 | 0 | 0.07 | 0.05 | 0.05 | 0.02 | 0.03 |
| 280 | 0.03 | 0 | 0 | 0 | 0.04 | 0 | 0.01 | 0 | 0.04 | 0 | 0 | 0 | 0 | 0.03 | 0 | 0.08 | 0.05 | 0.05 | 0.02 | 0.03 |
| 320 | 0.03 | 0 | 0 | 0 | 0.04 | 0 | 0.01 | 0 | 0.04 | 0 | 0 | 0 | 0 | 0.03 | 0 | 0.09 | 0.05 | 0.05 | 0.02 | 0.03 |
| 360 | 0.03 | 0 | 0 | 0 | 0.04 | 0 | 0.01 | 0 | 0.04 | 0 | 0 | 0 | 0 | 0.03 | 0 | 0.09 | 0.05 | 0.05 | 0.02 | 0.03 |
| 400 | 0.03 | 0 | 0 | 0 | 0.05 | 0 | 0 | 0 | 0.04 | 0 | 0 | 0 | 0 | 0.03 | 0 | 0.1 | 0.05 | 0.05 | 0.02 | 0.03 |
| 440 | 0.03 | 0 | 0 | 0 | 0.05 | 0 | 0 | 0 | 0.04 | 0 | 0 | 0 | 0 | 0.02 | 0 | 0.1 | 0.06 | 0.05 | 0.02 | 0.03 |
| 480 | 0.03 | 0 | 0 | 0 | 0.05 | 0 | 0 | 0 | 0.04 | 0 | 0 | 0 | 0 | 0.03 | 0 | 0.11 | 0.06 | 0.06 | 0.02 | 0.03 |
| 520 | 0.03 | 0 | 0 | 0 | 0.06 | 0 | 0 | 0 | 0.04 | 0 | 0 | 0 | 0 | 0.03 | 0 | 0.11 | 0.06 | 0.06 | 0.02 | 0.02 |
| 560 | 0.03 | | 0 | 0 | 0.06 | 0 | 0 | 0 | 0.04 | 0 | 0 | 0 | 0 | 0.02 | 0 | 0.11 | 0.06 | 0.06 | 0.02 | 0.02 |
| 600 | 0.03 | | 0 | 0 | 0.07 | 0 | 0 | 0 | 0.04 | 0 | 0 | 0 | 0 | 0.03 | 0 | 0.11 | 0.06 | 0.06 | 0.02 | 0.02 |
| rate/min | -0.001 | 0.000 | 0.000 | 0.000 | 0.002 | 0.000 | -0.002 | 0.000 | 0.002 | -0.002 | -0.001 | 0.000 | -0.001 | -0.001 | -0.001 | 0.018 | 0.000 | 0.001 | -0.002 | -0.002 |

Average of the first four minutes

Note: reaction conditions: estimated 0.1 u/1 ml reaction, 500 μg/ml substrate

FIGURE 7G

| TG Enz | 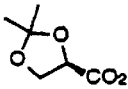 1R | 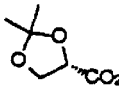 1S | 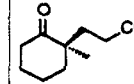 2R | 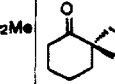 2S | 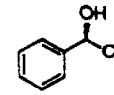 3R | 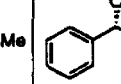 3S |
|---|---|---|---|---|---|---|
| E01 | - | - | - | - | - | - |
| E02 | 28 | 330 | 28 | 120 | 480 | 480 |
| E03 | 3 | 80 | 3 | 13 | 180 | 180 |
| E04 | 240 | 240 | 120 | 330 | NH | NH |
| E05 | 25 | 330 | 25 | 100 | o/n | o/n |
| E06 | 22 | 330 | 22 | 100 | o/n | o/n |
| E07 | 20 | 330 | 20 | 100 | o/n | o/n |
| E08 | 180 | 240 | 170 | >330 | NH | 480 |
| E09 | 240 | 240 | 240 | >330 | NH | 480 |
| E10 | 180 | 200 | 170 | o/n | NH | 480 |
| E11 | 240 | 240 | 240 | >330 | NH | 2d |
| E12 | 9 | 180 | 100 | 240 | - | - |
| E13 | 90 | 210 | 90 | o/n | NH | NH |
| E14 | 90 | 210 | 90 | o/n | NH | 2d |
| E15 | 90 | 210 | 90 | o/n | NH | 2d |
| E16 | 120 | 240 | 100 | o/n | NH | NH |
| E17 | 140 | 210 | 90 | >330 | NH | NH |
| E18 | - | - | - | - | - | - |
| E19 | 70 | >330 | 70 | 220 | 480 | 480 |
| E20 | 70 | >330 | 70 | 220 | 480 | 480 |
| Ctrl | 1440 | 1440 | not observed after 3 days | not observed after 3 days | not observed after 3 days | not observed after 3 days |
FIGURE 8B

FIGURE 8C

| TG<br>Enz | ![4R structure] CO2Me<br>4R | ![4S structure] CO2Me<br>4S | ![5R structure]<br>5R | ![5S structure]<br>5S | ![6R structure] Cl CO2Me<br>6R | ![6S structure] Cl CO2Me<br>6S |
|---|---|---|---|---|---|---|
| E01 | NH | NH | 20 | 20 | 20 | 5 |
| E02 | NH | NH | 20 | 20 | 20 | 5 |
| E03 | 30 | 30 | 2 | 4 | 4 | 2 |
| E04 | NH | NH | 20 | 20 | 20 | 4 |
| E05 | NH | NH | 15 | 30 | 40 | 20 |
| E06 | NH | NH | 15 | 30 | 40 | 20 |
| E07 | NH | NH | 15 | 30 | 40 | 20 |
| E08 | NH | NH | 15 | 18 | 15 | 5 |
| E09 | NH | NH | 20 | 20 | 15 | 4 |
| E10 | NH | NH | 20 | 20 | 15 | 8 |
| E11 | NH | NH | 20 | 20 | 20 | 10 |
| E12 | NH | NH | 4 | 10 | 2 | 2 |
| E13 | NH | NH | 15 | 15 | 25 | 6 |
| E14 | NH | NH | 20 | 20 | 30 | 15 |
| E15 | NH | NH | 20 | 20 | 25 | 4 |
| E16 | NH | NH | 30 | 30 | - | 20 |
| E17 | NH | NH | 15 | 15 | - | 15 |
| E18 | NH | NH | 25 | 25 | - | - |
| E19 | NH | NH | 20 | 20 | 30 | 15 |
| E20 | NH | NH | 20 | 20 | 40 | 20 |
| Ctrl | not observed after 3 days | not observed after 3 days | not observed after 3 days | not observed after 3 days | not observed after 3 days | not observed after 3 days |

| TG Enz | 7R (Ph-N-pyrrolidine-CO2Et) | 7S (Ph-N-pyrrolidine-CO2Et) | 8R (OH-CH-CO2Me) | 8S (OH-CH-CO2Me) | 9R (HO-CH-CO2Me) | 9S (HO-CH-CO2Me) |
|---|---|---|---|---|---|---|
| E01 | - | - | 90 | 90 | NH | NH |
| E02 | - | - | 90 | 240 | NH | NH |
| E03 | - | - | 3 | 6 | 1440 | o/n |
| E04 | - | - | 1080 | 120 | NH | NH |
| E05 | - | - | 90 | 240 | NH | NH |
| E06 | - | - | 90 | 240 | NH | NH |
| E07 | - | - | 90 | 240 | NH | NH |
| E08 | - | - | 240 | 90 | NH | NH |
| E09 | - | - | 240 | 90 | NH | NH |
| E10 | - | - | 240 | 90 | NH | NH |
| E11 | - | - | 240 | 90 | NH | NH |
| E12 | - | - | 60 | 60 | NH | NH |
| E13 | - | - | >1080 | 90 | NH | NH |
| E14 | - | - | 300 | 120 | NH | NH |
| E15 | - | - | >1080 | 120 | NH | NH |
| E16 | - | - | >1080 | >1080 | NH | NH |
| E17 | - | - | - | - | NH | NH |
| E18 | - | - | 90 | 90 | NH | NH |
| E19 | - | - | 90 | 90 | NH | NH |
| E20 | - | - | 90 | 90 | NH | NH |
| Ctrl | - | - | >1080 | >1080 | >1080 | >1080 |

FIGURE 8D

| Substrate | E001 | E002 | E003 | E004 | E005 | E006 | E007 | E008 | E009 | E010 | E011 | E012 | E013 | E014 | E015 | E016 | E017 | E019 | E020 |
|---|---|---|---|---|---|---|---|---|---|---|---|---|---|---|---|---|---|---|---|
| Arg-pNA | 0.223 | 0.082 | 0.656 | 0.38 | 0.187 | 0.2 | 0.072 | 0.063 | 0.115 | 0.05 | 0.109 | 0.26 | 0.056 | 0.136 | 0.88 | 0.186 | 0.172 | 0.054 | 0.61 |
| Lys-pNA | 0.25 | 0.062 | 0.574 | 0.364 | 0.186 | 0.183 | 0.051 | 0.058 | 0.093 | 0.026 | 0.086 | 0.026 | 0.025 | 0.101 | 0.815 | 0.146 | 0 | 0.04 | 0.555 |
| Glu-γ-pNA | 0.011 | 0.012 | 0.011 | 0.034 | 0.015 | 0.046 | 0.151 | 0.002 | 0.012 | 0.021 | 0.019 | 0.024 | 0.015 | 0.063 | 0.015 | 0.019 | 0.061 | 0.02 | 0.016 |
| Leu-pNA | 0.21 | 0.179 | 0.219 | 0.261 | 0.12 | 0.123 | 0.068 | 0.025 | 0.05 | 0.03 | 0.042 | 0.555 | 0.024 | 0.105 | 0.51 | 0.128 | 0.179 | 0.046 | 0.361 |
| Met-pNA | 0.137 | 0.197 | 0.168 | 0.147 | 0.08 | 0.087 | 0.085 | 0.046 | 0.075 | 0.066 | 0.066 | 0.049 | 0.048 | 0.116 | 0.317 | 0.097 | 0.206 | 0.052 | 0.185 |
| Phe-pNA | 0.192 | 0.496 | 0.168 | 0.494 | 0.153 | 0.15 | 0.18 | 0.315 | 0.473 | 0.495 | 0.125 | 0.322 | 0.495 | 0.489 | 0.4 | 0.205 | 0.812 | 0.118 | 0.214 |
| Pro-pNA | 0.018 | 0.024 | 0.014 | 0.048 | 0.015 | 0.016 | 0.017 | 0.007 | 0.011 | 0.003 | 0.007 | 0.017 | 0.026 | 0.06 | 0.024 | 0.029 | 0.053 | 0.017 | 0.021 |
| Arg-Pro-pNA | -0.101 | -0.067 | -0.033 | -0.063 | -0.102 | -0.121 | -0.095 | -0.046 | -0.041 | -0.098 | -0.076 | -0.002 | -0.065 | -0.054 | -0.078 | -0.084 | -0.134 | -0.065 | -0.065 |
| Gly-pNA | 0.067 | 0.232 | 0.237 | 0.111 | 0.094 | 0.086 | 0.08 | 0.026 | 0.035 | 0.027 | 0.029 | 0.031 | 0.02 | 0.069 | 0.328 | 0.1 | 0.08 | 0.057 | 0.188 |
| Val-pNA | 0.007 | 0.022 | 0.011 | 0.041 | 0.023 | 0.017 | 0.008 | 0.018 | 0.01 | 0.028 | 0.017 | 0.024 | 0.006 | 0.065 | 0.016 | 0.027 | 0.055 | 0.02 | 0.017 |
| Ala-pNA | 0.318 | 0.172 | 0.789 | 0.828 | 0.526 | 0.499 | 0.129 | 0.183 | 0.285 | 0.082 | 0.239 | 0.038 | 0.076 | 0.234 | 0.919 | 0.41 | 0.407 | 0.114 | 0.886 |
| Ala-Ala-pNA | 0.333 | 0.021 | 0.488 | 0.486 | 0.111 | 0.102 | 0.017 | 0.009 | 0.023 | 0.027 | 0.009 | 0.029 | 0.014 | 0.067 | 0.979 | 0.073 | 0.069 | 0.008 | 0.832 |
| Ala-Ala-Ala-pNA | 0.218 | 0.009 | 0.29 | 0.304 | 0.055 | 0.059 | 0.024 | 0.008 | 0.018 | 0.041 | 0.009 | 0.033 | 0.012 | 0.062 | 0.92 | 0.025 | 0.076 | 0.018 | 0.639 |
| Ala-Ala-Val-Ala-pNA | 0.021 | 0.018 | 0.008 | 0.037 | 0.022 | 0.026 | 0.038 | 0.001 | 0.002 | 0.026 | 0.008 | 0.019 | 0.007 | 0.054 | 0.006 | 0.02 | 0.034 | 0.011 | 0.034 |
| Glu-γ-3-carboxy-4-NA | 0.006 | 0.011 | 0.018 | 0.046 | 0.01 | 0.044 | 0.17 | 0.004 | 0.007 | 0.046 | 0.009 | 0.028 | 0.013 | 0.069 | 0.018 | 0.02 | 0.056 | 0.014 | 0.012 |
| N-Cbz-Phe-pNA | -0.004 | 0.196 | 0.197 | 0.254 | 0.226 | 0.185 | 0.134 | 0.157 | 0.166 | 0.175 | 0.245 | 0.305 | 0.237 | 0.234 | 0.172 | 0.315 | 0.159 | 0.389 | 0.258 |
| N-Cbz-Gly-Gly-Leu-pNA | 0.064 | 0.021 | 0.012 | 0.151 | 0.022 | 0.014 | 0.016 | 0.001 | 0.007 | 0.021 | 0.006 | 0.375 | 0.027 | 0.057 | 0.009 | 0.031 | 0.024 | 0.029 | 0.01 |
| N-Cbz-Ala-Ala-Leu-pNA | 0.058 | 0.008 | -0.003 | 0.121 | 0.28 | -0.03 | -0.047 | 0.061 | -0.011 | 0.061 | -0.081 | 0.209 | -0.014 | -0.01 | -0.046 | 0.045 | 0.047 | 0.016 | -0.043 |
| Nα-Cbz-Arg-pNA | 0.045 | 0.009 | 0.008 | 0.029 | 0.01 | 0.012 | 0.023 | 0.002 | 0.004 | 0.021 | 0.006 | 0.019 | 0 | 0.055 | 0.012 | 0.009 | 0.044 | 0.011 | 0.01 |
| N-Cbz-Val-Gly-Arg-pNA | 0.02 | 0.029 | 0.01 | 0.048 | 0.022 | 0.023 | 0.018 | 0.01 | 0.032 | 0.033 | 0.018 | 0.102 | 0.018 | 0.066 | 0.026 | 0.016 | 0.059 | 0.016 | 0.029 |
| N-Cbz-Gly-Pro-Citrulline-pNA | 0.036 | 0.017 | 0.003 | 0.054 | 0.012 | 0.02 | 0.017 | 0.011 | 0.009 | 0.021 | 0.008 | 0.027 | 0.004 | 0.053 | 0.018 | -0.011 | 0.046 | 0 | -0.003 |
| N-t-Boc-Ala-Ala-pNA | 0.023 | 0.019 | 0.009 | 0.051 | 0.016 | 0.021 | 0.031 | -0.001 | 0.011 | 0.015 | 0.005 | 0.046 | 0.021 | 0.05 | 0.02 | 0.02 | 0.064 | 0.012 | -0.016 |
| N-Acetyl-DL-Phe-pNA | 0.04 | 0.02 | -0.005 | 0.028 | 0.014 | 0.005 | -0.017 | 0.001 | -0.01 | 0.024 | 0.008 | 0.023 | 0.008 | 0.062 | -0.008 | -0.008 | 0.03 | 0.001 | 0.007 |
| N-Acetyl-L-Leu-pNA | 0.053 | 0.01 | 0.02 | 0.035 | 0.018 | 0.022 | 0.017 | 0.004 | 0.001 | 0.021 | 0.011 | 0.112 | 0.012 | 0.04 | 0.015 | 0.023 | 0.059 | 0.021 | 0.036 |
| N-Acetyl-L-Ala-pNA | 0.013 | 0.016 | 0.011 | 0.039 | 0.026 | 0.013 | 0.017 | -0.022 | 0.007 | 0.01 | -0.005 | 0.012 | 0.008 | 0.038 | 0.005 | 0.009 | 0.036 | 0.008 | 0.024 |
| N-t-Boc-L-Phe-pNP ester | 0.654 | 0.684 | 0.658 | 0.873 | 0.912 | 0.774 | 0.701 | 0.783 | 0.866 | 0.73 | 0.775 | 0.78 | 0.72 | 0.688 | 0.771 | 0.755 | 0.761 | 0.754 | 0.715 |
| N-t-Boc-D-Phe-pNP ester | 0.819 | 0.716 | 0.687 | 0.85 | 0.909 | 0.756 | 0.783 | 0.694 | 0.823 | 0.695 | 0.798 | 0.768 | 0.82 | 0.691 | 0.72 | 0.78 | 0.739 | 0.78 | 0.73 |
| p-NP-p'-guanido benzoate | 0.713 | 0.626 | 0.706 | 0.816 | 0.824 | 0.812 | 0.82 | 0.781 | 0.846 | 0.849 | 0.743 | 0.825 | 0.801 | 0.84 | 0.771 | 0.778 | 0.75 | 0.771 | 0.75 |
| Nα-t-Boc-D-Glu-pNP ester | -0.07 | -0.149 | -0.135 | 0.086 | -0.004 | -0.034 | -0.228 | -0.083 | 0.012 | -0.073 | -0.116 | 0.047 | -0.076 | 0.012 | -0.132 | -0.042 | -0.097 | -0.142 | -0.112 |
| Nα-t-Boc-L-Glu-pNP ester | -0.118 | -0.127 | -0.234 | -0.055 | -0.002 | -0.132 | -0.182 | -0.157 | -0.062 | -0.097 | -0.11 | 0.024 | -0.019 | -0.03 | -0.071 | -0.073 | -0.109 | -0.146 | -0.101 |

FIGURE 9

STABLE BIOCATALYSTS FOR ESTER HYDROLYSIS

This application is a continuation-in-part of U.S. Ser. No. 08/827,810 filed Apr. 11, 1997 (abandoned) which is a continuation-in-part of U.S. Ser. No. 08/781,802 filed Jan. 10, 1997 (now U.S. Pat. No. 5,969,121) which is a continuation-in-part of U.S. Ser. No. 08/694,078 filed Aug. 8, 1996 (pending) which claims priority to U.S. Ser. No. 60/019,580 filed Jun. 12, 1996 and U.S. Ser. No. 60/009,704 filed Jan. 11, 1996.

STATEMENT OF GOVERNMENT RIGHTS

The work disclosed in this application was supported in part by Grant Number: NCI 1-R43-CA63876-01 from the NIH-SBIR to ThermoGen Inc., therefore, the U.S. Government may have some rights in the present invention.

FIELD OF THE INVENTION

The instant disclosure is directed to the field of isolated stable biocatalysts that are suitable for enzymatic application in commercial pharmaceutical and chemical synthesis, DNA vectors for the production of recombinant ester hydrolyzing proteins, host cells transformed by such vectors, and recombinant ester hydrolyzing proteins produced by such vectors and transformed cells.

BACKGROUND OF THE INVENTION

Esterases and Lipases.

Esterases and lipases catalyze the hydrolysis of ester bonds to produce alcohols and carboxylic acids as shown below.

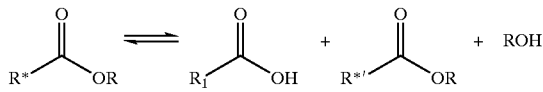

Esterases and lipases can be characterized by different substrate specificities, R group or chain length preference, and unique inhibitors (1, 2). The many esterases and lipases range from hydrolases such as the broad carboxyl esterases which preferentially hydrolyze esters with long carbon chain R groups, to choline esterases, and to acetyl esterases which act on very specific substrates. In many cases, these hydrolases are also known to show stereo- and regio-selective preferences resulting from the chiral nature inherent in protein active sites. This preferential hydrolytic activity make them useful for reactions requiring different regioselectivity and stereoselectivity or for kinetic resolution methods on racemic mixtures. For enzymes that demonstrate stereoselectivity, if R* is a racemic mixture, the product of enzyme catalyzed hydrolysis, $R_1$, would be the most rapidly hydrolyzed stereoisomer while the remaining ester designated R*' would be the enriched antipode mixed with any remaining $R_1$. The products can then be separated by chromatography to provide pure $R_1$. The availability of a large pool of esterases and lipases with varying specificities would be useful for screening the enzymes for specific reactions, and developing optimal protocols for specific chemical synthesis. The expedience of this process would facilitate the production scale-up of many useful pharmaceutical products.

In aqueous solvent systems, esterases and lipases carry out their natural reactions: the hydrolysis of ester bonds. In vitro, these enzymes can be used to carry out reactions on a wide variety of substrates, including esters containing cyclic and acyclic alcohols, mono- and di-esters, and lactams (3). By carrying out the reactions in organic solvents (4, 5) where water is excluded, the reactions of esterases and lipases can be reversed. These enzymes can catalyze esterification or acylation reactions to form ester bonds (3, 6, 7). This process can also be used in the transesterification of esters and in ring closure or opening reactions.

Optically pure chiral pharmaceuticals.

Currently, the majority of synthetic chiral pharmaceuticals are sold as racemic mixtures. However, due to advances in the synthesis of optically pure (single isomer) chiral compounds, this situation is changing (7). Racemic drugs often contain one isomer which is therapeutically active and the other enantiomer which is at best inactive and at worst a major cause of potentially harmful side effects. The non-useful isomer in a racemic drug is increasingly being viewed as a contaminant. Indeed, the FDA's Policy Statement for the Development of New Drugs recommends "that the pharmacokinetic profile of each isomer should be characterized in animals and later compared to the clinical pharmacokinetic profile obtained in Phase I" drug testing (8). Thus, pharmaceutical companies will need to develop a synthesis or separation route to produce each pure isomer of each new synthetic drug.

Enzymatic synthesis of optically pure pharmaceuticals and intermediates.

Since it is often very difficult to generate optically pure solutions of certain chiral molecules by classical chemical synthesis, new enzymatic biocatalysts will play a major role in this endeavor. In some cases, enzymes may be able to replace hazardous chemical synthesis procedures with more environmentally-friendly biological synthesis processes. It can also be much more cost effective to produce a pharmaceutical intermediate enzymatically if an enzyme can eliminate several chemical protection and deprotection steps at once (7). All six major classes of enzymes (oxidoreductases, transferases, hydrolases, lyases, isomerases, and ligases) have been useful in the synthesis of optically pure compounds as described in several detailed reviews (3, 7). The hydrolases have proven to be the most useful group of enzymes, due to the abundance of hydrolases, the information about them, their independence from cofactors, and the wide variety of substrates they can accept.

A survey of the literature shows many examples of mesophilic hydrolases particularly esterases and lipases used in chemical synthesis or chiral resolution. These include esterases from pig (9, 10) and horse (3) livers and a wide variety of lipases from Aspergillus sp. (11) Candida sp. (12–16), Pseudomonas sp., (17–19), Rhizopus sp. (20) and others. Several lipases have been used in the synthesis of propranolol (7), a beta-adrenergic blocking agent used in the treatment of angina and hypertension. Ibuprofen, a nonstearoidal antiinflammatory agent has been synthesized via stereo selective hydrolysis of its methyl ester using carboxyesterase (7). While these enzymes have begun to demonstrate the utility of biocatalysts in chemical synthesis, there is still a profound need for a wider variety of esterases and lipases which have varying substrate specificities, regioselectivities, and steroselectivities. In addition, since these enzymes need to be employed in a large-scale industrial setting, there is a need for them to have increased stability, higher thermotolerance and a longer "shelf life".

Thermostable enzymes.

Thermophilic organisms have already provided a rich source of useful proteins that catalyze reactions at higher temperatures and are stable for much longer periods of time (21, 22). One example is the DNA Polymerase I from *Thermus aquaticus* and its use in polymerase chain reaction (PCR) (23, 24). Thermophilic enzymes have become the most commercially successful enzymes in industry because of their long-term stability and ease of use. The most successful enzyme to date, alpha-amylase, is used in corn processing and comes from the moderate thermophile *B. stearothermophilus* (25). Another commercially successful industrial enzyme is subtilisin, a serine protease also found in various strains of Bacillus, has been widely used in laundry detergents and other cleaning solutions.

The commercial success of these enzymes can be attributed to their ease of use. In addition to functioning at high temperatures, thermostable enzymes generally posses an increased shelf life which markedly improves handling conditions, especially by those not trained in biochemistry to work with the specific range of conditions used for mesophilic enzymes. If enzymes are to play a significant role in large scale processing of chemicals, they must be able to endure the harsh conditions associated with these processes. Thermostable enzymes are easier to handle, last longer, and given the proper immobilization support should be reusable for multiple applications Finally, the hydrophobic and electrostatic forces that allow these enzymes to survive high temperatures also allow them to generally function better in organic solvents (26–31). While most enzymes lose a significant portion of their activity in organic solvents, thermostable enzymes may prove more tolerant to the denaturing conditions of many organic solvents. Highly thermostable esterases and lipases are necessary to expand the application of these biocatalysts in large scale industrial reactions.

Thermostable esterases and lipases.

To date, only one esterase and a few lipases have been reported with moderately thermostable characteristics. Tulin et al. (32) reported a *Bacillus stearothermophilus* esterase cloned into *Bacillus brevis* which was stable up to 10 minutes at 70° C. Sugihara et al.(33, 34) have isolated novel thermostable lipases from two microorganisms, A Bacillus soil isolate and a *Pseudomonas cepacia* soil isolate. The former lipase is stable up to 30 minutes at 65° C. but rapidly inactivated above this temperature. The lipase from *Pseudomonas cepacia* was stable when heated for 30 minutes at 75° C. and pH 6.5 but had only 10% of its activity when assayed at this temperature. A thermoalcalophilic lipase (35) was identified from a Bacillus species MC7 isolated by continuous culture and had a half-life of 3 hours at 70° C. Finally, Sigurgisladottir et al. (6) have reported the isolation of one Thermus and two Bacillus strains which posses lipases active on olive oil up to 80° C., although there was no report on enzyme stability in this study.

These enzymes offer only limited variations in substrate specificities and only moderate thermostability profiles. They do not address the need for different substrate specificities, the need to produce large scale quantities which can be economically commercialized, and many of them have only limited overall stability. In this patent application we have identified a series of esterases and lipases which offer a range of substrate specificities (including regioselectivity, stereoselectivity), enhanced enzyme stability, and can be produced in large quantities for commercial use.

SUMMARY OF THE INVENTION

The instant invention provides for the isolation and characterization of commercial grade enzyme preparations characterized by esterase activity, and corresponding to the data as disclosed in Table 1. In a preferred embodiment, the instant invention provides for the isolation, and characterization of specifically purified esterase which is characterized by esterase activity, and corresponding to the data as disclosed in Table 1. In a most preferred embodiment, the instant invention provides for proteins generated by recombinant DNA technology which have esterase activity. The instant invention encompasses lambda phage expression vectors which contain an insert that can be used for the production of recombinant ester hydrolyzing proteins of the instant invention, from a transformed cell host. The insert contained on the lambda phage expression vector may be used in, for example, a phage-plasmid hybrid expression vector or other suitable expression vector such as, but not limited to, plasmids, YACs, cosmids, phagemids, etc. In a preferred embodiment, a lambda expression vector is one of the vectors named in Table 7, or one which contains an insert which encodes for a substantially similar recombinant protein. The instant disclosure also provides for vectors which are capable of transforming a host cell, and which encode for recombinant ester hydrolyzing proteins, the transformed host cells, and the recombinant ester hydrolyzing protein. Appropriate host cells include but are not limited to: *E. coli*, Bacilli, Thermus sp., etc. The recombinant ester hydrolyzing protein encoded by the vector is capable of hydrolyzing 5-bromo-4-chloro-3-indolyl-acetate (X-acetate). The recombinant ester hydrolyzing protein produced by the vector can be further characterized by a half-life stability comparable to that of a corresponding protein purified from the isolates. The recombinant ester hydrolyzing protein is also characterized by the ability to remain stable at temperatures comparable to, or better than that of the corresponding protein from the original isolates. Recombinant ester hydrolyzing protein encoded for by the vector can also be characterized by certain substrate specificities as discussed below, which are comparable to those of the corresponding purified protein from the isolates. In a preferred embodiment the vector is a vector named in Table 7 or 8, or one which contains an insert which encodes for a substantially similar recombinant protein. In a preferred embodiment of the instant invention, a vector which encodes specific recombinant ester hydrolyzing protein is one of the vectors named and listed in Table 8.

The instant invention is directed to the novel nucleic acids, and the proteins encoded for therein, isolated from the expression vectors of the present invention. In particular, the present invention is directed towards the nucleic acid sequence for DNA insert of said vectors, and the the protein amino acid sequence(s) expressible therefrom.

BRIEF DESCRIPTION OF THE DRAWINGS

FIG. 1 depicts a sample activity profile which characterizes and enzyme of the instant disclosure. Graph 1 depicts the Temperature Profile of the enzyme plotting relative esterase activity versus temperature. Graph 2 depicts the Residual Esterase Activity of the listed enzyme plotting relative remaining activity versus time in hours, at 25° C., 40° C., and 65° C. Graph 3 depicts the pH profile for the listed enzyme plotting Relative Esterase Activity versus pH. Data for enzymes are summarized in Tables 1, 2 and 10.

FIG. 2. Kinetic analysis of E100. The enzyme displays normal Michaelis kinetics yielding linear data with both a) Lineweaver-Burke and b) Eadie-Hofstee analysis to give a $Km=7.2\times10^{-5}M$ and $Vmax=1.8\times10^{-5}$ $Mmin^{-1}$ using p-NP as the substrate.

FIGS. 3a–3b. Temperature and pH profiles of E100. a) Temperature profile of E100. Plot of E100 catalyzed hydrolysis of p-nitrophenyl proprionate as a function of temperature. Enzyme activity was determined upon exposure to different temperatures. Initial rates of nitrophenyl-proprionate hydrolysis were determined in 50 mM borate Buffer pH 8.5 equilibrated to the desired temperature to which 0.25 mM substrate dissolved in $CH_3CN$ was added followed by enzyme. Rates were determined by monitoring the change in absorbance at 405 nm and corrected for the spontaneous hydrolysis of substrate substituting bovine serum albumin for enzyme. b) pH profile of E100. The effect of pH on the hydrolysis of p-nitrophenyl proprionate catalyzed by E100. The pH profile of the enzyme was determined by preparing different buffers appropriate for the desired pH's at 10 mM concentration. Reactions were performed by addition of the substrate (0.25 mM) dissolved in CH3CN to the buffer solution followed by the enzyme. Reactions were incubated for 5 minutes after which the reaction was terminated by addition of 0.1 mM PMSF dissolved in $CH_3CN$. The pH of the mixture is adjusted to 8.5 by addition of 0.1 M Tris-HCl. Absorbances are recorded at 405 nm and concentrations calculated based on the $\epsilon=17$ $mM^{-1}$ $cm^{-1}$ for the product nitrophenol. Formation of products is corrected for the spontaneous hydrolysis of the substrate.

FIGS. 5A–5B. Substrates used to screen stereo- and regioselectivity. Esterases are versatile biocatalysts in the sense that stereo- and regio-selectivity can be mediated by substrate structure which fall into four types. The compounds listed represent a range of different structural features encountered in common substrates with potential importance for the chemical intermediate industry. Several of the substrates are commercially available in entantio- or diastereomerically pure form and can be used in qualitative screening procedures described in the text. Four classes of substrates most commonly associated with hydrolytic biocatalysts for chiral centers resolution are considered. A) Type I substrates position the desired product on the carboxylic acid side of the product, while Type II compounds the alcohol contains the requisite functionality. B) Type III and Type IV substrates can be considered subsets of Types I and II, but their unique properties dictate that they be classified separately. Type III molecules require that the enzyme differentiates a prochiral substrate while Type IV compounds are meso structures. These last two substrate types demonstrate the synthetic importance of biocatalyst based resolution methods as these types of compounds are very difficult to selectively operate upon by other chemical means.

FIGS. 6A–6U. Nucleic acid sequence and translated protein amino acid sequence. The isolation and cloning of the genes encoding for the enzymes of the instant invention will result in DNA segments in which an open reading frame (ORF) may be found which corresponds to translated protein amino acid sequence. Alternative start codons are recognized in the art, however the encoded protein will comprise at minimum a core protein ORF. FIG. 6A is an isolated nucleic acid sequence, and translated amino acid sequence which correspond to E001 (SEQ ID NO.:1 and SEQ ID NO.:2) enzyme ORF, alternative start codons are underlined. FIG. 6B is an isolated nucleic acid sequence, and translated amino acid sequence which correspond to E009 (SEQ ID NO.:3 and SEQ ID NO.:4) enzyme ORF, alternative start codons are underlined. FIG. 6C is an isolated nucleic acid sequence, and translated amino acid sequence which correspond to E011 (SEQ ID NO.:5 and SEQ ID NO.:6) enzyme ORF, alternative start codons are underlined. FIG. 6D is an isolated nucleic acid sequence, and translated amino acid sequence which correspond to E101 (SEQ ID NO.:7 and SEQ ID NO.:8) enzyme ORF, alternative start codons are underlined. FIG. 6E is an isolated nucleic acid sequence, and translated amino acid sequence which corresponds to E019 (SEQ ID NO.:9 and SEQ ID NO.:10) enzyme ORF, alternative start codons are underlined. FIG. 6F is an isolated nucleic acid sequence, and translated amino acid sequence which corresponds to E005 (SEQ ID NO.:11 and SEQ ID NO.:12) enzyme ORF, alternative start codons are underlined. FIG. 6G is the cloned isolated nucleic acid sequence which contains the E004 (SEQ ID NO.:13 and SEQ ID NO.:14) ORF, alternative start codons are underlined. FIG. 6H is the cloned isolated nucleic acid sequence which contains the E006 (SEQ ID NO.:15 and SEQ ID NO.:16) ORF, alternative start codons are underlined. FIG. 6I is the cloned isolated nucleic acid sequence which contains the E008 (SEQ ID NO.:17 and SEQ ID NO.:18) ORF, alternative start codons are underlined. FIG. 6J is the cloned isolated nucleic acid sequence which contains the E010 (SEQ ID NO.:19 and SEQ ID NO.:20) ORF, alternative start codons are underlined. FIG. 6K is the cloned isolated nucleic acid sequence which contains the E013 (SEQ ID NO.:21 and SEQ ID NO.:22) ORF, alternative start codons are underlined. FIG. 6L is the cloned isolated nucleic acid sequence which contains the E015 (SEQ ID NO.:23 and SEQ ID NO.:24) ORF, alternative start codons are underlined. FIG. 6M is the cloned isolated nucleic acid sequence which contains the E016 (SEQ ID NO.:25 and SEQ ID NO.:26) ORF, alternative start codons are underlined. FIG. 6N is the cloned isolated nucleic acid sequence which contains the E017 (SEQ ID NO.:27 and 28) ORF, alternative start codons are underlined. FIG. 6O is the cloned isolated nucleic acid sequence which contains the E020 (SEQ ID NO.:29 and SEQ ID NO.:30) ORF, alternative start codons are underlined. FIG. 6P is the cloned isolated nucleic acid sequence which contains the E027 (SEQ ID NO.:31 and SEQ ID NO.:32) ORF, alternative start codons are underlined. FIGS. 6Q (SEQ ID NO.:33), 6R (SEQ ID NO.:34), 6S (SEQ ID NO.:35), 6T (SEQ ID NO.:36) and 6U (SEQ ID NO.:37) are partial sequences.

FIGS. 7A–G. Substrate Chain Length Specificity FIG. 7A is a graph of data from a colorometric esterase assay performed on the substrate: bis-p-nitrophenyl-Carbonate. FIG. 7B is data from a colorometric esterase assay performed on the substrate: p-nitrophenyl-Acetate. FIG. 7C the substrate: bis-p-nitrophenyl-Propionate. FIG. 7D the substrate: bis-p-nitrophenyl-Butyrate. FIG. 7E the substrate: bis-p-nitrophenyl-Caproate. Figure the substrate: bis-p-nitrophenyl-Caprylate. FIG. 7G the substrate: bis-p-nitrophenyl-Laurate. Note that E009 is an 80× dilution compared to the other enzymes in b, c, d, and f.

FIGS. 8A–D. Entantiomer Substrate Specificity FIG. 8A summarizes the results of colorometric esterase activity assays for entantiomer specificity. FIGS. 8B–D reports quantitative colorometric assay data in terms of minutes required for detectable color change.

FIG. 9. Enzyme Activity against para-nitroanilide compounds Table lists the results of enzyme activity assay against various substrates. Data is reported as normalized OD readings.

DETAILED DESCRIPTION OF THE INVENTION

Figure 1B:
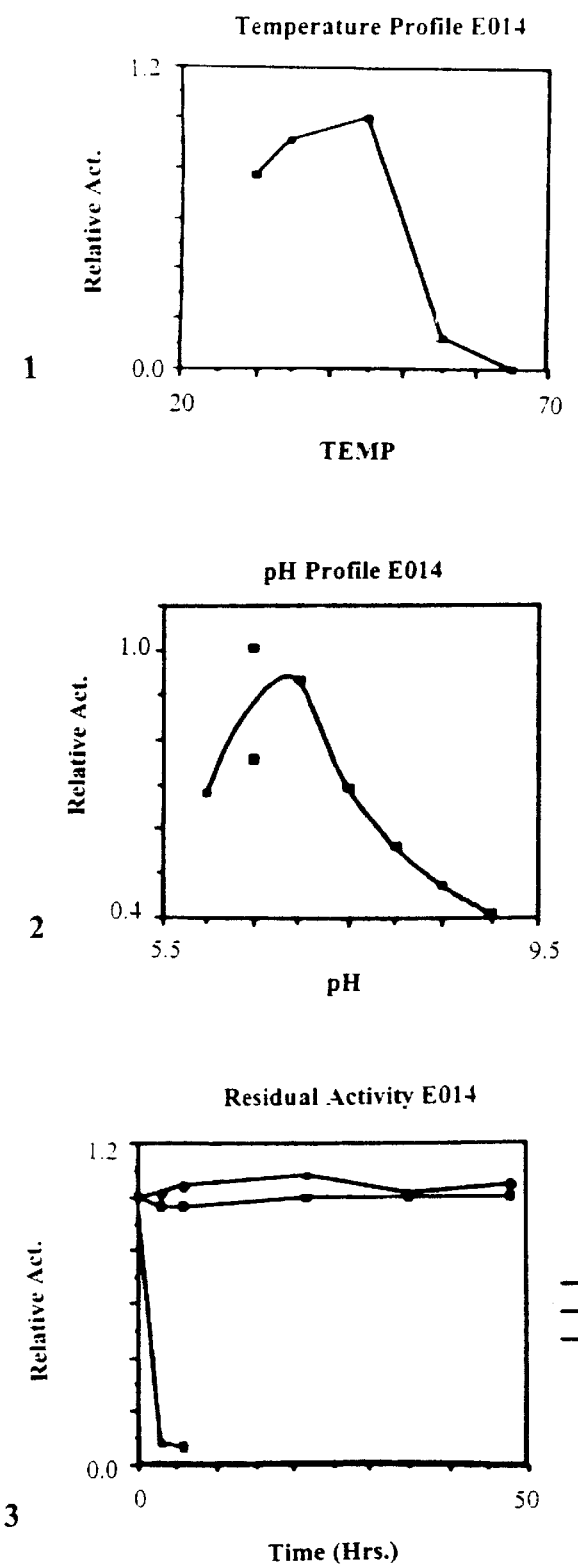
FIG. 1. Enzyme Characteristics.

The instant invention provides for isolated commercially useful protein preparations from themostable bacteria which are selected for enzymatic activity, and characterized by apparent molecular weight, pH, and temperature stability. The isolated protein of the instant disclosure can be used as molecular weight markers for finding similar enzymes, as well as functionally as enzymes for carrying out biocatalysis. Commercial chemical synthesis of specific racemic products often require the use of such isolated enzyme preparations.

The results of characterization assays demonstrate that the esterase enzymes described have a range of optimal parameters. For instance, E100 and E101 have optimal operating temperatures above 70° C. as would be consistent with enzymes isolated from an extreme thermophile, and E001–E021 have optimal commercial temperatures in the range of 40–50° C. as would be consistent with enzymes isolated from the more moderate thermophilic organisms. Both groups, however, provide added stability and functionality as compared to other known esterases from thermophilic bacteria. E001–E021 provide an optimal temperature environment for chemists who wish to work in less extreme temperature ranges, and also function well at room temperature. The results also demonstrate that the enzymes described posses a variety of pH optima including some with no apparent preference under the conditions of the experiment, however the trend for most of the proteins is to have pH optima near or slightly below neutral.

The following examples are meant by way of illustration, and not limitation, as to the specific embodiments of the instant invention. One of ordinary skill in the art would understand that many equivalents to the instant inventions can be made with no more than routine experimentation.

EXAMPLE 1

Isolation and Propagation of Thermophilic Organisms

Strains

Thermus sp. T351 (ATCC 31674) is available from the American Type Culture Collection (ATCC). All isolated strains and cultures are grown on TT medium (36). This medium consists of (per liter): BBL Polypeptone (8 gm), Difco Yeast Extract (4 gm), and NaCl (2 gm). Small scale cultures for screening are grown at 65° C. at 250–300 rpm with 1 liter of medium in a 2 liter flask. Larger scale production of cells for enzyme purification are grown in 17 liter fermentors (LH Fermentation, Model 2000 series 1). The fermentors have a working volume of 15 liters and cultures were grown in TT broth, 250 rpm, 0.3 to 0.5 vvm (volumes air/volume media per minute) at 65° C. Temperature is maintained by circulating 65° C. water from a 28 liter 65° C. water reservoir through hollow baffles within the stirred jars. E. coli strains are grown as described in (37).

Enrichment Procedures for Newly Isolated Thermophiles.

Multiple stream sediments, composting organic materials, and soil samples are used to isolate new strains. These samples are collected from numerous geographic sites ranging from the Midwest to the Southeast. Samples (~1 gm) are resuspended in 2 ml of TI broth and 50–100 $\mu$l of these samples were plated onto TT agar plates containing twice the usual amount of agar (3%). Agar is usually added to a final concentration of 1.5% for solid media This prevents highly motile microorganisms from overcrowding the plate at the expense of other microbes. Plates are incubated at 55° C. or 65° C. for one to two days and isolates then purified by numerous restreaks onto fresh plates for single colony isolation. The initial basis for differentiation is color, colony morphology, microscopic examination, temperature of growth, and lipase and esterase activities. Several hundred strains were initially isolated. 65 different microorganisms were chosen for further study.

EXAMPLE 2

Methods for Esterase Identification and Assay

Esterase Plate assay

Organisms are grown in liquid cultures on TT media at either 55° C. or 65° C. Cells are pelleted by centrifugation (3,000 RPM for 20 minutes) and the supernatants saved to be tested. Pellets are washed with 2 volumes of 10 mM Tris HCl pH 8.0 three times after which the cell pellets are resuspended in fresh Tris buffer and disrupted by sonication. Cell debris is removed by centrifugation and the crude extracts were tested for esterase activity on an esterase screening plate. Briefly, fifty microliters of cell extract is transferred to a well on a microtiter plate consisting of 0.1 mg/ml of either 5-bromo-4-chloro-3-indolyl acetate or butyrate (for esterase activities) suspended in 0.7% agarose and 0.1M Tris-HCl pH 8.0. Control wells consist of addition of either buffer, 20 U of Pig Liver Esterase (PLE), or 20 U of Porcine Pancreatic Lipase (PPL). Plates are incubated for sufficient time to allow full color development in control wells, usually about twenty minutes at 37° C. Dark wells represent positive activity.

Both cell extracts and culture supernatants are tested for esterase activity by this method. Only cell extracts showed significant esterase activity.

Esterase Liquid assay and determination of specific activity

Protein concentrations are determined by the Pierce BCA assay using defined concentrations of bovine serum albumin as the standard. Protein concentrations are obtained from the calibrated absorbance of the sample solutions at 562 nm and are expressed as milligrams of protein. Esterase activities are routinely measured by determining the rate of hydrolysis of p-nitrophenylproprionate (0.5 mM from a 10 mM stock dissolved in CH3CN) in 50 mM sodium phosphate buffer pH 7.0 equilibrated at 40° C. and monitored at 346 nm (isosbestic point for the acid/carboxylate couple $\epsilon$=4800). The specific activity is defined as the amount of p-nitrophenol produced in micromoles per minute per milligram of total protein.

Identification of extremely stable esterases.

Native (non denaturing) 10% polyacrylamide gels are run on crude extracts. After electrophoresis, the gels are equilibrated in pH 7.6 Trizma buffer and then stained for activity in either 0.15% X-acetate. The gels are then incubated at 55° C. for up to 30 minutes. These gels can then be stained with an esterase activity stain containing either 5-bromo-4-chloro-3-indolyl acetate (X-acetate), 5-bromo-4-chloro-3-indolyl butyrate (X-butyrate) or 5-bromo-4-chloro-3-indolyl caprylate (X-caprylate) and produced indigo precipitates. Two major bands were apparent in the lanes with Thermus crude extracts. A single small band of activity is seen in the E. coli control lanes. Esterases can be identified from Thermus sp. T351 and from several of the new isolates. Table 1 summarizes the activities which are found from these organisms.

TABLE 1

Summary of New Esterases and Strains Identified

| Isolate[1] | Esterase | Source | Growth Temp (° C.) 37 | 55 | 65 | Isolation Temp (° C.) | mw (kD)[2] | Specific Activity[3] |
|---|---|---|---|---|---|---|---|---|
| S1 | E001 | soil | nd | nd | + | 65 | 22 | 0.011 |
| 54 | E002 | compost | − | + | + | 65 | 28 | 0.87 |
| 50 | E003 | compost | − | + | + | 65 | 28 | 2.2 |
| GP1 | E004 | soil | nd | nd | + | 65 | 36 | 0.3 |
| C-1 | E005 | compost | nd | nd | + | 65 | 28 | 2.3 |
| 55 | E006 | compost | − | + | + | 65 | 36 | 2.1 |
| 46 | E007 | compost | − | + | + | 65 | 28 | 0.3 |
| 30 | E008 | soil | − | + | + | 55 | 28 | 2.1 |
| 28 | E009 | soil | − | + | + | 55 | 36 | 2.0 |
| 29 | E010 | soil | − | + | − | 55 | 46.5 | 2.3 |
| 31 | E011 | soil | − | + | − | 55 | 36 | 3.6 |
| 26b | E012 | soil | − | + | − | 55 | 28 | 5.2 |
| 27 | E013 | soil | − | + | + | 55 | 36 | 2.7 |
| 34 | E014 | soil | − | + | +/− | 55 | 36 | 0.8 |
| 62 | E015 | compost | − | + | + | 55 | 36 | 3.4 |
| 47 | E016 | compost | − | + | + | 65 | 28 | 0.8 |
| 49 | E017 | soil | − | + | + | 65 | 36 | 0.03 |
| C-3 | E018 | compost | nd | nd | + | 65 | 36 | 0.077 |
| 4 | E019 | compost | − | + | + | 55 | 30 | 0.4 |
| 7 | E020 | compost | − | + | + | 55 | 28 | 1.6 |
| 32 | E021/17b[4] | soil | − | + | +/− | 55 | 36 | 0.3 |
| Thermus sp. T351 | E100 | ATCC# 31674 | nd | + | + | 65 | 45 | 0.0032 |
| Thermus sp. T351 | E101 | ATCC# 31674 | nd | + | + | 65 | 135 | 0.032 |

[1]Isolates GP1, 27, 28, 29, 30, 31, 32, 34, 62 appear to be thermophilic Actinomyces.
[2]Approximate molecular weight as determined by chromatography for E001–E021 or SDS-PAGE for E100 and E101.
[3]Specific activity is the amount of p-nitrophenol produced in micromoles per minute per milligram of total protein at 40° C. after purification to homogeneity (for E100 and E101) or semi-purification (for E001–E021) as described in the Examples.
[4]E021 is also referred to as E017b.

EXAMPLE 3

Procedure for Purification of Esterase Activity to Homogeneity

Protein Isolation

A large batch cell culture is grown according to the methods described in Example 1 and the cell paste is collected by centrifugation and stored at −80° C. 100 g of cell paste is thawed in 200 ml of a stirred solution composed of 50 mM phosphate buffer at pH 7.5 containing 200 mM KCl and 0.1 mM EDTA. Once dissolved, the suspension is allowed to warm to room temperature and then treated with lysozyme (0.1 mg/ml) for 2 hours. The solution is then sonicated to completely disrupt the cells. Settings used on a 375 watt Sonics & Materials Vibra Cell sonicator with a standard ¼" horn were 5 minutes of power setting 8 disruption with a 50% pulse rate. Alternative methods for cell disruption can include processing the cells through a device such as a french press, Gaullen homogenizer, microfluidizer or other homogenizer. Cell debris is removed by centrifugation and proteins can be precipitated by $NH_4SO_4$ fractionation to 60% saturation. Precipitated protein is centrifuged and resuspended in minimal volume of 50 mM phosphate pH 6.5 containing 1 mM β-mercaptoethanol (BME).

DEAE Purification

The protein solution is dialyzed against the resuspension buffer 3 times using 10 Kd pore size dialysis tubing. The resulting protein solution is diluted two fold in the buffer and applied to a 100 ml bed volume DEAE column equilibrated in the same buffer. The column is washed with 200 ml equilibration buffer and then eluted with a linear gradient from 0 to 0.5 M NaCl.

Q Resin purification

Active fractions isolated from DEAE purification are pooled and dialyzed against three changes of equilibration buffer and dialysate was applied to a 50 ml bed volume of sepharose Q resin equilibrated with the buffer above. The column is washed with 100 ml of 50 mM phosphate pH 6.5 containing 0.1 M KCl and 1 mM BME and then eluted with 150 ml of a KCl gradient from 0.1 M to 0.6M added to the above buffer.

Ultrafiltration Concentration

Active fractions are pooled and concentrated using an Amicon Ultrafiltration system fitted with a 30 Kd cut off membrane.

Preparative SDS PAGE

Concentrated protein solutions are loaded to a preparative 10% SDS-PAGE gel using the standard SDS loading buffer without boiling the sample. After development, the gel is treated with 0.7% agarose containing 0.1M phosphate pH 7.5 and 0.1 mg/ml 5-bromo-4-chloro-indoylacetate. The resulting blue band was excised from the gel, placed in dialysis tubing and the protein is recovered by electroelution in 0.05M Tris buffer pH 8.5 for 1 hour. At this stage the protein is purified to homogeneity as observed by both native- and SDS-PAGE stained with either coomassie or silver stain. Protein can be stored at 4° C. for future use.

Gel filtration

A gel filtration column can also be used as a further or substituted purification step.

EXAMPLE 4

Method for Commercial Grade Preparation of Isolated Esterase

For many industrial applications, a completely purified preparation of enzyme is neither required nor desired due to production cost considerations. A rapid, inexpensive protocol to produce a protein of interest in a form which is isolated to contain protein with significant esterase activity is desired. One such semi-purification procedure is described here. 50 g of cell paste is thawed in 100 ml of 50 mM Tris HCl buffer at pH 7.5 containing 0.1M NaCl and 0.01 mM EDTA. Cells are disrupted by sonication and the cell debris is removed by centrifugation. The crude cell lysate is diluted by three fold with 50 mM Tris-HCl pH 7.5 and the material is loaded to a DEAE cellulose column (bed volume 60 ml) equilibrated with the dilution buffer. The column is washed with three column volumes of dilution buffer followed by a salt gradient of 0–0.5M NaCl over 4 column volumes. Active fractions eluted from the ion exchange resin in the salt gradient window of 0.25–0.35 M. Fractions were assayed for activity as described under determination of specific activity and those showing the highest activity were pooled and concentrated by ultrafiltration with 10 Kd molecular weight cut off membrane. Concentrated enzyme samples are stored at 4° C. for further use. In some instances, more than one ester hydrolysis activity may still be detected under long term exposure to substrate agarose overlays of proteins separated on native PAGE, indicating very small quantities of a second esterase activity which should not interfere with most industrial applications. A further purification (such as an Ammonium sulfate salt precipitation, gel filtration, or other methods as described in Example 3) can be applied if necessary. The process can be scaled up or down as desired.

EXAMPLE 5

Method for Determination of Temperature Profile

Optimal temperature profiles for an esterase protein is performed by measuring the activity of the esterase diluted into 0.1M sodium phosphate buffer pH 7.0 equilibrated at 30° C., 35° C., 45° C., 55° C. and 65° C. respectively for five minutes. The temperature profile is then determined by measuring the rate of hydrolysis of p-nitrophenylproprionate added to the equilibrated solution under reaction conditions described for determination of specific activity in Example 2 (modified by the various temperatures used in this experiment). Control reactions that substitute bovine serum albumin for esterase enzymes are used to allow correction for temperature dependent autohydrolysis of the substrate. The data is then plotted as relative activity versus the temperature of the reaction.

EXAMPLE 6

Method for Determination of Enzyme Stability

The long term catalytic stability the esterase enzyme is evaluated by testing the activity remaining after exposure to various temperatures. The enzyme stock solution is diluted into 0.1 M sodium phosphate buffer pH 7.0 and placed in a temperature bath equilibrated to 25° C., 40° C. or 60° C. respectively under sealed conditions to avoid concentration effects due to evaporation. Residual activity is then determined by removing aliquots at regular intervals and measuring the rate of hydrolysis of p-nitrophenyl-proprionate as described above. Results are plotted as relative activity vs. time. The results indicate that all enzymes tested retain most of the initial activity for at least 48 hours when exposed to temperatures up to and including 40° C. Activity does decrease at 60° C. particularly for enzymes isolated from organisms with optimal growth temperatures near 55° C.

Figure 4:
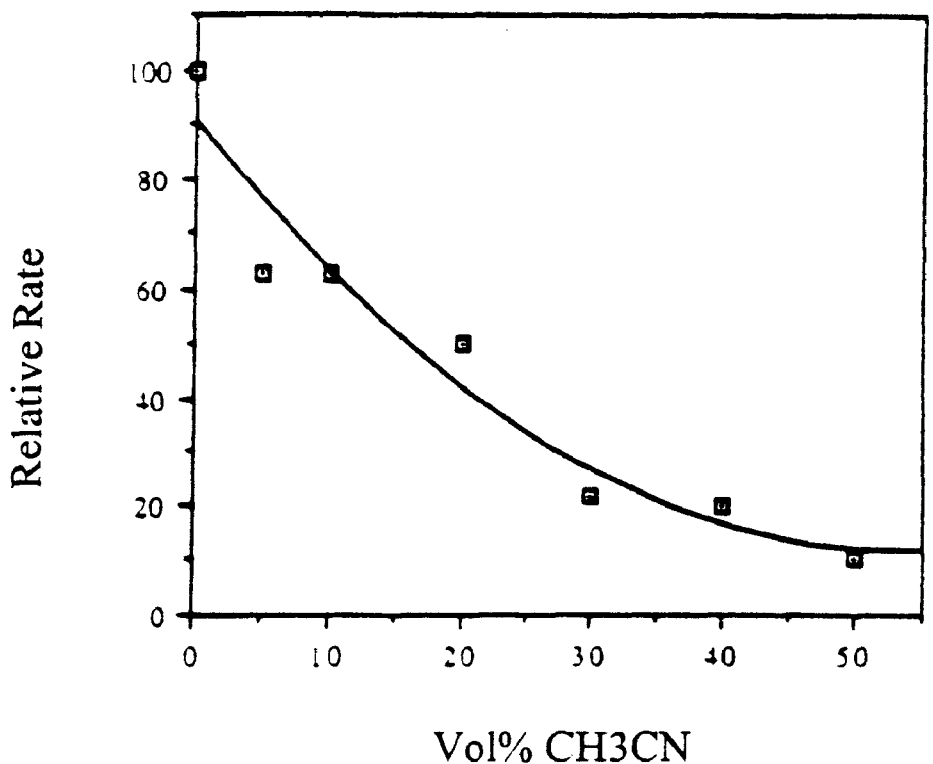
FIG. 4. The tolerance of E100 to the presence of organic cosolvents on the hydrolysis of p-nitrophenyl proprionate as determined by relative rates. Residual activity of the enzyme is determined in the presence of organic solvent by measuring the initial rate of enzyme catalyzed hydrolysis of pNP in the presence of various concentrations of $CH_3CN$. Reactions are run in 50 mM Tris-HCl pH 8.5 at 37° C. as described in determination of activity. Changes in absorbance are corrected for spontaneous hydrolysis of the substrate and the changes in extinction coefficient of the product in the presence of organic cosolvent.

FIG. 4 is an example of the typical data obtained. Data for enzymes are summarized in tables 1, 2 and 10.

EXAMPLE 7

Method for Determination of pH Profile

The pH profile of an esterase is determined as follows. The rate of p-nitrophenylproprionate hydrolysis is determined under reaction conditions similar to those described for determination of specific activity in Example 2 with buffers of wide useful pH windows that overlap with at least one data point. For the purposes of these experiments two buffers were selected that met the above criteria, Mes (useful range of 6–6.5) and Bis-tris propane (useful buffer range 6.5–9). All pH tests were corrected for spontaneous autohydrolysis by subtraction of experimental runs from controls substituting bovine serum albumen for esterase. This control data treatment becomes especially important for pH's greater than 7.5.

EXAMPLE 8

Solvent Effects on Esterase Activity

Industrial applications for biocatalysts often require that enzymes function under non-native and harsh conditions. Exposure to elevated temperatures and pH fluctuations are possible challenges to enzyme activity, however the lack aqueous solubility of many compounds that may serve as substrate targets for biocatalysts is a significant challenge to the industrial organic chemist. Organic cosolvents are commonly used in reactions and isolated enzymes must be able to survive under conditions of relatively high concentrations of cosolvent. Experiments are run in the presence of various organic solvents such as ethanol, acetonitrile, dimethylformamide, dioxane, toluene, hexane and detergents like SDS, triton X100 and Tween 20. Additional experiments are also performed to test the activity of isolated catalysts in nearly anhydrous solvent conditions in which the enzymes will be lyophilized from buffers and pH's of optimal activity.

EXAMPLE 9

Method for Protein Characterization by Migration on Native PAGE

The number of esterase enzymes in each semi-pure sample is determined from native gel PAGE using 4–15% acrylamide gradient (precast gels purchased from Bio-Rad laboratories) separating proteins based on their charge to size ratio. The gel shows trace contamination with other enzymes capable of indoylacetate hydrolysis that could not be detected easily with the HPLC because of column dilution effects. What is clear from the gel experiments is that most of the samples have a single major activity band or zone that have similar migration characteristics.

EXAMPLE 10

Determination of Relative Molecular Weight by Chromatography

The estimated native molecular weights for the protein of interest is determined by separation on a Pharmacia Superdex S200 FPLC column fitted to a Hitachi HPLC 6200 system. Proteins were separated by isocratic elution in 0.05 M sodium phosphate buffer at pH 7.0 containing 0.1 M NaCl. The solvent flow rate was maintained at 0.5 ml/min and protein was detected by UV at 280 nm. Esterase active fractions were detected initially by 5-bromo-3-chloro-3-indolyl-acetate plate assay with follow-up assay of most active fractions by p-nitrophenyl-proprionate hydrolysis (both methods are described in Example 2). Molecular weights are estimated by comparison to standard elution profiles (plotted as the log of molecular weight vs. time in minutes) generated by use of the following proteins: β-amylase 200 Kd, alcohol dehydrogenase 150 Kd, bovine serum albumin 66 Kd, carbonic anhydrase 29 Kd, cytochrome c 12.3 Kd.

EXAMPLE 11

Characterization of Substrate Specificities

Substrate preference of esterases for hydrolytic activity on various esters can be determined as follows. A grid of molecules is prepared on microtiter plates by dissolving each substrate (0.1 mM final concentration) in $CH_3CN$ and mixing with 0.1M phosphate buffer pH 7.5. Partially purified enzymes is then added to the wells and the reaction mixture is incubated for 30 minutes. Crude lysates can also be tested this way. Plates are checked after 10, 20 and 30 minutes to determine relative activities. For experiments with noncolored substrates, reactions are run in test tubes under the same conditions as described for the colored substrates except that the reactions are extracted three times with dichloromethane. The organic layers are combined, dried with $MgSO_4$ and concentrated to 0.1 ml in a nitrogen stream. The concentrates are then spotted to silica gel TLC plates and developed in a solvent mixture of 80:20:0.01 hexane:ethyl ether:acetic acid. TLC plates are visualized with UV and $I_2$.

EXAMPLE 12

Rapid Screen Assay for Quick Substrate Specificity Characterization

A new method was developed to rapidly screen for esterase activity based on the mechanism of the enzyme catalyzed hydrolysis reaction wherein the pH of the system is reduced by the release of protons upon ester hydrolysis. The proton flux in the reaction can be monitored by use of indicator dyes that have pH-dependent color transitions in the desired pH range of enzyme activity. The best indicators tested are phenol red for enzymes that function optimally at slightly elevated pHs (starting point pH 8.5) or bromothymol blue (starting point pH 7.2) for enzymes that operate well at more neutral conditions.

The indicator reactions are monitored by one of two methods. Spectroscopic studies are performed by measuring the UV/Vis maxima of a 0.001% solution of either phenol red or bromothymol blue dissolved in different pH buffers at 5 mM concentration. Hydrolytic reactions are then performed by adding the substrate (0.1 mM final concentration) to a 5 mM buffer solution (sodium phosphate pH 7.2 for bromothymol blue indicator and sodium borate pH 8.5 for phenol red indicator) and equilibrating the temperature at 25° C. for five minutes followed by initiation of the reaction by addition of 0.1 U target enzyme.

An alternative method for monitoring the hydrolytic reactions is useful for broad screening applications. 5 mM buffer containing 0.001% indicator dye and substrates dissolved in $CH_3CN$, DMF or DMSO to an organic solvent composition of no more than 10% is added to a stirred 24 well microtiter tray. The temperature is allowed to equilibrate for five minutes at 25° C. after which the reaction is initiated by addition of 0.1 U of the esterase. Reaction progress is monitored by solution color changes upon which, aliquots of NaOH are added to return the reaction color to the starting point. Reactions are determined to be complete when no further color change is detected after prolonged incubation. Product formation is verified by TLC analysis of reactions acidified with 0.1 M HCl, extracted with ethyl acetate, dried with $Na_2SO_4$ and concentrated under a stream of $N_2$. For testing substrates in which enzyme-based chiral resolution is being screened, products are separated and isolated by chiral phase HPLC and enantiomeric purity is determined by integration of peak areas for each isomer.

Rapid assay of a variety of hydrolytic activities, in this cases esterases, is determined in a microtiter plate experiment using several different enzymes and substrates. Accurate comparison of commercially available enzymes can be insured by using the same specific activity for each enzyme determined from the total protein and the initial rate of hydrolysis of the common substrate p-nitrophenylproprionate. The data are recorded as the time required to visualize a pH dependent color change for the given indicator dye. Control experiments using BSA as the protein source cause no change in indicator color and establish that pH changes in solution are the result of an enzyme catalyzed hydrolysis. Control tests of reaction solutions containing enzymes and indicators without substrates established that color changes in the solutions are not the result of buffer salts or the enzymes alone.

Studies performed to determine whether the microtiter plate format was amenable to small scale preparative chemistry are performed as follows. Using racemic phenethylacetate and pig liver esterase, reactions are run and titrated with aliquots of 0.1N NaOH to maintain original solution color until no further color changes occurred at which point the reactions are stopped. Products are isolated and tested by TLC and compared to total amount of base added to verify the extent of the reaction. Phenethyl alcohol is separated from starting acetyl ester by flash column chromatography followed by analysis by chiral phase HPLC. The enantiomeric excess of the hydrolysis products is determined from the peak integration and compared to an identical reaction run in the absence of indicator dye. The results from these experiments suggest that inclusion of indicator dye has no effect on the stereoselectivity of esterase catalyzed resolution of phenethylacetate.

In order to test the assay for usefulness in a broad-based enzyme screening method, seven organisms isolated from various sources in the environment were tested for their ability to produce enzymes that would catalyze the hydrolysis of a group of structurally diverse compounds. Table 2 shows the results of these studies.

TABLE 2

Substrate Specificity.

| Substrate | Lysate Hydrolytic Rate (min) | | | | | | | | |
|---|---|---|---|---|---|---|---|---|---|
| | N/E | E001 | E003 | E004 | E005 | E006 | E016 | E017 | E018 |
| Ethyl butyrate | — | 60 | 240 | 20 | <5 | <5 | — | — | 15 |
| Glyceryl tributyrate | — | 60 | 20 | <5 | <5 | <5 | <5 | 120 | 60 |
| (R)-Methyl mandelate | — | — | 240 | — | 120 | 240 | — | 300 | — |
| (S)-Methyl mandelate | — | — | 300 | 240 | 240 | 240 | — | — | 240 |
| 1-Phenylethyl acetate | — | 240 | 240 | 20 | 60 | 60 | 120 | 900 | 60 |
| Solvent Control | — | — | — | — | — | — | — | — | — |

Results are reported as the amount of time required to change indicator color. The data is indicative of variable substrate specificity between different environmental isolates. Of particular note is the suggestion of stereoselectivity as determined from the relative rates of hydrolysis for substrate enantiomers. Control reactions are similar to those described above in the substrate specificity studies with commercially available enzymes.

EXAMPLE 13

Further Characterization of Substrate Specificities

Depicted in FIG. 10 are examples of the substrates that can be tested with each enzyme activity. These molecules have been chosen specifically because of their importance as intermediates in the synthetic literature with the potential for industrial application. Experiments can be performed with crude lysates or proteins isolated from media broth in cases where the activities are known to rapidly assess the likely reaction chemistry including substrate preference and stereochemistry. All structure activity tests are compared to standard mesophile biocatalysts such as pig liver esterase. The reactions are monitored by TLC analysis to compare the products to standards purchased from commercial sources or prepared by chemical means (for example, base-catalyzed hydrolysis of esters).

Investigations of stereochemical preference by each esterase can be evaluated by one of two methods. In the first method, standard single stereoisomers of commercially available entantiomerically pure substrate esters are hydrolyzed by each enzyme and the relative rates of hydrolysis for each antipode are used as diagnostic qualitative determinants of potential chiral selectivity. In the second method, those molecules not commercially available as single stereoisomers are hydrolyzed as racemates using kinetic resolution methods (running the reaction generally less than 50% completion). The products of the reaction are isolated and analyzed for their enantiomeric excess (ee) by chiral phase HPLC (Diacel Chiralcel OD or OB) or $^1$H NMR of the corresponding diasteriomers prepared by derivatizing products to Mosher derivatives (alcohol products) or menthyl derivatives (carboxylate products). Diastereomeric ratios determined from the NMR spectra are based on corresponding peak integrations and compared to either literature values or standards obtained from commercial sources using of chiral shift reagents when necessary. Optical rotations and absolute configurations of the products are then determined by polarimetric analysis and compared to values found in the literature or determined from standards obtained from commercial suppliers.

EXAMPLE 14

Characterization of Proteins E001–E021/17b

Strains from the identified sources as listed in Table 1 were isolated by growth in TT media at 65° C. as described in Example 1 (ie. S1 from soil, etc.). Specific esterase hydrolytic activity was identified by the methods described in Example 2 and the isolated esterase protein assigned the identifier as listed in Table 1 (ie. E001 etc.) To prepare enzyme, a 15 liter culture of isolate is grown and the cells are spun down and collected as described in Example 1. The cells are lysed and a isolated preparation of was purified according to the procedures outlined in Example 4. The protein was characterized using the methods described in Example 5 to determine the temperature profile, Example 6 to determine protein stability, and Example 7 to determine the pH profile, and the results are shown in FIG. 4. The protein was characterized by migration on Native gradient PAGE as described in Example 9 and the data is shown in FIG. 2. The specific activity was determined as described in Example 2 and the molecular weight was determined by chromatography as described in Example 10 and are presented in Table 1. Substrate specificity for several proteins has been demonstrated and are shown in Table 2. Thus the identified and characterized esterases have been demonstrated to be useful, and to posesses unique activity at commercially useful purity. Certain results are summarized in Table 10.

EXAMPLE 15

Characterization of E100

Purification of E100

E100 is purified from Thermus sp. T351 over 300 fold by a series of four steps described in Example 3: DEAE purification, Q Resin purification, Ultrafiltration concentration, and preparative SDS PAGE. The specific activity could not be measured in the crude lysate since there was a secondary esterase activity present (E101). The secondary activity could be completely removed from the target esterase during the first chromatographic step in which the secondary esterase passed through the DEAE column unbound. For purification of various technical grades of E100, DEAE purification alone is sufficient to yield E100 enzyme substantially purified away from any other contaminating activity. Q Resin purification and ultrafiltration allow for higher purity product to be produced as required by specific applications. A final SDS PAGE purification step allows the protein to be purified to homogeneity for determination of molecular characteristics.

Protein Characterization

The active band is collected by electroelution on a preparative SDS-PAGE gel and rerun on 10% SDS-PAGE under denaturing conditions. This shows a single band with a relative molecular mass of about ~45 Kd. Unboiled samples run on the same SDS-PAGE gels show multiple bands in approximate increments of the proposed monomeric molecular mass. Additionally, the nonboiled sample can be stained for activity, however only bands corresponding to multimeric forms of the enzyme are found to retain activity beginning with dimeric species. The specific activity of the purified protein is approximately $3.2 \times 10^{-6}$ Mmin$^{-1}$mg$^{-1}$ using 4-methyl-umbelliferyl-butyrate (MUB) as the substrate.

Measurement of E100 Enzyme Activity

Esterase activity is measured by monitoring the hydrolysis of p-nitrophenylproprionate (pNP), or in some cases MUB. Each substrate is dissolved in acetonitrile and added to the reaction mixture (100 μM final concentration) which contain 50 mM Tris HCl pH 8.5 adjusted for temperature dependent pH variation. Reactions are thermally equilibrated at 37° C. for 5 minutes prior to initiation of the reaction by addition of 10 μL of enzyme sample, while control reactions substituted equivalent amounts of BSA. The reaction is monitored spectrophotometrically at 405 nm $\epsilon=17$ mM$^{-1}$cm$^{-1}$ for pNP and 360 nm $\epsilon=7.9$ mM$^{-1}$cm$^{-1}$ for MUB.

The rates of enzyme catalyzed hydrolysis are corrected for the spontaneous hydrolysis of the substrate. Protein concentrations are determined by either the absorbance at 280 nm or by Lowery assay. Crude activity is determined by a calorimetric assay based on the hydrolysis of 5-bromo-4-chloro-3-indoyl esters suspended in a 0.7% agar matrix on microtiter plates. A 0.1 mg/ml solution of the indolyl derivative is dissolved in a minimal volume of acetonitrile and added to a warm solution of 0.7% agar containing 0.1M phosphate buffer pH 7.5. 10 μL of this solution is distributed to microtiter plates which, when cooled, could be used with as much as 100 μL of enzyme sample and incubated at temperatures from ambient to >65° C.

E100 was effectively inhibited when exposed to tosyl fluoride but was unaffected by the presence of either metal ions, chelating agents or reducing molecules Table 3.

TABLE 3

Inhibition by reaction components on the hydrolysis of p-nitrophenylprorionate by E100

| Additive (concentration) | Relative Rate[a] (%) |
|---|---|
| None | 100 |
| PMSF (0.1 mM) | 0 |
| BME (10 mM) | 99 |
| DTT (1 mM) | 101 |
| CaCl$_2$ (10 mM) | 108 |
| MgCl$_2$ (10 mM) | 95 |
| ZnCl$_2$ (10 mM) | 90 |
| EDTA (1 mM) | 96 |

Reaction conditions are those described in the general experimental above except for the addition of specified components. Relative rates are corrected for the spontaneous rate of hydrolysis of the uncatalyzed reaction.

Substrate specificity of E100

The substrate specificity was tested as outlined as according to Example 11, and the results from the structure activity experiments for E100 are shown in summary Table 4. E100 displays a broad substrate specificity catalyzing the hydrolysis of a number of nitrophenyl, coumaryl and alkyl esters. The enzyme displays hydrolytic activity towards both straight chain and aromatic moieties on the carboxylate side of substrates however, carboxylate R groups of long alkyl chains >C8 or those containing naphthyl leaving groups are not substrates. The enzyme displays no significant activity towards either casein or milk as assayed by clearing zones on agar plates.

TABLE 4

Substrate Activity of E100

| Substrate | E100 | Control |
|---|---|---|
| I-acetate[a] | ++ | − |
| I-butyrate[a] | ++ | −− |
| I-caprylate[a] | + | −− |
| N-acetate[a] | −− | −− |
| U-acetate[a] | ++ | +/− |
| U-stearate[a] | −− | −− |
| pN-acetate[a] | ++ | −− |
| pN-proprionate[a] | ++ | −− |
| oN-proprionate[a] | ++ | −− |
| oN-caprylate[a] | + | − |
| oN-palmitate[a] | +− | − |
| oN-stearate[a] | − | −− |
| Me-PA[b] | + | −− |
| Et-PA[b] | + | −− |
| isoProp-PA[b] | + | −− |

Structure activity assay of partially purified esterase E100 from Thermus species. (++) highest activity as determined by [a]color formation in less then 10 min or significant product formation on [b]TLC. The remaining activity measurements follow the order: + > +/− > − > −−. Structure abbreviations are as follows: I, chloro-bromo-indoyl, N, a-napthyl, U, methylumbelliferyl, pN, p-nitrophenyl, oN, o-nitrophenyl, PA, phenylacetate.

Determination of Kinetic Characteristics

Kinetic characteristics are determined by measuring the concentration dependent initial rates of enzyme catalyzed hydrolysis of nitrophenyl proprionate. Reactions are run at pH 8.5 in 50 mM Tris-HCl buffer equilibrated to 37° C. and initiated by addition of enzyme. Rates are determined from the absorbance changes due to formation of product nitrophenol at 405 nm. Rates are corrected for the spontaneous hydrolysis of substrate during the course of the reaction. Concentration vs. rate data are analyzed by both double reciprocal plots and by HanesWolff plots to determine Km, Vmax and Vmax/Km. The kinetic characteristics of E100 determined from plots of the initial rates of hydrolytic reactions are shown in FIG. 6.

Determination of Temperature Profile and Optimal pH for E100

Figure 7A:
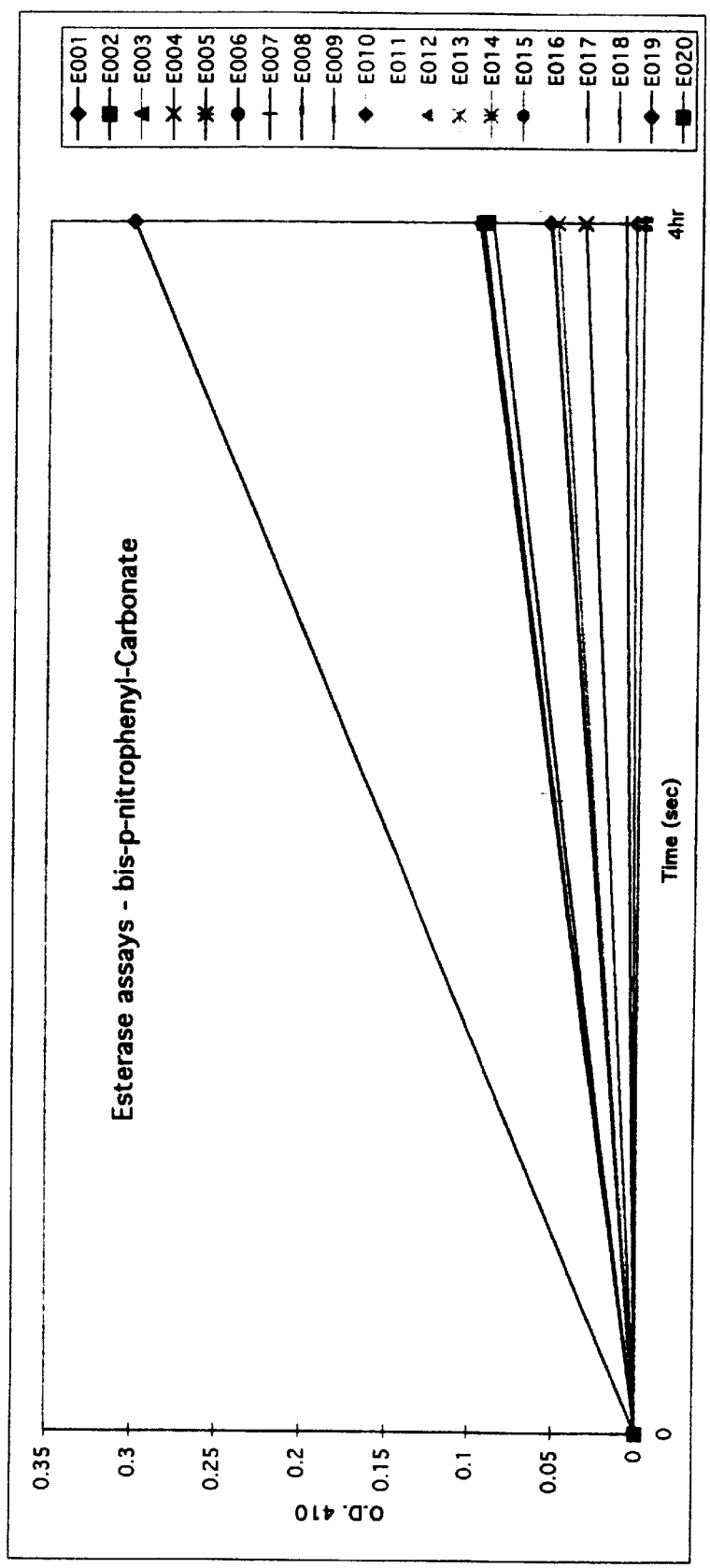

The temperature profile of the enzyme is determined as shown in FIG. 7a. Enzyme activity is observed to steadily increase to the limit of the assay, over 70° C., (where the background signal from autohydrolysis of the substrate became too high and is no longer correctable) as the temperature of the reaction is elevated and suggests that the low end for optimal activity for E100 is greater than 70° C. E100 displays a basic pH profile with a low end optimal activity observed to be approximately 9.0, the limit of substrate stability at 37° C. (FIG. 7b).

Determination of Enzyme Stability in the Presence of Organic Solvents

E100 is tested for tolerance to organic solvent composition using the polar aprotic cosolvent acetonitrile as a preliminary system. the enzyme retained 50% of its activity in a solvent mixture of 20 vol % organic cosolvent (FIG. 8).

N-Terminal Sequencing of E100

Purified proteins are run on 10% SDS-PAGE gels and then transferred to PVDF membranes by electroblotting. Membranes are washed with several changes of doubly distilled water to remove any remaining SDS or other contaminants and then stained with coomassie blue. Membranes were then destained with several changes of 50:40:10 MeOH:$H_2O$:AcOH followed by one wash of 10% MeOH. Membranes are then air dried and then submitted for sequencing. The N-terminal sequence of E100 was determined at the University of Illinois Urbana Champaign genetic engineering facility.

The N-terminus of E100 was determined by automated sequencing of the polypeptide purified by 10% SDS-PAGE and transferred to a PVDF support. The sequence obtained was: MKLLEWLK?EV, where the letters refer to the standard amino acid single letter code and the "?" refers to an indeterminate amino acid. Thus, E100 has been demonstrated to be a useful esterase with unique activity at commercially useful purity.

EXAMPLE 16

Characterization of E101

E101 is one of two esterase activities that are isolated from Thermus sp T351. E101 can be purified away from a second esterase, E100, in an early purification step.

Purification of E101

A Thermus sp. T351 supernatant prepared as described in Examples 1 and 2 is fractionated with $NH_4SO_4$ and the precipitated proteins are collected between 20– 60% saturation. Pellets are redissolved in 30 ml of buffer (50 mM Tris-HCl pH 8.0, 1 mM BME) and dialyzed against the same buffer using 30 Kd cutoff dialysis tubing. Dialysate is loaded to 100 ml bed volume of DEAE resin equilibrated with the buffer above and the column was washed with 150 ml of the equilibration buffer. Active protein is observed in the load and wash fractions, pooled, and concentrated with the use of an Amicon concentrator fitted with a YM30 membrane. Concentrated proteins are then loaded directly to a 25 ml bed volume of sepharose SP resin equilibrated with the above buffer. Active fractions appear in the load and wash fractions which are pooled and concentrated as above. Concentrate is then loaded to a Sephracryl HR200 gel filtration column (1×40 cm) and 0.5 ml fractions are collected at a flow rate of 2 ml/hr. Active fractions are collected and analyzed by SDS-PAGE. In order to perform N-terminal sequencing, fractions considered to be homogeneous are concentrated and submitted to a protein sequencing service center. The enzyme is stored at 4° C. for future use.

E101 can be purified over 35 fold by these methods and possesses characteristics dramatically different from E100, the other esterase which is isolated from this strain. Attempts to use ion exchange chromatography result in subtractive purification since in no instance was the protein retained. Resins investigated include DEAE, Q sepharose, CM cellulose, SP sepharose and hydroxyappatite under conditions that varied from pH 6.0 to 9.0, and buffers from phosphate to borate including Tris and Hepes. After two ion exchange steps the protein is purified to homogeneity by gel filtration chromatography however, the protein appears to have an interaction with the column as retention is considerably longer than the molecular weight would suggest. The molecular weight of the protein appears to be approximately 135 Kd with a monomer mass of ~35 Kd as determined from native and denaturing SDS-PAGE respectively.

E101 Characteristics

The specific activity of the enzyme is ten fold greater than observed for E100 with 4-methyl-umbelliferyl butyrate (MUB) as the substrate. E101 is inhibited by PMSF but is insensitive to metal ions or metal ion chelators. The specific activity of the purified protein was found to be $3.2 \times 10^{-5}$ mol $min^{-1} mg^{-1}$ and was determined from initial rates of hydrolysis using methyl umbelliferyl butyrate as a substrate. Table 5 outlines the inhibitory effect of various substances on E101 activity.

TABLE 5

The inhibitory effect of reaction components on the hydrolysis of p-nitrophenylprorionate by E101

| Additive (concentration) | Relative Rate[a] |
|---|---|
| None | 100% |
| PMSF (0.1 mM) | 0 |
| BME (10 mM) | 96 |
| DTT (1 mM) | 98 |
| $CaCl_2$ (10 mM) | 102 |
| $MgCl_2$ (10 mM) | 97 |
| $ZnCl_2$ (10 mM) | 100 |
| EDTA (1 mM) | 93 |

Reaction conditions are those described in the general experimental above except for the addition of specified components. Relative rates are corrected for the spontaneous rate of hydrolysis of the uncatalyzed reaction.

Substrate specificity of E101

The substrate specificity of E101 was determined as described in Example 11. The results from the structure activity experiments for E101 are shown in Table 6. The hydrolytic activity of the enzyme is similar to that observed for E100 and has no observable protease activity toward milk or casein.

TABLE 6

Substrate Activity of E101

| Substrate | E101 | Control |
|---|---|---|
| I-acetate[a] | ++ | -- |
| I-butyrate[a] | ++ | -- |
| I-caprylate[a] | + | -- |
| N-acetate[a] | -- | -- |
| U-acetate[a] | ++ | +/- |
| U-stearate[a] | +/- | -- |
| pN-acetate[a] | + | -- |
| pN-proprionate[a] | + | -- |
| oN-proprionate[a] | ++ | -- |
| oN-caprylate[a] | +/- | -- |
| oN-palmitate[a] | +/- | -- |
| oN-stearate[a] | -- | -- |
| Me-PA[b] | ++ | -- |
| Et-PA[b] | ++ | -- |
| isoProp-PA[b] | + | -- |

Structure activity assay of partially purified esterase E101 from Thermus species. (++) highest activity as determined by [a]color formation in less then 10 min or significant product formation on [b]TLC. The remaining activity measurements follow the order: + > +/- > - > --. Structure abbreviations are as follows: I, chloro-bromo-indoyl, N, a-napthyl, U, methylunmbelliferyl, pN, p-nitrophenyl, oN, o-nitrophenyl, PA, phenylacetate.

Thus, E101 has been demonstrated to be a useful esterase with unique activity at commercially useful purity.

EXAMPLE 17

Cloning of Esterase

General Cloning Strategy

The λ ZAP cloning system from Stratagene™ can be used for the library constructions and detection of esterase activity. Other cloning systems can also be used to yield similar results. The usual efficiency of cloning in λ vectors vary from $10^5$ to $10^7$ hybrid clones per mg of cloned DNA and is sufficient to produce a representative gene library from a convenient amount of size-selected chromosomal DNA fragments. We have found that detection of esterase activity in phage plaques, as opposed to bacterial colonies, is more efficient due to the easier access of substrate to the enzyme. Phages are generally less sensitive to the toxic action of cloned proteins and are also able to survive at the temperatures up to 70° C. The ability of the cloning system to tolerate elevated temperatures and potential toxicity of the cloned proteins is necessary for the detection of the activity of thermophilic proteins, such as the esterases described here.

Isolation of DNA for Construction of gene banks

Genomic DNA is prepared from a culture of the appropriate strain containing the esterase of interest as described in Example 1. Cells of different strains are grown to late log phase in 100 ml TT broth (8 g Polypeptone (BBL 11910), 4 g yeast extract, 2 g NaCl, per liter) at 55° C. or 65° C. overnight shaking at 250 RPM. Cells are recovered by centrifugation and the pellet is resuspended in 5 ml of lysis buffer (10 mM Tris-HCL, pH 7.0, 1 mM EDTA, and 10 mM NaCl). Lysozyme is added to a final concentration of 2 mg/ml. Cells are incubated at 37° C. for 15 minutes followed by the addition of SDS to 1%. The lysate is gently extracted three times with phenol/chloroform/iso-amyl alcohol (25/24/1) and the DNA spooled from a 95% ethanol overlay of the aqueous phase.

One of ordinary skill would find other methods for preparation of DNA which are well known in the art (37). For example, fresh colonies of a strain containing the esterase of interest are inoculated in 50 ml of TT media in 250 ml Erlenmeyer flask and incubated at 55° C. for 24 hours at 200 rpm in a New Brunswick Environmental Shaker. The cells are harvested by centrifugation at 3000 g for 15 min., resuspended in 5 ml of GTE buffer (50 mM Glucose, 25 mM Tris-HCl pH 8, 10 mM EDTA) and treated with 2 mg/ml of lysozyme at 37° C. for 10 min. Lysozyme-generated spheroplasts are lysed by the addition of 1% SDS and partially deproteinased by addition of 100 μg/ml of proteinase K at 24° C. for 10 min. Chromosomal DNA is further purified by three phenol/chloroform extractions, precipitated with 2.5 volumes of ethanol and resuspended in 1 ml of TE (10 mM Tris pH 8.0; 1 mM EDTA), after washing in 20 ml of 75% ethanol. The extracted fraction consists of DNA fragments larger than 50 kb, with a concentration of about 0.5 ng/μl, as detected by gel electrophoresis using a 0.7% agarose gel run at 10 V/cm for 4 hours.

Construction of Gene Libraries

Genomic DNA is partially digested with the restriction enzyme Sau3A and then ligated to predigested Lambda ZAP Express (Stratagene Cloning Systems). Products of ligation reactions are packed in vitro using λ packaging extracts which are purchased from Promega. This vector accommodates DNA up to 12 kb in length and allows identification of clones both by expression off the T3 and T7 promoters and by probe hybridization to plaques. The library is retained and screened for esterase activity. Other methods for generating genomic DNA libraries are also well known in the art.

Five samples of 10 μg of chromosomal DNA of each of the strains prepared as described above, are treated with different concentrations of Sau3A restriction endonuclease (New England BioLabs) according to the manufacturer's instructions for 30 min at 37° C. in a volume of 50 μl each. The concentration of Sau3A is varied from 0.1 u to 0.002 u/μg of the digested DNA in separate tubes. The reactions are stopped by heat inactivation of the endonuclease at 70° C. for 10 minutes and analyzed by gel electrophoresis on a 0.7% agarose gel run at 10 V/cm for 4 hours (a typical digestion pattern is obtained, data not shown). Fractions with an average fragment size of 5 kb are chosen for cloning. For native strains containing E001, E002, E003, E006, E007, E008, E009, E010, E012, E016, E020 these are the second of the five samples of digested chromosomal DNA with the concentration of Sau3A of about 0.02 u/μg of the DNA. For the rest of the strains, the proper degree of partial digestion is achieved in the first test tube with 0.1 u of Sau3A/μg of the DNA. Fifty ng of chromosomal DNA fragments are ligated with equimolar amounts of dephosphorilatyed BamHI-arms of the lambda ZAP phage vector (Stratagene) in 5 μl with 1 unit of ligase (New England Biolabs). Ligation reactions are performed at 1 8° C. for 8 hours and stopped by heat inactivation at 70° C. for 10 min. One μl of the ligation reaction, containing approximately 10 ng of DNA insert, is used for in vitro packaging with 10 μl of lambda proheads (produced by Promega Corp). The packaging reaction is performed at 28° C. for 90 min, combined with 100 μl of an overnight culture of E. coli XL1 Blue and plated using 2 ml of 0.7% top agar (0.8% NaCl, 10 mM MgSO4) per plate onto five 90-mm Petri plates containing LB media Serial dilutions of the packaging mixture are produced in order to determine the cloning efficiency which is generally about $1.0 \times 10^7$ hybrid phages/μg of cloned DNA. Cloning efficiencies for each individual strain varied, the size of the library generated fell within a range of 0.5 to $2.5 \times 10^5$ from which two to twelve positive clones were analyzed (data not shown). Hybrid phages from one plate are harvested to collect the amplified library, which is stored in 3 ml of LB media with 25% glycerol. The four other primary plates are treated with indicator agar containing 5-bromo-4-chloro-3-indolyl-acetate (X-Acetate) as described below, to find hybrid plaques carrying esterase genes.

Screening of gene banks for esterase activity

The products of the above packaging reactions are infected into E. coli XL1 blue MRF' (Stratagene). Primary plaques of an unamplified gene library are screened for enzyme activity by overlaying the plates with top agar containing X-Acetate for 30 minutes at 65° C. The concentration of substrate in the indicator overlay is diluted from a 4% stock in ethanol or N,N-dimethyl formamide to a concentration generally between 0.1 and 1% (usually about 0.4% is used) in the final solution. Other suitable substrates may be substituted in this procedure including, but not limited to, 5-bromo-4-chloro-3-indolyl-butyrate (X-butyrate), 5-bromo-4-chloro-3-indolyl-proprionate (X-proprionate), 5-bromo-4-chloro-3-indolyl-stearate (X-stearate), 4-methylumbelliferyl-acetate (MUA), 4-methylumbelliferyl-butyrate (MUB), 4-methylumbelliferyl-proprionate (MUP), or other 5-bromo-4-chloro-3-indolyl- or 4-methylumbelliferyl-esters which may be either synthesized or purchased from a commercial vendor such as Sigma Chemical. In order to inactivate background endogenous esterase activity from E. coli, the plates are preheated at 65° C. for 20 minutes. Hybrid phages surviving this procedure are picked and re-screened three times. The extracts are then analyzed for the presence of a protein band with the same mobility as the native protein as described below. The lambda ZAP cloning system permits an excision of smaller plasmid vector to simplify the insert characterization. While other methods may be employed for screening gene banks for esterase activity, i.e. isolation, purification, and N-terminal sequencing of protein; creation of degenerate nucleotide probes from N-terminal sequence; screening of gene bank with degenerate probes, the instant method is efficient and uniquely suited for the purpose of isolation of promising clones.

In particular, the four primary plates with phage colonies generated during the cloning described above, are incubated at 65° C. for 30 min. in order to inactivate some of the potential E. coli esterase activities. Approximately two ml of 0.7% top agar (0.8% NaCl, 10 mM MgSO$_4$) containing about 1 mg/ml of the colorimetric esterase substrate X-Acetate or other substrate (including but not limited to X-butyrate, X-proprionate, X-stearate, and 4-methylumbelliferyl based substrates) is overlaid onto each plate. Expression of cloned esterases can be detected by blue halos around phage colonies (or fluorescent halos in the case of the 4-methylumbelliferyl substates). A typical result for this process can yield a ratio of 1:3000 positive colonies to hybrid phages.

Between two and twelve primary positive phage plaques are generally picked up from each set of plates, resuspended in 50 μl of LB medium, and streaked onto a lawn of E. coli XL1 Blue using sterile paper strips. These purified phage plaques are then overlaid by indicator agar containing X-Acetate as before, and positive plaques were selected as in primary screening experiment. Three rounds of such purification by restreaking are generally sufficient to produce a pure hybrid phage clone expressing esterase activity. All these clone candidates demonstrate significant esterase activity in the X-Acetate plate assay. Several clone candidates from each strain are chosen for further analysis, each representing the progeny of single primary phage plaque.

Testing Protein Profiles Produced by Phage Clones

Production and analysis of protein from the phage clones is performed as follows, but alternative methods are possible: A single plaque from each clone is resuspended in 20 μl of an overnight culture of E. coli XL1 Blue (grown in LB medium with the presence of 10 mM of MgSO$_4$), incubated for 20 min at 24° C. in one well of a 96-well microtiter plate to allow adsorption, transferred into 15-ml test tube containing 2 ml of LB, and grown overnight at 37° C. in a New Brunswick Environmental Shaking incubator set at approximately 300 rpm. Cell debris can be removed by centrifugation at 12,000 g for 10 min. Phage lysates from the clones are then subjected to 4–15% gradient Native polyacrylamide gel electrophoresis (PAGE) for comparison to the native proteins purified from the original organisms. Precast gradient gels are purchased from BioRad Laboratories (catalog number 161-0902) and used according to the manufacturer's instructions for native gels. An esterase preparation from the original strain, purified by HPLC to a single protein band is used as a control on the same gel. Alternatively, a native protein preparation which has not been purified to homogeneity but is purified to a single esterase activity can be used as a control. Protein bands possessing an esterase activity can be detected by applying an X-Acetate overlay and incubating at room temperature for 5–20 min. The relative mobility of the clone candidates can be compared to the native esterase protein.

The data generated for 107 hybrid phage clone candidates from 20 strains are summarized in Table 7, which shows the results of the typical comparison of the esterase activities detected in lambda clones compared to the host strain. For each gene library screened, there is at least one clone candidate expressing an esterase protein with the mobility of the protein purified from the original strain. Several of the λ clone candidates express esterase activities which have mobilities that are different from the major component of the esterase specimens purified from the original strains. Similar sized bands possessing esterase activity are observed in the native organism as minor components (data not shown). These cloned ester hydrolyzing activities are given names depicted in Table 7.

Excision of the Plasmid Vector from the Phage

The lambda ZAP vector allows the phage clone to be conveniently converted into a plasmid vector to allow better physical characterization of the DNA insert and regulated expression of cloned genes. Induction of M13-specific replication by co-infection with the helper phage results in excision of a multi-copy plasmid carrying the cloned insert. 10 μl phage stocks of the lambda hybrids (with about $10^7$ Colony Forming Units (CFU)) and 1 μl of Exassist M13 helper phage (about $10^{10}$ CFU) are used to infect 20 μl of an overnight culture of the *E. coli* XL1 Blue grown in LB. After 20 min at 24° C., the cell suspension is transferred from one of the wells of a 96-well microtiter plate into a 15-ml culture tube, diluted with 2 ml of LB, grown overnight at 37° C. and 300 rpm, heated at 65° C. for 10 min, and cleared by centrifugation at 3000 g for 20 min. Excised plasmids packed in M13 particles are transduced into a lambda resistant strain, XLOLR, that does not permit the development of the M13 helper phage. Ten μl of excised phage lysate are mixed with 30 μl of the overnight culture of the *E. coli* XLOLR strain in one well of 96-well microtiter plate, incubated for 20 min at 37° C. to allow adsorption, diluted with 100 μl of LB, and incubated at 37° C. for 40 min to express the kanamycin (Km) resistance marker (neo) of the plasmid. Cells are plated onto two LB plates supplemented with 40 mg/ml Km. One of the plates also contains 50 μl of a 4% X-Acetate stock solution.

Preliminary experiments are performed by growing plates at 37° C. to demonstrate that a significant phenotypic segregation occurs with the transductant *E. coli* colonies expressing cloned thermophilic esterases. In an extreme case of the CE020 strain, very few colonies not expressing any esterase activity could be re-streaked from primary transductant colonies, which actively expressed esterase activity. Because of this segregation and apparent instability of plasmids containing the active clones, protocols for manipulation of most of the esterase clones needed to be modified as compared with the standard protocol of plasmid excision recommended by Stratagene. It was possible that the instability was due to the function of the cloned protein expressed in the cell, thus it was hypothesized that lowering the growth temperature might overcome the segregation problem, since the esterases were from thermophilic organisms and may not be as active at the lower temperatures.

Therefore, to overcome the problem of instability due to the activity of the esterase containing plasmids, cultivation of *E. coli* cells harboring thermophilic esterases is performed at 28° C. and 30° C., with the result that the effective phenotypic segregation is reduced. Thus, in the event that a cloned thermophilic esterase activity is lethal or partially lethal to the host cell, the growth temperature of the strain should be lowered to 30° C. or even room temperature. The recombinant strains harboring plasmids with active esterase proteins often exhibited a phenotypic segregation of the esterase activity on X-acetate plates. This segregation could be due to plasmid or insert loss if the esterase activity had toxic properties to the cell. To overcome this cells could be grown at lower temperatures (presumably reducing the activity of the cloned thermophilic esterases). Thus strains can be plated with X-Acetate at 28° C. and 37° C. Yellow colonies of faster growing segregants are visible at both temperatures, but contra-selection at 37° C. is much stronger. After determining that temperature makes a large difference in stability of the clone phenotype, further experiments are carried out by plating all plasmid based clones at 26° C., generally for 48 hours. *E. coli* cells are plated in a medium containing X-Acetate to detect expression of cloned esterase by the plasmid, and a degree of segregation in or between primary colonies. Thus, growth of the transformed cells at a temperature which reduces the activity of the cloned esterase is important to the effective isolation of productive plasmids.

In the specific case, eight bacterial colonies derived from each of the phage clones are picked from the plates without X-Acetate, transferred into 100 ml of LB supplemented with 40 mg/ml Km in a 96-well plate and grown overnight. Progeny of these colonies are analyzed by a spot-test using X-Acetate containing agar. Several plasmid clones derived from each phage are chosen for further study by picking ones producing brightest blue halos and least amount of the esterase⁻ segregants.

Selection for the Stable Plasmid Variants

Since it is determined that the plasmid-based vectors carrying esterase genes are often unstable, stable variants of the plasmids are isolated. One method for such isolation is as follows *E. coli* cells carrying excised plasmids are purified using LB plates supplemented with Km and a limited amount of X-Acetate to reduce any potential negative growth impacts from production of the somewhat lethal indole product of the calorimetric reaction. Colonies are selected by their phenotype (in general giving a modest growth rate and intensive blue color) and grown in 2 ml of LB with Km in 15 ml test tube for 48 hours to reach $OD_{600}$ of about 1.0 and harvested by centrifugation at 12,000 g for 1 min. Cell pellets are resuspended in 500 ml of 0.1 M Phosphate buffer pH 7.0 and sonicated using a Sonics & Materials Vibra Cell 375 Watt sonicator at 4° C. Sonication is performed using a microtip, 40% max capacity, 50% time pulse for 45 sec. Lysates are centrifuged at 12,000 g for 5 min and tested for its relative esterase activity. Variants with the highest activity are selected for the next round of growth and analysis. Three rounds of plating followed by growth in liquid medium and activity assays are performed to verify the stability of the clones.

Deviations in specific esterase activity among variants from the same plasmid lineage can be reduced to a factor of three from over a factor of 100 by this procedure. Stabilization of the activity generally occurs at the level corresponding to the highest activity values detected in the first round of stabilization. This could indicate that *E. coli* host mutations are being selected which allow higher tolerance of the cloned protein, rather than simply suppressed activity of cloned toxic gene.

Physical Characterization of Plasmid Clones

Plasmid DNA is extracted from *E. coli* cells using a standard alkali lysis procedure, or other procedures known in the art (37). The DNA is digested with a series of restriction endonucleases such as EcoRI, BamHI, HindIII, PstI, EcoRV, and XbaI to establish digestion pattern of the clone and to determine a size of the cloned DNA fragment. The physical map patterns for the production clones were determined. The insert sizes for each clone are calculated from this data and is summarized in Table 8.

TABLE 7

Cloned Esterase Candidates and Analysis

| # | Native Strain | Activity in phage lysate? | Recombinant Esterases Identified in Phage Lysate | Primary Clone Name | Derivative Plasmid Name | Active Plasmid Derivative | Specific Activity in Stabilized clone U/mg |
|---|---|---|---|---|---|---|---|
| 1 | S1 | + | E001 | lambdaTGE 1.1 | pTGE1.1 | + | 1536 |
| 2 | S1 | + | E001, E022 | lambdaTGE 1.2 | pTGE1.2 | + | |
| 3 | S1 | + | E001, E022 | lambdaTGE 1.3 | pTGE1.3 | + | |
| 4 | S1 | + | E001 | lambdaTGE 1.4 | pTGE1.4 | + | |
| 5 | S1 | + | E001 | lambdaTGE 1.5 | pTGE1.5 | + | 1489 |
| 6 | S1 | nt | nt | lambdaTGE 1.6 | pTGE1.6 | + | |
| 7 | S1 | nt | nt | lambdaTGE 1.7 | pTGE1.7 | + | |
| 8 | S1 | + | E022 | lambdaTGE 1.8 | pTGE1.8 | − | |
| 9 | 54 | + | E002 | lambdaTGE 2.1 | pTGE2.1 | + | 8300 |
| 10 | 54 | + | E023 | lambdaTGE 2.2 | pTGE2.2 | nt | 550 |
| 11 | 54 | + | E023 | lambdaTGE 2.3 | pTGE2.3 | + | |
| 12 | 54 | + | E002 | lambdaTGE 2.4 | pTGE2.4 | + | 2530 |
| 13 | 54 | + | E002 | lambdaTGE 2.8 | pTGE2.8 | − | |
| 14 | 50 | + | E003 | lambdaTGE 3.1 | pTGE3.1 | − | |
| 15 | 50 | + | E003 | lambdaTGE 3.2 | pTGE3.2 | + | 2610 |
| 16 | 50 | + | E003 | lambdaTGE 3.3 | pTGE3.3 | + | |
| 17 | 50 | + | E003 | lambdaTGE 3.4 | pTGE3.4 | + | |
| 18 | GP1 | + | E004 | lambdaTGE 4.1 | pTGE4.1 | − | |
| 19 | GP1 | + | E024 | lambdaTGE 4.2 | pTGE4.2 | + | |
| 20 | GP1 | + | E004 | lambdaTGE 4.3 | pTGE4.3 | + | 320 |
| 21 | GP1 | + | E004 | lambdaTGE 4.4 | pTGE4.4 | − | |
| 22 | GP1 | + | E004 | lambdaTGE 4.5 | pTGE4.5 | nt | |
| 23 | GP1 | + | E004 | lambdaTGE 4.6 | pTGE4.6 | + | 490 |
| 24 | C-1 | + | E005 | lambdaTGE 5.1 | pTGE5.1 | − | |
| 25 | C-1 | + | E025 | lambdaTGE 5.2 | pTGE5.2 | + | |
| 26 | C-1 | + | E005 | lambdaTGE 5.3 | pTGE5.3 | + | 984 |
| 27 | C-1 | − | | lambdaTGE 5.4 | pTGE5.4 | nt | |
| 28 | C-1 | + | E005 | lambdaTGE 5.5 | pTGE5.5 | nt | |
| 29 | 55 | + | E006 | lambdaTGE 6.1 | pTGE6.1 | − | |
| 30 | 55 | +/− | E026 | lambdaTGE 6.2 | pTGE6.2 | − | |
| 31 | 55 | + | E006 | lambdaTGE 6.3 | pTGE6.3 | + | 230 |
| 32 | 55 | + | E006 | lambdaTGE 6.4 | pTGE6.4 | − | |
| 33 | 55 | + | E006 | lambdaTGE 6.5 | pTGE6.5 | − | |
| 34 | 55 | + | E006 | lambdaTGE 6.6 | pTGE6.6 | − | |
| 35 | 46 | +− | *** | lambdaTGE 7.1 | pTGE7.1 | + | 210 |
| 36 | 46 | +− | *** | lambdaTGE 7.2 | pTGE7.2 | + | |
| 37 | 30 | + | E008 | lambdaTGE 8.1 | pTGE8.1 | − | |
| 38 | 30 | + | E008 | lambdaTGE 8.2 | pTGE8.2 | − | |
| 39 | 30 | + | E008 | lambdaTGE 8.3 | pTGE8.3 | + | |
| 40 | 30 | + | E008 | lambdaTGE 8.4 | pTGE8.4 | + | |
| 41 | 30 | + | E008 | lambdaTGE 8.5 | pTGE8.5 | + | 330 |
| 42 | 28 | − | | lambdaTGE 9.1 | pTGE9.1 | + | |
| 43 | 28 | − | | lambdaTGE 9.2 | pTGE9.2 | − | |
| 44 | 28 | + | E009 | lambdaTGE 9.3 | pTGE9.3 | + | 512 |
| 45 | 28 | + | E009 | lambdaTGE 9.4 | pTGE9.4 | + | >270 |
| 46 | 28 | + | E009 | lambdaTGE 9.5 | pTGE9.5 | − | |
| 47 | 28 | + | E009 | lambdaTGE 9.6 | pTGE9.6 | + | |
| 48 | 28 | + | E009 | lambdaTGE 9.7 | pTGE9.7 | + | |
| 49 | 29 | − | | lambdaTGE 10.1 | pTGE10.1 | − | |
| 50 | 29 | − | | lambdaTGE 10.2 | pTGE10.2 | − | |
| 51 | 29 | + | E010 | lambdaTGE 10.3 | pTGE10.3 | + | 546 |
| 52 | 29 | − | | lambdaTGE 10.4 | pTGE10.4 | + | >600 |
| 53 | 29 | + | E010 | lambdaTGE 10.5 | pTGE10.5 | + | |
| 54 | 29 | + | E010 | lambdaTGE 10.6 | pTGE10.6 | − | |
| 55 | 29 | − | | lambdaTGE 10.7 | pTGE10.7 | − | |
| 56 | 29 | + | E010 | lambdaTGE 10.8 | pTGE10.8 | + | |
| 57 | 31 | − | | lambdaTGE 11.1 | pTGE11.1 | + | |
| 58 | 31 | − | | lambdaTGE 11.2 | pTGE11.2 | − | |
| 59 | 31 | + | E011 | lambdaTGE 11.4 | pTGE11.4 | + | |
| 60 | 31 | + | E011 | lambdaTGE 11.9 | pTGE11.9 | + | |
| 61 | 31 | + | E011 | lambdaTGE 11.10 | pTGE11.10 | + | 1052 |
| 62 | 31 | − | | lambdaTGE 11.7 | pTGE11.7 | + | |
| 63 | 26b | + | | lambdaTGE 12.1 | pTGE12.1 | + | |
| 64 | 26b | + | | lambdaTGE 12.2 | pTGE12.2 | + | >600 |
| 65 | 26b | + | | lambdaTGE 12.3 | pTGE12.3 | + | |
| 66 | 26b | + | | lambdaTGE 12.4 | pTGE12.4 | + | |
| 67 | 26b | + | E029 | lambdaTGE 12.5 | pTGE12.5 | − | |
| 68 | 26b | + | E029 | lambdaTGE 12.6 | pTGE12.6 | − | |
| 69 | 27 | + | E013 | lambdaTGE 13.1 | pTGE13.1 | + | |
| 70 | 27 | + | E013 | lambdaTGE 13.2 | pTGE13.2 | + | 428 |
| 71 | 27 | + | E013 | lambdaTGE 13.3 | pTGE13.3 | + | 33 |
| 72 | 27 | + | E013 | lambdaTGE 13.4 | pTGE13.4 | + | |

TABLE 7-continued

Cloned Esterase Candidates and Analysis

| # | Native Strain | Activity in phage lysate? | Recombinant Esterases Identified in Phage Lysate | Primary Clone Name | Derivative Plasmid Name | Active Plasmid Derivative | Specific Activity in Stabilized clone U/mg |
|---|---|---|---|---|---|---|---|
| 73 | 34 | − | | lambdaTGE 14.2 | pTGE14.2 | − | |
| 74 | 34 | + | E014 | lambdaTGE 14.3 | pTGE14.3 | + | 460 |
| 75 | 34 | − | | lambdaTGE 14.4 | pTGE14.4 | − | |
| 76 | 34 | + | E014 | lambdaTGE 14.5 | pTGE14.5 | + | >1200 |
| 77 | 34 | + | E027 | lambdaTGE 14.6 | pTGE14.6 | + | >900 |
| 78 | 34 | − | | lambdaTGE 14.7 | pTGE14.7 | + | |
| 79 | 34 | + | E014 | lambdaTGE 14.8 | pTGE14.8 | − | |
| 80 | 34 | + | E014 | lambdaTGE 14.9 | pTGE14.9 | + | |
| 81 | 62 | + | E015 | lambdaTGE 15.1 | pTGE15.1 | + | |
| 82 | 62 | + | E015 | lambdaTGE 15.2 | pTGE15.2 | + | |
| 83 | 62 | + | E015 | lambdaTGE 15.3 | pTGE15.3 | + | |
| 84 | 62 | + | E015 | lambdaTGE 15.4 | pTGE15.4 | + | |
| 85 | 62 | + | E015 | lambdaTGE 15.5 | pTGE15.5 | + | |
| 86 | 62 | + | E015 | lambdaTGE 15.6 | pTGE15.6 | + | |
| 87 | 62 | + | E015 | lambdaTGE 15.7 | pTGE15.7 | + | |
| 89 | 62 | + | E015 | lambdaTGE 15.9 | pTGE15.9 | + | 4700 |
| 90 | 47 | + | E016 | lambdaTGE 16.1 | pTGE16.1 | + | 600 |
| 91 | 47 | + | | lambdaTGE 16.2 | pTGE16.2 | + | |
| 92 | 47 | + | E016 | lambdaTGE 16.3 | pTGE16.3 | + | >1200 |
| 93 | 47 | + | | lambdaTGE 16.4 | pTGE16.4 | + | |
| 94 | 47 | + | E016 | lambdaTGE 16.5 | pTGE16.5 | + | |
| 95 | 47 | + | | lambdaTGE 16.6 | pTGE16.6 | + | |
| 96 | 47 | + | | lambdaTGE 16.7 | pTGE16.7 | + | |
| 97 | C-3 | + | | lambdaTGE 18.1 | pTGE18.1 | + | nt |
| 98 | C-3 | + | | lambdaTGE 18.2 | pTGE18.2 | − | |
| 99 | 4 | + | E019 | lambdaTGE 19.1 | pTGE19.1 | + | >120 |
| 100 | 4 | + | E019 | lambdaTGE 19.2 | pTGE19.2 | + | |
| 101 | 4 | + | E019 | lambdaTGE 19.3 | pTGE19.3 | + | |
| 102 | 4 | + | E019 | lambdaTGE 19.4 | pTGE19.4 | + | 1960 |
| 103 | 4 | + | E019 | lambdaTGE 19.5 | pTGE19.5 | − | |
| 104 | 4 | + | E019 | lambdaTGE 19.6 | pTGE19.6 | + | |
| 105 | 7 | − | | lambdaTGE 20.1 | pTGE20.1 | + | |
| 105 | 7 | − | | lambdaTGE 20.2 | pTGE20.2 | + | |
| 106 | 7 | + | E020 | lambdaTGE 20.3 | pTGE20.3 | + | 2470 |
| 107 | 7 | + | E028 | lambdaTGE 20.4 | pTGE20.4 | + | |
| 108 | 7 | − | | lambdaTGE 20.5 | pTGE20.5 | + | |
| 109 | 7 | + | E020 | lambdaTGE 20.6 | pTGE20.6 | + | |
| 110–104 | 32 | − | | lambdaTGE 21.1–21.5 | pTGE21.1–21.5 | + | |
| 105 | 32 | + | E017b | lambdaTGE 21.6 | pTGE21.6 | + | |
| 106 | 32 | + | E017b | lambdaTGE 21.8 | pTGE21.8 | + | 930 |
| 107 | 32 | + | E017b | lambdaTGE 21.9 | pTGE21.9 | + | |

***No protein detected by activity stain.

TABLE 8

Production Clone Data

| Production Enzyme | Selected Production plasmid | Recombinant Strain Name | Approx. DNA Insert Size[1] (kb) | Specific Activity in Typical Recombinant Crude Extract[2] (U/mg) |
|---|---|---|---|---|
| recE001 | pTGE1.1 | CE001 | 3.5 | 1,536 |
| recE001.5 | pTGE1.5 | CE001.5 | nt | nt |
| recE002 | pTGE2.1 | CE002 | 2.5 | 8,300 |
| recE003 | pTGE3.2 | CE003 | 4.1 | 2,610 |
| recE004 | pTGE4.6 | CE004 | 3.4 | 490 |
| recE005 | pTGE5.3 | CE005 | 1.9 | 984 |
| recE006 | pTGE6.3 | CE006 | 6 | 230 |
| recE007 | pTGE7.1 | CE007 | 3.7 | 210 |
| recE008 | pTGE8.5 | CE008 | 3.2 | 330 |
| recE009 | pTGE9.4 | CE009 | 4.5 | 270 |
| recE010 | pTGE10.3 | CE010 | 2.5 | 546 |
| recE011 | pTGE11.10 | CE011 | 2.4 | 1,052 |
| recE029 | pTGE12.2 | CE029 | 4.2 | 600 |
| recE013 | pTGE13.2 | CE013 | 2.2 | 428 |
| recE014 | pTGE14.3 | CE014 | 2.5 | 460 |
| recE015 | pTGE15.9 | CE015 | 3.5 | 4,700 |
| recE016 | pTGE16.1 | CE016 | 2 | 600 |
| recE016.3 | pTGE16.3 | CE016.3 | 1.8 | 1,200 |
| recE017b | pTGE21.8 | CE017b | 3.8 | 930 |
| recE019 | pTGE19.4 | CE019 | 3.7 | 1,960 |
| recE020 | pTGE20.3 | CE020 | 2.7 | 2,470 |
| recE022 | pTGE1.8 | CE022 | nt | nt |
| recE023 | pTGE2.2 | CE023 | 3.7 | 550 |
| recE024 | pTGE4.2 | CE024 | nt | nt |
| recE025 | pTGE5.2 | CE025 | nt | nt |

TABLE 8-continued

Production Clone Data

| Production Enzyme | Selected Production plasmid | Recombinant Strain Name | Approx. DNA Insert Size[1] (kb) | Specific Activity in Typical Recombinant Crude Extract[2] (U/mg) |
|---|---|---|---|---|
| recE027 | pTGE14.6 | CE027 | 2.6 | 900 |
| recE028 | pTGE20.4 | CE028 | 2.5 | nt |

[1]Insert sizes are estimated from the agarose gel. The estimated insert size is based on a vector size of 4.5 kb and the accuracy which could be achieved analyzing each of the six digestion patterns.
[2]Specific activity is calculated as the amount of p-nitrophenol produced in micromoles per minute per milligram of total protein as described in Example 2. The numbers reported here are from a typical production batch and may vary.

Generation of the tag sequences for PCR identification of esterase containing inserts The DNA sequences of the ends of the insert fragment carrying esterase genes can be determined by sequencing the ends of the inserts using standard T7 and S6 primers to produce unique tags of the cloned DNA. Sequence analysis can be carried out to design PCR primers which can uniquely amplify the DNA inserts from both the clones and the host organisms. These tags can be potentially used to generate this DNA fragment from the chromosome of the studied organisms using PCR technique.

Screening of the Cosmid library with an oligonucleotide probe

For cloning of enzymes which cannot be cloned by activity, other methods are used. A degenerative probe is prepared to the N-terminal sequence of the protein and hybridized to plaques from the recombinant phage bank. Alternatively, degenerate PCR amplification probes can be made using the N-terminal sequence or sequences obtained from the n-termini of internal protein fragments which have been obtained after proteolytic digestion of the enzyme. Using these sequences, a probe can be made from an amplified region between the N-terminus and an internal fragment or between two internal fragment sequences to identify a clone carrying the DNA encoding for the enzyme of interest.

EXAMPLE 18

Overproduction and Overexpression of Esterases
Production of recombinant esterase The production strains used are listed in Table 8. Cloned enzymes are produced from *E. coli.* strain XLOLR. Alternatively, any suitable *E. coli* host may be used, including but not limited to HB101, C600, TG1 and XL1-Blue.

Several media can be used to produce cloned esterases. LB (10 gm/l tryptone, 5 gm/l yeast extract and 10 gm/l NaCl) and Terrific Broth (12 gm/l tryptone, 24 gm/l yeast extract and 4 ml/l glycerol supplemented with 100 ml of a sterile solution of 0.17 M $KH_2PO_4$, 0.72 M $K_2HPO_4$ after autoclaving) have been tested and the results from optimal growth conditions for the production strains listed in Table 9 below. Each media is supplemented with 10–50 μg/ml kanamycin.

Optimal production media depends on a number of factors, including media cost and specific activity of the produced proteins. TB media is a richer media and therefore more expensive. For instance, in the case of CE009, while more total units are produced in a single fermentation run, not enough is produced to justify the higher cost of the media. In addition, the specific activity is higher for the LB media preparation.

Fermentation production is run in 17 L Fermentors (15 L working volume/LH Fermentation) at 30° C., 600 RPM, and 0.5 vvm air flow. The seed train is established as follows. A loopful of a frozen production culture is used to inoculate 50 ml of production media in a 250 ml Erlenmeyer flask. The flask is incubated at 30° C. for two days (250 RPM) and then used to inoculate a 1 liter flask with 250 ml of production media. This flask is incubated 1 day at 30° C. and 250 RPM. The 1 liter flask is used to inoculate the fermentor.

Production of substantially purified preparations from a cell paste of strains producing the recombinant enzymes are carried out similar to the methods described in Example 4 and the specific protocols described in Examples 14–34 for the native proteins.

TABLE 9

Preferred media for Strains CE001–CE010

| | LB | | | TB | | | |
|---|---|---|---|---|---|---|---|
| Strain | Specific Activity (U/mg) | Total Cell mass (g) | Total Units | Specific Activity (U/mg) | Total Cell mass (g) | Total Units | Current Growth media of choice* |
| CE001 | 213 | 0.41 | 4500 | 138 | 0.84 | 6725 | TB |
| CE002 | 98 | 0.52 | 1625 | 101 | 0.93 | 4575 | TB |
| CE003 | 272 | 0.42 | 4200 | 22 | 0.87 | 1025 | LB |
| CE004 | 208 | 0.47 | 3650 | 28 | 0.90 | 1350 | LB |
| CE005 | 123 | 0.40 | 3675 | 125 | 1.00 | 7600 | TB |
| CE006 | 85 | 0.42 | 2125 | 71 | 0.62 | 2175 | LB |
| CE007 | 9 | 0.39 | 225 | 19 | 0.75 | 500 | TB |
| CE008 | 71 | 0.51 | 2775 | 45 | 0.80 | 2350 | LB |
| CE009 | 109 | 0.42 | 2650 | 74 | 0.81 | 3050 | LB |
| CE010 | 418 | 0.42 | 2200 | 225 | 0.95 | 8375 | TB |

*Given current media costs

Optimization of esterase production

Further optimization of esterase production is performed by media studies in shake flasks followed by further optimization at the 1 liter to 20 liter scale. Depending on the enzyme, final fermentation conditions can involve either a fed-batch or continuous fermentation process. Since the esterase activity being analyzed is intracellular, the use of a clear or defined media such as TT media is necessary.

Organisms of interest are grown and cell pellets are collected by centrifugation. Pellets are disrupted by sonication and enzymes can be purified using the standard techniques of ion exchange and gel permeation chromatography described in Examples 3 and 4. Growth conditions including media composition, pH, and temperature are optimized at the small scale (ie. shake flasks, and 1 liter fermentors) to give the highest cell density while retaining the highest amount of enzyme.

Isolation of High-production mutants

Several simple mutagenesis schemes are used to try and isolate high-producing mutants of the different activities of interest. These include mutagenesis with uv-light or chemical mutagens such as ethylmethane sulfanoate (EMS) or N-methyl-N'-nitro-N-nitrosoguanidine (MNNG). The cells are treated with varying concentrations of the mutagen (or varying exposure times with uv light) according to methods described in Miller (38). Optimal concentrations of the different mutagens with different organisms vary. In general, killing concentrations allowing 80% survival for EMS, approximately 50% survival for MNNG, or 10–50% survival for uv light are desired. Mutagenized cultures are then grown up, allowing the mutagen to wash out and plated onto solid media.

Mutants are identified by applying an esterase plate screen to the cells. For example with an esterase screen, an agar overlay containing a colorimetric or fluorogenic substrate such as 5-bromo-4-chloro-3-indolyl-acetate or 4-methyulumbelliferyl acetate will be applied. Colonies which show a significant increase in activity by hydrolysis of the substrate will be identified.

Candidate mutants are then analyzed by native polyacrylamide gel electrophoresis and compared to the parental strain. Standard assay methods described in Example 2 or the rapid esterase/lipase screen described in Example 12 can then be applied to identify any differences in amounts of enzyme activity. If a production level increase is large an increased band on either a Native or SDS polyacrylamide gel after coomassie staining may be seen. Strains with multiple activities can also be differentiated in this way, verifying that the increase is in the enzyme of interest. It is then confirmed that the mutants have unaltered kinetic and substrate properties as the parental enzyme. The majority of mutations identified by this approach are expression mutations which can be isolated in either a promoter region, repressor molecule, or other controlling element. Most mutations in the enzyme structural genes will likely inactivate the enzyme, however, an enhanced activity may also be isolated. If it is apparent that the mutation increases the activity of the desired protein band but not the intensity of the band on a coomassie stained gel, the mutant is recharacterized to determine if it is a more efficient biocatalyst.

EXAMPLE 19

Esterase Screening Kit

A large subset of enzymes can be packaged into an easy to use screening kit to rapidly analyze a large number of enzymes at once. The kits are formulated to eliminate as many potential errors as possible and each enzyme is provided in a lyophilized form if possible near its optimal buffer and reaction conditions.

Many different formats for the kit are possible, from a series of glass vials, to varying size microtiter plates constructed of different plastic materials. The microtiter plate is favored because of its ease of handling and manipulating. Most microtiter plates are made of polystyrene however, which will not stand up to most organic solvents. For experiments which utilize aqueous solvent, the polystyrene is not a problem. Other more tolerant plastics such as polypropylene are available and are ideal for the kit. Large size 24-well microtiter plates which allow 3 ml of sample to be assayed (allowing enough sample for multiple TLC or HPLC analysis) have been developed. Other formats may also be useful for different applications.

Each kit is prepared by addition of a stir bar, buffer (0.1M Na phosphate pH 7.0) and 1 U of each enzyme to each well of a 24 well polypropylene tray (Tomtec). Enzymes are aliquotted into each well or vial in set amounts so that it can be assured that an equal amount of activity is provided for comparison. The entire kit is then lyophilized, sealed with heat seal foil (3M) and labeled. Separate experiments found that there was no significant loss in enzyme activity when proteins were lyophilized in the kit trays as suggested by earlier experiments comparing glass to plastic. In addition to enzymes, each kit contains four control wells that are composed of buffers at pH's from 6–9 since it was found that some of the substrates tested tend to be unstable in buffered solutions which can confuse positive results with autohydrolysis. The rest of the kit is composed of an instruction manual, a data sheet, a sample preparation vial a glass eye dropper and a plastic eye dropper. The kit is formulated in such a way that only solvent and substrate need be added to each well. The rapid-screen indicator dye method described in Example 12 can also be included in each well or vial. This makes a preliminary qualitative determination of enzyme effectiveness simple and fast.

EXAMPLE 20

Cloning and Characterization of Recombinant Proteins

The cloning and characterization of recombinant proteins from strain isolates which produced the native isolated protein (as listed in Table 1) was carried out as described in Example 37. Lambda expression vectors were isolated as described above (specific named isolates are shown in Table 7). E. coli clones harboring the excised hybrid phage-plasmids were derived as summarized in Table 7, and were finally selected for esterase activity by subsequent screening, which after 3 rounds of stabilizing procedure was calculated to approximate units of activity per mg of total cell protein obtained. Esterase activity stain gel used to screen positive phage library candidates for the recombinant proteins allowed the identification of alternative recombinant proteins as well. Production of the recombinant protein is carried out as described above, using TB for the media and purifying the enzyme as described for the native (nonrecombinant) protein in Example 4.

EXAMPLE 21

Sequencing of Recombinant Proteins

The isolation and cloning of the genes encoding for the enzymes of the instant invention results in DNA segments in which an open reading frame (ORF) may be found which corresponds to translated protein amino acid sequence. Sequencing of the DNA inserts which contain the corresponding nucleic acid sequence which encode for the protein enzymes can be conducted by the usual methods, either manually or using automated apparatus.

Once obtained, analysis of the nucleic acid sequence can reveal the presence of alternative start codons, a phenomenon recognized in the art, however the encoded protein enzyme will comprise at minimum a core protein ORF. FIG. 6A is an isolated nucleic acid sequence, and translated amino acid sequence which correspond to E001 (SEQ ID NO.:1 and SEQ ID NO.:2) enzyme ORF, alternative start codons are underlined. FIG. 6B is an isolated nucleic acid sequence, and translated amino acid sequence which correspond to E009 (SEQ ID NO.:3 and SEQ ID NO.:4) enzyme ORF, alternative start codons are underlined. FIG. 6C is the cloned isolated nucleic acid sequence which contains the E011 (SEQ ID NO.:5 and SEQ ID NO.:6) ORF, alternative start codons are underlined. FIG. 6D is the cloned isolated nucleic acid sequence which contains the E101 (SEQ ID NO.:7 and SEQ ID NO.:8) ORF, alternative start codons are underlined. FIG. 6E is the cloned isolated nucleic acid sequence which contains the E019 (SEQ ID NO.:9 and SEQ ID NO.:10) ORF, alternative start codons are underlined. FIG. 6F is the cloned isolated nucleic acid sequence which contains the E005 (SEQ ID NO.:11 and SEQ ID NO.:12) ORF, alternative start codons are underlined. FIG. 6G is the cloned isolated nucleic acid sequence which contains the E004 (SEQ ID NO.:13 and SEQ ID NO.:14) ORF, alternative start codons are underlined. FIG. 6H is the cloned isolated nucleic acid sequence which contains the E006 (SEQ ID NO.:15 and SEQ ID NO.:16) ORF, alternative start codons are underlined. FIG. 6I is the cloned isolated nucleic acid sequence which contains the E008 (SEQ ID NO.:17 and SEQ ID NO.:18) ORF, alternative start codons are underlined. FIG. 6J is the cloned isolated nucleic acid sequence which contains the E010 (SEQ ID NO.:19 and SEQ ID NO.:20) ORF, alternative start codons are underlined. FIG. 6K is the cloned isolated nucleic acid sequence which contains the E013 (SEQ ID NO.:21 and SEQ ID NO.:22) ORF, alternative start codons are underlined. FIG. 6L is the cloned isolated nucleic acid sequence which contains the E015 (SEQ ID NO.:23 and SEQ ID NO.:24) ORF, alternative start codons are underlined. FIG. 6M is the cloned isolated nucleic acid sequence which contains the E016 (SEQ ID NO.:25 and SEQ ID NO.:26) ORF, alternative start codons are underlined. FIG. 6N is the cloned isolated nucleic acid sequence which contains the E017 (SEQ ID NO.:27 and SEQ ID NO.:28) ORF, alternative start codons are underlined. FIG. 6O is the cloned isolated nucleic acid sequence which contains the E020 (SEQ ID NO.:29 and SEQ ID NO.:30) ORF, alternative start codons are underlined. FIG. 6P is the cloned isolated nucleic acid sequence which contains the E027 (SEQ ID NO.:31 and SEQ ID NO.:32) ORF, alternative start codons are underlined. FIG. 6Q (SEQ ID NO.:33) contains the nucleic acid sequence of the 5' end, and FIG. 6R (SEQ ID NO.:34) contains the 3' end of the insert which contains the E003. FIG. 6S (SEQ ID NO.:35) contains the nucleic acid sequence of the 5' end, and FIG. 6T (SEQ ID NO.:36) contains the 3' end of the insert which contains the E004 ORF. FIG. 6U (SEQ ID NO.:37) contains the nucleic acid sequence of the 3' end of the insert which contains the E014 ORF. These nucleic acid sequences allow one of ordinary skill in the art, practicing routine methods to complete characterization of the full length nucleic acid sequence of the insert, the detection of clones via hybridization, and the creation of amplification primers for detecting, amplifying and generating full length homologous genes.

TABLE 10

ThermoCat ™ E001–E020 Spec comparison

| Biocatalyst | Specific Activity | MW | Temperature Opt. | Temperature Useful Range | pH Opt. | pH 50% Range | Half Life (hours) 40° C. | Half Life (hours) 60° C. |
|---|---|---|---|---|---|---|---|---|
| E001 | 0.5 u/mg | 22 kDal | 45° C. | RT–55° C. | 7.5 | broad | +++ | 34 |
| E002 | 1.0 u/mg | 28 kDal | 45° C. | RT–60° C. | 7.0 | broad | +++ | 30 |
| E003 | 0.5 u/mg | 28 kDal | 45° C. | RT–60° C. | 7.0 | broad | +++ | 60 |
| E004 | 0.6 u/mg | 36 kDal | 45° C. | RT–60° C. | 6.5 | <6.0–8.0 | +++ | 10 |
| E005 | 6.7 u/mg | 28 kDal | 45° C. | RT–60° C. | 7.0 | broad | +++ | 15 |
| E006 | 3.6 u/mg | 36 kDal | 45° C. | RT–60° C. | 6.5–7.0 | broad | +++ | 30 |
| E007 | 2.7 u/mg | 28 kDal | 35° C. | RT–60° C. | 7.0 | <6.0–8.0 | >480 | 90 |
| E008 | 1.5 u/mg | 28 kDal | 40° C. | RT–55° C. | 6.5–7.0 | <6.0–8.0 | 50 | <1 |
| E009 | 1.3 u/mg | 36 kDal | 45° C. | RT–50° C. | 6.5–7.0 | <6.0–8.0 | +++ | <1 |
| E010 | 4.9 u/mg | 46 kDal | 45° C. | RT–55° C. | 6.5 | <6.0–8.0 | +++ | <1 |
| E011 | 6.2 u/mg | 36 kDal | 45° C. | RT–60° C. | 6.5–7.0 | <6.0–8.0 | +++ | 4 |
| E012 | 10.7 u/mg | 28 kDal | 45° C. | RT–60° C. | <=6.0 | <6.0–7.5 | +++ | 240 |
| E013 | 5.3 u/mg | 36 kDal | 45° C. | RT–60° C. | 7.0 | <6.0–8.0 | >480 | 6 |
| E014 | 0.9 u/mg | 36 kDal | 45° C. | RT–50° C. | 7.0 | <6.0–8.0 | +++ | <1 |
| E015 | 3.0 u/mg | 36 kDal | 45° C. | RT–60° C. | >9.0 | 7.5–>9.0 | +++ | 6 |
| E016 | 1.2 u/mg | 28 kDal | 45° C. | RT–60° C. | nd | nd | +++ | 240 |
| E017b | 0.4 u/mg | 36 kDal | 40° C. | RT–50° C. | >9.0 | 7.5–>9.0 | +++ | 4 |
| E018 | 0.2 u/mg | nd | nd | nd | nd | nd | 120 | 30 |
| E019 | 0.9 u/mg | 30 kDal | 45° C. | RT–60° C. | >9.0 | broad | nd | 25 |
| E020 | 3.9 u/mg | 28 kDal | 45° C. | RT–60° C. | broad | broad | +++ | 12 |

*broad pH range refers to >50% activity through all pH tested (6.0–8.5)

EXAMPLE 22

Ester Chain Length Specificity Characterization

The enzymes of the instant invention can be further characterized by testing for enzymatic specificty for substrate esters of different chain length. Such assays can be conducted using the methods described above, selecting the appropriate substrates. FIG. 7 depicts the result of colormetric esterase activity assays of the various enzymes. The graphed data was obtained where the reaction conditions were estimated to be approximately 0.1 U/l ml reaction, with 500 ug/ml substrate, where 1 Unit (U) is calculated for each enzyme stock preparation in relation to esterase activity where 1 Unit is the amount of enzyme needed to hydrolize approximately 1 umol of p-nitrophenyl proprionate per minute. The data is reported as approximate maximum $OD_{410\,nm}$ during incubation.

FIG. 7A graphs data using the substrate bis-p-nitrophenyl-carbonate. The highest activity was found with enzyme E019, which showed an $OD_{410\ nm}$ of 0.30 after 4 hours incubation. FIG. 7B graphs data using the substrate p-nitrophenyl-acetate. The highest activity was found with enzyme E020, which showed an $OD_{410\ nm}$ of 3.571 after 400 seconds incubation. FIG. 7C graphs data using the substrate bis-p-nitrophenyl-propionate. The highest activity was found with enzyme E003, which showed an $OD_{410\ nm}$ of 1.4 after 600 seconds incubation. FIG. 7D graphs data using the substrate bis-p-nitrophenyl-butyrate. The highest activity was found with enzyme E020, which showed an $OD_{410\ nm}$ of 1.19 after 160 seconds incubation. FIG. 7E graphs data using the substrate bis-p-nitrophenyl-caproate. The highest activity was found with enzyme E009, which showed an $OD_{410\ nm}$ of 0.37 after 560 seconds incubation. FIG. 7F graphs data using the substrate bis-p-nitrophenyl-caprylate. The highest activity was found with enzyme E003, which showed an $OD_{410\ nm}$ of 0.07 after 360 seconds incubation. FIG. 7G graphs data using the substrate bis-p-nitrophenyl-laurate. The highest activity was found with enzyme E016, which showed an $OD_{410\ nm}$ of 0.11 after 480 seconds incubation.

EXAMPLE 23 pH Dependent Assay for Entantiomer Esterase Specificity

Figure 8A:
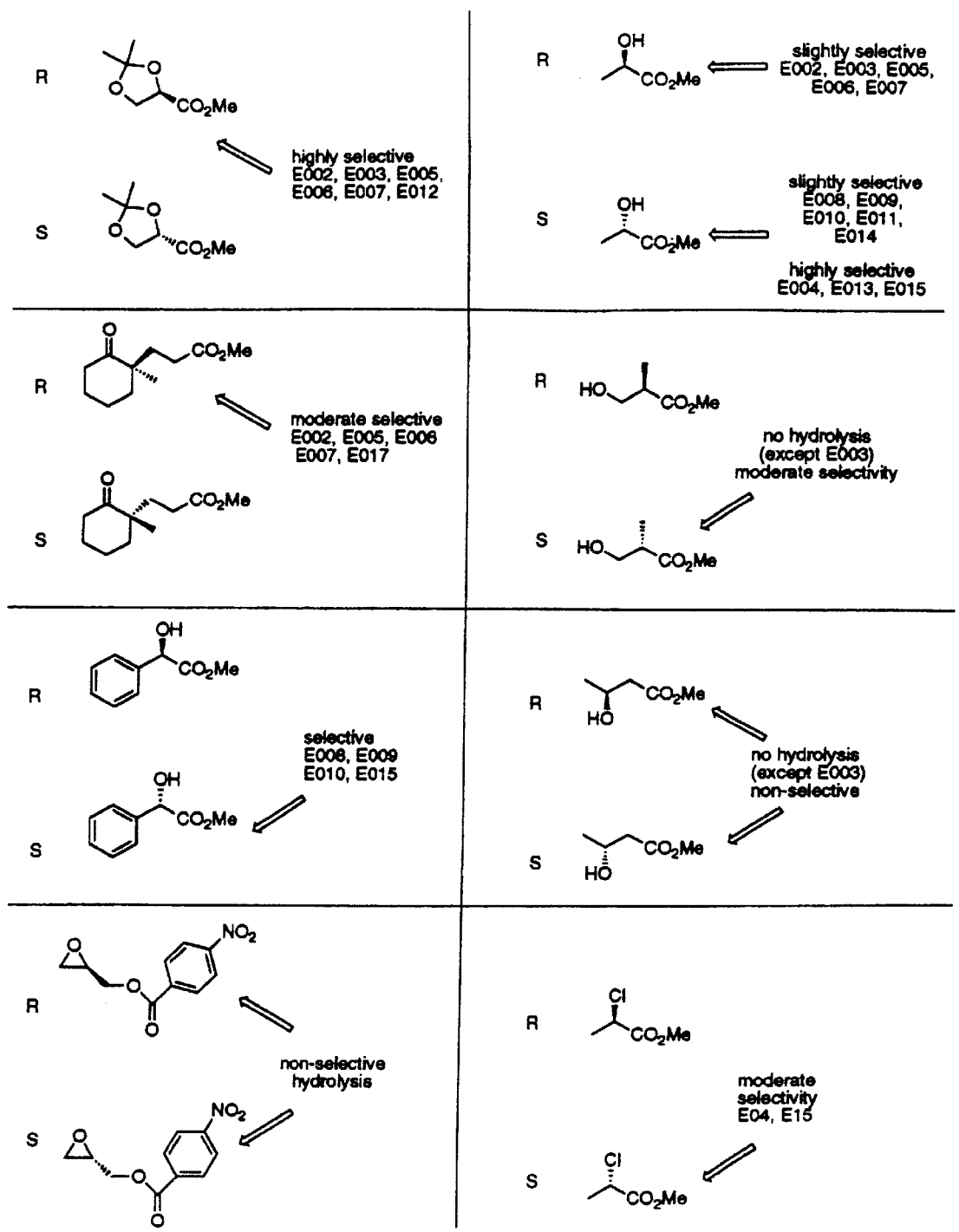

The enzymes of the invention can be further characterized by testing for enzymatic specificity for specific entantiomer substrate esters of different chiral structure. Such assays can be performed using the methods described above, selecting the appropriate substrate. The results of screening are depicted in FIG. 8. FIG. 8A summarizes the results of colorometric esterase activity assays for entaniomer specificity. FIG. 8B depicts quantitative colorometric assay data results in terms of minutes required for detectable color change, indicating pH change. The numbers report time in minutes following addition of enzyme. NH indicates no hydrolysis was detected after 3 days, and o/n indicates no hydrolysis after overnight incubation (approximately 6–15 hours). Substrates 1, 2, 4, 6, 8, and 9 were dissolved to a concentration of 40 mM in a 25 mM KPi buffer, pH=7.4, containing ~0.005% of bromothymol blue. Substrates 3, 5 and 7 were dissolved to a concentration of 10 mM in a 5 mM KPi buffer, pH=7.4, containing ~0.005% of bromothymol blue and up to 10% MeCN as cosolvent. The esterases tested were added in the amount of 1 U per well, as determined by hydrolysis of PNP-propionate. The control reaction was the substrate solution, with no added enzyme.

EXAMPLE 24

Characterization of Enzyme Activity Against Para-nitroanilide Compounds

The enzymes of the invention can be further characterized by testing for enzymatic specificity for alternative substrates which are similar to esters. Such assays can be performed using the methods described above, selecting the appropriate substrates. The enzymes of the invention were characterized against the anilides and esters listed below and the results depicted in FIG. 9. The assays were performed according to the general formula:

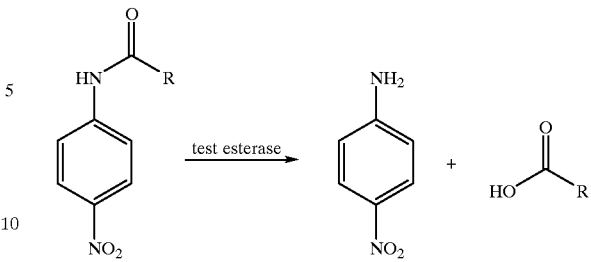

Test reactions were run in microtiter plates with each reaction in a total volume of about 100 ul. Each reaction consisted of about 75 ul of pH7.0 phosphate buffer, 5 ul of 5 mM substrate, and 20 ul of enzyme adjusted to 50 U/ml (where I U is approximatly the amount needed to hydrolize 1 uM of p-nitrophenyl-propionate in 1 minute). The final reaction mixture contained about 1 U enzyme and 0.25 mM substrate in each well. The reactions were incubated for about 2.5 hours at 37C. Control reactions, lacking enzyme, were run in adjacent wells. A control containing no substrate was also run on each plate. Following incubation, the plates were read at 405 nm in a BIORAD Model 3550 microplate reader. Values of the controls were subtracted from the experimental well values to determine net activity.

REFERENCES

1. Barman, T. E. *Enzyme Handbook,* Springer-Verlag, Berlin-Heidelberg. 1969.
2. Dixon, M., E. C. Webb, C. J. R. Thorne and K. F. Tipton. *Enzymes,* Academic Press, New York. 1979.
3. Santaniello, E., P. Ferraboschi, P. Grisenti and A. Manzocchi. (1992) The biocatalytic approach to the preparation of enantiomerically pure chiral building blocks. *Chem. Rev.* 92:1071–1140.
4. Klibanov, A. (1989) Enzymatic catalysis in anhydrous organic solvents. *TIBS.* 14:141–144.
5. Fitzpatrick, P. and A. Klibanov. (1991) How can the solvent affect enzyme enantioselectivity. *J Am Chem Soc.* 113:3166–3171.
6. Sigurgisladottir, S., M. Konraosdottir, A. Jonsson, J. K. Kristjansson and E. Matthiasson. (1993) Lipase Activity of Thermophilic Bacteria from Icelandic Hot Springs. *Biotechnol Lett.* 15:361–366.
7. Margolin, A. L. (1993) Enzymes in the Synthesis of Chiral Drugs—Review. *Enzyme Microb Technol.* 15:266–280.
8. Hodgson, J. (1992) Controlling chirality in enzymatic sysnthesis. *Biotechnology.* 10:1093–1097.
9. Klunder, A., F. Gastel and B. Zwanenburg. (1988) Structural requirements in the enzymatic optical resolution of bicyclic esters using pig liver esterase. *Tetrahedron Letters.* 29:2697–2700.
10. Rao, Y. K., C. K. Chen and J. Fried. (1993) Enantiospecific and Regiospecific Partial Hydrolysis of Racemic Diol Diacetates by Pig Liver Esterase. *J Org Chem.* 58:1882–1886.
11. Faulds, C. B. and G. Williamson. (1993) Ferulic Acid Esterase from *Aspergillus niger*—Purification and Partial Characterization of 2 Forms from a Commercial Source of Pectinase. *Biotechnol Appl Biochem.* 17:349–359.
12. Chattopadhyay, S. and V. R. Mamdapur. (1993) Enzymatic Esterification of 3-Hydroxybutyric Acid. *Biotechnol Lett.* 15:245–250.
13. Frykman, H., N. Ohrner, T. Norin and K. Hult. (1993) S-Ethyl Thiooctanoate as Acyl Donor in Lipase Catalysed Resolution of Secondary Alcohols. *Tetrahedron Lett.* 34:1367–1370.
14. Hedstrom, G., M. Backlund and J. Slotte. (1993) Enantioselective synthesis of ibuprofen esters in aot/isooctane microemulsions by *Candida cylindracea* lipase. *Biotech and Bioeng.* 42:618–624.
15. Pozo, M. and V. Gotor. (1993) Chiral carbamates through an enzymatic alkoxycarbonylation reaction. *Tetrahedron.* 49:4321–4326.
16. Puertas, S., R. Brieva, F. Rebolledo and V. Gotor. (1993) Lipase Catalyzed Aminolysis of Ethyl Propiolate and Acrylic Esters—Synthesis of Chiral Acrylamides. *Tetrahedron.* 49:4007–4014.
17. Bonini, C., R. Racioppi, G. Righi and L. Viggiani. (1993) Polyhydroxylated Chiral Building Block by Enzymatic Desymmetrization of Meso 1,3 Syn Diols. *J Org Chem.* 58:802–803.
18. Chenevert, R. and R. Gagnon. (1993) Lipase-Catalyzed Enantioselective Esterification or Hydrolysis of 1-O-Alkyl-3-O-Tosylglycerol Derivatives—Practical Synthesis of (S)-(+)-1-O-Hexadecyl-2,3-di-O-Hexadecanoylglycerol, a Marine Natural Product. *J Org Chem.* 58:1054–1057.
19. Henly, R., C. J. J. Elie, H. P. Buser, G. Ramos and H. E. Moser. (1993) The Influence of Protecting Groups on Lipase Catalyzed Transesterifications—Enzymatic Resolution of Racemic cis-1,3-Cyclopentanediol Derivatives. *Tetrahedron Let.* 34:2923–2926.
20. Patil, P., A. Chattopadhyay, S. Udupa and A. Banerji. (1993) Biotransformation with Rhizopus arrhizus: preparation of enantiomers of sulcatol. *Biotechnol Lett.* 15:367–372.
21. Ng, T. K. and W. F. Kenealy. Industrial Applications of Thermostable Enzymes. In *Thermophiles: General, Molecular, and Applied Microbiology.* Ed. by T. D. Brock, Wiley-Interscience, p. 197–215. 1986.
22. Wiegel, J. and L. G. Ljungdahl. (1986) The Importance of Thermophilic Bacteria in Biotechnology. *Crc Crit. Rev. of Biotech.* 3:39–108.
23. Saiki, R. K., D. H. Gelfand, S. Stoffel, S. J. Scharf, R. Higuchi, G. T. Horn, K. B. Mullis and H. A. Erlich. (1988) Primer-Directed Enzymatic Amplification of DNA with a Thermostable DNA Polymerase. *Science.* 239:487–491.
24. Stoflet, E. S., D. D. Koeberl, G. Sarkar and S. S. Sommer. (1988) Genomic Amplification with Transcript Sequencing. *Science.* 239:487–491.
25. Brumm, P., R. Hebeda and M. Teague. (1988) Purification and properties of a new, commercial, thermostable *Bacillis stearothermophilus* alpha-amylase. *Food Biotech.* 2:67–80.
26. Cowan, D. A. (1992) Enzymes from thermophilic archaebacteria: current and future applications in biotechnology. *Biochem Soc Symp.*
27. Mozhaev, V. V., K. G. Poltevsky, V. I. Slepnev, G. A. Badun and A. V. Levashov. (1991) Homogeneous solutions of hydrophilic enzymes in nonpolar organic solvents. New systems for fundamental studies and biocatalytic tansformations. *Febs Lett.* 292:159–61.
28. Puchegger, S., B. Redl and G. Stoffler. (1990) Purification and properties of a thermostable fumarate hydratase from the archaeobacterium Sulfolobus solfataricus. *J Gen Microbiol.*
29. Hanner, M., B. Redl and G. Stoffler. (1990) Isolation and characterization of an intracellular aminopeptidase from the extreme thermophilic archaebacterium Sulfolobus solfataricus. *Biochim Biophys Acta.* 1033:148–53.
30. Smith, L. D., N. Budgen, S. J. Bungard, M. J. Danson and D. W. Hough. (1989) Purification and characterization of glucose dehydrogenase from the thermoacidophilic archaebacterium Thermoplasma acidophilum. *Biochem J.* 261:973–7.
31. Veronese, F. M., E. Boccu, O. Schiavon, C. Grandi and A. Fontana. (1984) General stability of thermophilic enzymes: studies on 6-phosphogluconate dehydrogenase from *Bacillus stearothermophilus* and yeast. *J Appl Biochem.* 6:39–47.
32. Tulin, E. E., Y. Amaki, T. Nagasawa and T. Yamane. (1993) A *Bacillus stearothermophilus* Esterase Produced by a Recombinant *Bacillus brevis* Stabilized by Sulfhydryl Compounds. *Biosci Biotechnol Biochem.* 57:856–857.
33. Sugihara, A., M. Ueshima, Y. Shimada, S. Tsunasawa and Y. Tominaga. (1992) Purification and characterization of a novel thermostable lipase from *Pseudomonas cepacia.* *J Biochem.* 112:598–603.
34. Sugihara, A., T. Tani and Y. Tominaga. (1991) Purification and characterization of a novel thermostable lipase from Bacillus sp. *J Biochem.* 109:211–216.
35. Emanuilova, E., M. Kambourova, M. Dekovska and R. Manolov. (1993) Thermoalkalophilic Lipase-Producing Bacillus Selected by Continuous Cultivation. *FEMS Microbiol Lett.* 108:247–250.
36. Weber, J. M., S. Johnson, V. Vonstein, M. C. Casadaban and D. C. Demirjian. (1995) A chromosomal integration system for stable gene transfer into *Thermus flavus. Bio/Technology.* 13:271–275.
37. Sambrook, J., E. F. Fritsch and T. Maniatis. *Molecular Cloning, A Laboratory Manual* Cold Spring Harbor Laboratory Press, NY. 1989.
38. Miller, J. H. *A short course in bacterial genetics,* Cold Spring Harbor Laboratory Press, Cold Spring Harbor. 1992.
39. Wu, S. H., Z. W. Guo and C. J. Sih. (1990) Enhancing the enantioselectivity of Candida lipase catalyzed ester hydrolysis via noncovalent enzyme modification. *J. Am. Chem. Soc.* 112:1990.
40. Kazlauskas, R. J., A. N. E Weissfloch, A. T. Rappaport and L. A. Cuccia (1991) A rule to predict which enantiomer of a secondary alcohol reacts faster in reactions catalyzed by cholesterol esterase, lipase from *Pseudomonas cepacia,* and lipase from *Candida rugosa. J. Org. Chem.* 56:2656.
41. Sugai, Y., H. Kakeya and H. Ohta. (1990) Enzymatic preparations of enantiomerically enriched tertiary α-benzyloxyacid esters. Application to the synthesis of (s) (−) frontalin. *J. Org. Chem.* 55:4643.
42. Whitesell, J. K., H. H. Chen and R. M. Lawrence. (1985) Trans-2-phenylcyclohexanol. A powerful and readily available chiral auxiliary. *J. Org. Chem.* 50:4663.
43. Lin, J., T., T. Yamazki and T. Kitazume. (1987) A microbially based approach for the preparation of chiral molecules possessing the trifluoromethyl group. *J. Org. Chem.* 52:3211.
44. Hagan, D. and N. A. Zaidi. (1992) *J. Chem. Soc. Perkin Trans.* 947.
45. Kitazume, T., T. Sato, T. Kobayashi and J. T. Lin. (1986) Microbial approach to the practical monofluorinated chiral synthons. *J. Org. Chem.* 51:1003.
46. Cohen, S. G., A. Milovanovic, R. M. Shultz and S. Y. Weinstein. (1969) On the active site of alpha-chymotrypsin. Absolute configurations and kinetics of hydrolysis of cyclized and noncyclized substrates. *J. Biol. Chem.* 244:2664.
47. Crout, D. H., V. S. B. Gaundet, K. Lauman and M. Schneider. (1986) Enzymatic hydrolysis of (±)-trans-1,2- diacetoxycycloalkanes. A facile route to optically active cycloakane-1,2-diols. *Chem. Comm.* 808.
48. Sabbioni, G. and J. B. Jones. (1987) Enzymes in organic synthesis. 39. Preparations of chiral cyclic acid esters and bicyclic lactones via stereoselective pig liver esterase catalyzed hydrolyses of cyclic mesodiesters. *J. Org. Chem.* 52:4565.
49. Kobayashi, S., K. Kamijama, T. Iimori and M. Ohno. (1984) Creation of novel chiral synthons with enzymes and applications to natural products synthesis. 15. Efficient introduction of chiral centers into cyclobexane rings. *Tetrahedron Lett.* 25:2557.
50. Ladner, W. E. and G. M. Whitesides. (1984) Lipase catalyzed hydrolysis as a route to esters of chiral epoxy-alcohols. *J. Am. Chem. Soc.* 106:7250.
51. Mohr, P., N. Wacspe-Saracevic, C. Tamm, K. Gawronska and J. K. Gawronski. (1983) A study of stereoselective hydrolysis of symmetrical diesters with pig liver esterase. *Helv. Chim. Acta.* 66:2501.

We claim:

1. An isolated nucleic acid segment comprising the nucleic acid sequence of FIG. 6O (E020) (SEQ ID NO. 29).

2. An isolated nucleic acid segment comprising the nucleic acid sequence of an open reading frame encoded for by the nucleic acid of claim 1.

3. An expression vector nucleic acid construct comprising an expressible nucleic acid which is a nucleic acid of claim 2.

4. A host cell transformed with the expression vector construct of claim 3.

* * * * *

SEQUENCE LISTING

<160> NUMBER OF SEQ ID NOS: 37

<210> SEQ ID NO 1
<211> LENGTH: 3513
<212> TYPE: DNA
<213> ORGANISM: Artificial Sequence
<220> FEATURE:
<223> OTHER INFORMATION: Description of Artificial Sequence:cloned
      esterase gene from bacteria E001
<220> FEATURE:
<221> NAME/KEY: CDS
<222> LOCATION: (1182)..(2690)

<400> SEQUENCE: 1

```
gatcaagtgg cgatcgaccg cgcgttgatt gaacttgacg gcacggaaaa caaaggaaag      60
cttggggcga atgctatttt aggcgtgtcg ctcgcggtcg ctcgcgctgc ggctgatgag     120
cttggcttgc cgttgtacca atacttgggc ggctttaacg ctaaaacgct gcctgtaccg     180
atgatgaaca ttttaaacgg cggcgcgcat gcggacaaca acgttgacat tcaagaattc     240
atgatcatgc cggtcggtgc ggaaagcttc cgtgaagcgc tgcgcatggg tgcagaaatt     300
ttccatagct taaaagctgt gttaaaagcg aaaggctaca acacgctgt cggtgacgaa      360 ggcggatttg ctccgaactt aaaatcgaac gaagaagcgc tgcaaacgat cattgaagcg     420
atcgaaaaag ccggctacaa accaggcgaa caagtgatgc tcgctatgga cgttgcttcg     480
tcggagctgt acaacaaaga agatggcaaa tatcatttgg aaggcgaagg cgtcgtcaaa     540
acatcagaag aaatggttgc ttggtatgaa gagcttgtgt cgaaatatcc gatcatctcg     600
atcgaagacg gacttgacga aaatgactgg gaaggccata aactgcttac tgagcgcctt     660
ggccacaaag tgcagctcgt cggtgacgac ttgtttgtaa cgaacacgaa aaaactggcc     720
gaaggcattg aaaaaggcgt cggcaactcg atttaatta aagtgaacca aatcggtaca     780
ctgacggaaa cgttcgatgc cattgagatg gccaaacgcg ccggctacac ggcggttgtg     840
tcgcaccgtt ccggtgaaac ggaagacagc acgattgccg atatcgctgt cgcaacaaac     900
gctggccaaa tcaaaacggg agcaccgtcg cgtacggacc gcgtcgcaaa atacaaccag     960
ctgctccgca ttgaagacga acttggccac acggctattt accaaggcat tcgttcgttt    1020
tacaatttga aaaaataacg ggaatcaaca acaaagggtg tctccaacgt tgcgagacac    1080
cctctttaat tacgggaaac agaaatgatt tcctatcgat agcaaaaaat ggacgtgggt    1140
aaaccattcg tttataatat cttttttgtaa tcgttagaat a ttg aaa aag ggg atg   1196
                                              Leu Lys Lys Gly Met
                                                1               5 gga acc gtg atc gtg gaa aca aag tac ggt cgg ttg cgc ggg gga aca  1244
             Gly Thr Val Ile Val Glu Thr Lys Tyr Gly Arg Leu Arg Gly Gly Thr
                          10                  15                  20 aat gaa ggg gtt ttc tat tgg aaa ggg att ccg tac gcg aaa gcg ccg  1292
```

```
                                                       -continued

Asn Glu Gly Val Phe Tyr Trp Lys Gly Ile Pro Tyr Ala Lys Ala Pro
             25                   30                  35 gtc ggt gaa cgc cgt ttt ttg ccg ccg gaa ccg ccc gat gca tgg gac       1340
Val Gly Glu Arg Arg Phe Leu Pro Pro Glu Pro Pro Asp Ala Trp Asp
             40                  45                   50 gga gtg cgt gag gcg aca tcg ttt gga ccg gtc gtc atg cag ccg tcc       1388
Gly Val Arg Glu Ala Thr Ser Phe Gly Pro Val Val Met Gln Pro Ser
         55                  60                  65 gat tcg atg ttc agc cag ctg ctc gga cgg atg aat gaa cca atg agc       1436
Asp Ser Met Phe Ser Gln Leu Leu Gly Arg Met Asn Glu Pro Met Ser
70                  75                  80                   85 gag gat ggg ttg tat ctg aac att tgg tca ccg gcg gcg gat ggg aag       1484
Glu Asp Gly Leu Tyr Leu Asn Ile Trp Ser Pro Ala Ala Asp Gly Lys
                 90                  95                 100 aag cgc ccg gta ttg ttt tgg att cat ggc ggc gct ttt tta ttc ggc       1532
Lys Arg Pro Val Leu Phe Trp Ile His Gly Gly Ala Phe Leu Phe Gly
             105                 110                 115 tcc ggt tca ttt cca tgg tat gat gga acg gcg ttt gcc aaa cac ggc       1580
Ser Gly Ser Phe Pro Trp Tyr Asp Gly Thr Ala Phe Ala Lys His Gly
         120                 125                 130 gat gtc gtt gtc gtg acg atc aac tac cgg atg agc gtg ttt ggc ttt       1628
Asp Val Val Val Thr Ile Asn Tyr Arg Met Ser Val Phe Gly Phe
135                 140                 145 ttg tat ttg gga gat gcg ttt ggc gaa acg tat gcc cag gcg gga aat       1676
Leu Tyr Leu Gly Asp Ala Phe Gly Glu Thr Tyr Ala Gln Ala Gly Asn
150                 155                 160                 165 ctt ggc ata ttg gat caa gtg gcg gcg ctg cgc tgg gtg aaa gag aac       1724
Leu Gly Ile Leu Asp Gln Val Ala Ala Leu Arg Trp Val Lys Glu Asn
             170                 175                 180 att gag gcg ttc ggc ggt gat ccg gac aac att acg att ttt ggc gaa       1772
Ile Glu Ala Phe Gly Gly Asp Pro Asp Asn Ile Thr Ile Phe Gly Glu
         185                 190                 195 tca gcc gga gcg gca agc gtt ggc gtg ctg ttg tcg ctt ccg gaa gca       1820
Ser Ala Gly Ala Ala Ser Val Gly Val Leu Leu Ser Leu Pro Glu Ala
         200                 205                 210 agc ggg ctg ttt cga cgc gct ata ttg caa agc gga tcg ggt tcg ctt       1868
Ser Gly Leu Phe Arg Arg Ala Ile Leu Gln Ser Gly Ser Gly Ser Leu
             215                 220                 225 ctt ctt cgt tct ccg gag acg gcg atg gct ctg act gaa cgc att tta       1916
Leu Leu Arg Ser Pro Glu Thr Ala Met Ala Leu Thr Glu Arg Ile Leu
230                 235                 240                 245 gaa cgt gcc ggc atc cgt ccg ggt gac cgc gat cgg ctg ctg tcg att       1964
Glu Arg Ala Gly Ile Arg Pro Gly Asp Arg Asp Arg Leu Leu Ser Ile
             250                 255                 260 cca gca gca gag cta ttg cag gcg gcg atg tcg ctc ggc cca gga atc       2012
Pro Ala Ala Glu Leu Leu Gln Ala Ala Met Ser Leu Gly Pro Gly Ile
         265                 270                 275 acg tac ggt ccg gtg gtt gac gga cat gtg ttg cga cgc cat ccg atc       2060
Thr Tyr Gly Pro Val Val Asp Gly His Val Leu Arg Arg His Pro Ile
         280                 285                 290 gaa gcg ctc cac gac ggg gca gca agt gat att cca atc cta att ggc       2108
Glu Ala Leu His Asp Gly Ala Ala Ser Asp Ile Pro Ile Leu Ile Gly
295                 300                 305 gtg acg aaa gac gaa tac aat ttg ttt tca ttg act gat ccg tca ttg       2156
Val Thr Lys Asp Glu Tyr Asn Leu Phe Ser Leu Thr Asp Pro Ser Leu
310                 315                 320                 325 aca aga ctc gaa gaa aaa gaa ctg ctt gac cgg atg aac cgt gag gtc       2204
Thr Arg Leu Glu Glu Lys Glu Leu Leu Asp Arg Met Asn Arg Glu Val
                 330                 335                 340
```

```
ggg cct att ccg gag gag gcg gta cgc tat tac gcg gaa aca gcg gat    2252
Gly Pro Ile Pro Glu Glu Ala Val Arg Tyr Tyr Ala Glu Thr Ala Asp
            345                 350                 355 cgg tcg gca ccc gcg tgg caa aca tgg ctg cgc atc atg acg tac ctt    2300
Arg Ser Ala Pro Ala Trp Gln Thr Trp Leu Arg Ile Met Thr Tyr Leu
        360                 365                 370 gtt ttt gtc gac gga atg ttg cga acg gcg gat gcc caa gca gcg caa    2348
Val Phe Val Asp Gly Met Leu Arg Thr Ala Asp Ala Gln Ala Ala Gln
    375                 380                 385 ggg gcg aat gtg tac atg tat cgg ttt gat tat gaa acg ccg gcg ttc    2396
Gly Ala Asn Val Tyr Met Tyr Arg Phe Asp Tyr Glu Thr Pro Ala Phe
390                 395                 400                 405 ggt gga caa ctg aaa gcg tgc cat acg ctc gag ttg ccg ttt gtg ttt    2444
Gly Gly Gln Leu Lys Ala Cys His Thr Leu Glu Leu Pro Phe Val Phe
                410                 415                 420 cat aac ctc cat cag cct ggt gtc gag aat ttc gtc ggc aac cga cca    2492
His Asn Leu His Gln Pro Gly Val Glu Asn Phe Val Gly Asn Arg Pro
            425                 430                 435 gag cgt gag gcg att gcc agc gaa atg cat ggt gcc tgg ctt tcg ttc    2540
Glu Arg Glu Ala Ile Ala Ser Glu Met His Gly Ala Trp Leu Ser Phe
        440                 445                 450 gcc cgc acc ggc aac ccg aac ggc gct cat tta cca gag aag tgg ccc    2588
Ala Arg Thr Gly Asn Pro Asn Gly Ala His Leu Pro Glu Lys Trp Pro
    455                 460                 465 gta tac aca aaa gag cac aaa ccg gtg ttt gtc ttt tcg gct gcg agc    2636
Val Tyr Thr Lys Glu His Lys Pro Val Phe Val Phe Ser Ala Ala Ser
470                 475                 480                 485 cat gtg gaa gac gat ccg ttc ggt cgc gag cgg gaa gcg tgg caa gga    2684
His Val Glu Asp Asp Pro Phe Gly Arg Glu Arg Glu Ala Trp Gln Gly
                490                 495                 500 cgc ctt tgacgaaaaa atccataagc aacatgtgtt ctttgtctga acacgatcaa    2740
Arg Leu ggtacgcgca ttttcgcgga aaaagaccgt gggcaaacgt tcgcctttac ctctaaaagg    2800
aatgacgcaa catgtctgca cttcacagga aagaggacga aacggttggt tttcagaata    2860
ggaaaaggtg tcccgttttt tgggacacct tcttctatgt atcgctcaat catttgcttc    2920
tgtggcagga agcccgaatc gctcggcgag tgccggatca cgatcgatcg cctcaatcag    2980
tttccgcatg acgttcacat caaacgtaaa attcgaaccg attggcgagg tgacgaaaat    3040
tttcccttct ttcgcctcgc gtgctcgttt aaattgatag ccgtcaatcg caatgacgac    3100
tcgttcgtct ggccttgcca ttaggaatcc ctccatcgct gttttttctt tcattgtact    3160
tgattttgag gatgaacacc aacgttcatg acacgctctt aaggataacg gatgggagag    3220
cgttagaggg cggtgaattt catcaagaac gtagcacaaa acgacatttt ttcattatag    3280
acgtcttgat gtttggaatg atcggaaaag gcgattgtta ggcggggatc atgatccact    3340
agcggatgaa agtgaagagc aacgaaatag tctctttgtt tcacaacaaa tgaattggtg    3400
ccattcaggg cggagacagg tgagacagtt gctgcaaacg ataatgtatg gtatagtaaa    3460
aatattgcaa cgtaggtcgt tggaggtgtc aggcatgcat gccttgcttg tga          3513

<210> SEQ ID NO 2
<211> LENGTH: 503
<212> TYPE: PRT
<213> ORGANISM: Artificial Sequence
<220> FEATURE:
<223> OTHER INFORMATION: Description of Artificial Sequence:cloned
      esterase gene from bacteria E001

<400> SEQUENCE: 2
```

```
Leu Lys Lys Gly Met Gly Thr Val Ile Val Glu Thr Lys Tyr Gly Arg
 1               5                  10                  15

Leu Arg Gly Gly Thr Asn Glu Gly Val Phe Tyr Trp Lys Gly Ile Pro
             20                  25                  30

Tyr Ala Lys Ala Pro Val Gly Glu Arg Arg Phe Leu Pro Pro Glu Pro
         35                  40                  45

Pro Asp Ala Trp Asp Gly Val Arg Glu Ala Thr Ser Phe Gly Pro Val
     50                  55                  60

Val Met Gln Pro Ser Asp Ser Met Phe Ser Gln Leu Leu Gly Arg Met
 65              70                  75                  80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
                100                 105                 110

Ala Phe Leu Phe Gly Ser Gly Ser Phe Pro Trp Tyr Asp Gly Thr Ala
            115                 120                 125

Phe Ala Lys His Gly Asp Val Val Val Thr Ile Asn Tyr Arg Met
        130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Gly Asp Pro Asp Asn Ile
            180                 185                 190

Thr Ile Phe Gly Glu Ser Ala Gly Ala Ala Ser Val Gly Val Leu Leu
            195                 200                 205

Ser Leu Pro Glu Ala Ser Gly Leu Phe Arg Arg Ala Ile Leu Gln Ser
210                 215                 220

Gly Ser Gly Ser Leu Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                245                 250                 255

Arg Leu Leu Ser Ile Pro Ala Ala Glu Leu Leu Gln Ala Ala Met Ser
            260                 265                 270

Leu Gly Pro Gly Ile Thr Tyr Gly Pro Val Val Asp Gly His Val Leu
    275                 280                 285

Arg Arg His Pro Ile Glu Ala Leu His Asp Gly Ala Ala Ser Asp Ile
290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335

Met Asn Arg Glu Val Gly Pro Ile Pro Glu Glu Ala Val Arg Tyr Tyr
            340                 345                 350

Ala Glu Thr Ala Asp Arg Ser Ala Pro Ala Trp Gln Thr Trp Leu Arg
        355                 360                 365

Ile Met Thr Tyr Leu Val Phe Val Asp Gly Met Leu Arg Thr Ala Asp
    370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                405                 410                 415
```

```
Leu Pro Phe Val Phe His Asn Leu His Gln Pro Gly Val Glu Asn Phe
            420                 425                 430

Val Gly Asn Arg Pro Glu Arg Glu Ala Ile Ala Ser Glu Met His Gly
        435                 440                 445

Ala Trp Leu Ser Phe Ala Arg Thr Gly Asn Pro Asn Gly Ala His Leu
    450                 455                 460

Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
                485                 490                 495

Glu Ala Trp Gln Gly Arg Leu
            500

<210> SEQ ID NO 3
<211> LENGTH: 1896
<212> TYPE: DNA
<213> ORGANISM: Artificial Sequence
<220> FEATURE:
<223> OTHER INFORMATION: Description of Artificial Sequence:cloned
      esterase gene from bacteria E009
<220> FEATURE:
<221> NAME/KEY: CDS
<222> LOCATION: (211)..(1713)

<400> SEQUENCE: 3
tctaattcac gctggatctt tcctttgtgt tttaaaactt aaagcaccgg attgccggct      60
gtatggtccg gttggatatt gtcatcacat cgtggatatc agtggatccg gtgcgatgga     120
ttgcttcagg ggaacttta aacacttgag tttgacaacc actccttaat catttaagat     180
```

| | | |
|---|---|---|
| ttaaatgaaa attaaataa atcaaaaaga ttg att caa atg aat acg ttg gtg | 234 |
| Leu Ile Gln Met Asn Thr Leu Val | |
| 1               5 | |

```
gaa acc cgt ttt ggg aaa gtg caa ggc ggt aca gac gga gag gtt tgt      282
Glu Thr Arg Phe Gly Lys Val Gln Gly Gly Thr Asp Gly Glu Val Cys
    10                  15                  20 ttt tgg aaa ggg att cct tat gcg aaa cct ccg gtg gga aaa cgc cgc      330
Phe Trp Lys Gly Ile Pro Tyr Ala Lys Pro Pro Val Gly Lys Arg Arg
25                  30                  35                  40 ttt caa aaa ccg gaa ccg ccg gag aaa tgg gat ggc gtt tgg gag gcc      378
Phe Gln Lys Pro Glu Pro Pro Glu Lys Trp Asp Gly Val Trp Glu Ala
                45                  50                  55 acc cgg ttc cgg tcc atg gtg atg cag ccg tcc ggc acc acc ttc agc      426
Thr Arg Phe Arg Ser Met Val Met Gln Pro Ser Gly Thr Thr Phe Ser
            60                  65                  70 acc gtg ctc ggg gaa gcg gat ctt cct gtg agc gaa gac ggt ctt tat      474
Thr Val Leu Gly Glu Ala Asp Leu Pro Val Ser Glu Asp Gly Leu Tyr
        75                  80                  85 ctg aat atc tgg tcg ccg gca gcc gac gga aaa aag cgg ccg gtg ctc      522
Leu Asn Ile Trp Ser Pro Ala Ala Asp Gly Lys Lys Arg Pro Val Leu
    90                  95                  100 ttc tgg atc cat ggc ggc gcc tac cag ttt ggg tcc ggc gct tcc ccc      570
Phe Trp Ile His Gly Gly Ala Tyr Gln Phe Gly Ser Gly Ala Ser Pro
105                 110                 115                 120 tgg tat gac ggg acg gag ttt gcc aaa aac gga gat gtg gtg gtt gtc      618
Trp Tyr Asp Gly Thr Glu Phe Ala Lys Asn Gly Asp Val Val Val Val
                125                 130                 135 acg atc aac tac cgg ttg aac gcg ttt gga ttt ttg tac ttg gca gat      666
Thr Ile Asn Tyr Arg Leu Asn Ala Phe Gly Phe Leu Tyr Leu Ala Asp
            140                 145                 150 tgg ttc ggc gac gaa ttt tca gcg tcg ggc aac ctg gga att ttg gac      714
```

```
Trp Phe Gly Asp Glu Phe Ser Ala Ser Gly Asn Leu Gly Ile Leu Asp
            155                 160                 165 caa gtc gct gca ctg cgc tgg gtg aaa gaa aac att tcg gca ttc ggc       762
Gln Val Ala Ala Leu Arg Trp Val Lys Glu Asn Ile Ser Ala Phe Gly
        170                 175                 180 ggc gac ccg gag caa atc acc atc ttc ggg gag tcg gcc gga gcc gga       810
Gly Asp Pro Glu Gln Ile Thr Ile Phe Gly Glu Ser Ala Gly Ala Gly
185                 190                 195                 200 agc gtc ggg gtt ctg ctt tcc ctc ccg gaa acc aaa ggg ctg ttt caa       858
Ser Val Gly Val Leu Leu Ser Leu Pro Glu Thr Lys Gly Leu Phe Gln
                205                 210                 215 cgg gcg atc ttg caa agc gga tcg ggt gcc att ttg ctc cgt tcc tct       906
Arg Ala Ile Leu Gln Ser Gly Ser Gly Ala Ile Leu Leu Arg Ser Ser
        220                 225                 230 cag aca gcc tcg ggc atc gcg gaa caa att ctt acg aaa gcc ggc att       954
Gln Thr Ala Ser Gly Ile Ala Glu Gln Ile Leu Thr Lys Ala Gly Ile
        235                 240                 245 cga aaa gga gac cgc gac cgg ttg tta tcc atc ccg gcc ggt gaa ctc      1002
Arg Lys Gly Asp Arg Asp Arg Leu Leu Ser Ile Pro Ala Gly Glu Leu
250                 255                 260 ctt gaa gcc gca caa tcc gtg aat ccg gga atg gtt ttt ggt ccc gtt      1050
Leu Glu Ala Ala Gln Ser Val Asn Pro Gly Met Val Phe Gly Pro Val
265                 270                 275                 280 gtg gac ggc acc gta ttg aaa acc cat ccg att gaa gcg ttg gaa acc      1098
Val Asp Gly Thr Val Leu Lys Thr His Pro Ile Glu Ala Leu Glu Thr
                285                 290                 295 gga gcc gcc ggc gat atc ccg atc atc atc ggg gtg aca aag gat gag      1146
Gly Ala Ala Gly Asp Ile Pro Ile Ile Ile Gly Val Thr Lys Asp Glu
                300                 305                 310 tac aat tta ttt aca ctg act gac cct tcc tgg acg aca gcg gga aaa      1194
Tyr Asn Leu Phe Thr Leu Thr Asp Pro Ser Trp Thr Thr Ala Gly Lys
        315                 320                 325 gaa gaa ctg atg gac cgg atc gaa cag gaa atc ggg ccg gtt ccg gaa      1242
Glu Glu Leu Met Asp Arg Ile Glu Gln Glu Ile Gly Pro Val Pro Glu
        330                 335                 340 aaa gtt ttt cca tat tac tta tct ttt ggg gat cca tcg caa ccg gta      1290
Lys Val Phe Pro Tyr Tyr Leu Ser Phe Gly Asp Pro Ser Gln Pro Val
345                 350                 355                 360 tgg caa aag ctg ttg cgc gcc atg acc tac cac atc ttt acc cgg ggc      1338
Trp Gln Lys Leu Leu Arg Ala Met Thr Tyr His Ile Phe Thr Arg Gly
                365                 370                 375 atg tta aaa acg gct gac gcc caa atc aag caa ggc ggg aag gtt tgg      1386
Met Leu Lys Thr Ala Asp Ala Gln Ile Lys Gln Gly Gly Lys Val Trp
                380                 385                 390 gtt tac cgg ttt gat tac gaa acc ccg ctc ttt gac ggt cgg ttg aaa      1434
Val Tyr Arg Phe Asp Tyr Glu Thr Pro Leu Phe Asp Gly Arg Leu Lys
        395                 400                 405 gca tgt cac gca ctg gaa atc ccc ttt gtc ttt cac aac ctg cat caa      1482
Ala Cys His Ala Leu Glu Ile Pro Phe Val Phe His Asn Leu His Gln
        410                 415                 420 ccg ggg gtc gat gtg ttc acc ggc aca cat ccg aag cgg gag cta att      1530
Pro Gly Val Asp Val Phe Thr Gly Thr His Pro Lys Arg Glu Leu Ile
425                 430                 435                 440 tcc cgg caa atg cat gaa gca tgg att gcc ttt gcc cgg aca ggg gat      1578
Ser Arg Gln Met His Glu Ala Trp Ile Ala Phe Ala Arg Thr Gly Asp
                445                 450                 455 ccg aac ggc gac cat ctc ccc gat gcg tgg ttg ccc ttt gca caa aaa      1626
Pro Asn Gly Asp His Leu Pro Asp Ala Trp Leu Pro Phe Ala Gln Lys
                460                 465                 470
```

-continued

| | | | | | | | | | | | | |
|---|---|---|---|---|---|---|---|---|---|---|---|---|
| gac | cgg | ccg | gcc | atg | gtc | ttt | gac | acc | gaa | acc | aga | gcg gaa aag cat |
| Asp | Arg | Pro | Ala | Met | Val | Phe | Asp | Thr | Glu | Thr | Arg | Ala Glu Lys His |
| | | | 475 | | | | 480 | | | | 485 | |

1674

| | | | | | | | | | | |
|---|---|---|---|---|---|---|---|---|---|---|
| ctg | ttt | gac | cgc | gag | cag | gaa | ctg | tgg | gaa | tca aag gct tgagtgattt |
| Leu | Phe | Asp | Arg | Glu | Gln | Glu | Leu | Trp | Glu | Ser Lys Ala |
| | | 490 | | | | | 495 | | | 500 |

1723 gctcaagcct tttttgcatt tcacgtatgt attcggattt ggaattaaac aatggtgctt    1783 ttatcgaaat ggggagtgtt tgcttataat gaacgggttt acaaagcttg ttttggtacc    1843 ggattactga aatgatccgt gtttatcatt tggatgcttt ctattggaaa ccg          1896

<210> SEQ ID NO 4
<211> LENGTH: 501
<212> TYPE: PRT
<213> ORGANISM: Artificial Sequence
<220> FEATURE:
<223> OTHER INFORMATION: Description of Artificial Sequence:cloned
      esterase gene from bacteria E009

<400> SEQUENCE: 4

Leu Ile Gln Met Asn Thr Leu Val Glu Thr Arg Phe Gly Lys Val Gln
 1               5                  10                  15

Gly Gly Thr Asp Gly Glu Val Cys Phe Trp Lys Gly Ile Pro Tyr Ala
            20                  25                  30

Lys Pro Pro Val Gly Lys Arg Phe Gln Lys Pro Glu Pro Pro Glu
        35                  40                  45

Lys Trp Asp Gly Val Trp Glu Ala Thr Arg Phe Arg Ser Met Val Met
    50                  55                  60

Gln Pro Ser Gly Thr Thr Phe Ser Thr Val Leu Gly Glu Ala Asp Leu
65                  70                  75                  80

Pro Val Ser Glu Asp Gly Leu Tyr Leu Asn Ile Trp Ser Pro Ala Ala
                85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
                165                 170                 175

Lys Glu Asn Ile Ser Ala Phe Gly Gly Asp Pro Glu Gln Ile Thr Ile
            180                 185                 190

Phe Gly Glu Ser Ala Gly Ala Gly Ser Val Gly Val Leu Leu Ser Leu
        195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
                245                 250                 255

Leu Ser Ile Pro Ala Gly Glu Leu Leu Glu Ala Ala Gln Ser Val Asn
            260                 265                 270

Pro Gly Met Val Phe Gly Pro Val Val Asp Gly Thr Val Leu Lys Thr
        275                 280                 285

```
His Pro Ile Glu Ala Leu Glu Thr Gly Ala Ala Gly Asp Ile Pro Ile
    290                 295                 300
Ile Ile Gly Val Thr Lys Asp Glu Tyr Asn Leu Phe Thr Leu Thr Asp
305                 310                 315                 320
Pro Ser Trp Thr Thr Ala Gly Lys Glu Glu Leu Met Asp Arg Ile Glu
                325                 330                 335
Gln Glu Ile Gly Pro Val Pro Glu Lys Val Phe Pro Tyr Tyr Leu Ser
            340                 345                 350
Phe Gly Asp Pro Ser Gln Pro Val Trp Gln Lys Leu Leu Arg Ala Met
        355                 360                 365
Thr Tyr His Ile Phe Thr Arg Gly Met Leu Lys Thr Ala Asp Ala Gln
    370                 375                 380
Ile Lys Gln Gly Gly Lys Val Trp Val Tyr Arg Phe Asp Tyr Glu Thr
385                 390                 395                 400
Pro Leu Phe Asp Gly Arg Leu Lys Ala Cys His Ala Leu Glu Ile Pro
                405                 410                 415
Phe Val Phe His Asn Leu His Gln Pro Gly Val Asp Val Phe Thr Gly
            420                 425                 430
Thr His Pro Lys Arg Glu Leu Ile Ser Arg Gln Met His Glu Ala Trp
        435                 440                 445
Ile Ala Phe Ala Arg Thr Gly Asp Pro Asn Gly Asp His Leu Pro Asp
    450                 455                 460
Ala Trp Leu Pro Phe Ala Gln Lys Asp Arg Pro Ala Met Val Phe Asp
465                 470                 475                 480
Thr Glu Thr Arg Ala Glu Lys His Leu Phe Asp Arg Glu Gln Glu Leu
                485                 490                 495
Trp Glu Ser Lys Ala
            500

<210> SEQ ID NO 5
<211> LENGTH: 1952
<212> TYPE: DNA
<213> ORGANISM: Artificial Sequence
<220> FEATURE:
<223> OTHER INFORMATION: Description of Artificial Sequence:cloned
      esterase gene from bacteria E011
<220> FEATURE:
<221> NAME/KEY: CDS
<222> LOCATION: (197)..(1699)

<400> SEQUENCE: 5
gatctttcct ttgtgtttta aaacttaaag caccggattg ccggctgtat ggtccggttg      60
gatattgtca tcacatcgtg gatatcagtg gatccggtgc gatggattgc ttcaggggaa     120
cttttaaaca cttgagtttg acaaccactc cttaatcatt taagatttaa atgaaaatta     180
aaataaatca aaaaga gtg att caa atg aat acg ttg gtg gaa acc cgt ttt     232
              Val Ile Gln Met Asn Thr Leu Val Glu Thr Arg Phe
                1               5                  10 ggg aaa gtg caa ggc ggt aca gac gga gag gtt tgt ttt tgg aaa ggg     280
Gly Lys Val Gln Gly Gly Thr Asp Gly Glu Val Cys Phe Trp Lys Gly
          15                  20                  25 att cct tat gcg aaa cct ccg gtg gga aaa cgc cgc ttt caa aaa ccg     328
Ile Pro Tyr Ala Lys Pro Pro Val Gly Lys Arg Arg Phe Gln Lys Pro
      30                  35                  40 gaa ccg ccg gag aaa tgg gat ggc gtt tgg gag gcc acc cgg ttc cgg     376
Glu Pro Pro Glu Lys Trp Asp Gly Val Trp Glu Ala Thr Arg Phe Arg
45                  50                  55                  60 tcc atg gtg atg cag ccg tcc ggc acc acc ttc agc acc gtg ctc ggg     424
```

```
Ser Met Val Met Gln Pro Ser Gly Thr Thr Phe Ser Thr Val Leu Gly
             65                  70                  75 gaa gcg gat ctt cct gtg agc gaa gac ggt ctt tat ctg aat atc tgg       472
Glu Ala Asp Leu Pro Val Ser Glu Asp Gly Leu Tyr Leu Asn Ile Trp
         80                  85                  90 tcg ccg gca gcc gac gga aaa aag cgg ccg gtg ctc ttc tgg atc cat       520
Ser Pro Ala Ala Asp Gly Lys Lys Arg Pro Val Leu Phe Trp Ile His
             95                 100                 105 ggc ggc gcc tac cag ttt ggg tcc ggc gct tcc ccc tgg tat gac ggg       568
Gly Gly Ala Tyr Gln Phe Gly Ser Gly Ala Ser Pro Trp Tyr Asp Gly
        110                 115                 120 acg gag ttt gcc aaa aac gga gat gtg gtg gtt gtc acg atc aac tac       616
Thr Glu Phe Ala Lys Asn Gly Asp Val Val Val Val Thr Ile Asn Tyr
125                 130                 135                 140 cgg ttg aac gcg ttt gga ttt ttg tac ttg gca gat tgg ttc ggc gac       664
Arg Leu Asn Ala Phe Gly Phe Leu Tyr Leu Ala Asp Trp Phe Gly Asp
                145                 150                 155 gaa ttt tca gcg tcg ggc aac ctg gga att ttg gac caa gtc gct gca       712
Glu Phe Ser Ala Ser Gly Asn Leu Gly Ile Leu Asp Gln Val Ala Ala
            160                 165                 170 ctg cgc tgg gtg aaa gaa aac att tcg gca ttc ggc ggc gac ccg gag       760
Leu Arg Trp Val Lys Glu Asn Ile Ser Ala Phe Gly Gly Asp Pro Glu
        175                 180                 185 caa atc acc atc ttc ggg gag tcg gcc gga gcc gga agc gtc ggg gtt       808
Gln Ile Thr Ile Phe Gly Glu Ser Ala Gly Ala Gly Ser Val Gly Val
        190                 195                 200 ctg ctt tcc ctc ccg gaa acc aaa ggg ctg ttt caa cgg gcg atc ttg       856
Leu Leu Ser Leu Pro Glu Thr Lys Gly Leu Phe Gln Arg Ala Ile Leu
205                 210                 215                 220 caa agc gga tcg ggt gcc att ttg ctc cgt tcc tct cag aca gcc tcg       904
Gln Ser Gly Ser Gly Ala Ile Leu Leu Arg Ser Ser Gln Thr Ala Ser
                225                 230                 235 ggc atc gcg gaa caa att ctt acg aaa gcc ggc att cga aaa gga gac       952
Gly Ile Ala Glu Gln Ile Leu Thr Lys Ala Gly Ile Arg Lys Gly Asp
            240                 245                 250 cgc gac cgg ttg tta tcc atc ccg gcc ggt gaa ctc ctt gaa gcc gca      1000
Arg Asp Arg Leu Leu Ser Ile Pro Ala Gly Glu Leu Leu Glu Ala Ala
        255                 260                 265 caa tcc gtg aat ccg gga atg gtt ttt ggt ccc gtt gtg gac ggc acc      1048
Gln Ser Val Asn Pro Gly Met Val Phe Gly Pro Val Val Asp Gly Thr
        270                 275                 280 gta ttg aaa acc cat ccg att gaa gcg ttg gaa acc gga gcc gcc ggc      1096
Val Leu Lys Thr His Pro Ile Glu Ala Leu Glu Thr Gly Ala Ala Gly
285                 290                 295                 300 gat atc ccg atc atc atc ggg gtg aca aag gat gag tac aat tta ttt      1144
Asp Ile Pro Ile Ile Ile Gly Val Thr Lys Asp Glu Tyr Asn Leu Phe
                305                 310                 315 aca ctg act gac cct tcc tgg acg aca gcg gga aaa gaa gaa ctg atg      1192
Thr Leu Thr Asp Pro Ser Trp Thr Thr Ala Gly Lys Glu Glu Leu Met
            320                 325                 330 gac cgg atc gaa cag gaa atc ggg ccg gtt ccg gaa aaa gtt ttt cca      1240
Asp Arg Ile Glu Gln Glu Ile Gly Pro Val Pro Glu Lys Val Phe Pro
        335                 340                 345 tat tac tta tct ttt ggg gat cca tcg caa ccg gta tgg caa aag ctg      1288
Tyr Tyr Leu Ser Phe Gly Asp Pro Ser Gln Pro Val Trp Gln Lys Leu
        350                 355                 360 ttg cgc gcc atg acc tac cac atc ttt acc cgg ggc atg tta aaa acg      1336
Leu Arg Ala Met Thr Tyr His Ile Phe Thr Arg Gly Met Leu Lys Thr
365                 370                 375                 380
```

-continued

```
gct gac gcc caa atc aag caa ggc ggg aag gtt tgg gtt tac cgg ttt      1384
Ala Asp Ala Gln Ile Lys Gln Gly Gly Lys Val Trp Val Tyr Arg Phe
            385                 390                 395 gat tac gaa acc ccg ctc ttt gac ggt cgg ttg aaa gca tgt cac gca      1432
Asp Tyr Glu Thr Pro Leu Phe Asp Gly Arg Leu Lys Ala Cys His Ala
400                 405                 410 ctg gaa atc ccc ttt gtc ttt cac aac ctg cat caa ccg ggg gtc gat      1480
Leu Glu Ile Pro Phe Val Phe His Asn Leu His Gln Pro Gly Val Asp
            415                 420                 425 gtg ttc acc ggc aca cat ccg aag cgg gag cta att tcc cgg caa atg      1528
Val Phe Thr Gly Thr His Pro Lys Arg Glu Leu Ile Ser Arg Gln Met
430                 435                 440 cat gaa gca tgg att gcc ttt gcc cgg aca ggg gat ccg aac ggc gac      1576
His Glu Ala Trp Ile Ala Phe Ala Arg Thr Gly Asp Pro Asn Gly Asp
445                 450                 455                 460 cat ctc ccc gat gcg tgg ttg ccc ttt gca caa aaa gac cgg ccg gcc      1624
His Leu Pro Asp Ala Trp Leu Pro Phe Ala Gln Lys Asp Arg Pro Ala
                465                 470                 475 atg gtc ttt gac acc gaa acc aga gcg gaa aag cat ctg ttt gac cgc      1672
Met Val Phe Asp Thr Glu Thr Arg Ala Glu Lys His Leu Phe Asp Arg
            480                 485                 490 gag cag gaa ctg tgg gaa tca aag gct tgagtgattt gctcaagcct            1719
Glu Gln Glu Leu Trp Glu Ser Lys Ala
            495                 500 tttttgcatt tcacgtatgt attcggattt ggaattaaac aatggtgctt ttatcgaaat    1779
ggggagtgtt tgcttataat gaacgggttt acaaagcttg ttttggtacc ggattactga    1839
aatgatcaga aggaaatatc atgacgtaat aatcagggga tcttgagaaa gaaatacatg    1899
gagtgttatg tcccttgaaa aacagagacg ccggtggcat caccatcaca ggg           1952
```

<210> SEQ ID NO 6
<211> LENGTH: 501
<212> TYPE: PRT
<213> ORGANISM: Artificial Sequence
<220> FEATURE:
<223> OTHER INFORMATION: Description of Artificial Sequence:cloned esterase gene from bacteria E011

<400> SEQUENCE: 6

```
Val Ile Gln Met Asn Thr Leu Val Glu Thr Arg Phe Gly Lys Val Gln
1               5                   10                  15

Gly Gly Thr Asp Gly Glu Val Cys Phe Trp Lys Gly Ile Pro Tyr Ala
            20                  25                  30

Lys Pro Pro Val Gly Lys Arg Arg Phe Gln Lys Pro Glu Pro Pro Glu
        35                  40                  45

Lys Trp Asp Gly Val Trp Glu Ala Thr Arg Phe Arg Ser Met Val Met
    50                  55                  60

Gln Pro Ser Gly Thr Thr Phe Ser Thr Val Leu Gly Glu Ala Asp Leu
65                  70                  75                  80

Pro Val Ser Glu Asp Gly Leu Tyr Leu Asn Ile Trp Ser Pro Ala Ala
                85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
```

-continued

```
                 145                 150                 155                 160

Ser Gly Asn Leu Gly Ile Leu Asp Gln Val Ala Ala Leu Arg Trp Val
                        165                 170                 175

Lys Glu Asn Ile Ser Ala Phe Gly Gly Asp Pro Glu Gln Ile Thr Ile
                    180                 185                 190

Phe Gly Glu Ser Ala Gly Ala Gly Ser Val Gly Val Leu Leu Ser Leu
                    195                 200                 205

Pro Glu Thr Lys Gly Leu Phe Gln Arg Ala Ile Leu Gln Ser Gly Ser
                    210                 215                 220

Gly Ala Ile Leu Leu Arg Ser Ser Gln Thr Ala Ser Gly Ile Ala Glu
        225                 230                 235                 240

Gln Ile Leu Thr Lys Ala Gly Ile Arg Lys Gly Asp Arg Asp Arg Leu
                        245                 250                 255

Leu Ser Ile Pro Ala Gly Glu Leu Leu Glu Ala Ala Gln Ser Val Asn
                    260                 265                 270

Pro Gly Met Val Phe Gly Pro Val Asp Gly Thr Val Leu Lys Thr
                    275                 280                 285

His Pro Ile Glu Ala Leu Glu Thr Gly Ala Ala Gly Asp Ile Pro Ile
                    290                 295                 300

Ile Ile Gly Val Thr Lys Asp Glu Tyr Asn Leu Phe Thr Leu Thr Asp
        305                 310                 315                 320

Pro Ser Trp Thr Thr Ala Gly Lys Glu Glu Leu Met Asp Arg Ile Glu
                        325                 330                 335

Gln Glu Ile Gly Pro Val Pro Glu Lys Val Phe Pro Tyr Tyr Leu Ser
                    340                 345                 350

Phe Gly Asp Pro Ser Gln Pro Val Trp Gln Lys Leu Leu Arg Ala Met
                    355                 360                 365

Thr Tyr His Ile Phe Thr Arg Gly Met Leu Lys Thr Ala Asp Ala Gln
                    370                 375                 380

Ile Lys Gln Gly Gly Lys Val Trp Val Tyr Arg Phe Asp Tyr Glu Thr
        385                 390                 395                 400

Pro Leu Phe Asp Gly Arg Leu Lys Ala Cys His Ala Leu Glu Ile Pro
                        405                 410                 415

Phe Val Phe His Asn Leu His Gln Pro Gly Val Asp Val Phe Thr Gly
                    420                 425                 430

Thr His Pro Lys Arg Glu Leu Ile Ser Arg Gln Met His Glu Ala Trp
                    435                 440                 445

Ile Ala Phe Ala Arg Thr Gly Asp Pro Asn Gly Asp His Leu Pro Asp
                    450                 455                 460

Ala Trp Leu Pro Phe Ala Gln Lys Asp Arg Pro Ala Met Val Phe Asp
        465                 470                 475                 480

Thr Glu Thr Arg Ala Glu Lys His Leu Phe Asp Arg Glu Gln Glu Leu
                        485                 490                 495

Trp Glu Ser Lys Ala
                    500

<210> SEQ ID NO 7
<211> LENGTH: 3147
<212> TYPE: DNA
<213> ORGANISM: Artificial Sequence
<220> FEATURE:
<223> OTHER INFORMATION: Description of Artificial Sequence:cloned
      esterase gene from bacteria E101
<220> FEATURE:
<221> NAME/KEY: CDS
<222> LOCATION: (245)..(1231)
```

```
<400> SEQUENCE: 7
gatccgcttc atccagcagg tcctggagca gcgggagcgg gaggacacct tccgcctcaa        60
gcgcatcaag ggcaagatcg aggcccggga agcggaggag gggggcggc ccaaccccca        120 cctggagatc ggagcgggcc tctaaggccg ccccagcttg agccacccc caggcttccc        180 ctgggggtt taccttgac ccggtccaag gttttcgggt aggctcctcc tcggagggaa         240 aacc atg agg cgg ctt ttg ggg ctc ctt ttg ttc ctg gcc ttg gcc ttg         289
     Met Arg Arg Leu Leu Gly Leu Leu Leu Phe Leu Ala Leu Ala Leu
     1               5                   10                  15 gcg caa ggc ctt ggc cct tac tgg cag gag gtt cag gcc cag ggt acg         337
Ala Gln Gly Leu Gly Pro Tyr Trp Gln Glu Val Gln Ala Gln Gly Thr
                20                  25                  30 gtc tgc tcg gac ggc tcc ccc tgg cgg ttc tac gtg agc ccg ggg gac         385
Val Cys Ser Asp Gly Ser Pro Trp Arg Phe Tyr Val Ser Pro Gly Asp
            35                  40                  45 ccc aag aag gtc ctt ctg gac ttc cag ggg ggc ggg gcc tgc tgg gac         433
Pro Lys Lys Val Leu Leu Asp Phe Gln Gly Gly Gly Ala Cys Trp Asp
        50                  55                  60 gcc cag acc tgc ggt ccc cag agc cag acc tac cgg aag cgg gtg gac         481
Ala Gln Thr Cys Gly Pro Gln Ser Gln Thr Tyr Arg Lys Arg Val Asp
65                  70                  75 gtg cag gaa ctc ctc ctg gcc cag ggg atc tac aac cgg gcg agc atc         529
Val Gln Glu Leu Leu Leu Ala Gln Gly Ile Tyr Asn Arg Ala Ser Ile
 80                  85                  90                  95 gcc aac ccc ttc ttc ggc tgg acc cac gtc ttc atc ccc tac tgc acg         577
Ala Asn Pro Phe Phe Gly Trp Thr His Val Phe Ile Pro Tyr Cys Thr
                100                 105                 110 ggg gac ctg cac gtg ggc cgg gcc acg gtg gac tac ggc ggc ttt aag         625
Gly Asp Leu His Val Gly Arg Ala Thr Val Asp Tyr Gly Gly Phe Lys
            115                 120                 125 gtc cac cac cag ggg gcg cga aac gcc ctg gcc gcc ttg gag tac gtc         673
Val His His Gln Gly Ala Arg Asn Ala Leu Ala Ala Leu Glu Tyr Val
        130                 135                 140 ttc aag aac tac ccc aag gca gag cgg gtc ttc gtc acc ggg tgc agc         721
Phe Lys Asn Tyr Pro Lys Ala Glu Arg Val Phe Val Thr Gly Cys Ser
    145                 150                 155 gcc ggg ggg tac ggg gcg gtc ttc tgg gcg gac aag gtc ctt gcc acc         769
Ala Gly Gly Tyr Gly Ala Val Phe Trp Ala Asp Lys Val Leu Ala Thr
160                 165                 170                 175 tac aaa agc gcc cag atc gcc gtt tgc ggg gac gcc gcc ttg ggc gtg         817
Tyr Lys Ser Ala Gln Ile Ala Val Cys Gly Asp Ala Ala Leu Gly Val
                180                 185                 190 agc aca tcg gac ttc ccc ggg agc cgg gtt tgg aac gcc cgc ctg ccc         865
Ser Thr Ser Asp Phe Pro Gly Ser Arg Val Trp Asn Ala Arg Leu Pro
            195                 200                 205 gag ctt ccc ggc ctg ggc ccg aac ccc agc gtg gag gag atc tac cgg         913
Glu Leu Pro Gly Leu Gly Pro Asn Pro Ser Val Glu Glu Ile Tyr Arg
        210                 215                 220 gcc ctg gcc cgg gcc tac ccc ggc gcg gcc ttc gcc cag tac acc acc         961
Ala Leu Ala Arg Ala Tyr Pro Gly Ala Ala Phe Ala Gln Tyr Thr Thr
    225                 230                 235 cag ctg gac ggg acc cag atc tac ttc tac gcc ctc atg aag aag gag         1009
Gln Leu Asp Gly Thr Gln Ile Tyr Phe Tyr Ala Leu Met Lys Lys Glu
240                 245                 250                 255 gta ccc ccc tcc gag gcc acc gcc cgg gag tgg gcc gtc cgg gcc cag         1057
Val Pro Pro Ser Glu Ala Thr Ala Arg Glu Trp Ala Val Arg Ala Gln
                260                 265                 270
```

|     |      |
| --- | ---- |
| acc agc ctc cag agc ctg gcc cag gag tcc aac ttc acc tac tac ctg<br>Thr Ser Leu Gln Ser Leu Ala Gln Glu Ser Asn Phe Thr Tyr Tyr Leu<br>275                    280                   285 | 1105 |
| gcc ccg ggg agc caa cac tgc atc ctg ccc cgg ccc gag ctc tac acc<br>Ala Pro Gly Ser Gln His Cys Ile Leu Pro Arg Pro Glu Leu Tyr Thr<br>         290                   295                 300 | 1153 |
| ctg aag gtg ggg gag gtg agc gtt ctg gac tgg ctc agg agc ctg gcg<br>Leu Lys Val Gly Glu Val Ser Val Leu Asp Trp Leu Arg Ser Leu Ala<br>305                    310                   315 | 1201 |
| gag aag ggg cag gcc ccc cgc gta ggt ccg tgaggtcggg gagggcctcg<br>Glu Lys Gly Gln Ala Pro Arg Val Gly Pro<br>320                    325 | 1251 |
| aggaggaccc ggtacgcctc cttggggag ggggcctgga ggagggcccg gaggacccc | 1311 |
| tcccctttcg ccaccaggac gtccgccttc agggcgaaga ccccttggaa gtagagggcg | 1371 |
| tccgccaggc tggtgcggag ccggtcatag gcgctgaggc gggggttggg gggtcttagc | 1431 |
| cgggcgagga ggcgcgccca ggccaggtaa aggggtacc gctcagggta ggccccttc | 1491 |
| agggcgaaga ggaagaggta gttggccagg aactcgtcca gccagcggcg gccggtcctg | 1551 |
| agccgccagg ccacctggac cgcgtgggcg tgctcgtgcc cagggtgag gtccaagaac | 1611 |
| tcctccagcg ccccggggag accctcctcc gccacaggca ggaggacctg cgcaggcgg | 1671 |
| tggaggaggc gctcggggta gaccagaggg acgaagaggt aaagccgggt ccggctcgtc | 1731 |
| ctctggaagg ggaggccgta gggcacccgg gtcctctccc gccagtccct ctccgagagg | 1791 |
| acgaagaggt tcacggggg aaggggcgg tagcgggcca ggaggcggtg gagccctcc | 1851 |
| aggtaggcct ggacctgggc ggtgcgggcc ttcccccg gctgtagaa ggcggggagg | 1911 |
| tcggggtggg ggagggcgtt catatcacct cccggaaccc gatgcgctcc gcctgggcct | 1971 |
| ggagctcccg ccgcaggagg gggtgggcct cgaggcgggg gtccttctcc aggatctcct | 2031 |
| acaacgtgga cttctaaagc ccgccggcc ctccccccgc ccccggggc gggggttgg | 2091 |
| cctttttccg gccaggcca gggagccttg cgcgttcggc gtttggcgtt cagccttcgg | 2151 |
| cgtttggccc ataatcggga ccaggcgaaa cgggtatcat ggaggtatgc gctggctggg | 2211 |
| ggtgctcctc ctgggcctgg ccctggccca ggggctggac ctggcccagt cctcctgcg | 2271 |
| ccagggccaa tacgagcagg ccctggcccg gctggagcgg gagccccccg gcccggaggt | 2331 |
| cctggccctg aagggccggg cctacctgct cctgggccgg ccggaggcgg cccgggaggc | 2391 |
| cctggagggg gcgccccgcc tggccggggg ggcggaggtg gagcggctca aggggtggct | 2451 |
| ggccctggag gcgggaaagg ccgaggaggc ccggcggcc ttccaggccg cggccatcta | 2511 |
| ctcgggcctt ccccaagacg ccctcctctg gccctggcg gcttgggagg cgggccgctc | 2571 |
| ttccgaggag gccctggccc gggcggagcg ggcgggaggc gggcggagg cggccctcct | 2631 |
| taagggctc ttcctcctgg cccaggaccc ggcggaggcc ctggccgcct tccgccgggc | 2691 |
| gggggacggc cccttcaagg cccaggccct ctacctgcag ggcctggccc tcgaggccct | 2751 |
| gggccgggac ccggaggccc gggaggccta ccgccaggcc ctgaaggcct ccccggacta | 2811 |
| cctccccgcc cgccgggctt tagggctcta gtaccacccc atcctggcgt acgccaggat | 2871 |
| gggggccccg gtaaagcctt agccttccga cgaagcgggg aatgagggga agcctgaatg | 2931 |
| acggaaaaga ggatggaaaa atcggtcttc cgctaccaag gccccgagcc caaggggac | 2991 |
| cagcccaagg ccatccggga gctggtggag gccctggagg cggggagcg gttcgtcacc | 3051 |
| cttttggggg ccaccggcac ggggaagacg gtcaccatgg ccaaggtgat cgaggccctg | 3111 |
| ggcaggccca cctggtcct cgcccccaac aagatc | 3147 |

```
<210> SEQ ID NO 8
<211> LENGTH: 329
<212> TYPE: PRT
<213> ORGANISM: Artificial Sequence
<220> FEATURE:
<223> OTHER INFORMATION: Description of Artificial Sequence:cloned
      esterase gene from bacteria  E101

<400> SEQUENCE: 8

Met Arg Arg Leu Leu Gly Leu Leu Phe Leu Ala Leu Ala Leu Ala
 1               5                  10                  15

Gln Gly Leu Gly Pro Tyr Trp Gln Glu Val Gln Ala Gln Gly Thr Val
             20                  25                  30

Cys Ser Asp Gly Ser Pro Trp Arg Phe Tyr Val Ser Pro Gly Asp Pro
         35                  40                  45

Lys Lys Val Leu Leu Asp Phe Gln Gly Gly Ala Cys Trp Asp Ala
 50                  55                  60

Gln Thr Cys Gly Pro Gln Ser Gln Thr Tyr Arg Lys Arg Val Asp Val
 65                  70                  75                  80

Gln Glu Leu Leu Leu Ala Gln Gly Ile Tyr Asn Arg Ala Ser Ile Ala
                 85                  90                  95

Asn Pro Phe Phe Gly Trp Thr His Val Phe Ile Pro Tyr Cys Thr Gly
                100                 105                 110

Asp Leu His Val Gly Arg Ala Thr Val Asp Tyr Gly Gly Phe Lys Val
            115                 120                 125

His His Gln Gly Ala Arg Asn Ala Leu Ala Ala Leu Glu Tyr Val Phe
        130                 135                 140

Lys Asn Tyr Pro Lys Ala Glu Arg Val Phe Val Thr Gly Cys Ser Ala
145                 150                 155                 160

Gly Gly Tyr Gly Ala Val Phe Trp Ala Asp Lys Val Leu Ala Thr Tyr
                165                 170                 175

Lys Ser Ala Gln Ile Ala Val Cys Gly Asp Ala Ala Leu Gly Val Ser
            180                 185                 190

Thr Ser Asp Phe Pro Gly Ser Arg Val Trp Asn Ala Arg Leu Pro Glu
        195                 200                 205

Leu Pro Gly Leu Gly Pro Asn Pro Ser Val Glu Glu Ile Tyr Arg Ala
    210                 215                 220

Leu Ala Arg Ala Tyr Pro Gly Ala Ala Phe Ala Gln Tyr Thr Thr Gln
225                 230                 235                 240

Leu Asp Gly Thr Gln Ile Tyr Phe Tyr Ala Leu Met Lys Lys Glu Val
                245                 250                 255

Pro Pro Ser Glu Ala Thr Ala Arg Glu Trp Ala Val Arg Ala Gln Thr
            260                 265                 270

Ser Leu Gln Ser Leu Ala Gln Glu Ser Asn Phe Thr Tyr Tyr Leu Ala
        275                 280                 285

Pro Gly Ser Gln His Cys Ile Leu Pro Arg Pro Glu Leu Tyr Thr Leu
    290                 295                 300

Lys Val Gly Glu Val Ser Val Leu Asp Trp Leu Arg Ser Leu Ala Glu
305                 310                 315                 320

Lys Gly Gln Ala Pro Arg Val Gly Pro
                325

<210> SEQ ID NO 9
<211> LENGTH: 2315
<212> TYPE: DNA
```

```
<213> ORGANISM: Artificial Sequence
<220> FEATURE:
<223> OTHER INFORMATION: Description of Artificial Sequence:cloned
      esterase gene from bacteria E019
<220> FEATURE:
<221> NAME/KEY: CDS
<222> LOCATION: (312)..(1820)

<400> SEQUENCE: 9
acgattgccg atatcgctgt cgcaacaaac gctggccaaa tcaaaacggg agcaccgtcg      60
cgtacggacc gcgtcgcaaa atacaaccag ttgctccgca ttgaagacga acttggccac     120
acggctattt accaaggcat tcgttcgttt tacaatttga aaaaataacg ggaatcaaca     180
acaaagggtg tctccaacgt tgcgagacac cctctttaat tacgggaaac agaaatgatt     240
tcctatcgat agcaaaaaat ggacgtgggt aaaccattcg tttataatat cttttgtaa     300 tcgttagaat a ttg aaa aag ggg atg gga acc gtg atc gtg gaa aca aag      350
              Leu Lys Lys Gly Met Gly Thr Val Ile Val Glu Thr Lys
                1               5                  10 tac ggt cgg ttg cgc ggg gga aca aat gaa ggg gtt ttc tat tgg aaa       398
Tyr Gly Arg Leu Arg Gly Gly Thr Asn Glu Gly Val Phe Tyr Trp Lys
 15                  20                  25 ggg att ccg tac gcg aaa gcg ccg gtc ggt gaa cgc cgt ttt ttg ccg       446
Gly Ile Pro Tyr Ala Lys Ala Pro Val Gly Glu Arg Arg Phe Leu Pro
 30                  35                  40                  45 ccg gaa ccg ccc gat gca tgg gac gga gtg cgt gag gcg aca tcg ttt       494
Pro Glu Pro Pro Asp Ala Trp Asp Gly Val Arg Glu Ala Thr Ser Phe
                 50                  55                  60 gga ccg gtc gtc atg cag ccg tcc gat tcg atg ttc agc cag ctg ctc       542
Gly Pro Val Val Met Gln Pro Ser Asp Ser Met Phe Ser Gln Leu Leu
             65                  70                  75 gga cgg atg aat gaa cca atg agc gag gat ggg ttg tat ctg aac att       590
Gly Arg Met Asn Glu Pro Met Ser Glu Asp Gly Leu Tyr Leu Asn Ile
         80                  85                  90 tgg tca ccg gcg gcg gat ggg aag aag cgc ccg gta ttg ttt tgg att       638
Trp Ser Pro Ala Ala Asp Gly Lys Lys Arg Pro Val Leu Phe Trp Ile
     95                 100                 105 cat ggc ggc gct ttt tta ttc ggc tcc ggt tca ttt cca tgg tat gat       686
His Gly Gly Ala Phe Leu Phe Gly Ser Gly Ser Phe Pro Trp Tyr Asp
110                 115                 120                 125 gga acg gcg ttt gcc aaa cac ggc gat gtc gtt gtc gtg acg atc aac       734
Gly Thr Ala Phe Ala Lys His Gly Asp Val Val Val Val Thr Ile Asn
                130                 135                 140 tac cgg atg agc gtg ttt ggc ttt ttg tat ttg gga gat gcg ttt ggc       782
Tyr Arg Met Ser Val Phe Gly Phe Leu Tyr Leu Gly Asp Ala Phe Gly
            145                 150                 155 gaa acg tat gcc cag gcg gga aat ctt ggc ata ttg gat caa gtg gcg       830
Glu Thr Tyr Ala Gln Ala Gly Asn Leu Gly Ile Leu Asp Gln Val Ala
        160                 165                 170 gcg ctg cgc tgg gtg aaa gag aac att gag gcg ttc ggc ggt gat ccg       878
Ala Leu Arg Trp Val Lys Glu Asn Ile Glu Ala Phe Gly Gly Asp Pro
    175                 180                 185 gac aac att acg att ttt ggc gaa tca gcc gga gcg gca agc gtt ggc       926
Asp Asn Ile Thr Ile Phe Gly Glu Ser Ala Gly Ala Ala Ser Val Gly
190                 195                 200                 205 gtg ctg ttg tcg ctt ccg gaa gca agc ggg ctg ttt cga cgc gct ata       974
Val Leu Leu Ser Leu Pro Glu Ala Ser Gly Leu Phe Arg Arg Ala Ile
                210                 215                 220 ttg caa agc gga tcg ggt tcg ctt ctt ctt cgt tct ccg gag acg gcg      1022
Leu Gln Ser Gly Ser Gly Ser Leu Leu Leu Arg Ser Pro Glu Thr Ala
            225                 230                 235
```

-continued

```
atg gct ctg act gaa cgc att tta gaa cgt gcc ggc atc cgt ccg ggt    1070
Met Ala Leu Thr Glu Arg Ile Leu Glu Arg Ala Gly Ile Arg Pro Gly
        240                 245                 250 gac cgc gat cgg ctg ctg tcg att cca gca gca gag cta ttg cag gcg    1118
Asp Arg Asp Arg Leu Leu Ser Ile Pro Ala Ala Glu Leu Leu Gln Ala
    255                 260                 265 gcg atg tcg ctc ggc cca gga atc acg tac ggt ccg gtg gtt gac gga    1166
Ala Met Ser Leu Gly Pro Gly Ile Thr Tyr Gly Pro Val Val Asp Gly
270                 275                 280                 285 cat gtg ttg cga cgc cat ccg atc gaa gcg ctc cac gac ggg gca gca    1214
His Val Leu Arg Arg His Pro Ile Glu Ala Leu His Asp Gly Ala Ala
                290                 295                 300 agt gat att cca atc cta att ggc gtg acg aaa gac gaa tac aat ttg    1262
Ser Asp Ile Pro Ile Leu Ile Gly Val Thr Lys Asp Glu Tyr Asn Leu
            305                 310                 315 ttt tca ttg act gat ccg tca ttg aca aga ctc gaa gaa aaa gaa ctg    1310
Phe Ser Leu Thr Asp Pro Ser Leu Thr Arg Leu Glu Glu Lys Glu Leu
        320                 325                 330 ctt gac cgg atg aac cgt gag gtc ggg cct att ccg gag gag gcg gta    1358
Leu Asp Arg Met Asn Arg Glu Val Gly Pro Ile Pro Glu Glu Ala Val
    335                 340                 345 cgc tat tac gcg gaa aca gcg gat cgg tcg gca ccc gcg tgg caa aca    1406
Arg Tyr Tyr Ala Glu Thr Ala Asp Arg Ser Ala Pro Ala Trp Gln Thr
350                 355                 360                 365 tgg ctg cgc atc atg acg tac ctt gtt ttt gtc gac gga atg ttg cga    1454
Trp Leu Arg Ile Met Thr Tyr Leu Val Phe Val Asp Gly Met Leu Arg
                370                 375                 380 acg gcg gat gcc caa gca gcg caa ggg gcg aat gtg tac atg tat cgg    1502
Thr Ala Asp Ala Gln Ala Ala Gln Gly Ala Asn Val Tyr Met Tyr Arg
            385                 390                 395 ttt gat tat gaa acg ccg gcg ttt ggt gga caa ctg aaa gcg tgc cat    1550
Phe Asp Tyr Glu Thr Pro Ala Phe Gly Gly Gln Leu Lys Ala Cys His
        400                 405                 410 acg ctc gag ttg ccg ttt gtg ttt cat aac ctc cat cag cct ggt gtc    1598
Thr Leu Glu Leu Pro Phe Val Phe His Asn Leu His Gln Pro Gly Val
    415                 420                 425 gag aat ttc gtc ggc aac cga cca gag cgt gag gcg att gcc agc gaa    1646
Glu Asn Phe Val Gly Asn Arg Pro Glu Arg Glu Ala Ile Ala Ser Glu
430                 435                 440                 445 atg cat ggt gcc tgg ctt tcg ttc gcc cac acc ggc aac ccg aac ggc    1694
Met His Gly Ala Trp Leu Ser Phe Ala His Thr Gly Asn Pro Asn Gly
                450                 455                 460 gct cat tta cca gag aag tgg ccc gta tac aca aaa gag cac aaa ccg    1742
Ala His Leu Pro Glu Lys Trp Pro Val Tyr Thr Lys Glu His Lys Pro
            465                 470                 475 gtg ttt gtc ttt tcg gct gcg agc cat gtg gaa gac gat ccg ttc ggt    1790
Val Phe Val Phe Ser Ala Ala Ser His Val Glu Asp Asp Pro Phe Gly
        480                 485                 490 cgc gag cgg gaa gcg tgg caa gga cgc ctt tgacgaaaaa atccataagc      1840
Arg Glu Arg Glu Ala Trp Gln Gly Arg Leu
    495                 500 aacatgtgtt ctttgtctga acacgatcaa ggtacgcgca ttttcgcgga aaaagaccgt  1900
gggcaaacgt tcgcctttac ctctaaaagg aatgacgcaa catgtctgca cttcacagga  1960
aagaggacga aacggttggt tttcagaata ggaaaaggtg tcccgttttt tgggacacct  2020
tcttctatgt atcgctcaat catttgcttc tgtggcagga agcccgaatc gctcggcgag  2080
tgccggatcg gttgaaaaaa gtgatggatg agattcgcca agcaggcaac atcattttgt  2140
```

-continued

```
tcatcgatga gctccatacg ctaatcggcg ctggcggagc cgaaggagcg atccaaagaa    2200
ttcaaaaagc ttctcgagag tacttctaga gcggccgcgg gcccatcgat tttccacccg    2260
ggtggggtac caggtaagtg tacccaattc gccctatagt gagtcgtatt acaat         2315
```

<210> SEQ ID NO 10
<211> LENGTH: 503
<212> TYPE: PRT
<213> ORGANISM: Artificial Sequence
<220> FEATURE:
<223> OTHER INFORMATION: Description of Artificial Sequence:cloned
      esterase gene from bacteria E019

<400> SEQUENCE: 10

```
Leu Lys Lys Gly Met Gly Thr Val Ile Val Glu Thr Lys Tyr Gly Arg
  1               5                  10                  15

Leu Arg Gly Gly Thr Asn Glu Gly Val Phe Tyr Trp Lys Gly Ile Pro
                 20                  25                  30

Tyr Ala Lys Ala Pro Val Gly Glu Arg Arg Phe Leu Pro Pro Glu Pro
             35                  40                  45

Pro Asp Ala Trp Asp Gly Val Arg Glu Ala Thr Ser Phe Gly Pro Val
         50                  55                  60

Val Met Gln Pro Ser Asp Ser Met Phe Ser Gln Leu Leu Gly Arg Met
 65                  70                  75                  80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
            100                 105                 110

Ala Phe Leu Phe Gly Ser Gly Ser Phe Pro Trp Tyr Asp Gly Thr Ala
        115                 120                 125

Phe Ala Lys His Gly Asp Val Val Val Thr Ile Asn Tyr Arg Met
    130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Gly Asp Pro Asp Asn Ile
            180                 185                 190

Thr Ile Phe Gly Glu Ser Ala Gly Ala Ala Ser Val Gly Val Leu Leu
        195                 200                 205

Ser Leu Pro Glu Ala Ser Gly Leu Phe Arg Arg Ala Ile Leu Gln Ser
    210                 215                 220

Gly Ser Gly Ser Leu Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                245                 250                 255

Arg Leu Leu Ser Ile Pro Ala Ala Glu Leu Leu Gln Ala Ala Met Ser
            260                 265                 270

Leu Gly Pro Gly Ile Thr Tyr Gly Pro Val Val Asp Gly His Val Leu
        275                 280                 285

Arg Arg His Pro Ile Glu Ala Leu His Asp Gly Ala Ala Ser Asp Ile
    290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335
```

```
Met Asn Arg Glu Val Gly Pro Ile Pro Glu Ala Val Arg Tyr Tyr
        340                 345                 350
Ala Glu Thr Ala Asp Arg Ser Ala Pro Ala Trp Gln Thr Trp Leu Arg
        355                 360                 365
Ile Met Thr Tyr Leu Val Phe Val Asp Gly Met Leu Arg Thr Ala Asp
        370                 375                 380
Ala Gln Ala Ala Gln Gly Ala Asn Val Tyr Met Tyr Arg Phe Asp Tyr
385                 390                 395                 400
Glu Thr Pro Ala Phe Gly Gly Gln Leu Lys Ala Cys His Thr Leu Glu
                405                 410                 415
Leu Pro Phe Val Phe His Asn Leu His Gln Pro Gly Val Glu Asn Phe
                420                 425                 430
Val Gly Asn Arg Pro Glu Arg Glu Ala Ile Ala Ser Glu Met His Gly
                435                 440                 445
Ala Trp Leu Ser Phe Ala His Thr Gly Asn Pro Asn Gly Ala His Leu
        450                 455                 460
Pro Glu Lys Trp Pro Val Tyr Thr Lys Glu His Lys Pro Val Phe Val
465                 470                 475                 480
Phe Ser Ala Ala Ser His Val Glu Asp Asp Pro Phe Gly Arg Glu Arg
                485                 490                 495
Glu Ala Trp Gln Gly Arg Leu
            500
```

<210> SEQ ID NO 11
<211> LENGTH: 2643
<212> TYPE: DNA
<213> ORGANISM: Artificial Sequence
<220> FEATURE:
<223> OTHER INFORMATION: Description of Artificial Sequence:cloned
      esterase gene from bacteria E005
<220> FEATURE:
<221> NAME/KEY: CDS
<222> LOCATION: (1087)..(2595)

<400> SEQUENCE: 11

```
ttgattccaa gctcgaaatt aaccctcact aaagggaaca aaagctggag ctcgcgcgcc      60
tgcaggtcga cactagtgga tccccttttca tttatgattt tgcagcggtc gagctgcttt    120
tatgttgttg aatgaactgt tcaatttgat catgccggtc ggtgcggaaa gcttccgtga    180
agcgctgcgc atgggtgcag aaattttcca tagcttaaaa gctgtgttaa agcgaaaggg    240
ctacaacacg gctgtcggtg acgaaggcgg atttgctccg aacttaaaat cgaacgaaga    300
agcgctgcaa acgatcattg aagcgatcga aaaagccggc tacaaaccag gcgaacaagt    360
gatgctcgct atggacgttg cttcgtcgga gctgtacaac aaagaagatg gcaaatatca    420
tttggaaggc gaaggcgtcg tcaaaacatc agaagaaatg gttgcttggt atgaagagct    480
tgtgtcgaaa tatccgatca tctcgatcga agacggactt gacgaaaatg actgggaagg    540
ccataaactg cttactgagc gccttggcca caaagtgcag ctcgtcggtg acgacttgtt    600
tgtaacgaac acgaaaaaac tggccgaagg cattgaaaaa ggcgtcggca actcgatttt    660
aattaaagtg aaccaaatcg gtacactgac ggaaacgttc gatgccattg agatggccaa    720
acgcgccggc tacacggcgg ttgtgtcgca ccgttccggt gaaacggaag acagcacgat    780
tgccgatatc gctgtcgcaa caaacgctgc ccaaatcaaa acgggagcac cgtcgcgtac    840
ggaccgcgtc gcaaaataca accagctgct ccgcattgaa gacgaacttg ccacacggc     900
tatttaccaa ggcattcgtt cgttttacaa tttgaaaaaa taacgggaat caacaacaaa    960
```

```
gggtgtctcc aacgttgcga gacaccctct ttaattacgg gaaacagaaa tgatttccta      1020
tcgatagcaa aaaatggacg tgggtaaacc attcgtttat aatatctttt tgtaatcgtt      1080 agaata ttg aaa aag ggg atg gga acc gtg atc gtg gaa aca aag tac         1128
       Leu Lys Lys Gly Met Gly Thr Val Ile Val Glu Thr Lys Tyr
       1               5                  10 ggt cgg ttg cgc ggg gga aca aat gaa ggg gtt ttc tat tgg aaa ggg         1176
Gly Arg Leu Arg Gly Gly Thr Asn Glu Gly Val Phe Tyr Trp Lys Gly
15                  20                  25                  30 att ccg tac gcg aaa gcg ccg gtc ggt gaa cgc cgt ttt ttg ccg ccg         1224
Ile Pro Tyr Ala Lys Ala Pro Val Gly Glu Arg Arg Phe Leu Pro Pro
                35                  40                  45 gaa ccg ccc gat gca tgg gac gga gtg cgt gag gcg aca tcg ttt gga         1272
Glu Pro Pro Asp Ala Trp Asp Gly Val Arg Glu Ala Thr Ser Phe Gly
        50                  55                  60 ccg gtc gtc atg cag ccg tcc gat tcg atg ttc agc cag ctg ctc gga         1320
Pro Val Val Met Gln Pro Ser Asp Ser Met Phe Ser Gln Leu Leu Gly
65                  70                  75 cgg atg aat gaa cca atg agc gag gat ggg ttg tat ctg aac att tgg         1368
Arg Met Asn Glu Pro Met Ser Glu Asp Gly Leu Tyr Leu Asn Ile Trp
    80                  85                  90 tca ccg gcg gcg gat ggg aag aag cgc ccg gta ttg ttt tgg att cat         1416
Ser Pro Ala Ala Asp Gly Lys Lys Arg Pro Val Leu Phe Trp Ile His
95                  100                 105                 110 ggc ggc gct ttt tta ttc ggc tcc ggt tca ttt cca tgg tat gat gga         1464
Gly Gly Ala Phe Leu Phe Gly Ser Gly Ser Phe Pro Trp Tyr Asp Gly
                115                 120                 125 acg gcg ttt gcc aaa cac ggc gat gtc gtt gtc gtg acg atc aac tac         1512
Thr Ala Phe Ala Lys His Gly Asp Val Val Val Val Thr Ile Asn Tyr
        130                 135                 140 cgg atg agc gtg ttt ggc ttt ttg tat ttg gga gat gcg ttt ggc gaa         1560
Arg Met Ser Val Phe Gly Phe Leu Tyr Leu Gly Asp Ala Phe Gly Glu
145                 150                 155 acg tat gcc cag gcg gga aat ctt ggc ata ttg gat caa gtg gcg gcg         1608
Thr Tyr Ala Gln Ala Gly Asn Leu Gly Ile Leu Asp Gln Val Ala Ala
    160                 165                 170 ctg cgc tgg gtg aaa gag aac att gag gcg ttc ggc ggt gat ccg gac         1656
Leu Arg Trp Val Lys Glu Asn Ile Glu Ala Phe Gly Gly Asp Pro Asp
175                 180                 185                 190 aac att acg att ttt ggc gaa tca gcc gga gcg gca agc gtt ggc gtg         1704
Asn Ile Thr Ile Phe Gly Glu Ser Ala Gly Ala Ala Ser Val Gly Val
                195                 200                 205 ctg ttg tcg ctt ccg gaa gca agc ggg ctg ttt cga cgc gct ata ttg         1752
Leu Leu Ser Leu Pro Glu Ala Ser Gly Leu Phe Arg Arg Ala Ile Leu
        210                 215                 220 caa agc gga tcg ggt tcg ctt ctt ctt cgt tct ccg gag acg gcg atg         1800
Gln Ser Gly Ser Gly Ser Leu Leu Leu Arg Ser Pro Glu Thr Ala Met
225                 230                 235 gct ctg act gaa cgc att tta gaa cgt gcc ggc atc cgt ccg ggt gac         1848
Ala Leu Thr Glu Arg Ile Leu Glu Arg Ala Gly Ile Arg Pro Gly Asp
    240                 245                 250 cgc gat cgg ctg ctg tcg att cca gca gca gag cta ttg cag gcg gcg         1896
Arg Asp Arg Leu Leu Ser Ile Pro Ala Ala Glu Leu Leu Gln Ala Ala
255                 260                 265                 270 atg tcg ctc ggc cca gga atc acg tac ggt ccg gtg gtt gac gga cat         1944
Met Ser Leu Gly Pro Gly Ile Thr Tyr Gly Pro Val Val Asp Gly His
                275                 280                 285 gtg ttg cga cgc cat ccg atc gaa gcg ctc cac gac ggg gca gca agt         1992
Val Leu Arg Arg His Pro Ile Glu Ala Leu His Asp Gly Ala Ala Ser
```

```
                 290                 295                 300
gat att cca atc cta att ggc gtg acg aaa gac gaa tac aat ttg ttt      2040
Asp Ile Pro Ile Leu Ile Gly Val Thr Lys Asp Glu Tyr Asn Leu Phe
        305                 310                 315 tca ttg act gat ccg tca ttg aca aga ctc gaa gaa aaa gaa ctg ctt      2088
Ser Leu Thr Asp Pro Ser Leu Thr Arg Leu Glu Glu Lys Glu Leu Leu
320                 325                 330 gac cgg atg aac cgt gag gtc ggg cct att ccg gag gag gcg gta cgc      2136
Asp Arg Met Asn Arg Glu Val Gly Pro Ile Pro Glu Glu Ala Val Arg
335                 340                 345                 350 tat tac gcg gaa aca gcg gat cgg tcg gca ccc gcg tgg caa aca tgg      2184
Tyr Tyr Ala Glu Thr Ala Asp Arg Ser Ala Pro Ala Trp Gln Thr Trp
                355                 360                 365 ctg cgc atc atg acg tac ctt gtt ttt gtc gac gga atg ttg cga acg      2232
Leu Arg Ile Met Thr Tyr Leu Val Phe Val Asp Gly Met Leu Arg Thr
            370                 375                 380 gcg gat gcc caa gca gcg caa ggg gcg aat gtg tac atg tat cgg ttt      2280
Ala Asp Ala Gln Ala Ala Gln Gly Ala Asn Val Tyr Met Tyr Arg Phe
        385                 390                 395 gat tat gaa acg ccg gcg ttc ggt gga caa ctg aaa gcg tgc cat acg      2328
Asp Tyr Glu Thr Pro Ala Phe Gly Gly Gln Leu Lys Ala Cys His Thr
    400                 405                 410 ctc gag ttg ccg ttt gtg ttt cat aac ctc cat cag cct ggt gtc gag      2376
Leu Glu Leu Pro Phe Val Phe His Asn Leu His Gln Pro Gly Val Glu
415                 420                 425                 430 aat ttc gtc ggc aac cga cca gag cgt gag gcg att gcc agc gaa atg      2424
Asn Phe Val Gly Asn Arg Pro Glu Arg Glu Ala Ile Ala Ser Glu Met
                435                 440                 445 cat ggt gcc tgg ctt tcg ttc gcc cac acc ggc aac ccg aac ggc gct      2472
His Gly Ala Trp Leu Ser Phe Ala His Thr Gly Asn Pro Asn Gly Ala
            450                 455                 460 cat tta cca gag aag tgg ccc gta tac aca aaa gag cac aaa ccg gtg      2520
His Leu Pro Glu Lys Trp Pro Val Tyr Thr Lys Glu His Lys Pro Val
        465                 470                 475 ttt gtc ttt tcg gct gcg agc cat gtg gaa gac gat ccg ttc ggt cgc      2568
Phe Val Phe Ser Ala Ala Ser His Val Glu Asp Asp Pro Phe Gly Arg
    480                 485                 490 gag cgg gaa gcg tgg caa gga cgc ctt tgacgaaaaa atccataagc            2615
Glu Arg Glu Ala Trp Gln Gly Arg Leu
495                 500 aacatgtgtt ctttgtctga acacgatc                                       2643

<210> SEQ ID NO 12
<211> LENGTH: 503
<212> TYPE: PRT
<213> ORGANISM: Artificial Sequence
<220> FEATURE:
<223> OTHER INFORMATION: Description of Artificial Sequence:cloned
      esterase gene from bacteria E005

<400> SEQUENCE: 12

Leu Lys Lys Gly Met Gly Thr Val Ile Val Glu Thr Lys Tyr Gly Arg
  1               5                  10                  15

Leu Arg Gly Gly Thr Asn Glu Gly Val Phe Tyr Trp Lys Gly Ile Pro
             20                  25                  30

Tyr Ala Lys Ala Pro Val Gly Glu Arg Arg Phe Leu Pro Pro Glu Pro
         35                  40                  45

Pro Asp Ala Trp Asp Gly Val Arg Glu Ala Thr Ser Phe Gly Pro Val
     50                  55                  60
```

```
Val Met Gln Pro Ser Asp Ser Met Phe Ser Gln Leu Leu Gly Arg Met
 65                  70                  75                  80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
            100                 105                 110

Ala Phe Leu Phe Gly Ser Gly Ser Phe Pro Trp Tyr Asp Gly Thr Ala
            115                 120                 125

Phe Ala Lys His Gly Asp Val Val Val Thr Ile Asn Tyr Arg Met
130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Gly Asp Pro Asp Asn Ile
                180                 185                 190

Thr Ile Phe Gly Glu Ser Ala Gly Ala Ala Ser Val Gly Val Leu Leu
            195                 200                 205

Ser Leu Pro Glu Ala Ser Gly Leu Phe Arg Arg Ala Ile Leu Gln Ser
            210                 215                 220

Gly Ser Gly Ser Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                245                 250                 255

Arg Leu Leu Ser Ile Pro Ala Ala Glu Leu Leu Gln Ala Ala Met Ser
            260                 265                 270

Leu Gly Pro Gly Ile Thr Tyr Gly Pro Val Val Asp Gly His Val Leu
            275                 280                 285

Arg Arg His Pro Ile Glu Ala Leu His Asp Gly Ala Ala Ser Asp Ile
            290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335

Met Asn Arg Glu Val Gly Pro Ile Pro Glu Glu Ala Val Arg Tyr Tyr
            340                 345                 350

Ala Glu Thr Ala Asp Arg Ser Ala Pro Ala Trp Gln Thr Trp Leu Arg
            355                 360                 365

Ile Met Thr Tyr Leu Val Phe Val Asp Gly Met Leu Arg Thr Ala Asp
            370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                405                 410                 415

Leu Pro Phe Val Phe His Asn Leu His Gln Pro Gly Val Glu Asn Phe
            420                 425                 430

Val Gly Asn Arg Pro Glu Arg Glu Ala Ile Ala Ser Glu Met His Gly
            435                 440                 445

Ala Trp Leu Ser Phe Ala His Thr Gly Asn Pro Asn Gly Ala His Leu
            450                 455                 460

Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
```

```
                    485                 490                 495
Glu Ala Trp Gln Gly Arg Leu
                500

<210> SEQ ID NO 13
<211> LENGTH: 1699
<212> TYPE: DNA
<213> ORGANISM: Artificial Sequence
<220> FEATURE:
<223> OTHER INFORMATION: Description of Artificial Sequence:cloned
      esterase gene from bacteria  E004
<220> FEATURE:
<221> NAME/KEY: CDS
<222> LOCATION: (92)..(1594)

<400> SEQUENCE: 13
attgcttcag gggaactttt aaacacttga gtttgacaac cactccttaa tcatttaaga         60
tttaaatgaa aattaaaata aatcaaaaag a gtg att caa atg aat acg ttg          112
                                   Val Ile Gln Met Asn Thr Leu
                                     1               5 gtg gaa acc cgt ttt ggg aaa gta caa ggc ggt aca gac gga gag gtt         160
Val Glu Thr Arg Phe Gly Lys Val Gln Gly Gly Thr Asp Gly Glu Val
         10                  15                  20 tgt ttt tgg aaa ggg att cct tat gcg aaa cct ccg gtg gga aaa cgc         208
Cys Phe Trp Lys Gly Ile Pro Tyr Ala Lys Pro Pro Val Gly Lys Arg
 25                  30                  35 cgc ttt caa aaa ccg gaa ccg ccg gag aaa tgg gat ggc gtt tgg gag         256
Arg Phe Gln Lys Pro Glu Pro Pro Glu Lys Trp Asp Gly Val Trp Glu
 40                  45                  50                  55 gcc acc cgg ttc cgg tcc atg gtg atg cag ccg tcc ggc acc acc ttc         304
Ala Thr Arg Phe Arg Ser Met Val Met Gln Pro Ser Gly Thr Thr Phe
                 60                  65                  70 agc acc gtg ctc ggg gaa gcg gat ctt cct gtg agc gaa gac ggt ctt         352
Ser Thr Val Leu Gly Glu Ala Asp Leu Pro Val Ser Glu Asp Gly Leu
             75                  80                  85 tat ctg aat atc tgg tcg ccg gca gcc gac gga aaa aag cgg ccg gtg         400
Tyr Leu Asn Ile Trp Ser Pro Ala Ala Asp Gly Lys Lys Arg Pro Val
         90                  95                 100 ctc ttc tgg atc cat ggc ggc gcc tac cag ttt gga tcc ggc gct tcc         448
Leu Phe Trp Ile His Gly Gly Ala Tyr Gln Phe Gly Ser Gly Ala Ser
 105                 110                 115 ccc tgg tat gac ggg acg gag ttt gcc aaa aac gga gat gtg gtg gtt         496
Pro Trp Tyr Asp Gly Thr Glu Phe Ala Lys Asn Gly Asp Val Val Val
120                 125                 130                 135 gtc acg atc aac tac cgg ttg aac gcg ttt gga ttt ttg tac ttg gca         544
Val Thr Ile Asn Tyr Arg Leu Asn Ala Phe Gly Phe Leu Tyr Leu Ala
                140                 145                 150 gat tgg ttc ggc gac gaa ttt tca gcg tcg ggc aac ctg gga ata ttg         592
Asp Trp Phe Gly Asp Glu Phe Ser Ala Ser Gly Asn Leu Gly Ile Leu
            155                 160                 165 gac caa gtc gct gca ctg cgc tgg gtg aaa gaa aac att tcc gca ttc         640
Asp Gln Val Ala Ala Leu Arg Trp Val Lys Glu Asn Ile Ser Ala Phe
        170                 175                 180 ggc ggc gac ccg gag caa atc acc atc ttc ggg gag tcg gcc gga gcc         688
Gly Gly Asp Pro Glu Gln Ile Thr Ile Phe Gly Glu Ser Ala Gly Ala
    185                 190                 195 gga agc gtc ggg gtt ctg ctt tcc ctc ccg gaa acc aaa ggg ctg ttt         736
Gly Ser Val Gly Val Leu Leu Ser Leu Pro Glu Thr Lys Gly Leu Phe
200                 205                 210                 215 caa cgg gcg atc ttg caa agc gga tcg ggt gcc att ttg ctc cgt tcc         784
Gln Arg Ala Ile Leu Gln Ser Gly Ser Gly Ala Ile Leu Leu Arg Ser
```

```
              220                 225                 230
tct cag aca gcc tcg ggc atc gcg gaa caa att ctt acg aaa gcc ggc     832
Ser Gln Thr Ala Ser Gly Ile Ala Glu Gln Ile Leu Thr Lys Ala Gly
            235                 240                 245 att cga aaa gga gac cgc gac cgg ttg tta tcc atc ccg gcc ggt gaa     880
Ile Arg Lys Gly Asp Arg Asp Arg Leu Leu Ser Ile Pro Ala Gly Glu
        250                 255                 260 ctc ctt gaa gcc gca caa tcc gtg aat ccg gga atg gtt ttt ggt ccc     928
Leu Leu Glu Ala Ala Gln Ser Val Asn Pro Gly Met Val Phe Gly Pro
    265                 270                 275 gtt gtg gac ggc acc gta ttg aaa acc cat ccg att gaa gcg ttg gaa     976
Val Val Asp Gly Thr Val Leu Lys Thr His Pro Ile Glu Ala Leu Glu
280                 285                 290                 295 aac gga gcc gcc ggc gat atc ccg atc atc atc ggg gtg aca aag gat    1024
Asn Gly Ala Ala Gly Asp Ile Pro Ile Ile Ile Gly Val Thr Lys Asp
                300                 305                 310 gag tac aat tta ttt aca ctg act gac cct tcc tgg acg aca gcg gga    1072
Glu Tyr Asn Leu Phe Thr Leu Thr Asp Pro Ser Trp Thr Thr Ala Gly
            315                 320                 325 aaa gaa gaa ctg atg gac cgg atc gaa cag gaa atc ggg tcg gtt ccg    1120
Lys Glu Glu Leu Met Asp Arg Ile Glu Gln Glu Ile Gly Ser Val Pro
        330                 335                 340 gaa aaa gtt ttt cca tat tac tta tct tcc ggg gat cca tcg caa ccg    1168
Glu Lys Val Phe Pro Tyr Tyr Leu Ser Ser Gly Asp Pro Ser Gln Pro
    345                 350                 355 gta tgg caa aag ctg ttg cgc gcc atg acc tac cac atc ttt acc cgg    1216
Val Trp Gln Lys Leu Leu Arg Ala Met Thr Tyr His Ile Phe Thr Arg
360                 365                 370                 375 ggc atg tta aaa acg gct gac gcc caa atc aag caa ggc ggg aag gtt    1264
Gly Met Leu Lys Thr Ala Asp Ala Gln Ile Lys Gln Gly Gly Lys Val
                380                 385                 390 tgg gtt tac cgg ttt gat tac gaa acc ccg ctc ttt gac ggt cgg ttg    1312
Trp Val Tyr Arg Phe Asp Tyr Glu Thr Pro Leu Phe Asp Gly Arg Leu
            395                 400                 405 aaa gca tgt cac gca ctg gaa atc ccc ttt gtc ttt cac aac ctg cat    1360
Lys Ala Cys His Ala Leu Glu Ile Pro Phe Val Phe His Asn Leu His
        410                 415                 420 caa ccg ggg gtc gat gtg ttc acc ggc aca cat ccg aag cgg gag cta    1408
Gln Pro Gly Val Asp Val Phe Thr Gly Thr His Pro Lys Arg Glu Leu
    425                 430                 435 att tcc cgg caa atg cat gaa gca tgg att gcc ttt gcc cgg aca ggg    1456
Ile Ser Arg Gln Met His Glu Ala Trp Ile Ala Phe Ala Arg Thr Gly
440                 445                 450                 455 gat ccg aac ggc gac cat ctc ccc gat gcg tgg ttg ccc ttt gca caa    1504
Asp Pro Asn Gly Asp His Leu Pro Asp Ala Trp Leu Pro Phe Ala Gln
                460                 465                 470 aaa gac cgg ccg gcc atg gtc ttt gac acc gaa acc aga gcg gaa aag    1552
Lys Asp Arg Pro Ala Met Val Phe Asp Thr Glu Thr Arg Ala Glu Lys
            475                 480                 485 cat ctg ttt gac cgc gag cag gaa ctg tgg gaa tca aag gct               1594
His Leu Phe Asp Arg Glu Gln Glu Leu Trp Glu Ser Lys Ala
        490                 495                 500 tgagtgattt gctcaagcct tttttgcatt aacgtatgta ttcggatttg gaattaaaca    1654
atgggctttt atcgaatggg gagtgttgct tataatgaac gggtt                    1699

<210> SEQ ID NO 14
<211> LENGTH: 501
<212> TYPE: PRT
<213> ORGANISM: Artificial Sequence
```

-continued

```
<220> FEATURE:
<223> OTHER INFORMATION: Description of Artificial Sequence:cloned
      esterase gene from bacteria  E004

<400> SEQUENCE: 14

Val Ile Gln Met Asn Thr Leu Val Glu Thr Arg Phe Gly Lys Val Gln
 1               5                  10                  15

Gly Gly Thr Asp Gly Glu Val Cys Phe Trp Lys Gly Ile Pro Tyr Ala
             20                  25                  30

Lys Pro Pro Val Gly Lys Arg Arg Phe Gln Lys Pro Glu Pro Pro Glu
         35                  40                  45

Lys Trp Asp Gly Val Trp Glu Ala Thr Arg Phe Arg Ser Met Val Met
     50                  55                  60

Gln Pro Ser Gly Thr Thr Phe Ser Thr Val Leu Gly Glu Ala Asp Leu
 65                  70                  75                  80

Pro Val Ser Glu Asp Gly Leu Tyr Leu Asn Ile Trp Ser Pro Ala Ala
                 85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
                165                 170                 175

Lys Glu Asn Ile Ser Ala Phe Gly Gly Asp Pro Glu Gln Ile Thr Ile
            180                 185                 190

Phe Gly Glu Ser Ala Gly Ala Gly Ser Val Gly Val Leu Leu Ser Leu
        195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
                245                 250                 255

Leu Ser Ile Pro Ala Gly Glu Leu Leu Glu Ala Ala Gln Ser Val Asn
            260                 265                 270

Pro Gly Met Val Phe Gly Pro Val Asp Gly Thr Val Leu Lys Thr
        275                 280                 285

His Pro Ile Glu Ala Leu Glu Asn Gly Ala Ala Gly Asp Ile Pro Ile
    290                 295                 300

Ile Ile Gly Val Thr Lys Asp Glu Tyr Asn Leu Phe Thr Leu Thr Asp
305                 310                 315                 320

Pro Ser Trp Thr Thr Ala Gly Lys Glu Glu Leu Met Asp Arg Ile Glu
                325                 330                 335

Gln Glu Ile Gly Ser Val Pro Glu Lys Val Phe Pro Tyr Tyr Leu Ser
            340                 345                 350

Ser Gly Asp Pro Ser Gln Pro Val Trp Gln Lys Leu Leu Arg Ala Met
        355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
```

-continued

```
                385                 390                 395                 400
           Pro Leu Phe Asp Gly Arg Leu Lys Ala Cys His Ala Leu Glu Ile Pro
                           405                 410                 415

Phe Val Phe His Asn Leu His Gln Pro Gly Val Asp Val Phe Thr Gly
                       420                 425                 430

Thr His Pro Lys Arg Glu Leu Ile Ser Arg Gln Met His Glu Ala Trp
                   435                 440                 445

Ile Ala Phe Ala Arg Thr Gly Asp Pro Asn Gly Asp His Leu Pro Asp
               450                 455                 460

Ala Trp Leu Pro Phe Ala Gln Lys Asp Arg Pro Ala Met Val Phe Asp
           465                 470                 475                 480

Thr Glu Thr Arg Ala Glu Lys His Leu Phe Asp Arg Glu Gln Glu Leu
                           485                 490                 495

Trp Glu Ser Lys Ala
                       500

<210> SEQ ID NO 15
<211> LENGTH: 2345
<212> TYPE: DNA
<213> ORGANISM: Artificial Sequence
<220> FEATURE:
<223> OTHER INFORMATION: Description of Artificial Sequence:cloned
      esterase gene from bacteria E006
<220> FEATURE:
<221> NAME/KEY: CDS
<222> LOCATION: (196)..(1689)

<400> SEQUENCE: 15
cttcaactaa catgttggct tgcgggcgtt catgctcaga acaaggttg ggacaagcac      60 ttccaggcta acacagtcag aaatcgaaac gtactctcaa cagttcgctt aggcatggaa     120
gttttgcggc attctggcta cacaataaca agggaagact tactcgtggc tgcaacccta    180
ctagctcaaa attta atg agg gga tct ctc aga aca aag tac ggt cgg ttg     231
                Met Arg Gly Ser Leu Arg Thr Lys Tyr Gly Arg Leu
                  1               5                  10 cgc ggg gga aca aat gaa ggg gtt ttc tat tgg aaa ggg att ccg tac     279
Arg Gly Gly Thr Asn Glu Gly Val Phe Tyr Trp Lys Gly Ile Pro Tyr
            15                  20                  25 gcg aaa gcg ccg gtc ggt gaa cgc cgt ttt ttg ccg ccg gaa ccg ccc     327
Ala Lys Ala Pro Val Gly Glu Arg Arg Phe Leu Pro Pro Glu Pro Pro
        30                  35                  40 gat gca tgg gac gga gtg cgt gag gcg aca tcg ttt gga ccg gtc gtc     375
Asp Ala Trp Asp Gly Val Arg Glu Ala Thr Ser Phe Gly Pro Val Val
45                  50                  55                  60 atg cag ccg tcc gat tcg atg ttc agc cag ctg ctc gga cgg atg aat     423
Met Gln Pro Ser Asp Ser Met Phe Ser Gln Leu Leu Gly Arg Met Asn
                65                  70                  75 gaa cca atg agc gag gat ggg ttg tat ctg aac att tgg tca ccg gcg     471
Glu Pro Met Ser Glu Asp Gly Leu Tyr Leu Asn Ile Trp Ser Pro Ala
            80                  85                  90 gcg gat ggg aag aag cgc ccg gta ttg ttt tgg att cat ggc ggc gct     519
Ala Asp Gly Lys Lys Arg Pro Val Leu Phe Trp Ile His Gly Gly Ala
        95                 100                 105 ttt tta ttc ggc tcc ggt tca ttt cca tgg tat gat gga acg gcg ttt     567
Phe Leu Phe Gly Ser Gly Ser Phe Pro Trp Tyr Asp Gly Thr Ala Phe
    110                 115                 120 gcc aaa cac ggc gat gtc gtt gtc gtg acg atc aac tac cgg atg agc     615
Ala Lys His Gly Asp Val Val Val Val Thr Ile Asn Tyr Arg Met Ser
125                 130                 135                 140
```

-continued

| | | |
|---|---|---|
| gtg ttt ggc ttt ttg tat ttg gga gat gcg ttt ggc gaa acg tat gcc<br>Val Phe Gly Phe Leu Tyr Leu Gly Asp Ala Phe Gly Glu Thr Tyr Ala<br>                145                150                155 | 663 |
| cag gcg gga aat ctt ggc ata ttg gat caa gtg gcg gcg ctg cgc tgg<br>Gln Ala Gly Asn Leu Gly Ile Leu Asp Gln Val Ala Ala Leu Arg Trp<br>        160                165                170 | 711 |
| gtg aaa gag aac att gag gcg ttc ggc ggt gat ccg gac aac att acg<br>Val Lys Glu Asn Ile Glu Ala Phe Gly Gly Asp Pro Asp Asn Ile Thr<br>175                180                185 | 759 |
| att ttt ggc gaa tca gcc gga gcg gca agc gtt ggc gtg ctg ttg tcg<br>Ile Phe Gly Glu Ser Ala Gly Ala Ala Ser Val Gly Val Leu Leu Ser<br>    190                195                200 | 807 |
| ctt ccg gaa gca agc ggg ctg ttt cga cgc gct ata ttg caa agc gga<br>Leu Pro Glu Ala Ser Gly Leu Phe Arg Arg Ala Ile Leu Gln Ser Gly<br>205                210                215                220 | 855 |
| tcg ggt tcg ctt ctt ctt cgt tct ccg gag acg gcg atg gct ctg act<br>Ser Gly Ser Leu Leu Leu Arg Ser Pro Glu Thr Ala Met Ala Leu Thr<br>                225                230                235 | 903 |
| gaa cgc att tta gaa cgt gcc ggc atc cgt ccg ggt gac cgc gat cgg<br>Glu Arg Ile Leu Glu Arg Ala Gly Ile Arg Pro Gly Asp Arg Asp Arg<br>        240                245                250 | 951 |
| ctg ctg tcg att cca gca gca gag cta ttg cag gcg gcg atg tcg ctc<br>Leu Leu Ser Ile Pro Ala Ala Glu Leu Leu Gln Ala Ala Met Ser Leu<br>255                260                265 | 999 |
| ggc cca gga atc acg tac ggt ccg gtg gtt gac gga cat gtg ttg cga<br>Gly Pro Gly Ile Thr Tyr Gly Pro Val Val Asp Gly His Val Leu Arg<br>    270                275                280 | 1047 |
| cgc cat ccg atc gaa gcg ctc cac gac ggg gca gca agt gat att cca<br>Arg His Pro Ile Glu Ala Leu His Asp Gly Ala Ala Ser Asp Ile Pro<br>285                290                295                300 | 1095 |
| atc cta att ggc gtg acg aaa gac gaa tac aat ttg ttt tca ttg act<br>Ile Leu Ile Gly Val Thr Lys Asp Glu Tyr Asn Leu Phe Ser Leu Thr<br>                305                310                315 | 1143 |
| gat ccg tca ttg aca aga ctc gaa gaa aaa gaa ctg ctt gac cgg atg<br>Asp Pro Ser Leu Thr Arg Leu Glu Glu Lys Glu Leu Leu Asp Arg Met<br>        320                325                330 | 1191 |
| aac cgt gag gtc ggg cct att ccg gag gag gcg gta cgc tat tac gcg<br>Asn Arg Glu Val Gly Pro Ile Pro Glu Glu Ala Val Arg Tyr Tyr Ala<br>335                340                345 | 1239 |
| gaa aca gcg gat cgg tcg gca ccc gcg tgg caa aca tgg ctg cgc atc<br>Glu Thr Ala Asp Arg Ser Ala Pro Ala Trp Gln Thr Trp Leu Arg Ile<br>    350                355                360 | 1287 |
| atg acg tac ctt gtt ttt gtc gac gga atg ttg cga acg gcg gat gcc<br>Met Thr Tyr Leu Val Phe Val Asp Gly Met Leu Arg Thr Ala Asp Ala<br>365                370                375                380 | 1335 |
| caa gca gcg caa ggg gcg aat gtg tac atg tat cgg ttt gat tat gaa<br>Gln Ala Ala Gln Gly Ala Asn Val Tyr Met Tyr Arg Phe Asp Tyr Glu<br>        385                390                395 | 1383 |
| acg ccg gcg ttt ggt gga caa ctg aaa gcg tgc cat acg ctc gag ttg<br>Thr Pro Ala Phe Gly Gly Gln Leu Lys Ala Cys His Thr Leu Glu Leu<br>                400                405                410 | 1431 |
| ccg ttt gtg ttt cat aac ctc cat cag cct ggt gtc gag aat ttc gtc<br>Pro Phe Val Phe His Asn Leu His Gln Pro Gly Val Glu Asn Phe Val<br>            415                420                425 | 1479 |
| ggc aac cga cca gag cgt gag gcg att gcc agc gaa atg cat ggt gcc<br>Gly Asn Arg Pro Glu Arg Glu Ala Ile Ala Ser Glu Met His Gly Ala<br>        430                435                440 | 1527 |
| tgg ctt tcg ttc gcc cac acc ggc aac ccg aac ggc gct cat tta cca<br>Trp Leu Ser Phe Ala His Thr Gly Asn Pro Asn Gly Ala His Leu Pro<br>445                450                455                460 | 1575 |

-continued

```
gag aag tgg ccc gta tac aca aaa gag cac aaa ccg gtg ttt gtc ttt    1623
Glu Lys Trp Pro Val Tyr Thr Lys Glu His Lys Pro Val Phe Val Phe
            465                 470                 475 tcg gct gcg agc cat gtg gaa gac gat ccg ttc ggt cgc gag cgg gaa    1671
Ser Ala Ala Ser His Val Glu Asp Asp Pro Phe Gly Arg Glu Arg Glu
                480                 485                 490 gcg tgg caa gga cgc ctt tgacgaaaaa atccataagc aacatgtgtt           1719
Ala Trp Gln Gly Arg Leu
                495 ctttgtctga acacgatcaa ggtacgcgca ttttcgcgga aaaagaccgt gggcaaacgt  1779 tcgcctttac ctctaaaagg aatgacgcaa catgtctgca cttcacagga agaggacga   1839 aacggttggt tttcagaata ggaaaaggtg tcccgttttt tgggacacct tcttctatgt  1899 atcgctcaat catttgcttc tgtggcagga agcccgaatc gctcggcgag tgccggatca  1959 cgatcgatcg cctcaatcag tttccgcatg acgttcacat caaacgtaaa attcgaaccg  2019 attggcgagg tgacgaaaat tttcccttct ttcgcctcgc gtgctcgttt aaattgatag  2079 ccgtcaatcg caatgacgac tcgttcgtct ggccttgcca ttaggaatcc ctccatcgct  2139 gtttttcttt tcattgtact tgattttgag gatgaacacc aacgttcatg acacgctctt  2199 aaggataacg gatgggagag cgttagaggg cggtgaattt catcaagaac gtggcacaaa  2259 acgacatttt ttcattatag acgtcttgat gtttggaatg atcggaaaag gcgattgtta  2319 ggcggggatc atgatccact agcgga                                      2345
```

<210> SEQ ID NO 16
<211> LENGTH: 498
<212> TYPE: PRT
<213> ORGANISM: Artificial Sequence
<220> FEATURE:
<223> OTHER INFORMATION: Description of Artificial Sequence:cloned esterase gene from bacteria E006

<400> SEQUENCE: 16

```
Met Arg Gly Ser Leu Arg Thr Lys Tyr Gly Arg Leu Arg Gly Gly Thr
 1               5                  10                  15

Asn Glu Gly Val Phe Tyr Trp Lys Gly Ile Pro Tyr Ala Lys Ala Pro
            20                  25                  30

Val Gly Glu Arg Arg Phe Leu Pro Pro Glu Pro Pro Asp Ala Trp Asp
        35                  40                  45

Gly Val Arg Glu Ala Thr Ser Phe Gly Pro Val Met Gln Pro Ser
    50                  55                  60

Asp Ser Met Phe Ser Gln Leu Leu Gly Arg Met Asn Glu Pro Met Ser
65                  70                  75                  80

Glu Asp Gly Leu Tyr Leu Asn Ile Trp Ser Pro Ala Ala Asp Gly Lys
                85                  90                  95

Lys Arg Pro Val Leu Phe Trp Ile His Gly Gly Ala Phe Leu Phe Gly
            100                 105                 110

Ser Gly Ser Phe Pro Trp Tyr Asp Gly Thr Ala Phe Ala Lys His Gly
        115                 120                 125

Asp Val Val Val Thr Ile Asn Tyr Arg Met Ser Val Phe Gly Phe
    130                 135                 140

Leu Tyr Leu Gly Asp Ala Phe Gly Glu Thr Tyr Ala Gln Ala Gly Asn
145                 150                 155                 160

Leu Gly Ile Leu Asp Gln Val Ala Ala Leu Arg Trp Val Lys Glu Asn
                165                 170                 175
```

```
Ile Glu Ala Phe Gly Gly Asp Pro Asp Asn Ile Thr Ile Phe Gly Glu
            180                 185                 190

Ser Ala Gly Ala Ala Ser Val Gly Val Leu Leu Ser Leu Pro Glu Ala
        195                 200                 205

Ser Gly Leu Phe Arg Arg Ala Ile Leu Gln Ser Gly Ser Gly Ser Leu
        210                 215                 220

Leu Leu Arg Ser Pro Glu Thr Ala Met Ala Leu Thr Glu Arg Ile Leu
225                 230                 235                 240

Glu Arg Ala Gly Ile Arg Pro Gly Asp Arg Asp Arg Leu Leu Ser Ile
                245                 250                 255

Pro Ala Ala Glu Leu Leu Gln Ala Ala Met Ser Leu Gly Pro Gly Ile
            260                 265                 270

Thr Tyr Gly Pro Val Val Asp Gly His Val Leu Arg Arg His Pro Ile
        275                 280                 285

Glu Ala Leu His Asp Gly Ala Ala Ser Asp Ile Pro Ile Leu Ile Gly
        290                 295                 300

Val Thr Lys Asp Glu Tyr Asn Leu Phe Ser Leu Thr Asp Pro Ser Leu
305                 310                 315                 320

Thr Arg Leu Glu Glu Lys Glu Leu Leu Asp Arg Met Asn Arg Glu Val
                325                 330                 335

Gly Pro Ile Pro Glu Glu Ala Val Arg Tyr Tyr Ala Glu Thr Ala Asp
            340                 345                 350

Arg Ser Ala Pro Ala Trp Gln Thr Trp Leu Arg Ile Met Thr Tyr Leu
        355                 360                 365

Val Phe Val Asp Gly Met Leu Arg Thr Ala Asp Ala Gln Ala Ala Gln
        370                 375                 380

Gly Ala Asn Val Tyr Met Tyr Arg Phe Asp Tyr Glu Thr Pro Ala Phe
385                 390                 395                 400

Gly Gly Gln Leu Lys Ala Cys His Thr Leu Glu Leu Pro Phe Val Phe
                405                 410                 415

His Asn Leu His Gln Pro Gly Val Glu Asn Phe Val Gly Asn Arg Pro
            420                 425                 430

Glu Arg Glu Ala Ile Ala Ser Glu Met His Gly Ala Trp Leu Ser Phe
        435                 440                 445

Ala His Thr Gly Asn Pro Asn Gly Ala His Leu Pro Glu Lys Trp Pro
        450                 455                 460

Val Tyr Thr Lys Glu His Lys Pro Val Phe Val Phe Ser Ala Ala Ser
465                 470                 475                 480

His Val Glu Asp Asp Pro Phe Gly Arg Glu Arg Glu Ala Trp Gln Gly
                485                 490                 495

Arg Leu

<210> SEQ ID NO 17
<211> LENGTH: 1925
<212> TYPE: DNA
<213> ORGANISM: Artificial Sequence
<220> FEATURE:
<223> OTHER INFORMATION: Description of Artificial Sequence:cloned
      esterase gene from bacteria E008
<220> FEATURE:
<221> NAME/KEY: CDS
<222> LOCATION: (127)..(1581)

<400> SEQUENCE: 17
cccaacgacc cccgcccatt gacgtcaata atgacgtatg ttcccatagt aacgccaata      60
gggactttcc attgacgtca atgggtggag tatttacggt aaactgccca cttggcagta     120
```

```
catcaa gtg tat cat atg cca agt acg ccc cct att gac gtc aat gac      168
       Val Tyr His Met Pro Ser Thr Pro Pro Ile Asp Val Asn Asp
        1               5                  10 ggt aaa tgg ccc gcc tgg cat tat gcc cag tac atg acc tta tgg gac      216
Gly Lys Trp Pro Ala Trp His Tyr Ala Gln Tyr Met Thr Leu Trp Asp
 15              20                  25                  30 ttt cct act tgg cag tac atc tac gta tta gtc atc gct att acc atg      264
Phe Pro Thr Trp Gln Tyr Ile Tyr Val Leu Val Ile Ala Ile Thr Met
                 35                  40                  45 gtg aag cag ccg tcc ggc acc acc ttc agc acc gtg ctc ggg gaa gcg      312
Val Lys Gln Pro Ser Gly Thr Thr Phe Ser Thr Val Leu Gly Glu Ala
                     50                  55                  60 gat ctt cct gtg agc gaa gac ggt ctt tat ctg aat atc tgg tcg ccg      360
Asp Leu Pro Val Ser Glu Asp Gly Leu Tyr Leu Asn Ile Trp Ser Pro
             65                  70                  75 gca gcc gac gga aaa aag cgg ccg gtg ctc ttc tgg atc cat ggc ggc      408
Ala Ala Asp Gly Lys Lys Arg Pro Val Leu Phe Trp Ile His Gly Gly
         80                  85                  90 gcc tac cag ttt ggg tcc ggc gct tcc ccc tgg tat gac ggg acg gag      456
Ala Tyr Gln Phe Gly Ser Gly Ala Ser Pro Trp Tyr Asp Gly Thr Glu
 95                 100                 105                 110 ttt gcc aaa aac gga gat gtg gtg gtt gtc acg atc aac tac cgg ttg      504
Phe Ala Lys Asn Gly Asp Val Val Val Val Thr Ile Asn Tyr Arg Leu
                115                 120                 125 aac gcg ttt gga ttt ttg tac ttg gca gat tgg ttc ggc gac gaa ttt      552
Asn Ala Phe Gly Phe Leu Tyr Leu Ala Asp Trp Phe Gly Asp Glu Phe
            130                 135                 140 tca gcg tcg ggc aac ctg gga att ttg gac caa gtc gct gca ctg cgc      600
Ser Ala Ser Gly Asn Leu Gly Ile Leu Asp Gln Val Ala Ala Leu Arg
        145                 150                 155 tgg gtg aaa gaa aac att tcg gca ttc ggc ggc gac ccg gag caa atc      648
Trp Val Lys Glu Asn Ile Ser Ala Phe Gly Gly Asp Pro Glu Gln Ile
    160                 165                 170 acc atc ttc ggg gag tcg gcc gga gcc gga agc gtc ggg gtt ctg ctt      696
Thr Ile Phe Gly Glu Ser Ala Gly Ala Gly Ser Val Gly Val Leu Leu
175                 180                 185                 190 tcc ctc ccg gaa acc aaa ggg ctg ttt caa cgg gcg atc ttg caa agc      744
Ser Leu Pro Glu Thr Lys Gly Leu Phe Gln Arg Ala Ile Leu Gln Ser
                195                 200                 205 gga tcg ggt gcc att ttg ctc cgt tcc tct cag aca gcc tcg ggc atc      792
Gly Ser Gly Ala Ile Leu Leu Arg Ser Ser Gln Thr Ala Ser Gly Ile
            210                 215                 220 gcg gaa caa att ctt acg aaa gcc ggc att cga aaa gga gac cgc gac      840
Ala Glu Gln Ile Leu Thr Lys Ala Gly Ile Arg Lys Gly Asp Arg Asp
        225                 230                 235 cgg ttg tta tcc atc ccg gcc ggt gaa ctc ctt gaa gcc gca caa tcc      888
Arg Leu Leu Ser Ile Pro Ala Gly Glu Leu Leu Glu Ala Ala Gln Ser
    240                 245                 250 gtg aat ccg gga atg gtt ttt ggt ccc gtt gtg gac ggc acc gta ttg      936
Val Asn Pro Gly Met Val Phe Gly Pro Val Val Asp Gly Thr Val Leu
255                 260                 265                 270 aaa acc cat ccg att gaa gcg ttg gaa acc gga gcc gcc ggc gat atc      984
Lys Thr His Pro Ile Glu Ala Leu Glu Thr Gly Ala Ala Gly Asp Ile
                275                 280                 285 ccg atc atc atc ggg gtg aca aag gat gag tac aat tta ttt aca ctg     1032
Pro Ile Ile Ile Gly Val Thr Lys Asp Glu Tyr Asn Leu Phe Thr Leu
            290                 295                 300 act gac cct tcc tgg acg aca gcg gga aaa gaa gaa ctg atg gac cgg     1080
Thr Asp Pro Ser Trp Thr Thr Ala Gly Lys Glu Glu Leu Met Asp Arg
```

```
                305                    310                    315
atc gaa cag gaa atc ggg ccg gtt ccg gaa aaa gtt ttt cca tat tac    1128
Ile Glu Gln Glu Ile Gly Pro Val Pro Glu Lys Val Phe Pro Tyr Tyr
    320                    325                    330 tta tct ttt ggg gat cca tcg caa ccg gta tgg caa aag ctg ttg cgc    1176
Leu Ser Phe Gly Asp Pro Ser Gln Pro Val Trp Gln Lys Leu Leu Arg
335                    340                    345                    350 gcc atg acc tac cac atc ttt acc cgg ggc atg tta aaa acg gct gac    1224
Ala Met Thr Tyr His Ile Phe Thr Arg Gly Met Leu Lys Thr Ala Asp
                355                    360                    365 gcc caa atc aag caa ggc ggg aag gtt tgg gtt tac cgg ttt gat tac    1272
Ala Gln Ile Lys Gln Gly Gly Lys Val Trp Val Tyr Arg Phe Asp Tyr
            370                    375                    380 gaa acc ccg ctc ttt gac ggt cgg ttg aaa gca tgt cac gca ctg gaa    1320
Glu Thr Pro Leu Phe Asp Gly Arg Leu Lys Ala Cys His Ala Leu Glu
        385                    390                    395 atc ccc ttt gtc ttt cac aac ctg cat caa ccg ggg gtc gat gtg ttc    1368
Ile Pro Phe Val Phe His Asn Leu His Gln Pro Gly Val Asp Val Phe
    400                    405                    410 acc ggc aca cat ccg aag cgg gag cta att tcc cgg caa atg cat gaa    1416
Thr Gly Thr His Pro Lys Arg Glu Leu Ile Ser Arg Gln Met His Glu
415                    420                    425                    430 gca tgg att gcc ttt gcc cgg aca ggg gat ccg aac ggc gac cat ctc    1464
Ala Trp Ile Ala Phe Ala Arg Thr Gly Asp Pro Asn Gly Asp His Leu
                435                    440                    445 ccc gat gcg tgg ttg ccc ttt gca caa aaa gac cgg ccg gcc atg gtc    1512
Pro Asp Ala Trp Leu Pro Phe Ala Gln Lys Asp Arg Pro Ala Met Val
            450                    455                    460 ttt gac acc gaa acc aga gcg gaa aag cat ctg ttt gac cgc gag cag    1560
Phe Asp Thr Glu Thr Arg Ala Glu Lys His Leu Phe Asp Arg Glu Gln
        465                    470                    475 gaa ctg tgg gaa tca aag gct tgagtgattt gctcaagcct tttttgcatt       1611
Glu Leu Trp Glu Ser Lys Ala
    480                    485 tcacgtatgt attcggattt ggaattaaac aatggtgctt ttatcgaaat ggggagtgtt  1671
tgcttataat gaacgggttt acaaagcttg ttttggtacc ggattactga aatgatcaga  1731
aggaaatatc atgacgtaat aatcagggga tcttgagaaa gaaatacatg gagtgttatg  1791
tcccttgaaa aacagagacg ccggtggcat caccatcaca gggtctttct tttcaaatca  1851
tggtttgtag ttttataatg caaactaatt aatcatacat atggagtgtg ggttccattg  1911
atgccccttt aagg                                                    1925

<210> SEQ ID NO 18
<211> LENGTH: 485
<212> TYPE: PRT
<213> ORGANISM: Artificial Sequence
<220> FEATURE:
<223> OTHER INFORMATION: Description of Artificial Sequence:cloned
      esterase gene from bacteria E008

<400> SEQUENCE: 18

Val Tyr His Met Pro Ser Thr Pro Ile Asp Val Asn Asp Gly Lys
 1               5                  10                  15

Trp Pro Ala Trp His Tyr Ala Gln Tyr Met Thr Leu Trp Asp Phe Pro
            20                  25                  30

Thr Trp Gln Tyr Ile Tyr Val Leu Val Ile Ala Ile Thr Met Val Lys
        35                  40                  45

Gln Pro Ser Gly Thr Thr Phe Ser Thr Val Leu Gly Glu Ala Asp Leu
```

-continued

```
                50                  55                  60
Pro Val Ser Glu Asp Gly Leu Tyr Leu Asn Ile Trp Ser Pro Ala Ala
 65                  70                  75                  80

Asp Gly Lys Lys Arg Pro Val Leu Phe Trp Ile His Gly Gly Ala Tyr
                 85                  90                  95

Gln Phe Gly Ser Gly Ala Ser Pro Trp Tyr Asp Gly Thr Glu Phe Ala
                100                 105                 110

Lys Asn Gly Asp Val Val Val Thr Ile Asn Tyr Arg Leu Asn Ala
                115                 120                 125

Phe Gly Phe Leu Tyr Leu Ala Asp Trp Phe Gly Asp Glu Phe Ser Ala
                130                 135                 140

Ser Gly Asn Leu Gly Ile Leu Asp Gln Val Ala Ala Leu Arg Trp Val
145                 150                 155                 160

Lys Glu Asn Ile Ser Ala Phe Gly Gly Asp Pro Glu Gln Ile Thr Ile
                165                 170                 175

Phe Gly Glu Ser Ala Gly Ala Gly Ser Val Gly Val Leu Leu Ser Leu
                180                 185                 190

Pro Glu Thr Lys Gly Leu Phe Gln Arg Ala Ile Leu Gln Ser Gly Ser
                195                 200                 205

Gly Ala Ile Leu Leu Arg Ser Ser Gln Thr Ala Ser Gly Ile Ala Glu
210                 215                 220

Gln Ile Leu Thr Lys Ala Gly Ile Arg Lys Gly Asp Arg Asp Arg Leu
225                 230                 235                 240

Leu Ser Ile Pro Ala Gly Glu Leu Leu Glu Ala Ala Gln Ser Val Asn
                245                 250                 255

Pro Gly Met Val Phe Gly Pro Val Val Asp Gly Thr Val Leu Lys Thr
                260                 265                 270

His Pro Ile Glu Ala Leu Glu Thr Gly Ala Ala Gly Asp Ile Pro Ile
                275                 280                 285

Ile Ile Gly Val Thr Lys Asp Glu Tyr Asn Leu Phe Thr Leu Thr Asp
                290                 295                 300

Pro Ser Trp Thr Thr Ala Gly Lys Glu Glu Leu Met Asp Arg Ile Glu
305                 310                 315                 320

Gln Glu Ile Gly Pro Val Pro Glu Lys Val Phe Pro Tyr Tyr Leu Ser
                325                 330                 335

Phe Gly Asp Pro Ser Gln Pro Val Trp Gln Lys Leu Leu Arg Ala Met
                340                 345                 350

Thr Tyr His Ile Phe Thr Arg Gly Met Leu Lys Thr Ala Asp Ala Gln
                355                 360                 365

Ile Lys Gln Gly Gly Lys Val Trp Val Tyr Arg Phe Asp Tyr Glu Thr
                370                 375                 380

Pro Leu Phe Asp Gly Arg Leu Lys Ala Cys His Ala Leu Glu Ile Pro
385                 390                 395                 400

Phe Val Phe His Asn Leu His Gln Pro Gly Val Asp Val Phe Thr Gly
                405                 410                 415

Thr His Pro Lys Arg Glu Leu Ile Ser Arg Gln Met His Glu Ala Trp
                420                 425                 430

Ile Ala Phe Ala Arg Thr Gly Asp Pro Asn Gly Asp His Leu Pro Asp
                435                 440                 445

Ala Trp Leu Pro Phe Ala Gln Lys Asp Arg Pro Ala Met Val Phe Asp
                450                 455                 460

Thr Glu Thr Arg Ala Glu Lys His Leu Phe Asp Arg Glu Gln Glu Leu
465                 470                 475                 480
```

```
Trp Glu Ser Lys Ala
            485

<210> SEQ ID NO 19
<211> LENGTH: 1957
<212> TYPE: DNA
<213> ORGANISM: Artificial Sequence
<220> FEATURE:
<223> OTHER INFORMATION: Description of Artificial Sequence:cloned
      esterase gene from bacteria E010
<220> FEATURE:
<221> NAME/KEY: CDS
<222> LOCATION: (88)..(1590)

<400> SEQUENCE: 19
cttcagggga actttttaaac acttgagttt gacaaccact ccttaatcat ttaagattta        60
aatgaaaatt aaaataaatc aaaaaga gtg att caa atg aat acg ttg gtg gaa       114
                             Val Ile Gln Met Asn Thr Leu Val Glu
                              1               5 acc cgt ttt ggg aaa gtg caa ggc ggt aca gac gga gag gtt tgt ttt         162
Thr Arg Phe Gly Lys Val Gln Gly Gly Thr Asp Gly Glu Val Cys Phe
 10              15                  20                  25 tgg aaa ggg att cct tat gcg aaa cct ccg gtg gga aaa cgc cgc ttt         210
Trp Lys Gly Ile Pro Tyr Ala Lys Pro Pro Val Gly Lys Arg Arg Phe
             30                  35                  40 caa aaa ccg gaa ccg ccg gag aaa tgg gat ggc gtt tgg gag gcc acc         258
Gln Lys Pro Glu Pro Pro Glu Lys Trp Asp Gly Val Trp Glu Ala Thr
         45                  50                  55 cgg ttc cgg tcc atg gtg atg cag ccg tcc ggc acc acc ttc agc acc         306
Arg Phe Arg Ser Met Val Met Gln Pro Ser Gly Thr Thr Phe Ser Thr
     60                  65                  70 gtg ctc ggg gaa gcg gat ctt cct gtg agc gaa gac ggt ctt tat ctg         354
Val Leu Gly Glu Ala Asp Leu Pro Val Ser Glu Asp Gly Leu Tyr Leu
 75                  80                  85 aat atc tgg tcg ccg gca gcc gac gga aaa aag cgg ccg gtg ctc ttc         402
Asn Ile Trp Ser Pro Ala Ala Asp Gly Lys Lys Arg Pro Val Leu Phe
 90                  95                 100                 105 tgg atc cat ggc ggc gcc tac cag ttt ggg tcc ggc gct tcc ccc tgg         450
Trp Ile His Gly Gly Ala Tyr Gln Phe Gly Ser Gly Ala Ser Pro Trp
             110                 115                 120 tat gac ggg acg gag ttt gcc aaa aac gga gat gtg gtg gtt gtc acg         498
Tyr Asp Gly Thr Glu Phe Ala Lys Asn Gly Asp Val Val Val Val Thr
         125                 130                 135 atc aac tac cgg ttg aac gcg ttt gga ttt ttg tac ttg gca gat tgg         546
Ile Asn Tyr Arg Leu Asn Ala Phe Gly Phe Leu Tyr Leu Ala Asp Trp
     140                 145                 150 ttc ggc gac gaa ttt tca gcg tcg ggc aac ctg gga att ttg gac caa         594
Phe Gly Asp Glu Phe Ser Ala Ser Gly Asn Leu Gly Ile Leu Asp Gln
155                 160                 165 gtc gct gca ctg cgc tgg gtg aaa gaa aac att tcg gca ttc ggc ggc         642
Val Ala Ala Leu Arg Trp Val Lys Glu Asn Ile Ser Ala Phe Gly Gly
170                 175                 180                 185 gac ccg gag caa atc acc atc ttc ggg gag tcg gcc gga gcc gga agc         690
Asp Pro Glu Gln Ile Thr Ile Phe Gly Glu Ser Ala Gly Ala Gly Ser
             190                 195                 200 gtc ggg gtt ctg ctt tcc ctc ccg gaa acc aaa ggg ctg ttt caa cgg         738
Val Gly Val Leu Leu Ser Leu Pro Glu Thr Lys Gly Leu Phe Gln Arg
         205                 210                 215 gcg atc ttg caa agc gga tcg ggt gcc att ttg ctc cgt tcc tct cag         786
Ala Ile Leu Gln Ser Gly Ser Gly Ala Ile Leu Leu Arg Ser Ser Gln
     220                 225                 230
```

```
aca gcc tcg ggc atc gcg gaa caa att ctt acg aaa gcc ggc att cga        834
Thr Ala Ser Gly Ile Ala Glu Gln Ile Leu Thr Lys Ala Gly Ile Arg
    235                 240                 245 aaa gga gac cgc gac cgg ttg tta tcc atc ccg gcc ggt gaa ctc ctt        882
Lys Gly Asp Arg Asp Arg Leu Leu Ser Ile Pro Ala Gly Glu Leu Leu
250                 255                 260                 265 gaa gcc gca caa tcc gtg aat ccg gga atg gtt ttt ggt ccc gtt gtg        930
Glu Ala Ala Gln Ser Val Asn Pro Gly Met Val Phe Gly Pro Val Val
                270                 275                 280 gac ggc acc gta ttg aaa acc cat ccg att gaa gcg ttg gaa acc gga        978
Asp Gly Thr Val Leu Lys Thr His Pro Ile Glu Ala Leu Glu Thr Gly
            285                 290                 295 gcc gcc ggc gat atc ccg atc atc atc ggg gtg aca aag gat gag tac       1026
Ala Ala Gly Asp Ile Pro Ile Ile Ile Gly Val Thr Lys Asp Glu Tyr
        300                 305                 310 aat tta ttt aca ctg act gac cct tcc tgg acg aca gcg gga aaa gaa       1074
Asn Leu Phe Thr Leu Thr Asp Pro Ser Trp Thr Thr Ala Gly Lys Glu
    315                 320                 325 gaa ctg atg gac cgg atc gaa cag gaa atc ggg ccg gtt ccg gaa aaa       1122
Glu Leu Met Asp Arg Ile Glu Gln Glu Ile Gly Pro Val Pro Glu Lys
330                 335                 340                 345 gtt ttt cca tat tac tta tct ttt ggg gat cca tcg caa ccg gta tgg       1170
Val Phe Pro Tyr Tyr Leu Ser Phe Gly Asp Pro Ser Gln Pro Val Trp
                350                 355                 360 caa aag ctg ttg cgc gcc atg acc tac cac atc ttt acc cgg ggc atg       1218
Gln Lys Leu Leu Arg Ala Met Thr Tyr His Ile Phe Thr Arg Gly Met
            365                 370                 375 tta aaa acg gct gac gcc caa atc aag caa ggc ggg aag gtt tgg gtt       1266
Leu Lys Thr Ala Asp Ala Gln Ile Lys Gln Gly Gly Lys Val Trp Val
        380                 385                 390 tac cgg ttt gat tac gaa acc ccg ctc ttt gac ggt cgg ttg aaa gca       1314
Tyr Arg Phe Asp Tyr Glu Thr Pro Leu Phe Asp Gly Arg Leu Lys Ala
    395                 400                 405 tgt cac gca ctg gaa atc ccc ttt gtc ttt cac aac ctg cat caa ccg       1362
Cys His Ala Leu Glu Ile Pro Phe Val Phe His Asn Leu His Gln Pro
410                 415                 420                 425 ggg gtc gat gtg ttc acc ggc aca cat tcg aag cgg gag cta att tcc       1410
Gly Val Asp Val Phe Thr Gly Thr His Ser Lys Arg Glu Leu Ile Ser
                430                 435                 440 cgg caa atg cat gaa gca tgg att gcc ttt gcc cgg aca ggg gat ccg       1458
Arg Gln Met His Glu Ala Trp Ile Ala Phe Ala Arg Thr Gly Asp Pro
            445                 450                 455 aac ggc gac cat ctc ccc gat gcg tgg ttg ccc ttt gca caa aaa gac       1506
Asn Gly Asp His Leu Pro Asp Ala Trp Leu Pro Phe Ala Gln Lys Asp
        460                 465                 470 cgg ccg gcc atg gtc ttt gac acc gaa acc aga gcg gaa aag cat ctg       1554
Arg Pro Ala Met Val Phe Asp Thr Glu Thr Arg Ala Glu Lys His Leu
    475                 480                 485 ttt gac cgc gag cag gaa ctg tgg gaa tca aag gct tgagtgattt            1600
Phe Asp Arg Glu Gln Glu Leu Trp Glu Ser Lys Ala
490                 495                 500 gctcaagcct ttttgcatt tcacgtatgt attcggattt ggaattaaac aatggtgctt      1660
ttatcgaaat ggggagtgtt tgcttataat gaacggggtt acaaagcttg ttttggtacc     1720
ggattactga aatgatcaga aggaaatatc atgacgtaat aatcagggga tcttgagaaa     1780
gaaatacatg gagtgttatg tcccttgaaa acagagacg ccgtggcat caccatcaca      1840 gggtctttct tttcaaatca tggtttgtag tttataatgc aaactagttt aatcatacat    1900
```

```
attggaagtg tggttccatt tgatgccctt ttaaggaaat ggcaaaaact tgaatta       1957
```

<210> SEQ ID NO 20
<211> LENGTH: 501
<212> TYPE: PRT
<213> ORGANISM: Artificial Sequence
<220> FEATURE:
<223> OTHER INFORMATION: Description of Artificial Sequence:cloned esterase gene from bacteria E010

<400> SEQUENCE: 20

| | | | | | | | | | | | | | | |
|---|---|---|---|---|---|---|---|---|---|---|---|---|---|---|
| Val | Ile | Gln | Met | Asn | Thr | Leu | Val | Glu | Thr | Arg | Phe | Gly | Lys | Val | Gln |
| 1 | | | | 5 | | | | | 10 | | | | | 15 | |
| Gly | Gly | Thr | Asp | Gly | Glu | Val | Cys | Phe | Trp | Lys | Gly | Ile | Pro | Tyr | Ala |
| | | | 20 | | | | | 25 | | | | | 30 | | |
| Lys | Pro | Pro | Val | Gly | Lys | Arg | Arg | Phe | Gln | Lys | Pro | Glu | Pro | Pro | Glu |
| | | 35 | | | | | 40 | | | | | 45 | | | |
| Lys | Trp | Asp | Gly | Val | Trp | Glu | Ala | Thr | Arg | Phe | Arg | Ser | Met | Val | Met |
| | 50 | | | | | 55 | | | | | 60 | | | | |
| Gln | Pro | Ser | Gly | Thr | Thr | Phe | Ser | Thr | Val | Leu | Gly | Glu | Ala | Asp | Leu |
| 65 | | | | | 70 | | | | | 75 | | | | | 80 |
| Pro | Val | Ser | Glu | Asp | Gly | Leu | Tyr | Leu | Asn | Ile | Trp | Ser | Pro | Ala | Ala |
| | | | | 85 | | | | | 90 | | | | | 95 | |
| Asp | Gly | Lys | Lys | Arg | Pro | Val | Leu | Phe | Trp | Ile | His | Gly | Gly | Ala | Tyr |
| | | | 100 | | | | | 105 | | | | | 110 | | |
| Gln | Phe | Gly | Ser | Gly | Ala | Ser | Pro | Trp | Tyr | Asp | Gly | Thr | Glu | Phe | Ala |
| | | 115 | | | | | 120 | | | | | 125 | | | |
| Lys | Asn | Gly | Asp | Val | Val | Val | Thr | Ile | Asn | Tyr | Arg | Leu | Asn | Ala |
| | 130 | | | | | 135 | | | | | 140 | | | | |
| Phe | Gly | Phe | Leu | Tyr | Leu | Ala | Asp | Trp | Phe | Gly | Asp | Glu | Phe | Ser | Ala |
| 145 | | | | | 150 | | | | | 155 | | | | | 160 |
| Ser | Gly | Asn | Leu | Gly | Ile | Leu | Asp | Gln | Val | Ala | Ala | Leu | Arg | Trp | Val |
| | | | | 165 | | | | | 170 | | | | | 175 | |
| Lys | Glu | Asn | Ile | Ser | Ala | Phe | Gly | Gly | Asp | Pro | Glu | Gln | Ile | Thr | Ile |
| | | | 180 | | | | | 185 | | | | | 190 | | |
| Phe | Gly | Glu | Ser | Ala | Gly | Ala | Gly | Ser | Val | Gly | Val | Leu | Leu | Ser | Leu |
| | | 195 | | | | | 200 | | | | | 205 | | | |
| Pro | Glu | Thr | Lys | Gly | Leu | Phe | Gln | Arg | Ala | Ile | Leu | Gln | Ser | Gly | Ser |
| | 210 | | | | | 215 | | | | | 220 | | | | |
| Gly | Ala | Ile | Leu | Leu | Arg | Ser | Ser | Gln | Thr | Ala | Ser | Gly | Ile | Ala | Glu |
| 225 | | | | | 230 | | | | | 235 | | | | | 240 |
| Gln | Ile | Leu | Thr | Lys | Ala | Gly | Ile | Arg | Lys | Gly | Asp | Arg | Asp | Arg | Leu |
| | | | | 245 | | | | | 250 | | | | | 255 | |
| Leu | Ser | Ile | Pro | Ala | Gly | Glu | Leu | Leu | Glu | Ala | Ala | Gln | Ser | Val | Asn |
| | | | 260 | | | | | 265 | | | | | 270 | | |
| Pro | Gly | Met | Val | Phe | Gly | Pro | Val | Asp | Gly | Thr | Val | Leu | Lys | Thr |
| | | 275 | | | | | 280 | | | | | 285 | | | |
| His | Pro | Ile | Glu | Ala | Leu | Glu | Thr | Gly | Ala | Ala | Gly | Asp | Ile | Pro | Ile |
| | 290 | | | | | 295 | | | | | 300 | | | | |
| Ile | Ile | Gly | Val | Thr | Lys | Asp | Glu | Tyr | Asn | Leu | Phe | Thr | Leu | Thr | Asp |
| 305 | | | | | 310 | | | | | 315 | | | | | 320 |
| Pro | Ser | Trp | Thr | Thr | Ala | Gly | Lys | Glu | Glu | Leu | Met | Asp | Arg | Ile | Glu |
| | | | | 325 | | | | | 330 | | | | | 335 | |
| Gln | Glu | Ile | Gly | Pro | Val | Pro | Lys | Val | Phe | Pro | Tyr | Tyr | Leu | Ser |
| | | | 340 | | | | | 345 | | | | | 350 | | |

```
Phe Gly Asp Pro Ser Gln Pro Val Trp Gln Lys Leu Leu Arg Ala Met
        355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
385                 390                 395                 400

Pro Leu Phe Asp Gly Arg Leu Lys Ala Cys His Ala Leu Glu Ile Pro
                405                 410                 415

Phe Val Phe His Asn Leu His Gln Pro Gly Val Asp Val Phe Thr Gly
                420                 425                 430

Thr His Ser Lys Arg Glu Leu Ile Ser Arg Gln Met His Glu Ala Trp
            435                 440                 445

Ile Ala Phe Ala Arg Thr Gly Asp Pro Asn Gly Asp His Leu Pro Asp
        450                 455                 460

Ala Trp Leu Pro Phe Ala Gln Lys Asp Arg Pro Ala Met Val Phe Asp
465                 470                 475                 480

Thr Glu Thr Arg Ala Glu Lys His Leu Phe Asp Arg Glu Gln Glu Leu
                485                 490                 495

Trp Glu Ser Lys Ala
                500

<210> SEQ ID NO 21
<211> LENGTH: 1753
<212> TYPE: DNA
<213> ORGANISM: Artificial Sequence
<220> FEATURE:
<223> OTHER INFORMATION: Description of Artificial Sequence:cloned
      esterase gene from bacteria E013
<220> FEATURE:
<221> NAME/KEY: CDS
<222> LOCATION: (128)..(1630)

<400> SEQUENCE: 21
atcacatcgt ggatatcagt ggatccggtg cgatggattg cttcagggga acttttaaac      60
acttgagttt gacaaccact ccttaatcat ttaagattta aatgaaaatt aaataaaatc     120 aaaaaga gtg att caa atg aat acg ttg gtg gaa acc cgt ttt ggg aaa      169
        Val Ile Gln Met Asn Thr Leu Val Glu Thr Arg Phe Gly Lys
        1               5                   10 gtg caa ggc ggt aca gac gga gag gtt tgt ttt tgg aaa ggg att cct      217
Val Gln Gly Gly Thr Asp Gly Glu Val Cys Phe Trp Lys Gly Ile Pro
15                  20                  25                  30 tat gcg aaa cct ccg gtg gga aaa cgc cgc ttt caa aaa ccg gaa ccg      265
Tyr Ala Lys Pro Pro Val Gly Lys Arg Arg Phe Gln Lys Pro Glu Pro
                35                  40                  45 ccg gag aaa tgg gat ggc gtt tgg gag gcc acc cgg ttc cgg tcc atg      313
Pro Glu Lys Trp Asp Gly Val Trp Glu Ala Thr Arg Phe Arg Ser Met
            50                  55                  60 gtg atg cag ccg tcc ggc acc acc ttc agc acc gtg ctc ggg gaa gcg      361
Val Met Gln Pro Ser Gly Thr Thr Phe Ser Thr Val Leu Gly Glu Ala
        65                  70                  75 gat ctt cct gtg agc gaa gac ggt ctt tat ctg aat atc tgg tcg ccg      409
Asp Leu Pro Val Ser Glu Asp Gly Leu Tyr Leu Asn Ile Trp Ser Pro
    80                  85                  90 gca gcc gac gga aaa aag cgg ccg gtg ctc ttc tgg atc cat ggc ggc      457
Ala Ala Asp Gly Lys Lys Arg Pro Val Leu Phe Trp Ile His Gly Gly
95                  100                 105                 110 gcc tac cag ttt ggg tcc ggc gct tcc ccc tgg tat gac ggg acg gag      505
Ala Tyr Gln Phe Gly Ser Gly Ala Ser Pro Trp Tyr Asp Gly Thr Glu
                115                 120                 125
```

```
ttt gcc aaa aac gga gat gtg gtg gtt gtc acg atc aac tac cgg ttg      553
Phe Ala Lys Asn Gly Asp Val Val Val Val Thr Ile Asn Tyr Arg Leu
            130                 135                 140 aac gcg ttt gga ttt ttg tac ttg gca gat tgg ttc ggc gac gaa ttt      601
Asn Ala Phe Gly Phe Leu Tyr Leu Ala Asp Trp Phe Gly Asp Glu Phe
        145                 150                 155 tca gcg tcg ggc aac ctg gga att ttg gac caa gtc gct gca ctg cgc      649
Ser Ala Ser Gly Asn Leu Gly Ile Leu Asp Gln Val Ala Ala Leu Arg
    160                 165                 170 tgg gtg aaa gaa aac att tcg gca ttc ggc ggc gac ccg gag caa atc      697
Trp Val Lys Glu Asn Ile Ser Ala Phe Gly Gly Asp Pro Glu Gln Ile
175                 180                 185                 190 acc atc ttc ggg gag tcg gcc gga gcc gga agc gtc ggg gtt ctg ctt      745
Thr Ile Phe Gly Glu Ser Ala Gly Ala Gly Ser Val Gly Val Leu Leu
                195                 200                 205 tcc ctc ccg gaa acc aaa ggg ctg ttt caa cgg gcg atc ttg caa agc      793
Ser Leu Pro Glu Thr Lys Gly Leu Phe Gln Arg Ala Ile Leu Gln Ser
            210                 215                 220 gga tcg ggt gcc att ttg ctc cgt tcc tct cag aca gcc tcg ggc atc      841
Gly Ser Gly Ala Ile Leu Leu Arg Ser Ser Gln Thr Ala Ser Gly Ile
        225                 230                 235 gcg gaa caa att ctt acg aaa gcc ggc att cga aaa gga gac cgc gac      889
Ala Glu Gln Ile Leu Thr Lys Ala Gly Ile Arg Lys Gly Asp Arg Asp
    240                 245                 250 cgg ttg tta tcc atc ccg gcc ggt gaa ctc ctt gaa gcc gca caa tcc      937
Arg Leu Leu Ser Ile Pro Ala Gly Glu Leu Leu Glu Ala Ala Gln Ser
255                 260                 265                 270 gtg aat ccg gga atg gtt ttt ggt ccc gtt gtg gac ggc acc gta ttg      985
Val Asn Pro Gly Met Val Phe Gly Pro Val Val Asp Gly Thr Val Leu
                275                 280                 285 aaa acc cat ccg att gaa gcg ttg gaa acc gga gcc gcc ggc gat atc     1033
Lys Thr His Pro Ile Glu Ala Leu Glu Thr Gly Ala Ala Gly Asp Ile
            290                 295                 300 ccg atc atc atc ggg gtg aca aag gat gag tac aat tta ttt aca ctg     1081
Pro Ile Ile Ile Gly Val Thr Lys Asp Glu Tyr Asn Leu Phe Thr Leu
        305                 310                 315 act gac cct tcc tgg acg aca gcg gga aaa gaa gaa ctg atg gac cgg     1129
Thr Asp Pro Ser Trp Thr Thr Ala Gly Lys Glu Glu Leu Met Asp Arg
    320                 325                 330 atc gaa cag gaa atc ggg ccg gtt ccg gaa aaa gtt ttt cca tat tac     1177
Ile Glu Gln Glu Ile Gly Pro Val Pro Glu Lys Val Phe Pro Tyr Tyr
335                 340                 345                 350 tta tct ttt ggg gat cca tcg caa ccg gta tgg caa aag ctg ttg cgc     1225
Leu Ser Phe Gly Asp Pro Ser Gln Pro Val Trp Gln Lys Leu Leu Arg
                355                 360                 365 gcc atg acc tac cac atc ttt acc cgg ggc atg tta aaa acg gct gac     1273
Ala Met Thr Tyr His Ile Phe Thr Arg Gly Met Leu Lys Thr Ala Asp
            370                 375                 380 gcc caa atc aag caa ggc ggg aag gtt tgg gtt tac cgg ttt gat tac     1321
Ala Gln Ile Lys Gln Gly Gly Lys Val Trp Val Tyr Arg Phe Asp Tyr
        385                 390                 395 gaa acc ccg ctc ttt gac ggt cgg ttg aaa gca tgt cac gca ctg gaa     1369
Glu Thr Pro Leu Phe Asp Gly Arg Leu Lys Ala Cys His Ala Leu Glu
    400                 405                 410 atc ccc ttt gtc ttt cac aac ctg cat caa ccg ggg gtc gat gtg ttc     1417
Ile Pro Phe Val Phe His Asn Leu His Gln Pro Gly Val Asp Val Phe
415                 420                 425                 430 acc ggc aca cat ccg aag cgg gag cta att tcc cgg caa atg cat gaa     1465
Thr Gly Thr His Pro Lys Arg Glu Leu Ile Ser Arg Gln Met His Glu
```

-continued

```
                  435                 440                 445
gca tgg att gcc ttt gcc cgg aca ggg gat ccg aac ggc gac cat ctc   1513
Ala Trp Ile Ala Phe Ala Arg Thr Gly Asp Pro Asn Gly Asp His Leu
        450                 455                 460 ccc gat gcg tgg ttg ccc ttt gca caa aaa gac cgg ccg gcc atg gtc   1561
Pro Asp Ala Trp Leu Pro Phe Ala Gln Lys Asp Arg Pro Ala Met Val
        465                 470                 475 ttt gac acc gaa acc aga gcg gaa aag cat ctg ttt gac cgc gag cag   1609
Phe Asp Thr Glu Thr Arg Ala Glu Lys His Leu Phe Asp Arg Glu Gln
    480                 485                 490 gaa ctg tgg gaa tca aag gct tgagtgattt gctcaagcct tttttgcatt     1660
Glu Leu Trp Glu Ser Lys Ala
495             500 tcacgtatgt attcggattt ggaattaaac aatggtgctt ttatcgaaat ggggagtgtt 1720
tgcttataat gaacgggttt acaaagcttg ttt                            1753
```

<210> SEQ ID NO 22
<211> LENGTH: 501
<212> TYPE: PRT
<213> ORGANISM: Artificial Sequence
<220> FEATURE:
<223> OTHER INFORMATION: Description of Artificial Sequence:cloned
      esterase gene from bacteria E013

<400> SEQUENCE: 22

```
Val Ile Gln Met Asn Thr Leu Val Glu Thr Arg Phe Gly Lys Val Gln
 1               5                  10                  15

Gly Gly Thr Asp Gly Glu Val Cys Phe Trp Lys Gly Ile Pro Tyr Ala
            20                  25                  30

Lys Pro Pro Val Gly Lys Arg Phe Gln Lys Pro Glu Pro Pro Glu
        35                  40                  45

Lys Trp Asp Gly Val Trp Glu Ala Thr Arg Phe Arg Ser Met Val Met
     50                  55                  60

Gln Pro Ser Gly Thr Thr Phe Ser Thr Val Leu Gly Glu Ala Asp Leu
 65                  70                  75                  80

Pro Val Ser Glu Asp Gly Leu Tyr Leu Asn Ile Trp Ser Pro Ala Ala
                85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
                165                 170                 175

Lys Glu Asn Ile Ser Ala Phe Gly Gly Asp Pro Glu Gln Ile Thr Ile
            180                 185                 190

Phe Gly Glu Ser Ala Gly Ala Gly Ser Val Gly Val Leu Leu Ser Leu
        195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
```

```
                      245                 250                 255
Leu Ser Ile Pro Ala Gly Glu Leu Leu Glu Ala Ala Gln Ser Val Asn
            260                 265                 270

Pro Gly Met Val Phe Gly Pro Val Val Asp Gly Thr Val Leu Lys Thr
        275                 280                 285

His Pro Ile Glu Ala Leu Glu Thr Gly Ala Ala Gly Asp Ile Pro Ile
    290                 295                 300

Ile Ile Gly Val Thr Lys Asp Glu Tyr Asn Leu Phe Thr Leu Thr Asp
305                 310                 315                 320

Pro Ser Trp Thr Thr Ala Gly Lys Glu Glu Leu Met Asp Arg Ile Glu
            325                 330                 335

Gln Glu Ile Gly Pro Val Pro Glu Lys Val Phe Pro Tyr Tyr Leu Ser
        340                 345                 350

Phe Gly Asp Pro Ser Gln Pro Val Trp Gln Lys Leu Leu Arg Ala Met
    355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
385                 390                 395                 400

Pro Leu Phe Asp Gly Arg Leu Lys Ala Cys His Ala Leu Glu Ile Pro
            405                 410                 415

Phe Val Phe His Asn Leu His Gln Pro Gly Val Asp Val Phe Thr Gly
        420                 425                 430

Thr His Pro Lys Arg Glu Leu Ile Ser Arg Gln Met His Glu Ala Trp
    435                 440                 445

Ile Ala Phe Ala Arg Thr Gly Asp Pro Asn Gly Asp His Leu Pro Asp
    450                 455                 460

Ala Trp Leu Pro Phe Ala Gln Lys Asp Arg Pro Ala Met Val Phe Asp
465                 470                 475                 480

Thr Glu Thr Arg Ala Glu Lys His Leu Phe Asp Arg Glu Gln Glu Leu
            485                 490                 495

Trp Glu Ser Lys Ala
            500

<210> SEQ ID NO 23
<211> LENGTH: 1776
<212> TYPE: DNA
<213> ORGANISM: Artificial Sequence
<220> FEATURE:
<223> OTHER INFORMATION: Description of Artificial Sequence:cloned
      esterase gene from bacteria E015
<220> FEATURE:
<221> NAME/KEY: CDS
<222> LOCATION: (128)..(1630)

<400> SEQUENCE: 23
atcacatcgt ggatatcagt ggatccggtg cgatggattg cttcagggga acttttaaac      60
acttgagttt gacaaccact ccttaatcat ttaagattta aatgaaaatt aaataaatc     120 aaaaaga gtg att caa atg aat acg ttg gtg gaa acc cgt ttt ggg aaa     169
        Val Ile Gln Met Asn Thr Leu Val Glu Thr Arg Phe Gly Lys
         1               5                  10 gtg caa ggc ggt aca gac gga gag gtt tgt ttt tgg aaa ggg att cct     217
Val Gln Gly Gly Thr Asp Gly Glu Val Cys Phe Trp Lys Gly Ile Pro
 15                  20                  25                  30 tat gcg aaa cct ccg gtg gga aaa cgc cgc ttt caa aaa ccg gaa ccg     265
Tyr Ala Lys Pro Pro Val Gly Lys Arg Arg Phe Gln Lys Pro Glu Pro
                35                  40                  45
```

```
ccg gag aaa tgg gat ggc gtt tgg gag gcc acc cgg ttc cgg tcc atg      313
Pro Glu Lys Trp Asp Gly Val Trp Glu Ala Thr Arg Phe Arg Ser Met
         50                  55                  60 gtg atg cag ccg tcc ggc acc acc ttc agc acc gtg ctc ggg gaa gcg      361
Val Met Gln Pro Ser Gly Thr Thr Phe Ser Thr Val Leu Gly Glu Ala
             65                  70                  75 gat ctt cct gtg agc gaa gac ggt ctt tat ctg aat atc tgg tcg ccg      409
Asp Leu Pro Val Ser Glu Asp Gly Leu Tyr Leu Asn Ile Trp Ser Pro
         80                  85                  90 gca gcc gac gga aaa aag cgg ccg gtg ctc ttc tgg atc cat ggc ggc      457
Ala Ala Asp Gly Lys Lys Arg Pro Val Leu Phe Trp Ile His Gly Gly
 95                 100                 105                 110 gcc tac cag ttt ggg tcc ggc gct tcc ccc tgg tat gac ggg acg gag      505
Ala Tyr Gln Phe Gly Ser Gly Ala Ser Pro Trp Tyr Asp Gly Thr Glu
                115                 120                 125 ttt gcc aaa aac gga gat gtg gtg gtt gtc acg atc aac tac cgg ttg      553
Phe Ala Lys Asn Gly Asp Val Val Val Val Thr Ile Asn Tyr Arg Leu
            130                 135                 140 aac gcg ttt gga ttt ttg tac ttg gca gat tgg ttc ggc gac gaa ttt      601
Asn Ala Phe Gly Phe Leu Tyr Leu Ala Asp Trp Phe Gly Asp Glu Phe
        145                 150                 155 tca gcg tcg ggc aac ctg gga att ttg gac caa gtc gct gca ctg cgc      649
Ser Ala Ser Gly Asn Leu Gly Ile Leu Asp Gln Val Ala Ala Leu Arg
    160                 165                 170 tgg gtg aaa gaa aac att tcg gca ttc ggc ggc gac ccg gag caa atc      697
Trp Val Lys Glu Asn Ile Ser Ala Phe Gly Gly Asp Pro Glu Gln Ile
175                 180                 185                 190 acc atc ttc ggg gag tcg gcc gga gcc gga agc gtc ggg gtt ctg ctt      745
Thr Ile Phe Gly Glu Ser Ala Gly Ala Gly Ser Val Gly Val Leu Leu
                195                 200                 205 tcc ctc ccg gaa acc aaa ggg ctg ttt caa cgg gcg atc ttg caa agc      793
Ser Leu Pro Glu Thr Lys Gly Leu Phe Gln Arg Ala Ile Leu Gln Ser
            210                 215                 220 gga tcg ggt gcc att ttg ctc cgt tcc tct cag aca gcc tcg ggc atc      841
Gly Ser Gly Ala Ile Leu Leu Arg Ser Ser Gln Thr Ala Ser Gly Ile
        225                 230                 235 gcg gaa caa att ctt acg aaa gcc ggc att cga aaa gga gac cgc gac      889
Ala Glu Gln Ile Leu Thr Lys Ala Gly Ile Arg Lys Gly Asp Arg Asp
    240                 245                 250 cgg ttg tta tcc atc ccg gcc ggt gaa ctc ctt gaa gcc gca caa tcc      937
Arg Leu Leu Ser Ile Pro Ala Gly Glu Leu Leu Glu Ala Ala Gln Ser
255                 260                 265                 270 gtg aat ccg gga atg gtt ttt ggt ccc gtt gtg gac ggc acc gta ttg      985
Val Asn Pro Gly Met Val Phe Gly Pro Val Val Asp Gly Thr Val Leu
                275                 280                 285 aaa acc cat ccg att gaa gcg ttg gaa acc gga gcc gcc ggc gat atc     1033
Lys Thr His Pro Ile Glu Ala Leu Glu Thr Gly Ala Ala Gly Asp Ile
            290                 295                 300 ccg atc atc atc ggg gtg aca aag gat gag tac aat tta ttt aca ctg     1081
Pro Ile Ile Ile Gly Val Thr Lys Asp Glu Tyr Asn Leu Phe Thr Leu
        305                 310                 315 act gac cct tcc tgg acg aca gcg gga aaa gaa gaa ctg atg gac cgg     1129
Thr Asp Pro Ser Trp Thr Thr Ala Gly Lys Glu Glu Leu Met Asp Arg
    320                 325                 330 atc gaa cag gaa atc ggg ccg gtt ccg gaa aaa gtt ttt cca tat tac     1177
Ile Glu Gln Glu Ile Gly Pro Val Pro Glu Lys Val Phe Pro Tyr Tyr
335                 340                 345                 350 tta tct ttt ggg gat cca tcg caa ccg gta tgg caa aag ctg ttg cgc     1225
Leu Ser Phe Gly Asp Pro Ser Gln Pro Val Trp Gln Lys Leu Leu Arg
```

```
                   355                 360                 365
gcc atg acc tac cac atc ttt acc cgg ggc atg tta aaa acg gct gac    1273
Ala Met Thr Tyr His Ile Phe Thr Arg Gly Met Leu Lys Thr Ala Asp
            370                 375                 380 gcc caa atc aag caa ggc ggg aag gtt tgg gtt tac cgg ttt gat tac    1321
Ala Gln Ile Lys Gln Gly Gly Lys Val Trp Val Tyr Arg Phe Asp Tyr
                385                 390                 395 gaa acc ccg ctc ttt gac ggt cgg ttg aaa gca tgt cac gca ctg gaa    1369
Glu Thr Pro Leu Phe Asp Gly Arg Leu Lys Ala Cys His Ala Leu Glu
    400                 405                 410 atc ccc ttt gtc ttt cac aac ctg cat caa ccg ggg gtc gat gtg ttc    1417
Ile Pro Phe Val Phe His Asn Leu His Gln Pro Gly Val Asp Val Phe
415                 420                 425                 430 acc ggc aca cat ccg aag cgg gag cta att tcc cgg caa atg cat gaa    1465
Thr Gly Thr His Pro Lys Arg Glu Leu Ile Ser Arg Gln Met His Glu
                435                 440                 445 gca tgg att gcc ttt gcc cgg aca ggg gat ccg aac ggc gac cat ctc    1513
Ala Trp Ile Ala Phe Ala Arg Thr Gly Asp Pro Asn Gly Asp His Leu
            450                 455                 460 ccc gat gcg tgg ttg ccc ttt gca caa aaa gac cgg ccg gcc atg gtc    1561
Pro Asp Ala Trp Leu Pro Phe Ala Gln Lys Asp Arg Pro Ala Met Val
        465                 470                 475 ttt gac acc gaa acc aga gcg gaa aag cat ctg ttt gac cgc gag cag    1609
Phe Asp Thr Glu Thr Arg Ala Glu Lys His Leu Phe Asp Arg Glu Gln
    480                 485                 490 gaa ctg tgg gaa tca aag gct tgagtgattt gctcaagcct tttttgcatt       1660
Glu Leu Trp Glu Ser Lys Ala
495                 500 tcacgtatgt attcggattt ggaattaaac aatggtgctt ttatcgaaat ggggagtgtt  1720
tgcttataat gaacgggttt acaaagcttg ttttggtacc ggattactga aaatga     1776

<210> SEQ ID NO 24
<211> LENGTH: 501
<212> TYPE: PRT
<213> ORGANISM: Artificial Sequence
<220> FEATURE:
<223> OTHER INFORMATION: Description of Artificial Sequence:cloned
      esterase gene from bacteria E015

<400> SEQUENCE: 24

Val Ile Gln Met Asn Thr Leu Val Glu Thr Arg Phe Gly Lys Val Gln
 1               5                  10                  15

Gly Gly Thr Asp Gly Glu Val Cys Phe Trp Lys Gly Ile Pro Tyr Ala
            20                  25                  30

Lys Pro Pro Val Gly Lys Arg Phe Gln Lys Pro Glu Pro Pro Glu
        35                  40                  45

Lys Trp Asp Gly Val Trp Glu Ala Thr Arg Phe Arg Ser Met Val Met
    50                  55                  60

Gln Pro Ser Gly Thr Thr Phe Ser Thr Val Leu Gly Glu Ala Asp Leu
65                  70                  75                  80

Pro Val Ser Glu Asp Gly Leu Tyr Leu Asn Ile Trp Ser Pro Ala Ala
                85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Thr Ile Asn Tyr Arg Leu Asn Ala
    130                 135                 140
```

```
Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
            165                 170                 175

Lys Glu Asn Ile Ser Ala Phe Gly Asp Pro Glu Gln Ile Thr Ile
                180                 185                 190

Phe Gly Glu Ser Ala Gly Ala Gly Ser Val Gly Val Leu Leu Ser Leu
            195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
                245                 250                 255

Leu Ser Ile Pro Ala Gly Glu Leu Leu Glu Ala Ala Gln Ser Val Asn
            260                 265                 270

Pro Gly Met Val Phe Gly Pro Val Val Asp Gly Thr Val Leu Lys Thr
            275                 280                 285

His Pro Ile Glu Ala Leu Glu Thr Gly Ala Ala Gly Asp Ile Pro Ile
    290                 295                 300

Ile Ile Gly Val Thr Lys Asp Glu Tyr Asn Leu Phe Thr Leu Thr Asp
305                 310                 315                 320

Pro Ser Trp Thr Thr Ala Gly Lys Glu Glu Leu Met Asp Arg Ile Glu
                325                 330                 335

Gln Glu Ile Gly Pro Val Pro Glu Lys Val Phe Pro Tyr Tyr Leu Ser
            340                 345                 350

Phe Gly Asp Pro Ser Gln Pro Val Trp Gln Lys Leu Leu Arg Ala Met
            355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
385                 390                 395                 400

Pro Leu Phe Asp Gly Arg Leu Lys Ala Cys His Ala Leu Glu Ile Pro
            405                 410                 415

Phe Val Phe His Asn Leu His Gln Pro Gly Val Asp Val Phe Thr Gly
            420                 425                 430

Thr His Pro Lys Arg Glu Leu Ile Ser Arg Gln Met His Glu Ala Trp
    435                 440                 445

Ile Ala Phe Ala Arg Thr Gly Asp Pro Asn Gly Asp His Leu Pro Asp
450                 455                 460

Ala Trp Leu Pro Phe Ala Gln Lys Asp Arg Pro Ala Met Val Phe Asp
465                 470                 475                 480

Thr Glu Thr Arg Ala Glu Lys His Leu Phe Asp Arg Glu Gln Glu Leu
                485                 490                 495

Trp Glu Ser Lys Ala
            500

<210> SEQ ID NO 25
<211> LENGTH: 1777
<212> TYPE: DNA
<213> ORGANISM: Artificial Sequence
<220> FEATURE:
<223> OTHER INFORMATION: Description of Artificial Sequence:cloned
      esterase gene from bacteria E016
<220> FEATURE:
```

```
<221> NAME/KEY: CDS
<222> LOCATION: (123)..(1631)

<400> SEQUENCE: 25
gtctccaacg ttgcgagaca cccctcttta attacgggaa ccagaaatga tttcctatcg      60
atagcaaaaa atggacgtgg gtaaaccatt cgttaataat atcttttgta atcgttagaa     120 ta ttg aaa aag ggg atg gga ccc gtg atc gtg gaa aca aag tac ggt       167
   Leu Lys Lys Gly Met Gly Pro Val Ile Val Glu Thr Lys Tyr Gly
   1               5                   10                  15 cgg ttg cgc ggg gga aca aat gaa ggg gtt ttc tat tgg aaa ggg att       215
Arg Leu Arg Gly Gly Thr Asn Glu Gly Val Phe Tyr Trp Lys Gly Ile
                20                  25                  30 ccg tac gcg aaa gcg ccg gtc ggt gaa cgc cgt ttt ttg ccg ccg gaa       263
Pro Tyr Ala Lys Ala Pro Val Gly Glu Arg Arg Phe Leu Pro Pro Glu
            35                  40                  45 ccg ccc gat gca tgg gac gga gtg cgt gag gcg aca tcg ttt gga ccg       311
Pro Pro Asp Ala Trp Asp Gly Val Arg Glu Ala Thr Ser Phe Gly Pro
        50                  55                  60 gtc gtc atg cag ccg tcc gat tcg atg ttc agc cag ctg ctc gga cgg       359
Val Val Met Gln Pro Ser Asp Ser Met Phe Ser Gln Leu Leu Gly Arg
65                  70                  75 atg aat gaa cca atg agc gag gat ggg ttg tat ctg aac att tgg tca       407
Met Asn Glu Pro Met Ser Glu Asp Gly Leu Tyr Leu Asn Ile Trp Ser
 80                  85                  90                  95 ccg gcg gcg gat ggg aag aag cgc ccg gta ttg ttt tgg att cat ggc       455
Pro Ala Ala Asp Gly Lys Lys Arg Pro Val Leu Phe Trp Ile His Gly
                100                 105                 110 ggc gct ttt tta ttc ggc tcc ggt tca ttt cca tgg tat gat gga acg       503
Gly Ala Phe Leu Phe Gly Ser Gly Ser Phe Pro Trp Tyr Asp Gly Thr
            115                 120                 125 gcg ttt gcc aaa cac ggc gat gtc gtt gtc gtg acg atc aac tac cgg       551
Ala Phe Ala Lys His Gly Asp Val Val Val Val Thr Ile Asn Tyr Arg
        130                 135                 140 atg agc gtg ttt ggc ttt ttg tat ttg gga gat gcg ttt ggc gaa acg       599
Met Ser Val Phe Gly Phe Leu Tyr Leu Gly Asp Ala Phe Gly Glu Thr
    145                 150                 155 tat gcc cag gcg gga aat ctt ggc ata ttg gat caa gtg gcg gcg ctg       647
Tyr Ala Gln Ala Gly Asn Leu Gly Ile Leu Asp Gln Val Ala Ala Leu
160                 165                 170                 175 cgc tgg gtg aaa gag aac att gag gcg ttc ggc ggt gat ccg gac aac       695
Arg Trp Val Lys Glu Asn Ile Glu Ala Phe Gly Gly Asp Pro Asp Asn
                180                 185                 190 att acg att ttt ggc gaa tca gcc gga gcg gca agc gtt ggc gtg ctg       743
Ile Thr Ile Phe Gly Glu Ser Ala Gly Ala Ala Ser Val Gly Val Leu
            195                 200                 205 ttg tcg ctt ccg gaa gca agc ggg ctg ttt cga cgc gct ata ttg caa       791
Leu Ser Leu Pro Glu Ala Ser Gly Leu Phe Arg Arg Ala Ile Leu Gln
        210                 215                 220 agc gga gcg ggt tcg ctt ctt ctt cgt tct ccg gag acg gcg atg gct       839
Ser Gly Ala Gly Ser Leu Leu Leu Arg Ser Pro Glu Thr Ala Met Ala
    225                 230                 235 ctg act gaa cgc att tta gaa cgt gcc ggc atc cgt ccg ggt gac cgc       887
Leu Thr Glu Arg Ile Leu Glu Arg Ala Gly Ile Arg Pro Gly Asp Arg
240                 245                 250                 255 gat cgg ctg ctg tcg att cca gca gca gag cta ttg cag gcg gcg atg       935
Asp Arg Leu Leu Ser Ile Pro Ala Ala Glu Leu Leu Gln Ala Ala Met
                260                 265                 270 tcg ctc ggc cca gga atc acg tac ggt ccg gtg gtt gac gga cat gtg       983
Ser Leu Gly Pro Gly Ile Thr Tyr Gly Pro Val Val Asp Gly His Val
```

-continued

```
                    275                 280                 285
ttg cga cgc cat ccg atc gaa gcg ctc cac gac ggg gca gca agt gat       1031
Leu Arg Arg His Pro Ile Glu Ala Leu His Asp Gly Ala Ala Ser Asp
            290                 295                 300 att cca atc cta att ggc gtg acg aaa gac gaa tac aat ttg ttt tca       1079
Ile Pro Ile Leu Ile Gly Val Thr Lys Asp Glu Tyr Asn Leu Phe Ser
305                 310                 315 ttg act gat ccg tca ttg aca aga ctc gaa gaa aaa gaa ctg ctt gac       1127
Leu Thr Asp Pro Ser Leu Thr Arg Leu Glu Glu Lys Glu Leu Leu Asp
320                 325                 330                 335 cgg atg aac cgt gag gtc ggg cct att ccg gag aag ccg gta cgc tat       1175
Arg Met Asn Arg Glu Val Gly Pro Ile Pro Glu Lys Pro Val Arg Tyr
            340                 345                 350 tac gcg gaa aca gcg gat cgg tcg gca ccc gcg tgg caa aca tgg ctg       1223
Tyr Ala Glu Thr Ala Asp Arg Ser Ala Pro Ala Trp Gln Thr Trp Leu
            355                 360                 365 cgc atc atg acg tac ctt gtt ttt gtc gac gga atg ttg cga acg gcg       1271
Arg Ile Met Thr Tyr Leu Val Phe Val Asp Gly Met Leu Arg Thr Ala
            370                 375                 380 gat gcc caa gca gcg caa ggg gcg aat gtg tac atg tat cgg ttt gat       1319
Asp Ala Gln Ala Ala Gln Gly Ala Asn Val Tyr Met Tyr Arg Phe Asp
385                 390                 395 tat gaa acg ccg gcg ttc ggt gga caa ctg aaa gcg tgc cat acg ctc       1367
Tyr Glu Thr Pro Ala Phe Gly Gly Gln Leu Lys Ala Cys His Thr Leu
400                 405                 410                 415 gag ttg ccg ttt gtg ttt cat aac ctc cat cag cct ggt gtc gag aat       1415
Glu Leu Pro Phe Val Phe His Asn Leu His Gln Pro Gly Val Glu Asn
            420                 425                 430 ttc gtc ggc aac cga cca gag cgt gag gcg att gcc agc gaa atg cat       1463
Phe Val Gly Asn Arg Pro Glu Arg Glu Ala Ile Ala Ser Glu Met His
            435                 440                 445 ggt gcc tgg ctt tcg ttc gcc cac acc ggc aac ccg aac ggc gct cat       1511
Gly Ala Trp Leu Ser Phe Ala His Thr Gly Asn Pro Asn Gly Ala His
            450                 455                 460 tta cca gag aag tgg ccc gta tac aca aaa gag cac aaa ccg gtg ttt       1559
Leu Pro Glu Lys Trp Pro Val Tyr Thr Lys Glu His Lys Pro Val Phe
465                 470                 475 gtc ttt tcg gct gcg agc cat gtg gaa gac gat ccg ttc ggt cgc gag       1607
Val Phe Ser Ala Ala Ser His Val Glu Asp Asp Pro Phe Gly Arg Glu
480                 485                 490                 495 cgg gaa gcg tgg caa gga cgc ctt tgacgaaaaa atccataagc aacatgtgtt     1661
Arg Glu Ala Trp Gln Gly Arg Leu
                500 ctttgtctga acacgatcca aagaattcaa aaagcttctc gagagtactt ctagagcggc    1721 cgcgggccca tcgattttcc acccgggtgg ggtaccaggt aagtgtaccc aattcg         1777
```

<210> SEQ ID NO 26
<211> LENGTH: 503
<212> TYPE: PRT
<213> ORGANISM: Artificial Sequence
<220> FEATURE:
<223> OTHER INFORMATION: Description of Artificial Sequence:cloned
      esterase gene from bacteria E016

<400> SEQUENCE: 26

```
Leu Lys Lys Gly Met Gly Pro Val Ile Val Glu Thr Lys Tyr Gly Arg
  1               5                  10                  15

Leu Arg Gly Gly Thr Asn Glu Gly Val Phe Tyr Trp Lys Gly Ile Pro
             20                  25                  30
```

-continued

```
Tyr Ala Lys Ala Pro Val Gly Glu Arg Arg Phe Leu Pro Pro Glu Pro
         35                  40                  45

Pro Asp Ala Trp Asp Gly Val Arg Glu Ala Thr Ser Phe Gly Pro Val
     50                  55                  60

Val Met Gln Pro Ser Asp Ser Met Phe Ser Gln Leu Leu Gly Arg Met
 65              70                  75                      80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
             100                 105                 110

Ala Phe Leu Phe Gly Ser Gly Ser Phe Pro Trp Tyr Asp Gly Thr Ala
         115                 120                 125

Phe Ala Lys His Gly Asp Val Val Val Thr Ile Asn Tyr Arg Met
         130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
             165                 170                 175

Trp Val Lys Glu Asn Ile Glu Ala Phe Gly Gly Asp Pro Asp Asn Ile
             180                 185                 190

Thr Ile Phe Gly Glu Ser Ala Gly Ala Ala Ser Val Gly Val Leu Leu
         195                 200                 205

Ser Leu Pro Glu Ala Ser Gly Leu Phe Arg Arg Ala Ile Leu Gln Ser
    210                 215                 220

Gly Ala Gly Ser Leu Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                 245                 250                 255

Arg Leu Leu Ser Ile Pro Ala Ala Glu Leu Leu Gln Ala Ala Met Ser
             260                 265                 270

Leu Gly Pro Gly Ile Thr Tyr Gly Pro Val Val Asp Gly His Val Leu
         275                 280                 285

Arg Arg His Pro Ile Glu Ala Leu His Asp Gly Ala Ala Ser Asp Ile
290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                 325                 330                 335

Met Asn Arg Glu Val Gly Pro Ile Pro Glu Lys Pro Val Arg Tyr Tyr
             340                 345                 350

Ala Glu Thr Ala Asp Arg Ser Ala Pro Ala Trp Gln Thr Trp Leu Arg
         355                 360                 365

Ile Met Thr Tyr Leu Val Phe Val Asp Gly Met Leu Arg Thr Ala Asp
    370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                 405                 410                 415

Leu Pro Phe Val Phe His Asn Leu His Gln Pro Gly Val Glu Asn Phe
             420                 425                 430

Val Gly Asn Arg Pro Glu Arg Glu Ala Ile Ala Ser Glu Met His Gly
         435                 440                 445

Ala Trp Leu Ser Phe Ala His Thr Gly Asn Pro Asn Gly Ala His Leu
```

```
                450             455             460
Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
                485                 490                 495

Glu Ala Trp Gln Gly Arg Leu
            500

<210> SEQ ID NO 27
<211> LENGTH: 2405
<212> TYPE: DNA
<213> ORGANISM: Artificial Sequence
<220> FEATURE:
<223> OTHER INFORMATION: Description of Artificial Sequence:cloned
      esterase gene from bacteria E017
<220> FEATURE:
<221> NAME/KEY: CDS
<222> LOCATION: (258)..(1766)

<400> SEQUENCE: 27
ccgtcgcgta cggaccgcgt cgcaaaatac aaccagttgc tccgcattga agacgaactt      60
ggccacacgg ctatttacca aggcattcgt tcgttttaca atttgaaaaa ataacgggaa     120
tcaacaacaa agggtgtctc caacgttgcg agacaccctc tttaattacg ggaaacagaa     180
atgatttcct atcgatagca aaaatggacg tgggtaaac cattcgttta taatatcttt      240
ttgtaatcgt tagaata ttg aaa aag ggg atg gga acc gtg atc gtg gaa         290
                  Leu Lys Lys Gly Met Gly Thr Val Ile Val Glu
                    1               5                  10 aca aag tac ggt cgg ttg cgc ggg gga aca aat gaa ggg gtt ttc tat       338
Thr Lys Tyr Gly Arg Leu Arg Gly Gly Thr Asn Glu Gly Val Phe Tyr
            15                  20                  25 tgg aaa ggg att ccg tac gcg aaa gcg ccg gtc ggt gaa cgc cgt ttt       386
Trp Lys Gly Ile Pro Tyr Ala Lys Ala Pro Val Gly Glu Arg Arg Phe
        30                  35                  40 ttg ccg ccg gaa ccg ccc gat gca tgg gac gga gtg cgt gag gcg aca       434
Leu Pro Pro Glu Pro Pro Asp Ala Trp Asp Gly Val Arg Glu Ala Thr
    45                  50                  55 tcg ttt gga ccg gtc gtc atg cag ccg tcc gat tcg atg ttc agc cag       482
Ser Phe Gly Pro Val Val Met Gln Pro Ser Asp Ser Met Phe Ser Gln
60                  65                  70                  75 ctg ctc gga cgg atg aat gaa cca atg agc gag gat ggg ttg tat ctg       530
Leu Leu Gly Arg Met Asn Glu Pro Met Ser Glu Asp Gly Leu Tyr Leu
                80                  85                  90 aac att tgg tca ccg gcg gcg gat ggg aag aag cgc ccg gta ttg ttt       578
Asn Ile Trp Ser Pro Ala Ala Asp Gly Lys Lys Arg Pro Val Leu Phe
            95                 100                 105 tgg att cat ggc ggc gct ttt tta ttc ggc tcc ggt tca ttt cca tgg       626
Trp Ile His Gly Gly Ala Phe Leu Phe Gly Ser Gly Ser Phe Pro Trp
       110                  115                 120 tat gat gga acg gcg ttt gcc aaa cac ggc gat gtc gtt gtc gtg acg       674
Tyr Asp Gly Thr Ala Phe Ala Lys His Gly Asp Val Val Val Val Thr
   125                 130                 135 atc aac tac cgg atg agc gtg ttt ggc ttt ttg tat ttg gga gat gcg       722
Ile Asn Tyr Arg Met Ser Val Phe Gly Phe Leu Tyr Leu Gly Asp Ala
140                 145                 150                 155 ttt ggc gaa acg tat gcc cag gcg gga aat ctt ggc ata ttg gat caa       770
Phe Gly Glu Thr Tyr Ala Gln Ala Gly Asn Leu Gly Ile Leu Asp Gln
                160                 165                 170 gtg gcg gcg ctg cgc tgg gtg aaa gag aac att gag gcg ttc ggc ggt       818
Val Ala Ala Leu Arg Trp Val Lys Glu Asn Ile Glu Ala Phe Gly Gly
```

```
                    175                 180                 185
gat ccg gac aac att acg att ttt ggc gaa tca gcc gga gcg gca agc      866
Asp Pro Asp Asn Ile Thr Ile Phe Gly Glu Ser Ala Gly Ala Ala Ser
        190                 195                 200 gtt ggc gtg ctg ttg tcg ctt ccg gaa gca agc ggg ctg ttt cga cgc      914
Val Gly Val Leu Leu Ser Leu Pro Glu Ala Ser Gly Leu Phe Arg Arg
205                 210                 215 gct ata ttg caa agc gga tcg ggt tcg ctt ctt ctt cgt tct ccg gag      962
Ala Ile Leu Gln Ser Gly Ser Gly Ser Leu Leu Leu Arg Ser Pro Glu
220                 225                 230                 235 acg gcg atg gct ctg act gaa cgc att tta gaa cgt gcc ggc atc cgt     1010
Thr Ala Met Ala Leu Thr Glu Arg Ile Leu Glu Arg Ala Gly Ile Arg
                240                 245                 250 ccg ggt gac cgc gat cgg ctg ctg tcg att cca gca cca gag cta ttg     1058
Pro Gly Asp Arg Asp Arg Leu Leu Ser Ile Pro Ala Pro Glu Leu Leu
                255                 260                 265 cag gcg gcg atg tcg ctc ggc cca gga atc acg tac ggt ccg gtg gtt     1106
Gln Ala Ala Met Ser Leu Gly Pro Gly Ile Thr Tyr Gly Pro Val Val
            270                 275                 280 gac gga cat gtg ttg cga cgc cat ccg atc gaa gcg ctc cac gac ggg     1154
Asp Gly His Val Leu Arg Arg His Pro Ile Glu Ala Leu His Asp Gly
285                 290                 295 gca gca agt gat att cca atc cta att ggc gtg acg aaa gac gaa tac     1202
Ala Ala Ser Asp Ile Pro Ile Leu Ile Gly Val Thr Lys Asp Glu Tyr
300                 305                 310                 315 aat ttg ttt tca ttg act gat ccg tca ttg aca aga ctc gaa gaa aaa     1250
Asn Leu Phe Ser Leu Thr Asp Pro Ser Leu Thr Arg Leu Glu Glu Lys
                320                 325                 330 gaa ctg ctt gac cgg atg aac cgt gag gtc ggg cct att ccg gag gag     1298
Glu Leu Leu Asp Arg Met Asn Arg Glu Val Gly Pro Ile Pro Glu Glu
                335                 340                 345 gcg gta cgc tat tac gcg gaa aca gcg gat cgg tcg gca ccc gcg tgg     1346
Ala Val Arg Tyr Tyr Ala Glu Thr Ala Asp Arg Ser Ala Pro Ala Trp
            350                 355                 360 caa aca tgg ctg cgc atc atg acg tac ctt gtt ttt gtc gac gga atg     1394
Gln Thr Trp Leu Arg Ile Met Thr Tyr Leu Val Phe Val Asp Gly Met
365                 370                 375 ttg cga acg gcg gat gcc caa gca gcg caa ggg gcg aat gtg tac atg     1442
Leu Arg Thr Ala Asp Ala Gln Ala Ala Gln Gly Ala Asn Val Tyr Met
380                 385                 390                 395 tat cgg ttt gat tat gaa acg ccg gcg ttc ggt gga caa ctg aaa gcg     1490
Tyr Arg Phe Asp Tyr Glu Thr Pro Ala Phe Gly Gly Gln Leu Lys Ala
                400                 405                 410 tgc cat acg ctc gag ttg ccg ttt gtg ttt cat aac ctc cat cag cct     1538
Cys His Thr Leu Glu Leu Pro Phe Val Phe His Asn Leu His Gln Pro
                415                 420                 425 ggt gtc gag aat ttc gtc ggc aac cga cca gag cgt gag gcg att gcc     1586
Gly Val Glu Asn Phe Val Gly Asn Arg Pro Glu Arg Glu Ala Ile Ala
            430                 435                 440 agc gaa atg cat ggt gcc tgg ctt tcg ttc gcc cac acc ggc aac ccg     1634
Ser Glu Met His Gly Ala Trp Leu Ser Phe Ala His Thr Gly Asn Pro
445                 450                 455 aac ggc gct cat tta cca gag aag tgg ccc gta tac aca aaa gag cac     1682
Asn Gly Ala His Leu Pro Glu Lys Trp Pro Val Tyr Thr Lys Glu His
460                 465                 470                 475 aaa ccg gtg ttt gtc ttt tcg gct gcg agc cat gtg gaa gac gat ccg     1730
Lys Pro Val Phe Val Phe Ser Ala Ala Ser His Val Glu Asp Asp Pro
                480                 485                 490 ttc ggt cgc gag cgg gaa gcg tgg caa gga cgc ctt tgacgaaaaa          1776
Phe Gly Arg Glu Arg Glu Ala Trp Gln Gly Arg Leu
```

Phe Gly Arg Glu Arg Glu Ala Trp Gln Gly Arg Leu
            495                 500

| | |
|---|---:|
| atccataagc aacatgtgtt ctttgtctga acacgatcaa ggtacgcgca ttttcgcgga | 1836 |
| aaaagaccgt gggcaaacgt tcgcctttac ctctaaaagg aatgacgcaa catgtctgca | 1896 |
| cttcacagga aagaggacga aacggttggt tttcagaata ggaaaaggtg tcccgttttt | 1956 |
| tgggacacct tcttctatgt atcgctcaat catttgcttc tgtggcagga agcccgaatc | 2016 |
| gctcggcgag tgccggatca cgatcgatcg cctcaatcag tttccgcatg acgttcacat | 2076 |
| caaacgtaaa attcgaaccg attggcgagg tgacgaaaat ttcccttctt tcgcctcgcg | 2136 |
| tgctcgttta aattgatagc cgtcaatcgc aatgacgact cgttcgtctg gccttgccat | 2196 |
| taggaatccc tccatcgctg ttttttcttt cattgtactt gattttgagg atgaacacca | 2256 |
| acgttcatga cacgctctta aggataacgg atgggagagc gttagagggc ggtgaatttc | 2316 |
| atcaagaacg tggcacaaaa cgacattttt tcattataga cgtcttgatg tttggaatga | 2376 |
| tcggaaaagg cgattgttag gcggggatc | 2405 |

<210> SEQ ID NO 28
<211> LENGTH: 503
<212> TYPE: PRT
<213> ORGANISM: Artificial Sequence
<220> FEATURE:
<223> OTHER INFORMATION: Description of Artificial Sequence:cloned
      esterase gene from bacteria E017

<400> SEQUENCE: 28

Leu Lys Lys Gly Met Gly Thr Val Ile Val Glu Thr Lys Tyr Gly Arg
  1               5                  10                  15

Leu Arg Gly Gly Thr Asn Glu Gly Val Phe Tyr Trp Lys Gly Ile Pro
             20                  25                  30

Tyr Ala Lys Ala Pro Val Gly Glu Arg Arg Phe Leu Pro Pro Glu Pro
         35                  40                  45

Pro Asp Ala Trp Asp Gly Val Arg Glu Ala Thr Ser Phe Gly Pro Val
     50                  55                  60

Val Met Gln Pro Ser Asp Ser Met Phe Ser Gln Leu Leu Gly Arg Met
 65                  70                  75                  80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
            100                 105                 110

Ala Phe Leu Phe Gly Ser Gly Ser Phe Pro Trp Tyr Asp Gly Thr Ala
        115                 120                 125

Phe Ala Lys His Gly Asp Val Val Val Thr Ile Asn Tyr Arg Met
    130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Asp Pro Asp Asn Ile
            180                 185                 190

Thr Ile Phe Gly Glu Ser Ala Gly Ala Ala Ser Val Gly Val Leu Leu
        195                 200                 205

Ser Leu Pro Glu Ala Ser Gly Leu Phe Arg Arg Ala Ile Leu Gln Ser
    210                 215                 220

Gly Ser Gly Ser Leu Leu Leu Arg Ser Pro Glu Thr Ala Met Ala Leu

-continued

```
                225                 230                 235                 240
        Thr Glu Arg Ile Leu Glu Arg Ala Gly Ile Arg Pro Gly Asp Arg Asp
                        245                 250                 255

Arg Leu Leu Ser Ile Pro Ala Pro Glu Leu Leu Gln Ala Ala Met Ser
                        260                 265                 270

Leu Gly Pro Gly Ile Thr Tyr Gly Pro Val Val Asp Gly His Val Leu
                        275                 280                 285

Arg Arg His Pro Ile Glu Ala Leu His Asp Gly Ala Ala Ser Asp Ile
                290                 295                 300

Pro Ile Leu Ile Gly Val Thr Lys Asp Glu Tyr Asn Leu Phe Ser Leu
        305                 310                 315                 320

Thr Asp Pro Ser Leu Thr Arg Leu Glu Glu Lys Glu Leu Leu Asp Arg
                        325                 330                 335

Met Asn Arg Glu Val Gly Pro Ile Pro Glu Glu Ala Val Arg Tyr Tyr
                        340                 345                 350

Ala Glu Thr Ala Asp Arg Ser Ala Pro Ala Trp Gln Thr Trp Leu Arg
                        355                 360                 365

Ile Met Thr Tyr Leu Val Phe Val Asp Gly Met Leu Arg Thr Ala Asp
                370                 375                 380

Ala Gln Ala Ala Gln Gly Ala Asn Val Tyr Met Tyr Arg Phe Asp Tyr
        385                 390                 395                 400

Glu Thr Pro Ala Phe Gly Gly Gln Leu Lys Ala Cys His Thr Leu Glu
                        405                 410                 415

Leu Pro Phe Val Phe His Asn Leu His Gln Pro Gly Val Glu Asn Phe
                        420                 425                 430

Val Gly Asn Arg Pro Glu Arg Glu Ala Ile Ala Ser Glu Met His Gly
                        435                 440                 445

Ala Trp Leu Ser Phe Ala His Thr Gly Asn Pro Asn Gly Ala His Leu
                        450                 455                 460

Pro Glu Lys Trp Pro Val Tyr Thr Lys Glu His Lys Pro Val Phe Val
        465                 470                 475                 480

Phe Ser Ala Ala Ser His Val Glu Asp Asp Pro Phe Gly Arg Glu Arg
                        485                 490                 495

Glu Ala Trp Gln Gly Arg Leu
                    500

<210> SEQ ID NO 29
<211> LENGTH: 1924
<212> TYPE: DNA
<213> ORGANISM: Artificial Sequence
<220> FEATURE:
<223> OTHER INFORMATION: Description of Artificial Sequence:cloned
      esterase gene from bacteria E020
<220> FEATURE:
<221> NAME/KEY: CDS
<222> LOCATION: (271)..(1779)

<400> SEQUENCE: 29
aaaaacggga gcaccgtcgc gtacggaccg cgtcgcaaaa tacaaccagc tgctccgcat      60
tgaagacgaa cttggccaca cggctatttta ccaaggcatt cgttcgtttt acaatttgaa   120 aaataacgg gaatcaacaa caagggtgt ctccaacgtt gcgagacacc ctctttaatt      180
acgggaaaca gaaatgattt cctatcgata gcaaaaaatg gacgtgggta accattcgt     240 ttataatatc ttttttgtaat cgttagaata ttg aaa aag ggg atg gga acc gtg   294
                                    Leu Lys Lys Gly Met Gly Thr Val
                                     1               5
```

```
atc gtg gaa aca aag tac ggt cgg ttg cgc ggg gga aca aat gaa ggg      342
Ile Val Glu Thr Lys Tyr Gly Arg Leu Arg Gly Gly Thr Asn Glu Gly
     10              15                  20 gtt ttc tat tgg aaa ggg att ccg tac gcg aaa gcg ccg gtc ggt gaa      390
Val Phe Tyr Trp Lys Gly Ile Pro Tyr Ala Lys Ala Pro Val Gly Glu
 25              30                  35                  40 cgc cgt ttt ttg ccg ccg gaa ccg ccc gat gca tgg gac gga gtg cgt      438
Arg Arg Phe Leu Pro Pro Glu Pro Pro Asp Ala Trp Asp Gly Val Arg
                 45                  50                  55 gag gcg aca tcg ttt gga ccg gtc gtc atg cag ccg tcc gat tcg atg      486
Glu Ala Thr Ser Phe Gly Pro Val Val Met Gln Pro Ser Asp Ser Met
             60                  65                  70 ttc agc cag ctg ctc gga cgg atg aat gaa cca atg agc gag gat ggg      534
Phe Ser Gln Leu Leu Gly Arg Met Asn Glu Pro Met Ser Glu Asp Gly
         75                  80                  85 ttg tat ctg aac att tgg tca ccg gcg gcg gat ggg aag aag cgc ccg      582
Leu Tyr Leu Asn Ile Trp Ser Pro Ala Ala Asp Gly Lys Lys Arg Pro
     90                  95                 100 gta ttg ttt tgg att cat ggc ggc gct ttt tta ttc ggc tcc ggt tca      630
Val Leu Phe Trp Ile His Gly Gly Ala Phe Leu Phe Gly Ser Gly Ser
105                 110                 115                 120 ttt cca tgg tat gat gga acg gcg ttt gcc aaa cac ggc gat gtc gtt      678
Phe Pro Trp Tyr Asp Gly Thr Ala Phe Ala Lys His Gly Asp Val Val
                125                 130                 135 gtc gtg acg atc aac tac cgg atg agc gtg ttt ggc ttt ttg tat ttg      726
Val Val Thr Ile Asn Tyr Arg Met Ser Val Phe Gly Phe Leu Tyr Leu
            140                 145                 150 gga gat gcg ttt ggc gaa acg tat gcc cag gcg gga aat ctt ggc ata      774
Gly Asp Ala Phe Gly Glu Thr Tyr Ala Gln Ala Gly Asn Leu Gly Ile
        155                 160                 165 ttg gat caa gtg gcg gcg ctg cgc tgg gtg aaa gag aac att gag gcg      822
Leu Asp Gln Val Ala Ala Leu Arg Trp Val Lys Glu Asn Ile Glu Ala
170                 175                 180 ttc ggc ggt gat ccg gac aac att acg att ttt ggc gaa tca gcc gga      870
Phe Gly Gly Asp Pro Asp Asn Ile Thr Ile Phe Gly Glu Ser Ala Gly
185                 190                 195                 200 gcg gca agc gtt ggc gtg ctg ttg tcg ctt ccg gaa gca agc ggg ctg      918
Ala Ala Ser Val Gly Val Leu Leu Ser Leu Pro Glu Ala Ser Gly Leu
                205                 210                 215 ttt cga cgc gct ata ttg caa agc gga tcg ggt tcg ctt ctt ctt cgt      966
Phe Arg Arg Ala Ile Leu Gln Ser Gly Ser Gly Ser Leu Leu Leu Arg
            220                 225                 230 tct ccg gag acg gcg atg gct ctg act gaa cgc att tta gaa cgt gcc     1014
Ser Pro Glu Thr Ala Met Ala Leu Thr Glu Arg Ile Leu Glu Arg Ala
        235                 240                 245 ggc atc cgt ccg ggt gac cgc gat cgg ctg ctg tcg att cca gca gca     1062
Gly Ile Arg Pro Gly Asp Arg Asp Arg Leu Leu Ser Ile Pro Ala Ala
250                 255                 260 gag cta ttg cag gcg gcg atg tcg ctc ggc cca gga atc acg tac ggt     1110
Glu Leu Leu Gln Ala Ala Met Ser Leu Gly Pro Gly Ile Thr Tyr Gly
265                 270                 275                 280 ccg gtg gtt gac gga cat gtg ttg cga cgc cat ccg atc gaa gcg ctc     1158
Pro Val Val Asp Gly His Val Leu Arg Arg His Pro Ile Glu Ala Leu
                285                 290                 295 cac gac ggg gca gca agt gat att cca atc cta att ggc gtg acg aaa     1206
His Asp Gly Ala Ala Ser Asp Ile Pro Ile Leu Ile Gly Val Thr Lys
            300                 305                 310 gac gaa tac aat ttg ttt tca ttg act gat ccg tca ttg aca aga ctc     1254
Asp Glu Tyr Asn Leu Phe Ser Leu Thr Asp Pro Ser Leu Thr Arg Leu
315                 320                 325
```

-continued

```
gaa gaa aaa gaa ctg ctt gac cgg atg aac cgt gag gtc ggg cct att    1302
Glu Glu Lys Glu Leu Leu Asp Arg Met Asn Arg Glu Val Gly Pro Ile
        330                 335                 340 ccg gag gag gcg gta cgc tat tac gcg gaa aca gcg gat cgg tcg gca    1350
Pro Glu Glu Ala Val Arg Tyr Tyr Ala Glu Thr Ala Asp Arg Ser Ala
345                 350                 355                 360 ccc gcg tgg caa aca tgg ctg cgc atc atg acg tac ctt gtt ttt gtc    1398
Pro Ala Trp Gln Thr Trp Leu Arg Ile Met Thr Tyr Leu Val Phe Val
                365                 370                 375 gac gga atg ttg cga acg gcg gat gcc caa gca gcg caa ggg gcg aat    1446
Asp Gly Met Leu Arg Thr Ala Asp Ala Gln Ala Ala Gln Gly Ala Asn
        380                 385                 390 gtg tac atg tat cgg ttt gat tat gaa acg ccg gcg ttt ggt gga caa    1494
Val Tyr Met Tyr Arg Phe Asp Tyr Glu Thr Pro Ala Phe Gly Gly Gln
            395                 400                 405 ctg aaa gcg tgc cat acg ctc gag ttg ccg ttt gtg ttt cat aac ctc    1542
Leu Lys Ala Cys His Thr Leu Glu Leu Pro Phe Val Phe His Asn Leu
        410                 415                 420 cat cag cct ggt gtc gag aat ttc gtc ggc aac cga cca gag cgt gag    1590
His Gln Pro Gly Val Glu Asn Phe Val Gly Asn Arg Pro Glu Arg Glu
425                 430                 435                 440 gcg att gcc agc gaa atg cat ggt gcc tgg ctt tcg ttc gcc cac acc    1638
Ala Ile Ala Ser Glu Met His Gly Ala Trp Leu Ser Phe Ala His Thr
                445                 450                 455 ggc aac ccg aac ggc gct cat tta cca gag aag tgg ccc gta tac aca    1686
Gly Asn Pro Asn Gly Ala His Leu Pro Glu Lys Trp Pro Val Tyr Thr
            460                 465                 470 aaa gag cac aaa ccg gtg ttt gtc ttt tcg gct gcg agc cat gtg gaa    1734
Lys Glu His Lys Pro Val Phe Val Phe Ser Ala Ala Ser His Val Glu
        475                 480                 485 gac gat ccg ttc ggt cgc gag cgg gaa gcg tgg caa gga cgc ctt        1779
Asp Asp Pro Phe Gly Arg Glu Arg Glu Ala Trp Gln Gly Arg Leu
    490                 495                 500 tgacgaaaaa atccataagc aacatgtgtt ctttgtctga acacgatcca aagaattcaa  1839
aaagcttctc gagagtactt ctagagcggc cgcgggccca tcgattttcc acccgggtgg  1899
ggtaccaggt aagtgtaccc aattc                                       1924
```

<210> SEQ ID NO 30
<211> LENGTH: 503
<212> TYPE: PRT
<213> ORGANISM: Artificial Sequence
<220> FEATURE:
<223> OTHER INFORMATION: Description of Artificial Sequence:cloned esterase gene from bacteria E020

<400> SEQUENCE: 30

```
Leu Lys Lys Gly Met Gly Thr Val Ile Val Glu Thr Lys Tyr Gly Arg
  1               5                  10                  15

Leu Arg Gly Gly Thr Asn Glu Gly Val Phe Tyr Trp Lys Gly Ile Pro
             20                  25                  30

Tyr Ala Lys Ala Pro Val Gly Glu Arg Arg Phe Leu Pro Pro Glu Pro
         35                  40                  45

Pro Asp Ala Trp Asp Gly Val Arg Glu Ala Thr Ser Phe Gly Pro Val
     50                  55                  60

Val Met Gln Pro Ser Asp Ser Met Phe Ser Gln Leu Leu Gly Arg Met
 65                  70                  75                  80

Asn Glu Pro Met Ser Glu Asp Gly Leu Tyr Leu Asn Ile Trp Ser Pro
                 85                  90                  95
```

-continued

```
Ala Ala Asp Gly Lys Lys Arg Pro Val Leu Phe Trp Ile His Gly Gly
            100                 105                 110
Ala Phe Leu Phe Gly Ser Gly Ser Phe Pro Trp Tyr Asp Gly Thr Ala
        115                 120                 125
Phe Ala Lys His Gly Asp Val Val Val Thr Ile Asn Tyr Arg Met
    130                 135                 140
Ser Val Phe Gly Phe Leu Tyr Leu Gly Asp Ala Phe Gly Glu Thr Tyr
145                 150                 155                 160
Ala Gln Ala Gly Asn Leu Gly Ile Leu Asp Gln Val Ala Ala Leu Arg
                165                 170                 175
Trp Val Lys Glu Asn Ile Glu Ala Phe Gly Asp Pro Asp Asn Ile
            180                 185                 190
Thr Ile Phe Gly Glu Ser Ala Gly Ala Ala Ser Val Gly Val Leu Leu
        195                 200                 205
Ser Leu Pro Glu Ala Ser Gly Leu Phe Arg Arg Ala Ile Leu Gln Ser
    210                 215                 220
Gly Ser Gly Ser Leu Leu Leu Arg Ser Pro Glu Thr Ala Met Ala Leu
225                 230                 235                 240
Thr Glu Arg Ile Leu Glu Arg Ala Gly Ile Arg Pro Gly Asp Arg Asp
                245                 250                 255
Arg Leu Leu Ser Ile Pro Ala Ala Glu Leu Leu Gln Ala Ala Met Ser
            260                 265                 270
Leu Gly Pro Gly Ile Thr Tyr Gly Pro Val Val Asp Gly His Val Leu
        275                 280                 285
Arg Arg His Pro Ile Glu Ala Leu His Asp Gly Ala Ala Ser Asp Ile
    290                 295                 300
Pro Ile Leu Ile Gly Val Thr Lys Asp Glu Tyr Asn Leu Phe Ser Leu
305                 310                 315                 320
Thr Asp Pro Ser Leu Thr Arg Leu Glu Glu Lys Glu Leu Leu Asp Arg
                325                 330                 335
Met Asn Arg Glu Val Gly Pro Ile Pro Glu Glu Ala Val Arg Tyr Tyr
            340                 345                 350
Ala Glu Thr Ala Asp Arg Ser Ala Pro Ala Trp Gln Thr Trp Leu Arg
        355                 360                 365
Ile Met Thr Tyr Leu Val Phe Val Asp Gly Met Leu Arg Thr Ala Asp
    370                 375                 380
Ala Gln Ala Ala Gln Gly Ala Asn Val Tyr Met Tyr Arg Phe Asp Tyr
385                 390                 395                 400
Glu Thr Pro Ala Phe Gly Gly Gln Leu Lys Ala Cys His Thr Leu Glu
                405                 410                 415
Leu Pro Phe Val Phe His Asn Leu His Gln Pro Gly Val Glu Asn Phe
            420                 425                 430
Val Gly Asn Arg Pro Glu Arg Glu Ala Ile Ala Ser Glu Met His Gly
        435                 440                 445
Ala Trp Leu Ser Phe Ala His Thr Gly Asn Pro Asn Gly Ala His Leu
    450                 455                 460
Pro Glu Lys Trp Pro Val Tyr Thr Lys Glu His Lys Pro Val Phe Val
465                 470                 475                 480
Phe Ser Ala Ala Ser His Val Glu Asp Asp Pro Phe Gly Arg Glu Arg
                485                 490                 495
Glu Ala Trp Gln Gly Arg Leu
            500
```

<210> SEQ ID NO 31
<211> LENGTH: 1756
<212> TYPE: DNA
<213> ORGANISM: Artificial Sequence
<220> FEATURE:
<223> OTHER INFORMATION: Description of Artificial Sequence:cloned
esterase gene from bacteria E027
<220> FEATURE:
<221> NAME/KEY: CDS
<222> LOCATION: (130)..(1632)

<400> SEQUENCE: 31

```
acatcacatc gtggatatca gtggatccgg tgcgatggat tgcttcaggg gaacttttaa      60
acacttgagt ttgacaacca ctccttaatc atttaagatt taaatgaaaa ttaaaataaa     120 tcaaaaaga gtg att caa atg aat acg ttg gtg gaa acc cgt ttt ggg aaa    171
          Val Ile Gln Met Asn Thr Leu Val Glu Thr Arg Phe Gly Lys
            1               5                  10 gtg caa ggc ggt aca gac gga gag gtt tgt ttt tgg aaa ggg att cct      219
Val Gln Gly Gly Thr Asp Gly Glu Val Cys Phe Trp Lys Gly Ile Pro
 15                  20                  25                  30 tat gcg aaa cct ccg gtg gga aaa cgc cgc ttt caa aaa ccg gaa ccg      267
Tyr Ala Lys Pro Pro Val Gly Lys Arg Arg Phe Gln Lys Pro Glu Pro
                 35                  40                  45 ccg gag aaa tgg gat ggc gtt tgg gag gcc acc cgg ttc cgg tcc atg      315
Pro Glu Lys Trp Asp Gly Val Trp Glu Ala Thr Arg Phe Arg Ser Met
             50                  55                  60 gtg atg cag ccg tcc ggc acc acc ttc agc acc gtg ctc ggg gaa gcg      363
Val Met Gln Pro Ser Gly Thr Thr Phe Ser Thr Val Leu Gly Glu Ala
         65                  70                  75 gat ctt cct gtg agc gaa gac ggt ctt tat ctg aat atc tgg tcg ccg      411
Asp Leu Pro Val Ser Glu Asp Gly Leu Tyr Leu Asn Ile Trp Ser Pro
     80                  85                  90 gca gcc gac gga aaa aag cgg ccg gtg ctc ttc tgg atc cat ggc ggc      459
Ala Ala Asp Gly Lys Lys Arg Pro Val Leu Phe Trp Ile His Gly Gly
 95                 100                 105                 110 gcc tac cag ttt ggg tcc ggc gct tcc ccc tgg tat gac ggg acg gag      507
Ala Tyr Gln Phe Gly Ser Gly Ala Ser Pro Trp Tyr Asp Gly Thr Glu
                115                 120                 125 ttt gcc aaa aac gga gat gtg gtg gtt gtc acg atc aac tac cgg ttg      555
Phe Ala Lys Asn Gly Asp Val Val Val Val Thr Ile Asn Tyr Arg Leu
            130                 135                 140 aac gcg ttt gga ttt ttg tac ttg gca gat tgg ttc ggc gac gaa ttt      603
Asn Ala Phe Gly Phe Leu Tyr Leu Ala Asp Trp Phe Gly Asp Glu Phe
        145                 150                 155 tca gcg tcg ggc aac ctg gga att ttg gac caa gtc gct gca ctg cgc      651
Ser Ala Ser Gly Asn Leu Gly Ile Leu Asp Gln Val Ala Ala Leu Arg
    160                 165                 170 tgg gtg aaa gaa aac att tcg gca ttc ggc ggc gac ccg gag caa atc      699
Trp Val Lys Glu Asn Ile Ser Ala Phe Gly Gly Asp Pro Glu Gln Ile
175                 180                 185                 190 acc atc ttc ggg gag tcg gcc gga gcc gga agc gtc ggg gtt ctg ctt      747
Thr Ile Phe Gly Glu Ser Ala Gly Ala Gly Ser Val Gly Val Leu Leu
                195                 200                 205 tcc ctc ccg gaa acc aaa ggg ctg ttt caa cgg gcg atc ttg caa agc      795
Ser Leu Pro Glu Thr Lys Gly Leu Phe Gln Arg Ala Ile Leu Gln Ser
            210                 215                 220 gga tcg ggt gcc att ttg ctc cgt tcc tct cag aca gcc tcg ggc atc      843
Gly Ser Gly Ala Ile Leu Leu Arg Ser Ser Gln Thr Ala Ser Gly Ile
        225                 230                 235 gcg gaa caa att ctt acg aaa gcc ggc att cga aaa gga gac cgc gac      891
```

```
Ala Glu Gln Ile Leu Thr Lys Ala Gly Ile Arg Lys Gly Asp Arg Asp
    240                 245                 250 cgg ttg tta tcc atc ccg gcc ggt gaa ctc ctt gaa gcc gca caa tcc       939
Arg Leu Leu Ser Ile Pro Ala Gly Glu Leu Leu Glu Ala Ala Gln Ser
255                 260                 265                 270 gtg aat ccg gga atg gtt ttt ggt ccc gtt gtg gac ggc acc gta ttg       987
Val Asn Pro Gly Met Val Phe Gly Pro Val Val Asp Gly Thr Val Leu
                275                 280                 285 aaa acc cat ccg att gaa gcg ttg gaa acc gga gcc gcc ggc gat atc      1035
Lys Thr His Pro Ile Glu Ala Leu Glu Thr Gly Ala Ala Gly Asp Ile
            290                 295                 300 ccg atc atc atc ggg gtg aca aag gat gag tac aat tta ttt aca ctg      1083
Pro Ile Ile Ile Gly Val Thr Lys Asp Glu Tyr Asn Leu Phe Thr Leu
        305                 310                 315 act gac cct tcc tgg acg aca gcg gga aaa gaa gaa ctg atg gac cgg      1131
Thr Asp Pro Ser Trp Thr Thr Ala Gly Lys Glu Glu Leu Met Asp Arg
    320                 325                 330 atc gaa cag gaa atc ggg ccg gtt ccg gaa aaa gtt ttt cca tat tac      1179
Ile Glu Gln Glu Ile Gly Pro Val Pro Glu Lys Val Phe Pro Tyr Tyr
335                 340                 345                 350 tta tct ttt ggg gat cca tcg caa ccg gta tgg caa aag ctg ttg cgc      1227
Leu Ser Phe Gly Asp Pro Ser Gln Pro Val Trp Gln Lys Leu Leu Arg
                355                 360                 365 gcc atg acc tac cac atc ttt acc cgg ggc atg tta aaa acg gct gac      1275
Ala Met Thr Tyr His Ile Phe Thr Arg Gly Met Leu Lys Thr Ala Asp
            370                 375                 380 gcc caa atc aag caa ggc ggg aag gtt tgg gtt tac cgg ttt gat tac      1323
Ala Gln Ile Lys Gln Gly Gly Lys Val Trp Val Tyr Arg Phe Asp Tyr
        385                 390                 395 gaa acc ccg ctc ttt gac ggt cgg ttg aaa gca tgt cac gca ctg gaa      1371
Glu Thr Pro Leu Phe Asp Gly Arg Leu Lys Ala Cys His Ala Leu Glu
    400                 405                 410 atc ccc ttt gtc ttt cac aac ctg cat caa ccg ggg gtc gat gtg ttc      1419
Ile Pro Phe Val Phe His Asn Leu His Gln Pro Gly Val Asp Val Phe
415                 420                 425                 430 acc ggc aca cat ccg aag cgg gag cta att tcc cgg caa atg cat gaa      1467
Thr Gly Thr His Pro Lys Arg Glu Leu Ile Ser Arg Gln Met His Glu
                435                 440                 445 gca tgg att gcc ttt gcc cgg aca ggg gat ccg aac ggc gac cat ctc      1515
Ala Trp Ile Ala Phe Ala Arg Thr Gly Asp Pro Asn Gly Asp His Leu
            450                 455                 460 ccc gat gcg tgg ttg ccc ttt gca caa aaa gac cgg ccg gcc atg gtc      1563
Pro Asp Ala Trp Leu Pro Phe Ala Gln Lys Asp Arg Pro Ala Met Val
        465                 470                 475 ttt gac acc gaa acc aga gcg gaa aag cat ctg ttt gac cgc gag cag      1611
Phe Asp Thr Glu Thr Arg Ala Glu Lys His Leu Phe Asp Arg Glu Gln
    480                 485                 490 gaa ctg tgg gaa tca aag gct tgagtgattt gctcaagcct tttttgcatt        1662
Glu Leu Trp Glu Ser Lys Ala
495                 500 tcacgtatgt attcggattt ggaattaaac aatggtgctt ttatcgaaat ggggagtgtt    1722
tgcttataat gaacgggttt acaaagcttg tttt                                1756

<210> SEQ ID NO 32
<211> LENGTH: 501
<212> TYPE: PRT
<213> ORGANISM: Artificial Sequence
<220> FEATURE:
<223> OTHER INFORMATION: Description of Artificial Sequence:cloned
      esterase gene from bacteria E027
```

-continued

<400> SEQUENCE: 32

```
Val Ile Gln Met Asn Thr Leu Val Glu Thr Arg Phe Gly Lys Val Gln
  1               5                  10                  15
Gly Gly Thr Asp Gly Glu Val Cys Phe Trp Lys Gly Ile Pro Tyr Ala
             20                  25                  30
Lys Pro Pro Val Gly Lys Arg Arg Phe Gln Lys Pro Glu Pro Pro Glu
         35                  40                  45
Lys Trp Asp Gly Val Trp Glu Ala Thr Arg Phe Arg Ser Met Val Met
     50                  55                  60
Gln Pro Ser Gly Thr Thr Phe Ser Thr Val Leu Gly Glu Ala Asp Leu
 65                  70                  75                  80
Pro Val Ser Glu Asp Gly Leu Tyr Leu Asn Ile Trp Ser Pro Ala Ala
                 85                  90                  95
Asp Gly Lys Lys Arg Pro Val Leu Phe Trp Ile His Gly Gly Ala Tyr
            100                 105                 110
Gln Phe Gly Ser Gly Ala Ser Pro Trp Tyr Asp Gly Thr Glu Phe Ala
        115                 120                 125
Lys Asn Gly Asp Val Val Val Thr Ile Asn Tyr Arg Leu Asn Ala
    130                 135                 140
Phe Gly Phe Leu Tyr Leu Ala Asp Trp Phe Gly Asp Glu Phe Ser Ala
145                 150                 155                 160
Ser Gly Asn Leu Gly Ile Leu Asp Gln Val Ala Ala Leu Arg Trp Val
                165                 170                 175
Lys Glu Asn Ile Ser Ala Phe Gly Gly Asp Pro Glu Gln Ile Thr Ile
            180                 185                 190
Phe Gly Glu Ser Ala Gly Ala Gly Ser Val Gly Val Leu Leu Ser Leu
        195                 200                 205
Pro Glu Thr Lys Gly Leu Phe Gln Arg Ala Ile Leu Gln Ser Gly Ser
    210                 215                 220
Gly Ala Ile Leu Leu Arg Ser Ser Gln Thr Ala Ser Gly Ile Ala Glu
225                 230                 235                 240
Gln Ile Leu Thr Lys Ala Gly Ile Arg Lys Gly Asp Arg Asp Arg Leu
                245                 250                 255
Leu Ser Ile Pro Ala Gly Glu Leu Leu Glu Ala Ala Gln Ser Val Asn
            260                 265                 270
Pro Gly Met Val Phe Gly Pro Val Asp Gly Thr Val Leu Lys Thr
        275                 280                 285
His Pro Ile Glu Ala Leu Glu Thr Gly Ala Ala Gly Asp Ile Pro Ile
    290                 295                 300
Ile Ile Gly Val Thr Lys Asp Glu Tyr Asn Leu Phe Thr Leu Thr Asp
305                 310                 315                 320
Pro Ser Trp Thr Thr Ala Gly Lys Glu Glu Leu Met Asp Arg Ile Glu
                325                 330                 335
Gln Glu Ile Gly Pro Val Pro Glu Lys Val Phe Pro Tyr Tyr Leu Ser
            340                 345                 350
Phe Gly Asp Pro Ser Gln Pro Val Trp Gln Lys Leu Leu Arg Ala Met
        355                 360                 365
Thr Tyr His Ile Phe Thr Arg Gly Met Leu Lys Thr Ala Asp Ala Gln
    370                 375                 380
Ile Lys Gln Gly Gly Lys Val Trp Val Tyr Arg Phe Asp Tyr Glu Thr
385                 390                 395                 400
Pro Leu Phe Asp Gly Arg Leu Lys Ala Cys His Ala Leu Glu Ile Pro
```

```
                405                 410                 415
Phe Val Phe His Asn Leu His Gln Pro Gly Val Asp Val Phe Thr Gly
            420                 425                 430

Thr His Pro Lys Arg Glu Leu Ile Ser Arg Gln Met His Glu Ala Trp
            435                 440                 445

Ile Ala Phe Ala Arg Thr Gly Asp Pro Asn Gly Asp His Leu Pro Asp
    450                 455                 460

Ala Trp Leu Pro Phe Ala Gln Lys Asp Arg Pro Ala Met Val Phe Asp
465                 470                 475                 480

Thr Glu Thr Arg Ala Glu Lys His Leu Phe Asp Arg Glu Gln Glu Leu
                485                 490                 495

Trp Glu Ser Lys Ala
            500

<210> SEQ ID NO 33
<211> LENGTH: 168
<212> TYPE: DNA
<213> ORGANISM: Artificial Sequence
<220> FEATURE:
<223> OTHER INFORMATION: Description of Artificial Sequence:partial
      clone of esterase gene from bacteria E007 5'end

<400> SEQUENCE: 33
ctagtgattc cctcctttcg tgcccattag tactttcggt tgcgcggtga acaaatgaag      60
gggttttcta ttggaaaggg attccgtacg cgaaagctcc ggtcggtgaa cgccgatttt    120
tgccgccgga accgccgat gcatgggacg atgcgtgagg ccgacatc                  168

<210> SEQ ID NO 34
<211> LENGTH: 140
<212> TYPE: DNA
<213> ORGANISM: Artificial Sequence
<220> FEATURE:
<223> OTHER INFORMATION: Description of Artificial Sequence:partial
      cloned sequence of esterase gene from bacteria E007 3'end

<400> SEQUENCE: 34
gggcaagctt ctacatgcat cgccccgagc atgaaacgtc ggcgtccggt ggaaaactga     60
acgggtgcca tacacgaggg tttctcgttt cggattcata accttaatga accccttgtc   120
gagaatttcc gcgtaaactg                                                140

<210> SEQ ID NO 35
<211> LENGTH: 234
<212> TYPE: DNA
<213> ORGANISM: Artificial Sequence
<220> FEATURE:
<223> OTHER INFORMATION: Description of Artificial Sequence:partial
      cloned esterase gene from bacteria E002 5'end

<400> SEQUENCE: 35 aaatttaaa ccgaagccac cgcaaagcca aagaaaggg aaaaaatttt tcaaggtcaa       60
cctttagcca aatcgccggt tccaaaacgc cgtttttacg gttttaatgt gaaacgtcaa   120
tcggaaagac tgaattaagg cgatccgaat cggtgataac gggcgtcact tagcccgacg   180
attacggggc tttccctgcc acagaagcaa atgatttgag cgaatacata gaag          234

<210> SEQ ID NO 36
<211> LENGTH: 2122
<212> TYPE: DNA
<213> ORGANISM: Artificial Sequence
<220> FEATURE:
```

<223> OTHER INFORMATION: Description of Artificial Sequence:partial
      cloned esterase gene from bacteria E002 3'end

<400> SEQUENCE: 36

```
gaacggcgtt tgccaaacac ggcgatgtcg ttgtcgtgac gatcaactac cggatgagcg      60
tgtttggctt tttgtatttg ggagatgcgt gcggtgatcc ggacaacatt acgatttttg     120
gcgaatcaag ccggagcggc aagcgttggc gtgctgttgt cgctttcgga gcggtgatcc     180
ggacaacatt acgatttttg gcgaatcaag ccggagcggc aagcgttggc gtgctgttgt     240
cgctttcgga gcggtgatcc ggacaacatt acgatttttg gcgaatcaag ccggagcggc     300
aagcgttggc gtgctgttgt cgctttcgga gaacgcattt ttataaaccg tgcccggtaa     360
tttcgttccg gttggacccg caatccggct gcttgttctt ccaagcaac taacgcattt      420
ttataaaccg tgcccggtaa tttcgttccg gttggacccg caatccggcg tcttgttctt     480
tccaagcaac taacgcattt ttataaaccg ttcccggtaa tttcgttccg gttggacccg     540
caatccggct gcttgttctt ccaagcaac tcaatccggc tgcttgttct ttccaagcaa      600
ctgaccttt gcaagcggct aatgttcctc tcgggcccca ggaaatcacg tacgttcccg      660
tggttcccca ggcgggaaat cttggcatat ggatcaagt ggcggcgctg cgctgggtga      720
aagagaacat tgaggcgttc ggcggtgatc cggacaacat tacgattttt ggcgaatcag     780
ccggagcggc aagcgttggc gtgctgttgt cgcttccgga agcaagcggg ctgtttcgac     840
gcgctatatt gcaagcggat cgggttcgct tcttcttcgt tctccggaga cggcgatggc     900
tctgactgaa cgcattttag aacgtgccgg catccgtccg ggtgaccgcg atcggctgct     960
gtcgattcca gcagcagagc tattgcagcg gcgatgtcgc tcggcccagg aatcacgtac    1020
ggtccggtgg ttacggacat gtgttgcgac gccatccgat cgaagcgctc cacgacgggg    1080
cagcaagtga tattccaatc ctaattggcg tgacgaaaga cgaatacaat ttgttttcat    1140
tgactgatcc cgtcattgac aagactcgaa gaaaagaac tgcttgaccg gatgaaccgt     1200
gaggtcgggc ctattccgga ggaaggcggt accgctatta cgcggaaacc agcggatcgg    1260
gtcgggcacc ccgcgtggca acatggctg cgcatcatga cgtaccttgt ttttgtcgac     1320
ggaatgttgc gaacggcgga tgcccaagca gcgcaagggg cgaatgtgta catgtatcgg    1380
tttgattatg aaacgccggc gttcggtgga caactgaaag cgtgccatac gctcgagttg    1440
ccgtttgtgt ttcataacct ccatcagcct ggtgtcgaga atttcgtcgg caaccgacca    1500
gagcgtgagg cgattgccag cgaaatgcat ggtgcctggc tttcgttcgc ccacaccggc    1560
aacccgaacg gcgctcattt accagagaag tggcccgtat acacaaaaga gcacaaaccg    1620
gtgtttgtct tttcggctgc gagccatgtg aagacgatc cgttcggtgc gagcgggaag    1680
gtggcaagga cgccttttgac gaaaaaatcc ataagcaaca tgtgttcttt gtctgaacac    1740
gatcaaggta ccgcgcattt tcgcggaaaa agaccgtggg caaacgttcg cctttacctc    1800
taaaaggaat gacgcaacat gtctgcactt cacaggaaag aggacgaaac ggttggtttt    1860
taagaatagg aaaggtgtc ccgttttttt gggacaccct cttctatgta ttcgctcaaa     1920
tcatttgctt ctgtggcagg gaaagccccg taatcgtcgg gctaagtgcc gttatcacc    1980
gattcggatc gccttaattc agttttccga ttgacgtttc acattaaaac cgtaaaaaat    2040
tttggaaccc gatttggcta aaggttgacc gaaaattttt ttcccttcct tttggctttg    2100
cggtggcttc ggtttaaaat tt                                             2122
```

<210> SEQ ID NO 37

```
<211> LENGTH: 386
<212> TYPE: DNA
<213> ORGANISM: Artificial Sequence
<220> FEATURE:
<223> OTHER INFORMATION: Description of Artificial Sequence:partial
      cloned esterase gene from bacteria E014 3'end

<400> SEQUENCE: 37
cctgcacaaa tccgatgtga aatgttttgg gatattcggc ttgccttcct tttcattaaa      60
gccagtaaca tcccttgatt taacagagta aacgagtcgc cgcgggtagt cacggttttc     120
agatcgaaat atttcttcaa cagcgaatcg ctcttcagtg gcttgaacgt cagtaaccgt     180
cagattcaga tggttgagat tcatcgaatc tcctctcatg attttttttgt aaaaatgatc    240 gctgttttag tgatccttaa cgatggcttt catgtacaaa tttacaatcg cttcaaggtc     300
ttttgggtat caggttgttg gggtggacgg tgtcgacaaa tgagtccggc aagcaggata     360
taaagtaagc cgaatgggtc cgacaa                                          386
```